US010517941B2

(12) United States Patent
Meijberg et al.

(10) Patent No.: US 10,517,941 B2
(45) Date of Patent: Dec. 31, 2019

(54) INFLUENZA VIRUS VACCINES AND USES THEREOF

(71) Applicant: Janssen Vaccines & Prevention B.V., Leiden (NL)

(72) Inventors: Jan Willem Meijberg, Leiden (NL); Antonietta Impagliazzo, Leiden (NL); Katarina Radosevic, Nootdorp (NL); Jehangir Wadia, San Diego, CA (US); Robert Anthony Williamson, London (GB); Michelle Wagner, San Diego, CA (US); Zhaoqing Ding, San Diego, CA (US)

(73) Assignee: Janssen Vaccines & Prevention B.V., Leiden (NL)

( * ) Notice: Subject to any disclaimer, the term of this patent is extended or adjusted under 35 U.S.C. 154(b) by 346 days.

(21) Appl. No.: 14/952,794

(22) Filed: Nov. 25, 2015

(65) Prior Publication Data

US 2016/0136262 A1 May 19, 2016

Related U.S. Application Data

(63) Continuation of application No. PCT/EP2014/060997, filed on May 27, 2014.

(30) Foreign Application Priority Data

May 30, 2013 (EP) .................................... 13169830

(51) Int. Cl.
*A61K 39/145* (2006.01)
*C07K 14/005* (2006.01)
*C12N 7/00* (2006.01)
*A61K 39/00* (2006.01)

(52) U.S. Cl.
CPC .......... *A61K 39/145* (2013.01); *C07K 14/005* (2013.01); *C12N 7/00* (2013.01); *A61K 2039/57* (2013.01); *C07K 2319/40* (2013.01); *C07K 2319/91* (2013.01); *C12N 2760/16134* (2013.01); *C12N 2760/16151* (2013.01); *C12N 2760/16171* (2013.01)

(58) Field of Classification Search
None
See application file for complete search history.

(56) References Cited

U.S. PATENT DOCUMENTS

| 5,057,540 | A | 10/1991 | Kensil et al. | |
|---|---|---|---|---|
| 2010/0297174 | A1 | 11/2010 | Garcia-Sastre et al. | |
| 2013/0129761 | A1 | 5/2013 | Garcia-Sastre et al. | |
| 2014/0357845 | A1* | 12/2014 | Meijberg | A61K 39/12 |
| | | | | 530/396 |

FOREIGN PATENT DOCUMENTS

| EP | 11173953.8 | 7/2011 |
|---|---|---|
| WO | 9003184 | 4/1990 |
| WO | 90003184 A1 | 4/1990 |
| WO | 9014837 | 12/1990 |
| WO | 199014837 A1 | 12/1990 |
| WO | 9611711 | 4/1996 |
| WO | 9611711 A1 | 4/1996 |
| WO | 2004004762 | 1/2004 |
| WO | 2005002620 | 1/2005 |
| WO | 2008028946 | 3/2008 |
| WO | 2010117786 | 10/2010 |
| WO | 2010130636 | 11/2010 |
| WO | 2011123495 | 10/2011 |
| WO | 2013007770 | 1/2013 |
| WO | 2013079473 | 6/2013 |
| WO | 2013079473 A1 | 6/2013 |
| WO | 2014191435 | 12/2014 |
| WO | 2014191435 A1 | 12/2014 |
| WO | 2016005480 A1 | 1/2016 |
| WO | 2016005482 A1 | 1/2016 |

OTHER PUBLICATIONS

Devereux et al., "A Comprehensive Set of Sequence Analysis Pograms for the VAX", Nucleic Acids Research, vol. 12, No. 1, 9 pgs (1984).
Ekiert et al., "A Highly Conserved Neutralizing Epitope on Group 2 Influenza A Viruses", Science, vol. 333, pp. 843-850, 8 pgs (Aug. 2011).
Ekiert et al., "Antibody Recognition of a Highly Conserved Infuenza Virus Epitope", Science, vol. 324, pp. 246-251 (Apr. 2009).
Ferguson et al., "Ecological and Immunological Determinants of Influenza Evolution", Nature, vol. 422, pp. 428-433 (Mar. 2003).
Lorieau et al., "The Complete Influenza Hemagglutinin Fusion Domain Adopts a Tight Helical Hairpin Arrangement at the Lipid:Water Interface", PNAS, vol. 107, No. 25, pp. 11341-11346 (Jun. 2010).
Steel et al., "Influenza Virus Based on the Conserved Hemagglutinin Stalk Domain", MBio, vol. 1, No. 1, 9 pgs (Apr. 2010).

(Continued)

*Primary Examiner* — Benjamin P Blumel
(74) *Attorney, Agent, or Firm* — Panitch Schwarze Belisario & Nadel LLP

(57) ABSTRACT

Provided are influenza hemagglutinin stem domain polypeptides comprising (a) an influenza hemagglutinin HA1 domain that comprises an HA1 N-terminal stem segment comprising the amino acids from position 1 to position x, preferably from position p to position x, of the HA1 domain, covalently linked by a linking sequence of 0-50 amino acid residues to an HA1 C-terminal stem segment, comprising the amino acids from position y to and including the C-terminal amino acid of the HA1 domain; and (b) an influenza hemagglutinin HA2 domain, wherein the hemagglutinin stem domain polypeptide is resistant to protease cleavage at the junction between HA1 and HA2, and wherein one or more amino acid of the amino acids at positions 337, 340, 352, 353, 402, 406, 409, 413 and/or 416 have been mutated, as compared to the corresponding positions in wild-type influenza HA.

26 Claims, 26 Drawing Sheets

Specification includes a Sequence Listing.

(56) References Cited

OTHER PUBLICATIONS

Throsby et al., "Heterosubtypic Neutralizing Monoclonal Antibodies Cross-Protective Against H5N1 and H1N1 Recovered from Human IgM Memory B Cells", PLOS ONE, vol. 3, No. 12, 15 pgs (Dec. 2008).
Dopheide et al., "The Location of the Bromelain Cleavage Site in a Hong Kong Influenza Virus Haemmagglutinin", J. Ge. Virol., vol. 52, pp. 367-370 (1981).
Wilson et al., "Structure of the Haemagglutinin Membrane Glycoprotein of Influenza Virus at 3 A Resolution", Nature, vol. 289, pp. 366-373 (Jan. 1981).
PCT International Search Report dated Sep. 16, 2014, PCT/EP2014/060997.
PCT Written Opinion dated Sep. 16, 2014, PCT/EP2014/060997.
G. Bommakanti et al., Design of *Escherichia coli*-Expressed Stalk Domain Immunogens of H1N1 Hemagglutinin That Protect Mice from Lethal Challenge, Journal of Virology, Sep. 26, 2012, pp. 13434-13444, vol. 86, No. 24.
Sagawa et al., The immunological activity of a deletion mutant of influenza virus haemagglutinin lacking the globular region, Journal of General Virology, Jan. 1, 1996, pp. 1483-1487, vol. 77, No. 7.
John Steel et al., Influenza virus vaccinebased on the conserved hemagglutinin stalk domain, MBIO, May 18, 2010, pp. 1-9, vol. 1, Issue 1, American Society for Microbiology.
Gayathri Bommakanti et al., Design of an HA2-based *Escherichia coli* expressed influenza immunogen that protects mice from pathogenic challenge, Proceedings of the National Academy of Sciences, Aug. 3, 2010, pp. 13701-13706, vol. 107, No. 31.
Alberini et al., "Pseudoparticle Neutralization is a Reliable Assay to Measure Immunity and Cross-Reactivity to H5N1 Influenza Viruses", Vaccine, vol. 27, pp. 5998-6003 (2009).
Bommakanti et al., "Design of *Escherichia coli*-Expressed Stalk Domain Immunogens of H1N1 Hemagglutinin That Protect Mice from Lethal Challenge", Journ. of Virology, vol. 86, No. 24, pp. 13434-13444 (Dec. 2012).
Cheng et al., "Development of a Robust Reporter-based ADCC Assay with Frozen, Thaw-and-use Cells to Measure Fc Effector Function of Therapeutic Antibodies", Journ. Immunol. Methods, vol. 414, pp. 69-81 (2014).
Coffman et al., "Vaccine Adjuvants" Putting Innate Immunity to Work, Immunity, vol. 33, pp. 492-503(Oct. 2010).
DiLillo et al., "Broadly Neutralizing Hemagglutinin Stalk-Specific Antibodies Require FcγR Interactions for Protection Against Influenza Virus in Vivo", Nat. Med., vol. 20, No. 2, pp. 143-153 (Feb. 2014).
Devereux et al., "A Comprehensive Set of Sequence Analysis Programs for the VAX", Nucl. Acids Res., vol. 12, No. 1, pp.387-395 (1984).
Dopheide et al., "The Location of the Bromelain Cleavage Site in a Hong Kong Influenza Virus Haemagglutinin", Journ. Gen. Virol., vol. 52, pp. 367-370 (1981).
Ekiert et al., "A Highly Conserved Neutralizing Epitope on Group 2 Influenza A Viruses", Science, vol. 333, No. 6044, pp. 843-850 (2011).
Ferguson et al., "Ecological and Immunological Determinants of Influenza Evolution", Nature, vol. 422, pp. 428-443 (Mar. 2003).
Lorieau et al., "The Complete Influenza Hemagglutinin Fusion Domain Adopts a Tight Helical Hairpin Arrangement at the Lipid:Waler Interface", Proc. Natl. Acad. Sci., vol. 107, No. 25, pp. 11341-11346 (Jun. 2010)
Parekh et al., "Development and Validation of an Antibody-Dependent Cell-Mediated Cytotoxicity-Reporter Gene Assay", mAbs, vol. 4, No. 3, pp. 310-318 (2012).
Schnueriger et al., "Development of a Quantitative, Cell-Line Based Assay to Measure ADCC Activity Mediated by Therapeutic Antibodies", Molec. Immun., vol. 48, pp. 1512-1517 (2011)
Steel et al., "Influenza Virus Vaccine Based on the Conserved Hemagglutinin Stalk Domain", mBio, vol. 1, No. 1, pp. 1-9 (Apr. 2010)

Stevens et al., "Structure of the Uncleaved Human H1 Hemagglutinin from the Extinct 1918 Influenza Virus", Science, vol. 303, pp. 1866-1870 (Mar. 2004).
Stevens et al., "Structure and Receptor Specificity of the Hemagglutinin from an H5N1 Influenza Virus", Science, vol. 312, pp. 404-410 (Apr. 2006).
Temperton et al., "A Sensitive Retroviral Pseudotype Assay for Influenza H5N1-Neutralizing Antibodies", Viruses, vol. 1, No. 3 pp. 105-112 (2007).
Bommakanti et al., Supporting Information, 10.1073/PNAS.1007465107, pp. 1-6, 2010.
LU et al., "Production and Stabilization of the Trimeric Influenza Hemagglutinin Stem Domain for Potentially Broadly Protective Influenza Vaccines", Proc. of the Nat. Acad. of Sciences, pp. 1-27 (2013).
Zhirnov et al., "Cleavage of Influenza A Virus Hemagglutinin in Human Respiratory Epithelium is Cell Associated and Sensitive to Exogenous Antiproteases", Journal of Virology, vol. 76, No. 17, pp. 8682-8689, Sep. 2002.
Ekiert et al., "Antibody Recognition of a Highly Conserved Influenza Virus Epitope", Science, vol. 324, pp. 246-251 (Apr. 2009).
Mallajosyula et al., "Influenza Hemagglutinin Stem-Fragment Immunogen Elicts Broadly Neutralizing Antibodies and Confers Heterologous Protection", Proc. of the Nat. Acad. of Sciences, vol. 111, No. 25, pp. E2514-E2523 (Jun. 2014).
DeGorce et al., "HTRF: A technology tailored for drug discovery-a review of theoretical aspects and recent applications," Curr. Chem. Genomics 3:22-32 (2009).
Bommakanti et al., "Design of an HA2-based *Escherichia coli* expressed influenza immunogen that protects mice from pathogenic challenge", Proceedings of the National Academy of Sciences of the United States of America, vol. 107, No. 31, pp. 13701-13706, 2010.
Int'l Search Report and Written Opinion dated Sep. 16, 2014 in Int'l Application No. PCT/EP2014/060997.
Ichihashi et al., "Cross-Protective Peptide Vaccine against Influenza A Viruses developed in HLA-A *2402 Human Immunity Model", PLoS One, vol. 6, Issue 9, pp. 1-9, Sep. 2011.
Atsmon et al., "Safety and Immunogenicity of Multimeric-001-a Novel Universal Influenza Vaccine", Journ. Clin Immunol., vol. 32, pp. 595-603 (2012).
Safronetz et al., "Pandemic Swine-Origin H1N1 Influenza A Virus Isolates Show Heterogeneous Virulence in Macaques", Journ. of Virol., vol. 85, No. 3, pp. 1214-1223 (Feb. 2011).
Sun et al., "Modifications to the Hemagglutinin Cleavage Site Control the Virulence of a Neurotropic H1N1 Influenza Virus", Journ. of Virology, vol. 84, No. 17, pp. 8683-8690 (2010).
Kodihalli et al., "Strategies for inducing protection against avian influenza A virus subtypes with DNA vaccines", Vaccine,18(23)2592-2599, 2000.
Sagawa et al., The immunological activity of a deletion mutant of influenza virus haemagglutinin lacking the globular region, Journal of General Virology, pp. 1483-87, vol. 77, No. 7., 1996.
Eang et al., Vaccination with a synthetic peptide from the influenza virus hemagglutinin provides protection against distinct viral subtypes, Proceedings of the National Academy of Sciences of the United States of America, pp. 18979-18984, vol. 107, No. 44., Nov. 2010.
Bianchi et al., Universal influenza B vaccine based on the maturational cleavage site of the hemagglutinin precursor, Journal of Virology, The American Society for Microbiology, pp. 7380-7388, vol. 79, No. 12, 2005.
Kang et al., Novel vaccines against influenza viruses, Virus Research, pp. 31-38, vol. 162, No. 1., Oct. 1, 2011.
Eckert et al., Stalking influenza, Proceedings of the National Academy of Sciences of the United States of America, , pp. 13563-13564, vol. 107, No. 31, Aug. 3, 2010.
Steel et al., Live Attenuated Influenza Viruses Containing NS1 Truncations as Vaccine Candidates against H5N1 Highly Pathogenic Avian influenza, Journal of Virology, pp. 1742-1753, vol. 83, No. 4, Feb. 2009.

* cited by examiner s127H1 SEQ ID NO: 66

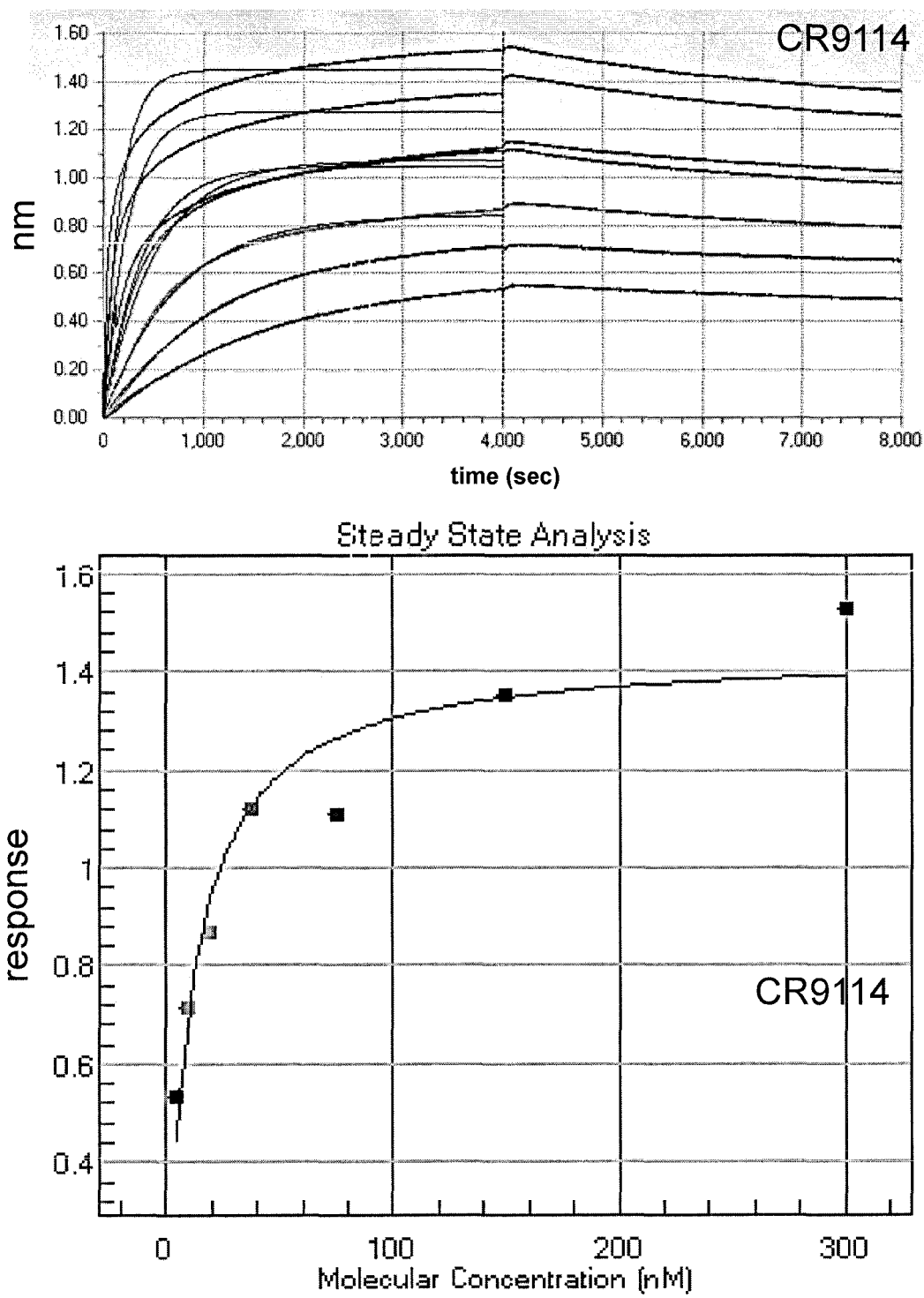
s127H1 SEQ ID NO: 66
FIG.2A - continued s86B4 SEQ ID NO: 67

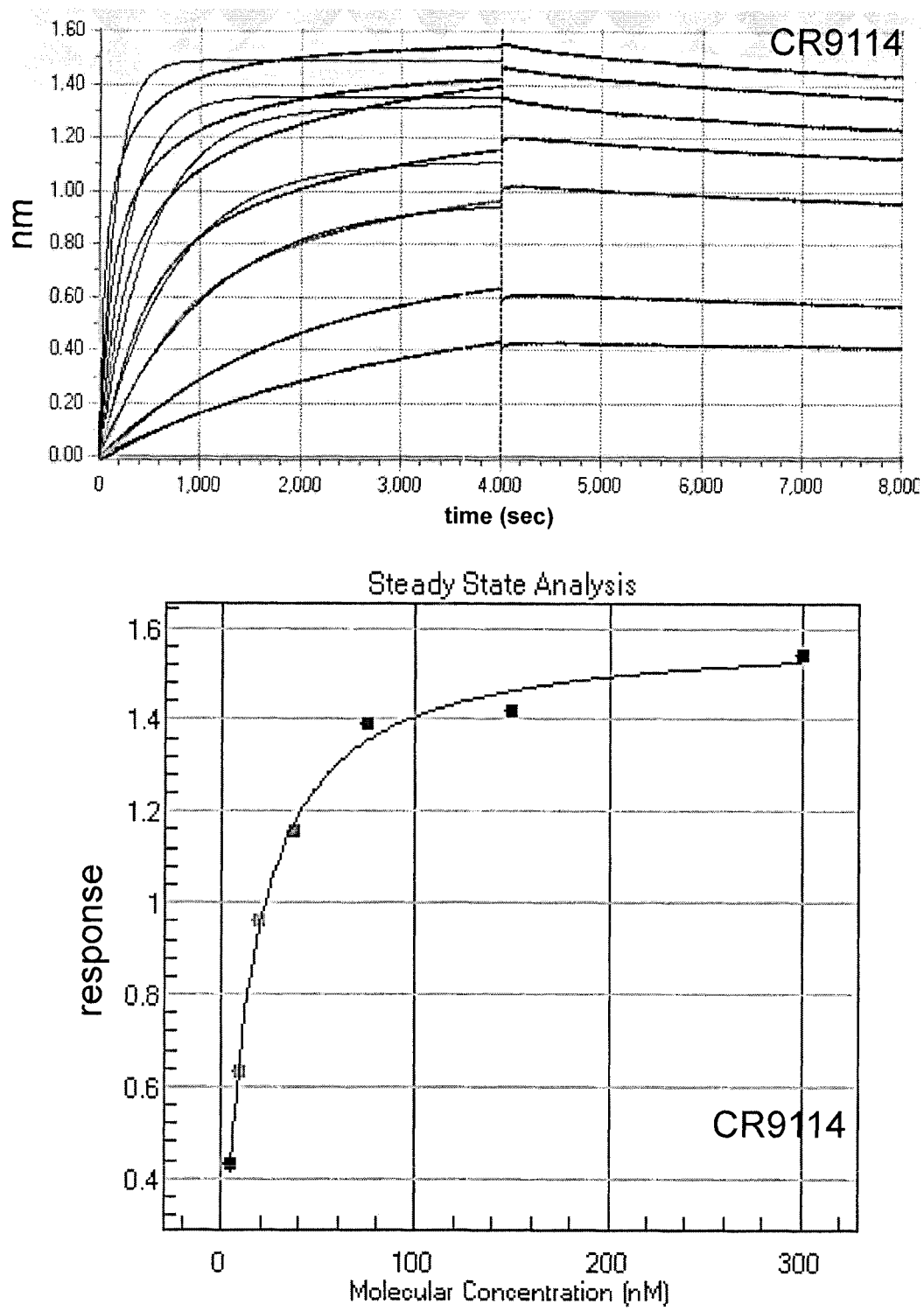
s86B4 SEQ ID NO: 67
FIG. 2B – continued s74H9 SEQ ID NO: 65

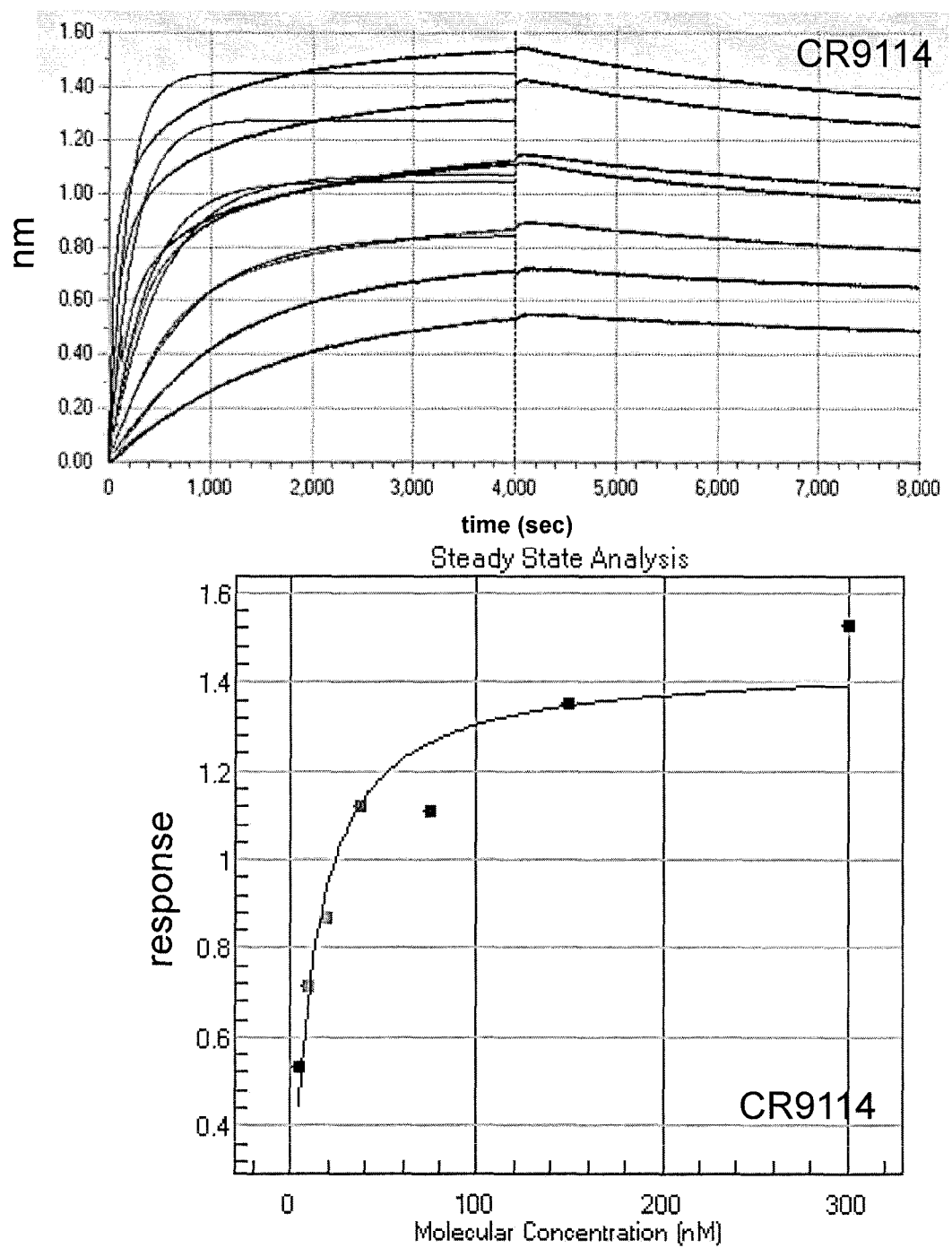
s74H9 SEQ ID NO: 65
FIG. 2C - continued s6E12 SEQ ID NO: 69

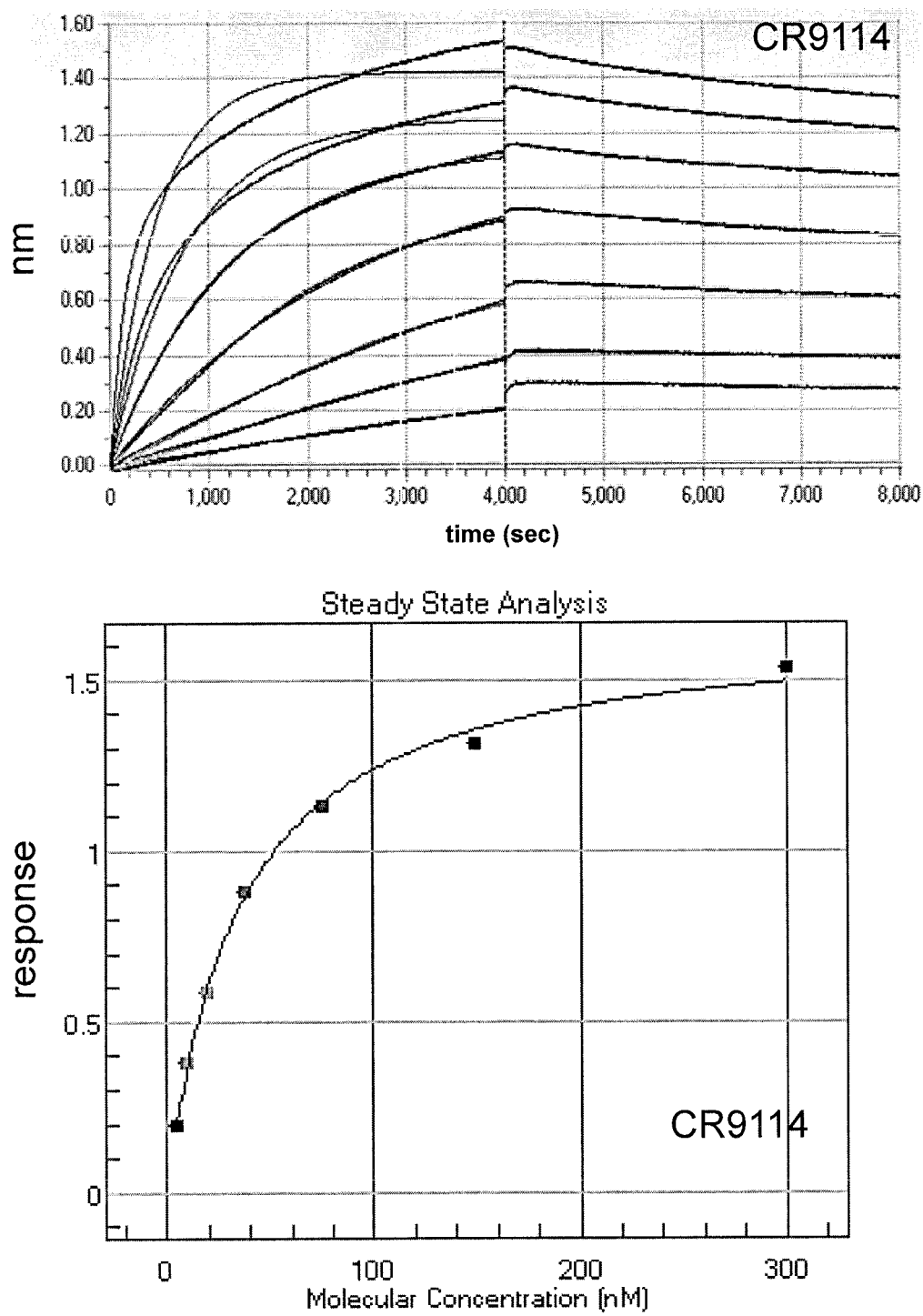
s6E12 SEQ ID NO: 69
FIG. 2D - continued s55G7 SEQ ID NO: 68

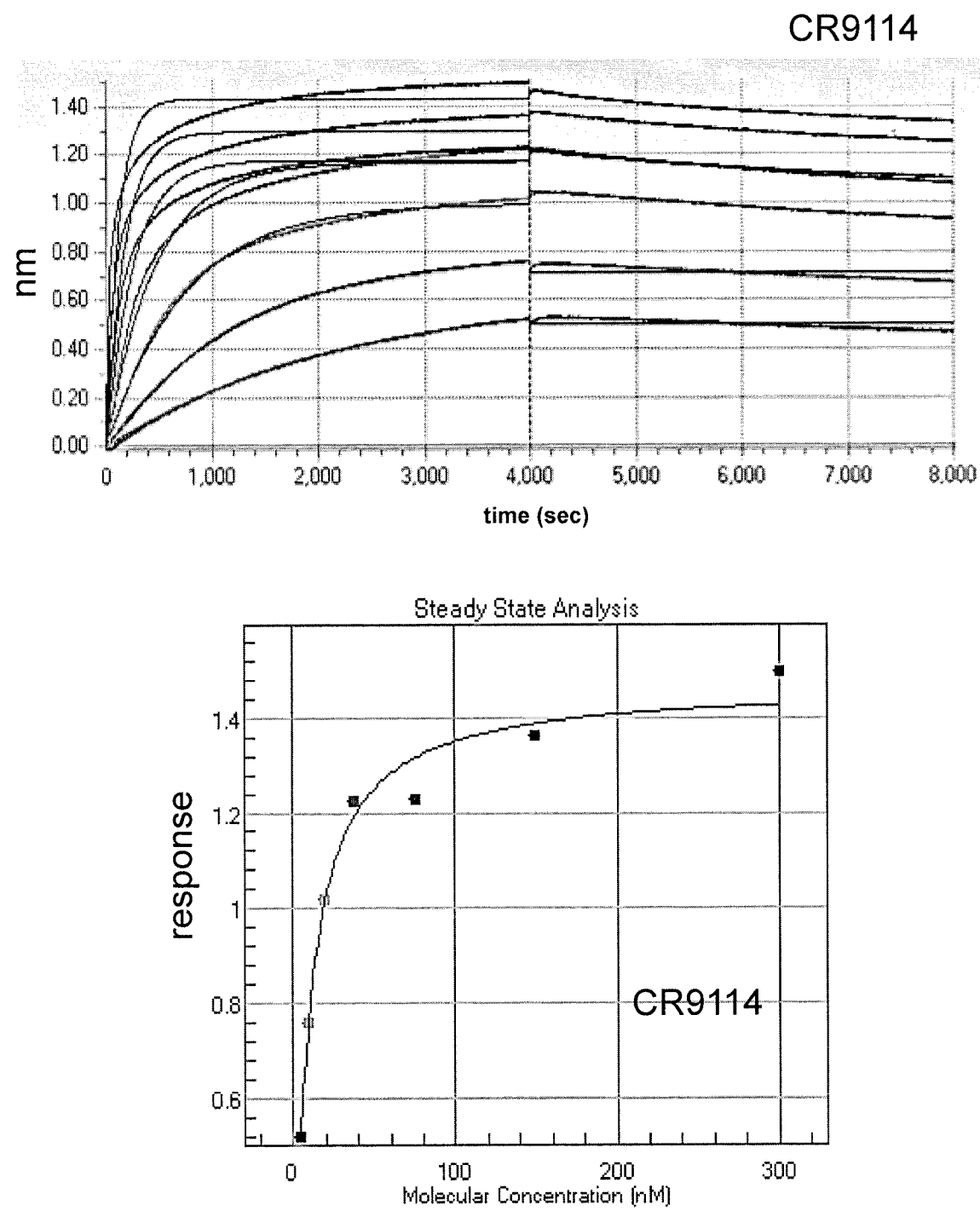
s55G7 SEQ ID NO: 68
FIG. 2E - continued s74H9 SEQ ID NO: 34 s6E12 SEQ ID NO: 38

INFLUENZA VIRUS VACCINES AND USES THEREOF

CROSS-REFERENCE TO RELATED APPLICATIONS

This application is a continuation of International Patent Application PCT/EP2014/060997, filed May 27, 2014, designating the United States of America and published in English as International Patent Publication WO 2014/191435 A1 on Dec. 4, 2014, which claims the benefit under Article 8 of the Patent Cooperation Treaty and under 35 U.S.C. § 119(e) to European Patent Application Serial No. 13169830.0, filed May 30, 2013, the disclosure of each of which is hereby incorporated herein in its entirety by this reference.

STATEMENT ACCORDING TO 37 C.F.R. § 1.821(c) or (e)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

TECHNICAL FIELD

The disclosure relates to the field of medicine. Provided herein are influenza hemagglutinin stem domain polypeptides, methods for providing hemagglutinin stem domain polypeptides, compositions comprising the same, vaccines comprising the same and methods of their use, in particular, in the detection, prevention and/or treatment of influenza.

BACKGROUND

Influenza viruses are major human pathogens, causing a respiratory disease (commonly referred to as "influenza" or "the flu") that ranges in severity from sub-clinical infection to primary viral pneumonia, which can result in death. The clinical effects of infection vary with the virulence of the influenza strain and the exposure, history, age, and immune status of the host. Every year, it is estimated that approximately 1 billion people worldwide undergo infection with influenza virus, leading to severe illness in 3-5 million cases and an estimated 300,000 to 500,000 of influenza-related deaths. The bulk of these infections can be attributed to influenza A viruses carrying H1 or H3 hemagglutinin subtypes, with a smaller contribution from Influenza B viruses and, therefore, representatives of all three are included in the seasonal vaccine. The current immunization practice relies on early identification of circulating influenza viruses to allow for timely production of an effective seasonal influenza vaccine. Apart from the inherent difficulties in predicting the strains that will be dominant during the next season, antiviral resistance and immune escape also play a role in failure of current vaccines to prevent morbidity and mortality. In addition to this, the possibility of a pandemic caused by a highly virulent viral strain originating from animal reservoirs and reassorted to increase human-to-human spread, poses a significant and realistic threat to global health.

Influenza A viruses are widely distributed in nature and can infect a variety of birds and mammals. Influenza viruses are enveloped RNA viruses that belong to the family of Orthomyxoviridae. Their genomes consist of eight single-stranded RNA segments that code for eleven different proteins, one nucleoprotein (NP), three polymerase proteins (PA, PB1, and PB2), two matrix proteins (M1 and M2), three non-structural proteins (NS1, NS2, and PB1-F2), and two external glycoproteins (hemagglutinin (HA) and neuraminidase (NA)). The viruses are classified on the basis of differences in antigenic structure of the HA and NA proteins, with their different combinations representing unique virus subtypes that are further classified into specific influenza virus strains. Although all known subtypes can be found in birds, currently circulating human influenza A subtypes are H1N1 and H3N2. Phylogenetic analysis has demonstrated a subdivision of hemagglutinins into two main groups: inter alia, the H1, H2, H5 and H9 subtypes in phylogenetic group 1 and, inter alia, the H3, H4 and H7 subtypes in phylogenetic group 2.

The influenza type B virus strains are strictly human. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and BNictoria/2/87 (B/Victoria) lineages (Ferguson et al., 2003). Although the spectrum of disease caused by influenza B viruses is generally milder than that caused by influenza A viruses, severe illness requiring hospitalization is still frequently observed with influenza B infection.

It is known that antibodies that neutralize the influenza virus are primarily directed against hemagglutinin (HA). Hemagglutinin or HA is a trimeric glycoprotein that is anchored to the viral coat and has a dual function: it is responsible for binding to the cell surface receptor sialic acid and, after uptake, it mediates the fusion of the viral and endosomal membrane leading to release of the viral RNA in the cytosol of the cell. HA comprises a large head domain and a smaller stem domain. Attachment to the viral membrane is mediated by a C-terminal anchoring sequence connected to the stem domain. The protein is post-transiationaily cleaved in a designated loop to yield two polypeptides, HA1 and HA2 (the full sequence is referred to as HA0). The membrane distal head region is mainly derived from HA1 and the membrane proximal stem region primarily from HA2 (FIG. 1).

The reason that the seasonal influenza vaccine must be updated every year is the large variability of the virus. In the hemagglutinin molecule, this variation is particularly manifested in the head domain where antigenic drift and shift have resulted in a large number of different variants. Since this is also the area that is immunodominant, most neutralizing antibodies are directed against this domain and act by interfering with receptor binding. The combination of immunodominance and large variation of the head domain also explains why infection with a particular strain does not lead to immunity to other strains: the antibodies elicited by the first infection only recognize a limited number of strains closely related to the virus of the primary infection.

Recently, influenza hemagglutinin stem domain polypeptides, lacking all or substantially all of the influenza hemagglutinin globular head domain, have been described and used to generate an immune response to one or more conserved epitopes of the stem domain polypeptide. It is believed that epitopes of the stem domain polypeptide are less immunogenic than the highly immunogenic regions of a globular head domain, thus, the absence of a globular head domain in the stem domain polypeptide might allow an immune response against one or more epitopes of the stem domain polypeptide to develop (Steel et al., 2010). Steel et al. thus have created a new molecule by deleting amino acid residues 53 to 276 of HA1 of the A/Puerto Rico/8/1934 (H1N1) and A/Hong Kong/1968 (H3N2) strains from the HA primary sequence, and replacing this by a short flexible linking sequence GGGG (SEQ ID NO:77). Vaccination of mice with the H3 HK68 construct did not elicit antisera that were cross-reactive with group 1 HAs. In addition, as shown in PCT/EP2012/073706, the stem domain polypeptides were highly unstable and did not adopt the correct conformation as proven by the lack of binding of antibodies that were shown to bind to conserved epitopes in the stem region.

In addition, Bommakanti et al. (2010) described an HA2-based polypeptide comprising amino acid residues 1-172 of HA2, a 7-amino acid linker (GSAGSAG (SEQ ID NO:15)), amino acid residues 7-46 of HA1, a 6-amino acid linker GSAGSA (SEQ ID NO:16), followed by residues 290-321 of HA1, with the mutations V297T, I300E, Y302T and C305T in HA1. The design was based on the sequence of H3 HA (A/Hong Kong/1968). The polypeptide only provided cross-protection against another influenza virus strain within the H3 subtype (A/Phil/2/82 but not against an H1 subtype (A/PR/8/34)). In a more recent paper by Bommakanti et al. (2012), a stem domain sequence based on HA from H1N1 A/Puerto Rico/8/1934 (H1HA0HA6) is described. In this polypeptide, the equivalent of residues 55 to 302 have been deleted and mutations I311T, V314T, I316N, C319S, F406D, F409T, and L416D have been made. Both the H3- and HA-based polypeptides were expressed in E. coli and, therefore, lack the glycans that are a part of the naturally occurring HA proteins. When expressed in E. coli, the polypeptide is recovered mainly as high molecular weight aggregates and a minor monomeric fraction. The polypeptide binds CR6261 with two apparent dissociation constants of 9 and 0.2 µM. The authors show that mice can survive a challenge with 1LD90 of the homologous H1N1 A/Puerto Rico/8/1934 virus after immunization (twice, four-week interval) with 20 µg of protein adjuvanted with 100 µg of CpG7909. The authors also describe circularly permutated polypeptides comparable to those described above for A/Hong Kong/1/1968-derived polypeptides. These polypeptides are derived from HAs from H1N1 A/Puerto Rico/8/1934, H1N1 A/North Carolina/20/99 or H1N1 A/California/07/2009 and can provide partial protection in a mild challenge (1LD90) model in mice of H1N1 A/Puerto Rico/8/1934 (i.e., within the same subtype). Sera from guinea pigs immunized with these polypeptides did not exhibit detectable levels of neutralization when tested in a neutralization assay.

There thus still exists a need for a safe and effective universal vaccine that stimulates the production of a robust, broadly neutralizing antibody response and that offers protection against a broad set of current and future influenza virus strains (both seasonal and pandemic), in particular, providing protection against one or more influenza A virus subtypes within phylogenetic group 1 and/or group 2, for effective prevention and therapy of influenza.

BRIEF SUMMARY

Provided herein are influenza hemagglutinin stem domain polypeptides, methods for providing stem domain polypeptides, compositions comprising the same, vaccines comprising the same, and methods of their use.

In a first aspect, provided are immunogenic polypeptides comprising an influenza hemagglutinin stem domain and lacking the globular head, referred to as influenza hemagglutinin (HA) stem domain polypeptides. The polypeptides are capable of inducing an immune response when administered to a subject, in particular, a human subject. The polypeptides of the disclosure present conserved epitopes of the membrane proximal stem domain HA molecule to the immune system in the absence of dominant epitopes that are present in the membrane distal head domain. To this end, part of the primary sequence of the HA0 protein making up the head domain is removed and the remaining amino acid sequence is reconnected, either directly or, in some embodiments, by introducing a short flexible linking sequence ("linker") to restore the continuity of the amino acid chain. The resulting sequence is further modified by introducing specific mutations that stabilize the native three-dimensional structure of the remaining part of the HA0 molecule. The immunogenic polypeptides do not comprise the full-length HA1 and/or HA2 of an influenza virus.

The polypeptides are preferably based on HA of influenza A viruses of the H1 subtype.

Provided are influenza hemagglutinin stem domain polypeptides comprising (a) an influenza hemagglutinin HA1 domain that comprises an HA1 N-terminal stem segment, covalently linked by a linking sequence of 0-50 amino acid residues to an HA1 C-terminal stem segment, and (b) an influenza hemagglutinin HA2 domain, wherein the hemagglutinin stem domain polypeptides are resistant to protease cleavage at the junction between HA1 and HA2, and wherein one or more amino acids in the amino acid sequence connecting the A helix and the helix CD of HA2 have been mutated as compared to a wild-type influenza HA2 domain.

In certain embodiments, the polypeptides comprise one or more mutations on position 337, 340, 352 or 353 of SEQ ID NO:1, or equivalent positions in other influenza viruses of the H1 subtype. A mutation means that an amino acid on a specific position has been substituted by another amino acid which is not present on the corresponding position in the wild-type influenza HA, i.e., the HA of the influenza virus on which the stem polypeptide is based.

In certain embodiments, the polypeptides of the disclosure further comprise one or more mutations in the HA2 amino acid sequence connecting the C-terminal residue of helix A to the N-terminal residue of helix CD, as indicated in FIG. 1.

In certain embodiments, the HA1 N-terminal stem segment comprises the amino acids 1-x of HA1, and the HA1 C-terminal stem segment comprises the amino acids y-end (i.e., the C-terminal amino acid of HA1) of HA1. Thus, in certain embodiments, the deletion in the HA1 segment comprises the amino acid sequence from the amino acid at position x+1 up to and including the amino acid at position y-1.

In certain embodiments, the polypeptides do not comprise the signal sequence. In certain embodiments, the HA1 N-terminal segment thus comprises the amino acid p-x of HA1, wherein p is the first amino acid of the mature HA molecule (e.g., p=18 in case of SEQ ID NO:1). The person of ordinary skill in the art will be able to prepare the polypeptides described herein without the signal peptides (e.g., amino acids 1-17 of SEQ ID NO:1).

In certain embodiments, the polypeptides of the disclosure contain the intracellular sequences of HA and the transmembrane domain. In other embodiments, the polypeptides of the disclosure do not comprise the intracellular sequences of HA and the transmembrane domain. In certain embodiments, the intracellular and transmembrane sequences, e.g., the amino acid sequence from position (or the equivalent of) 519, 520, 521, 522, 523, 524, 525, 526, 527, 526, 528, 529, or 530 of the HA2 domain to the C-terminus of the HA2 domain, have been removed.

The polypeptides do not comprise the full-length HA1.

In certain embodiments, the polypeptides are glycosylated.

In certain embodiments, the immunogenic polypeptides are substantially smaller than HA0, preferably lacking all or substantially all of the globular head of HA. Preferably, the immunogenic polypeptides are no more than 360, preferably no more than 350, 340, 330, 320, 310, 305, 300, 295, 290, 285, 280, 275, or 270 amino acids in length. In certain embodiments, the immunogenic polypeptides are from about 250 to about 350, preferably from about 260 to about 340, preferably from about 270 to about 330, preferably from about 270 to about 330 amino acids in length.

In certain embodiments, the polypeptides further comprise one or more additional mutations in the HA1 and/or HA2 domain, as compared to the amino acid sequence of the HA on which the HA1 and HA2 domains are based.

The polypeptides comprise the conserved stem domain epitopes of the group 1 cross-neutralizing antibody CR6261 (as disclosed in WO2008/028946) and/or of the antibody CR9114 (as described in WO2013/007770), an antibody capable of binding to and neutralizing both group 1 and group 2 influenza A viruses, as well as influenza B viruses. It is thus another aspect of the disclosure to provide HA stem domain polypeptides, wherein the polypeptides stably present the epitopes of the antibody CR6261 and/or CR9114, as indicated by binding of the antibody or antibodies to the polypeptides. In an embodiment, the polypeptides do not bind to CR8020 and CR8057 (described in WO 2010/130636), which are monoclonal antibodies that bind to H3 influenza viruses only. The influenza hemagglutinin stem domain polypeptides provided herein are suitable for use in immunogenic compositions (e.g., vaccines) capable of generating immune responses against a plurality of influenza virus A and/or B strains. In an embodiment, the influenza hemagglutinin stem domain polypeptides are capable of generating immune responses against influenza A virus strains of phylogenetic group 1 and/or group 2, in particular, against influenza virus strains of both phylogenetic group 1 and group 2. In an embodiment, the polypeptides are capable of generating an immune response against homologous influenza virus strains. In an embodiment, the polypeptides are capable of generating an immune response against heterologous influenza virus strains of the same and/or different subtypes. In a further embodiment, the polypeptides are capable of generating an immune response to influenza virus strains of both phylogenetic group 1 and group 2 and influenza B virus strains.

The polypeptides hereof may be used, e.g., in stand-alone therapy and/or prophylaxis and/or diagnosis of a disease or condition caused by an influenza virus, in particular, a phylogenetic group 1 or 2 influenza A virus and/or an influenza B virus, or in combination with other prophylactic and/or therapeutic treatments, such as (existing or future) vaccines, antiviral agents and/or monoclonal antibodies.

In a further aspect, provided are nucleic acid molecules encoding the influenza HA stem domain polypeptides. In yet another aspect, provided are vectors comprising the nucleic acid molecules encoding the immunogenic polypeptides.

In a further aspect, provided are methods for inducing an immune response in a subject, the method comprising administering to the subject a polypeptide and/or nucleic acid molecule as described herein.

In another aspect, provided are immunogenic compositions comprising a polypeptide and/or a nucleic acid molecule as described herein. The immunogenic compositions provided herein can be in any form that allows for the compositions to be administered to a subject, e.g., mice, ferrets or humans. In a specific embodiment, the immunogenic compositions are suitable for human administration. The polypeptides, nucleic acid molecules and compositions may be used in methods of preventing and/or treating an influenza virus disease and/or for diagnostic purposes. The compositions may further comprise a pharmaceutically acceptable carrier or excipient. In certain embodiments, the compositions described herein comprise, or are administered in combination with, an adjuvant.

In another aspect, provided are polypeptides, nucleic acid molecules and/or immunogenic compositions for use as a vaccine. The disclosure, in particular, relates to immunogenic polypeptides, nucleic acid molecules, and/or immunogenic compositions for use as a vaccine in the prevention and/or treatment of a disease or condition caused by an influenza virus A subtype of phylogenetic group 1 and/or 2 and/or influenza B virus.

The various embodiments and uses of the polypeptides hereof will become more clear from the following detailed description of the disclosure.

BRIEF DESCRIPTION OF THE DRAWINGS

FIG. 2A: s127H1 SEQ ID NO:66. FIG. 2B: s86B4 SEQ ID NO:67. FIG. 2C: s74H9 SEQ ID NO:65. FIG. 2D: s6E12 SEQ ID NO:69. FIG. 2E: s55G7 SEQ ID NO:68.

FIG. 3A: s127H1 SEQ ID NO:66. FIG. 3B: s86B4 SEQ ID NO:67. FIG. 3C: s74H9 SEQ ID NO:65. FIG. 3D: s6E12 SEQ ID NO:69. FIG. 3E: s55G7 SEQ ID NO:68.

FIG. 4A: Top row, survival, mean body weight change and median clinical score for the negative (PBS) and positive control (CR6261) groups; Bottom row, survival, mean body weight change and median clinical score for the experimental groups immunized with s74H9 or s86B4. For reasons of comparison, the negative control PBS group is also shown. FIG. 4B: Immunogenicity of s74119 (SEQ ID NO:65) and s86B4 (SEQ ID NO:67). Top row, left and middle panels, immunization induces antibodies capable of recognizing the cognate antigen (s74H9 left panel, s86B4 middle panel) as well as full-length HA from H1N1 A/Brisbane/59/07 (right panel) as determined by ELISA; Bottom row, the induced antibodies are capable of competing with CR9114 for binding to full-length HA from H1N1 A/Brisbane/59/07 in a competition ELISA (left panel). For reasons of comparison, competition levels by unlabeled CR9114 (i.e., self-competition) and the non-binding monoclonal antibody CR8020, both serially diluted from 5 μg/ml starting concentration, are indicated in a separate graph.

FIG. 5A: Top row, survival, mean body weight change and median clinical score for the negative (PBS) and positive control (CR6261) groups; Bottom row, survival, mean body weight change and median clinical score for the experimental group immunized with s127H1 (SEQ ID NO:35). For reasons of comparison, the negative control PBS group is also shown. FIG. 5B: Immunogenicity of s127H1 (SEQ ID NO:35). Top row, immunization induces antibodies capable of recognizing the cognate antigen s127H1 (SEQ ID NO:35) (left panel) as well as full-length HA from H1N1 A/Brisbane/59/07 (right panel) as determined by ELISA; Bottom row, the induced antibodies are capable of competing with CR9114 for binding to full-length HA from H1N1 A/Brisbane/59/07 in a competition ELISA (left panel). For reasons of comparison, competition levels by unlabeled CR9114 (i.e., self-competition) and the non-binding monoclonal antibody CR8020, both serially diluted from 5 μg/ml starting concentration, are indicated in a separate graph.

FIG. 7A: Analysis of combination sequences in the fusion peptide area. FIG. 7B: Analysis of the B-loop area.

FIG. 9A: Analysis of combination sequences in the fusion peptide area. FIG. 9B: Analysis of the B-loop area.

DETAILED DESCRIPTION

Definitions

Figure 1:
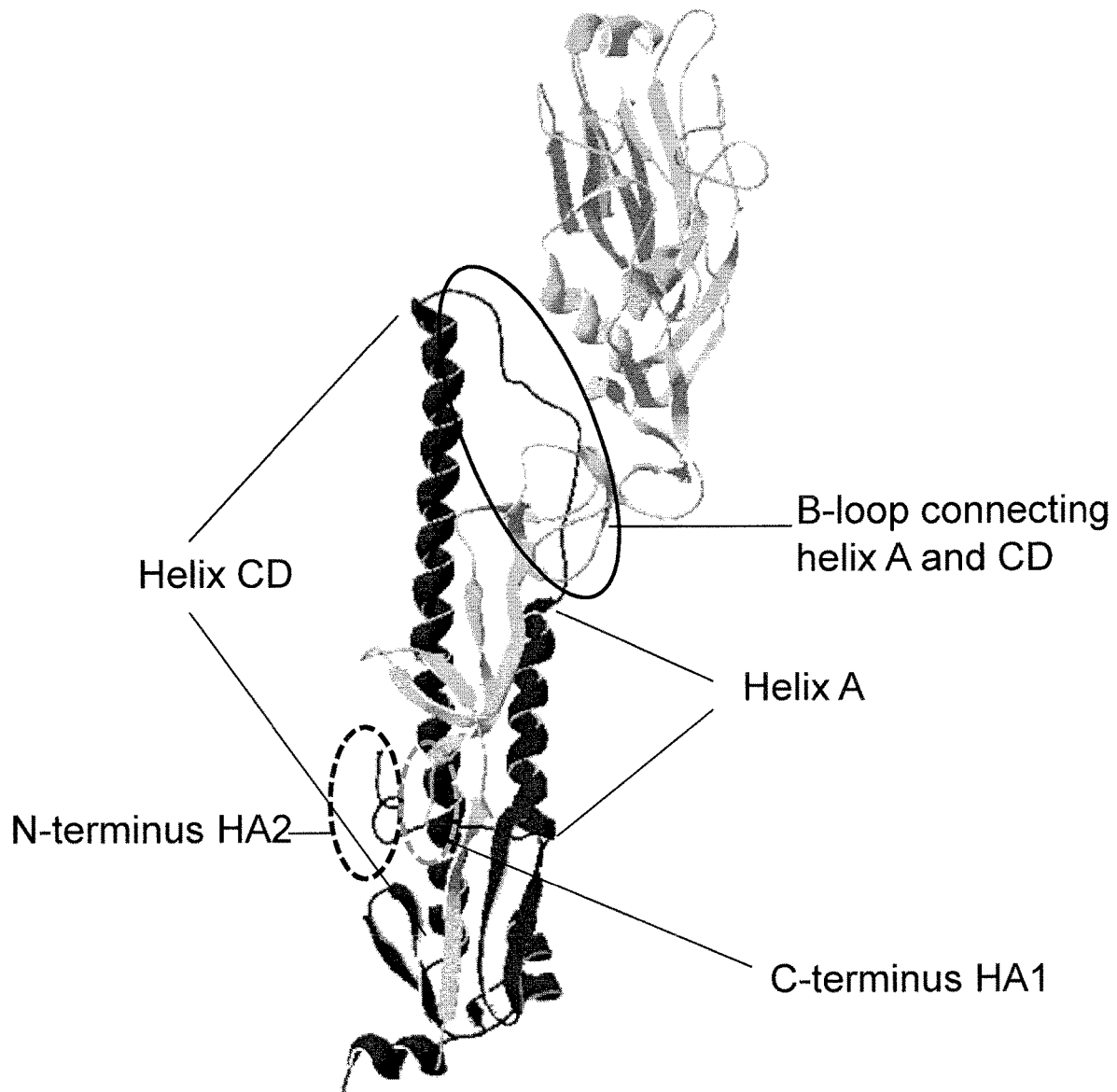
FIG. 1. Model of the HA monomer in the pre-fusion state as present in the native trimer. HA1 is shown in light grey; HA2 is shown in dark grey. Helix A (an important part of the epitope of CR6261) and helix CD (part of the trimer interface) are indicated, as is the loop connecting these secondary structure elements. The C-terminus of HA1 and the N-terminus of HA2 are also indicated. The fusion peptide is located at the N-terminus of HA2.
Figure 2A:
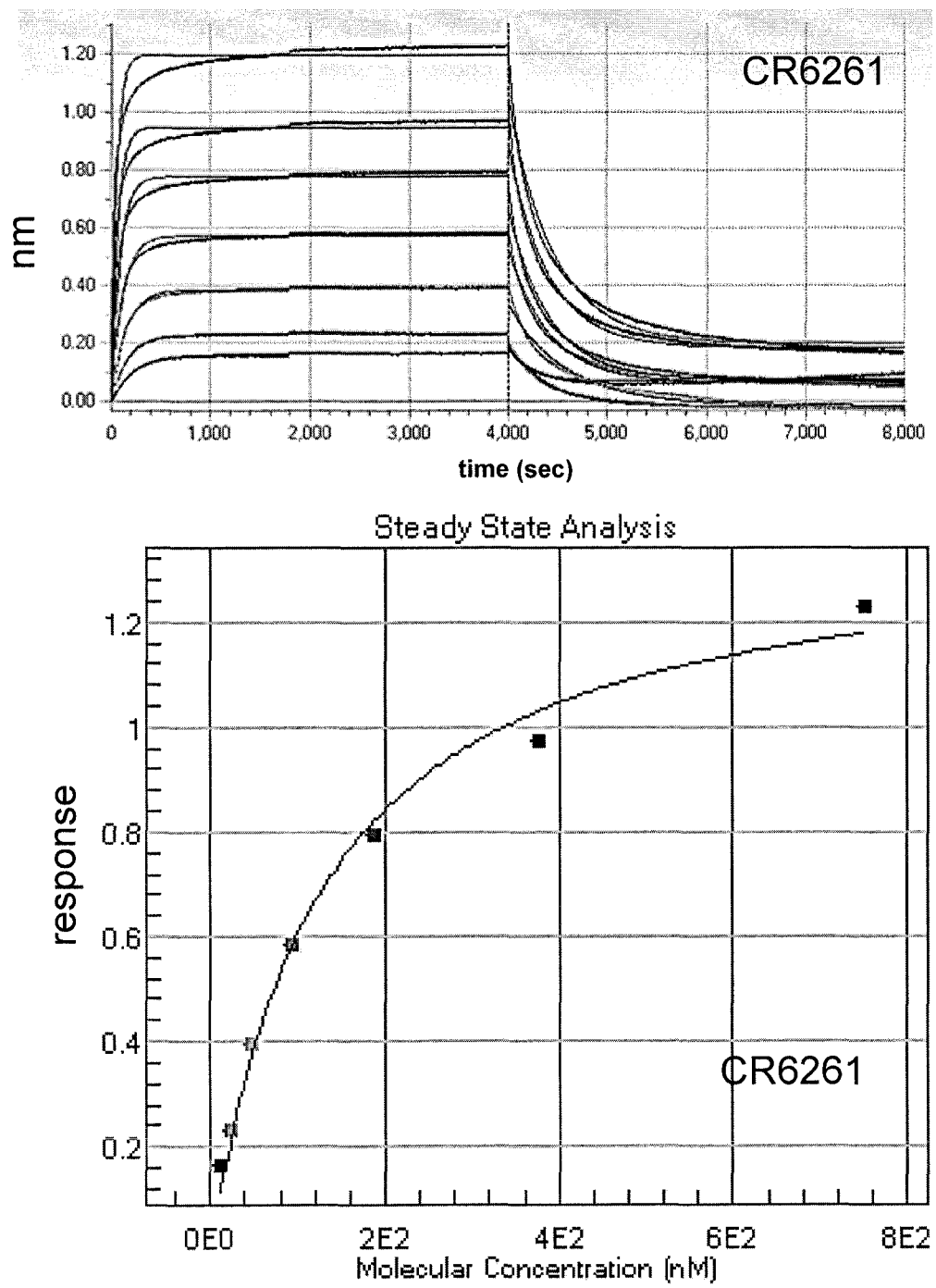
FIGS. 2A-2E. Binding of soluble polypeptides of the disclosure to monoclonal antibodies CR6261 and CR9114 using biolayer interferometry. Top panels show individual binding curves for immobilized monoclonal antibodies exposed to varying concentrations of soluble polypeptides of the disclosure; bottom panels show the steady-state analysis used to estimate $K_d$.
Figure 2B:
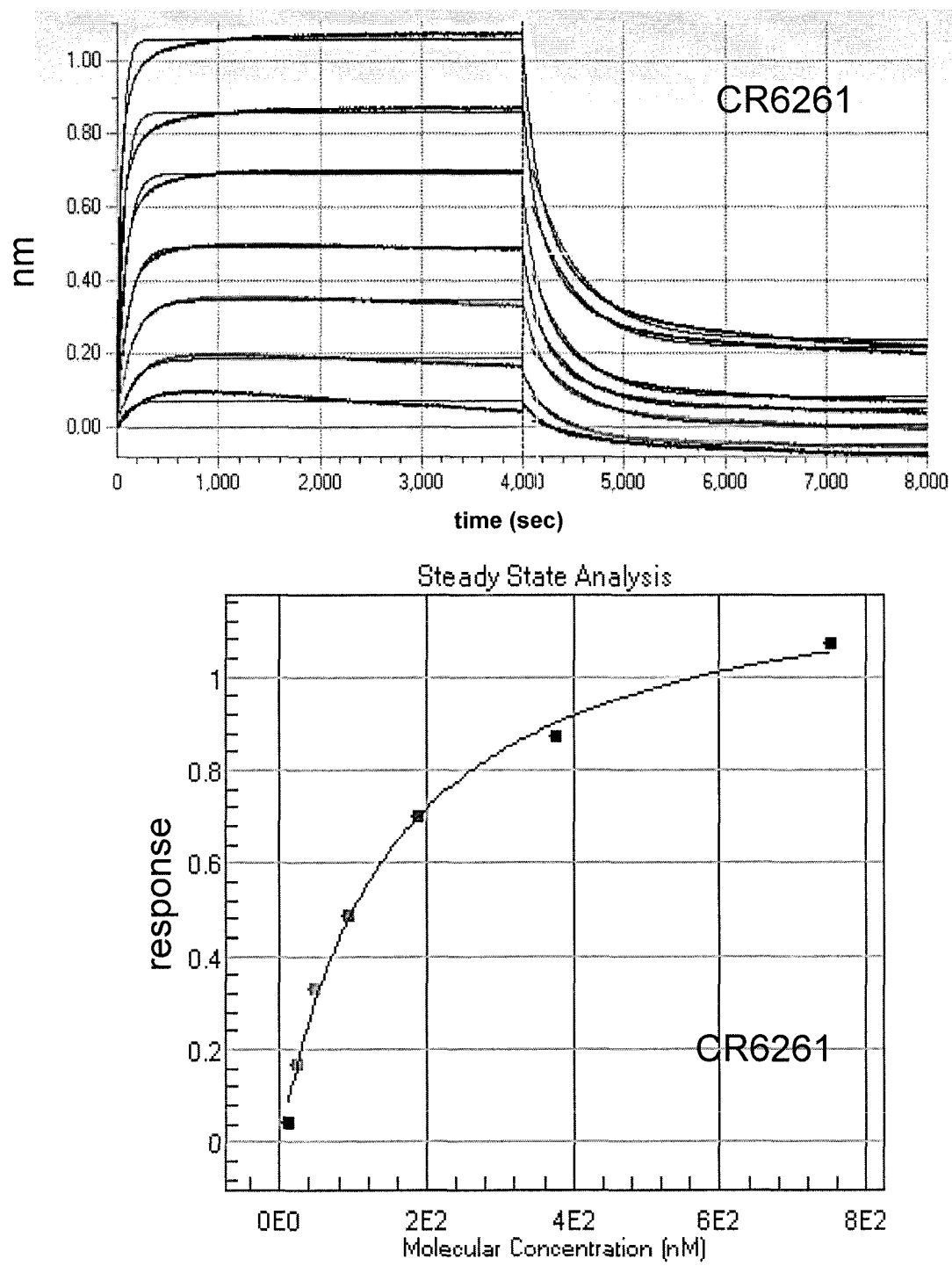
Figure 2C:
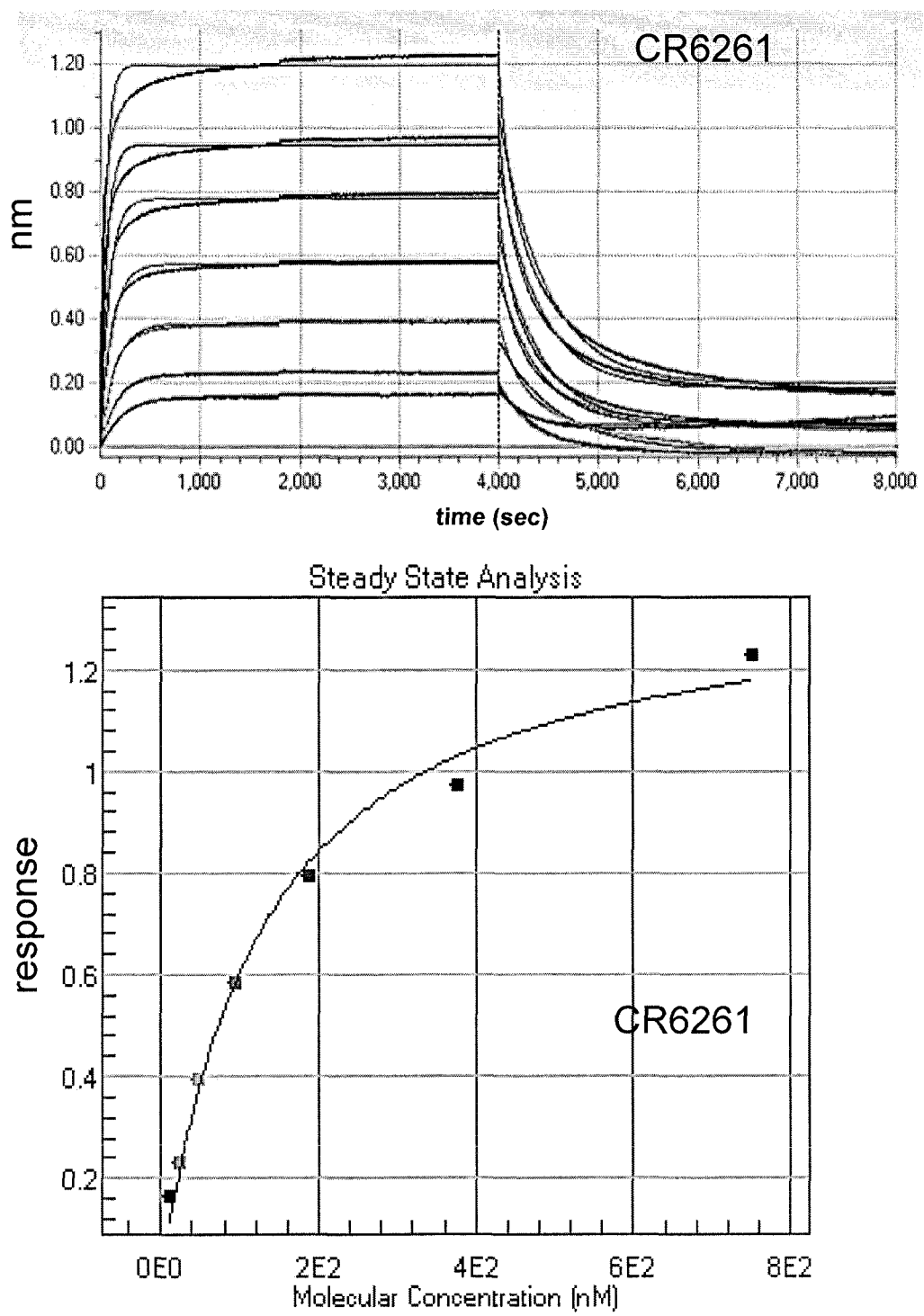
Figure 2D:
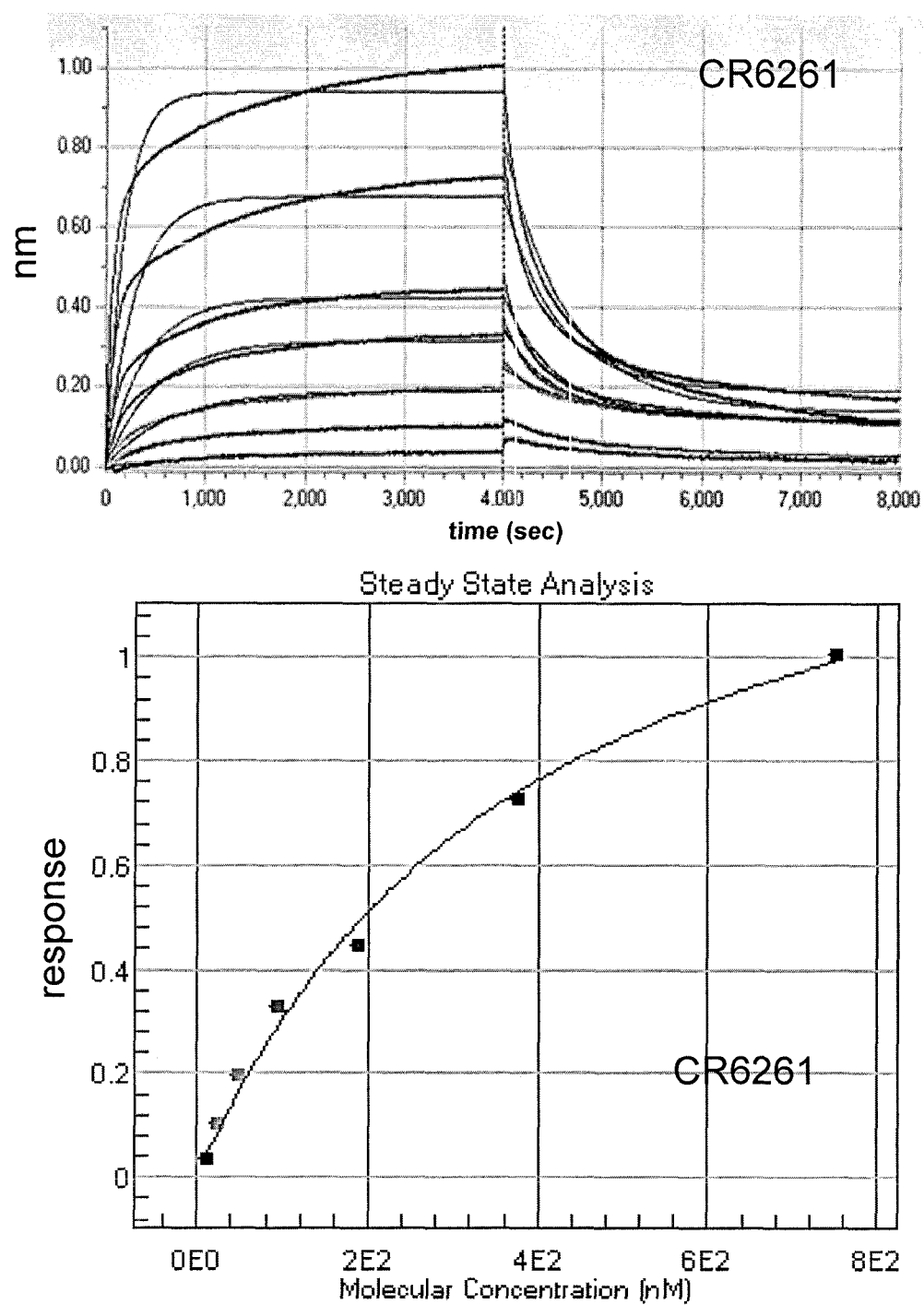
Figure 2E:
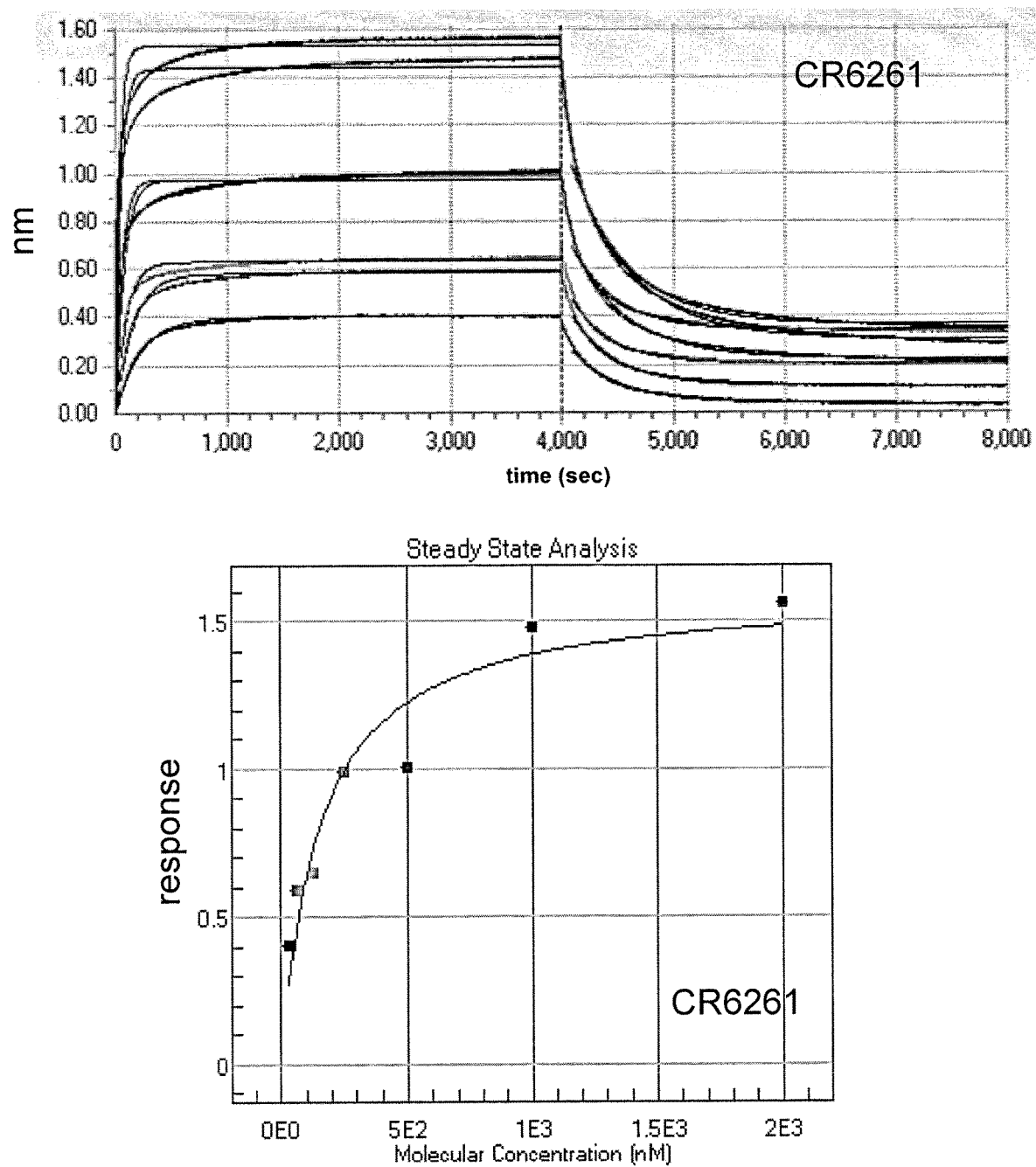
Figure 3A:
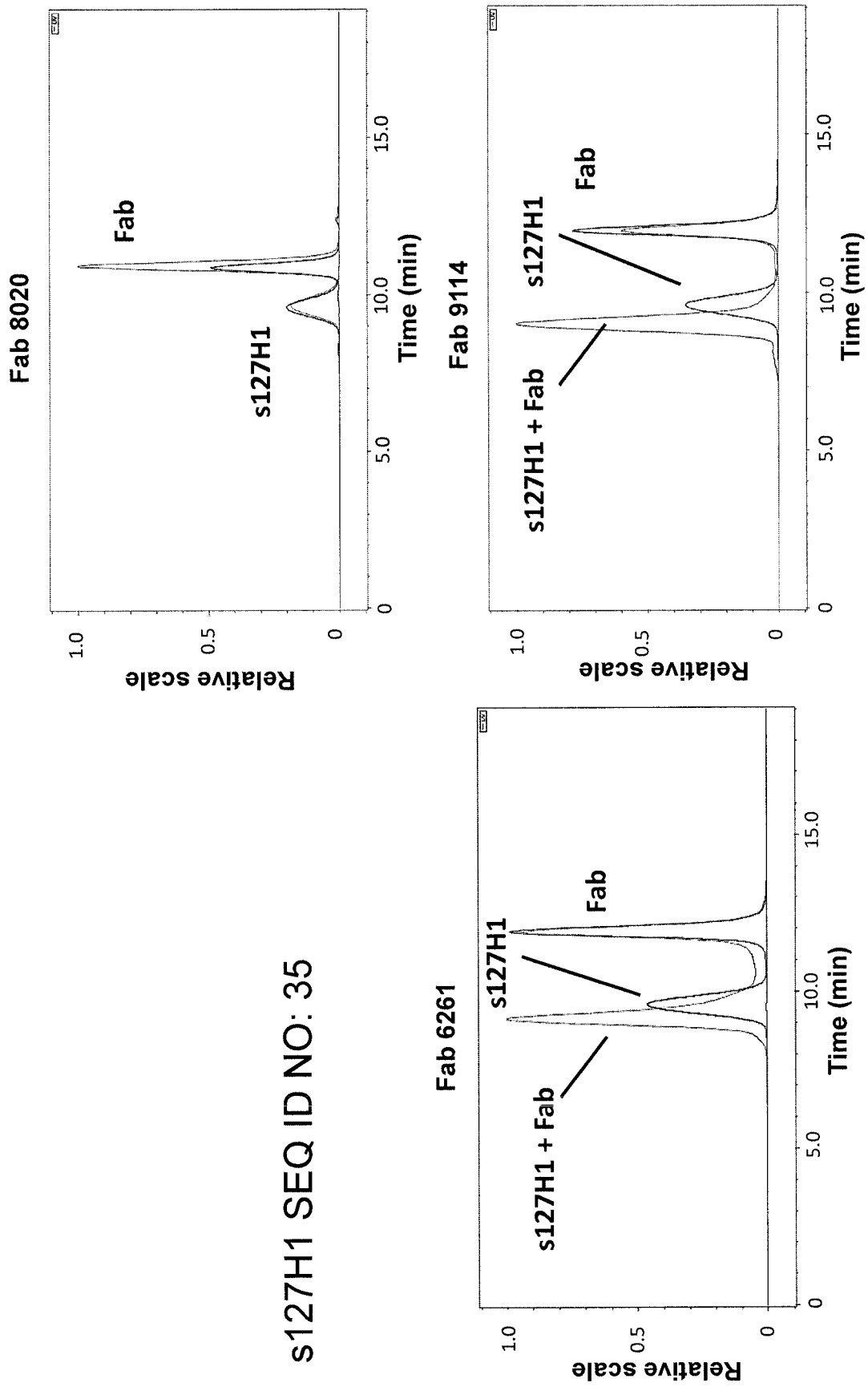
FIGS. 3A-3E. Size exclusion chromatograms of soluble polypeptides of the disclosure in the absence and presence of Fab Fragments of CR8020, CR6261 and CR9114. For all soluble polypeptides of the disclosure, complex formation is observed for CR6261 and CR9114 Fab fragments, but not for CR8020 Fab fragments.
Figure 3B:
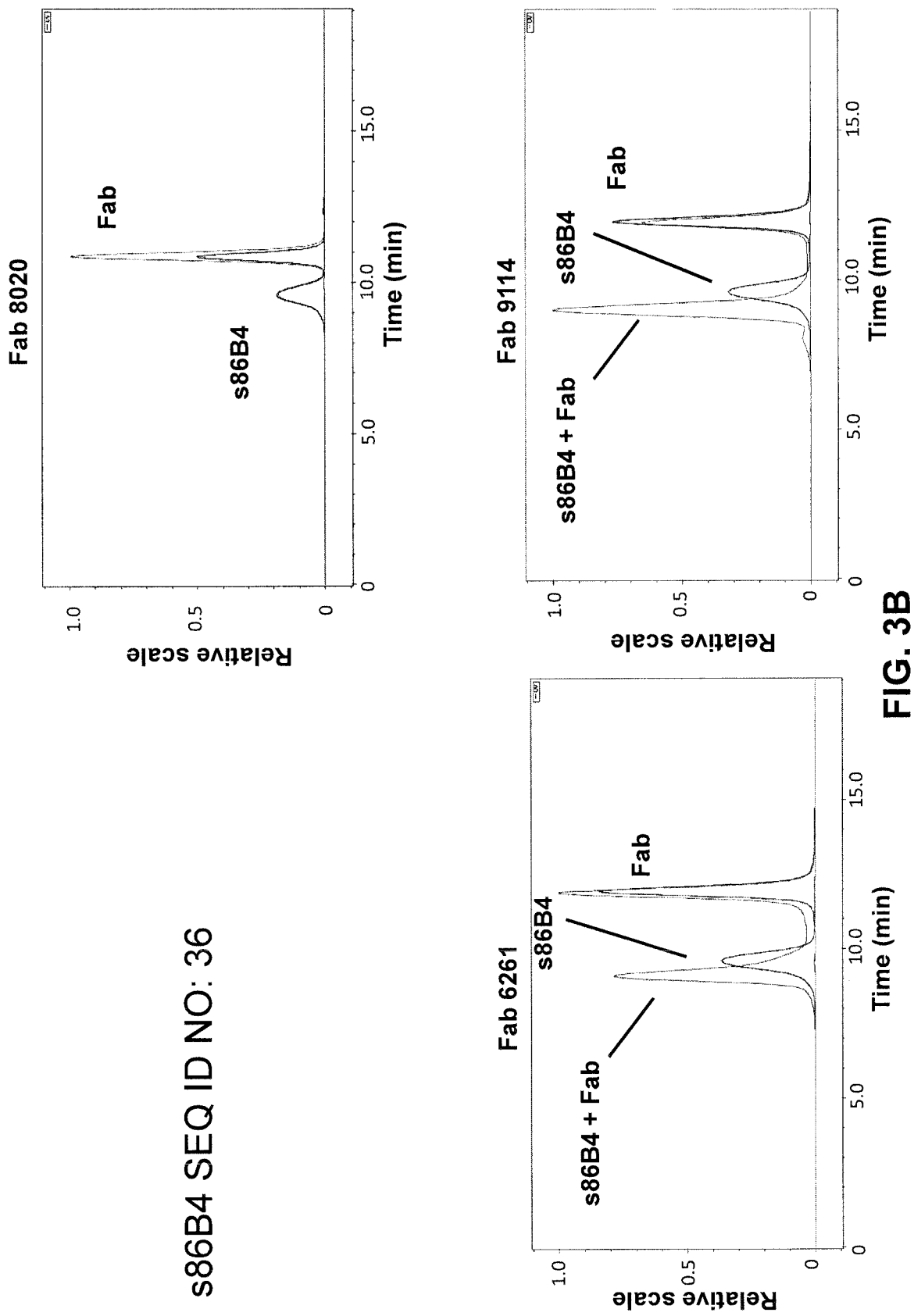
Figure 3C:
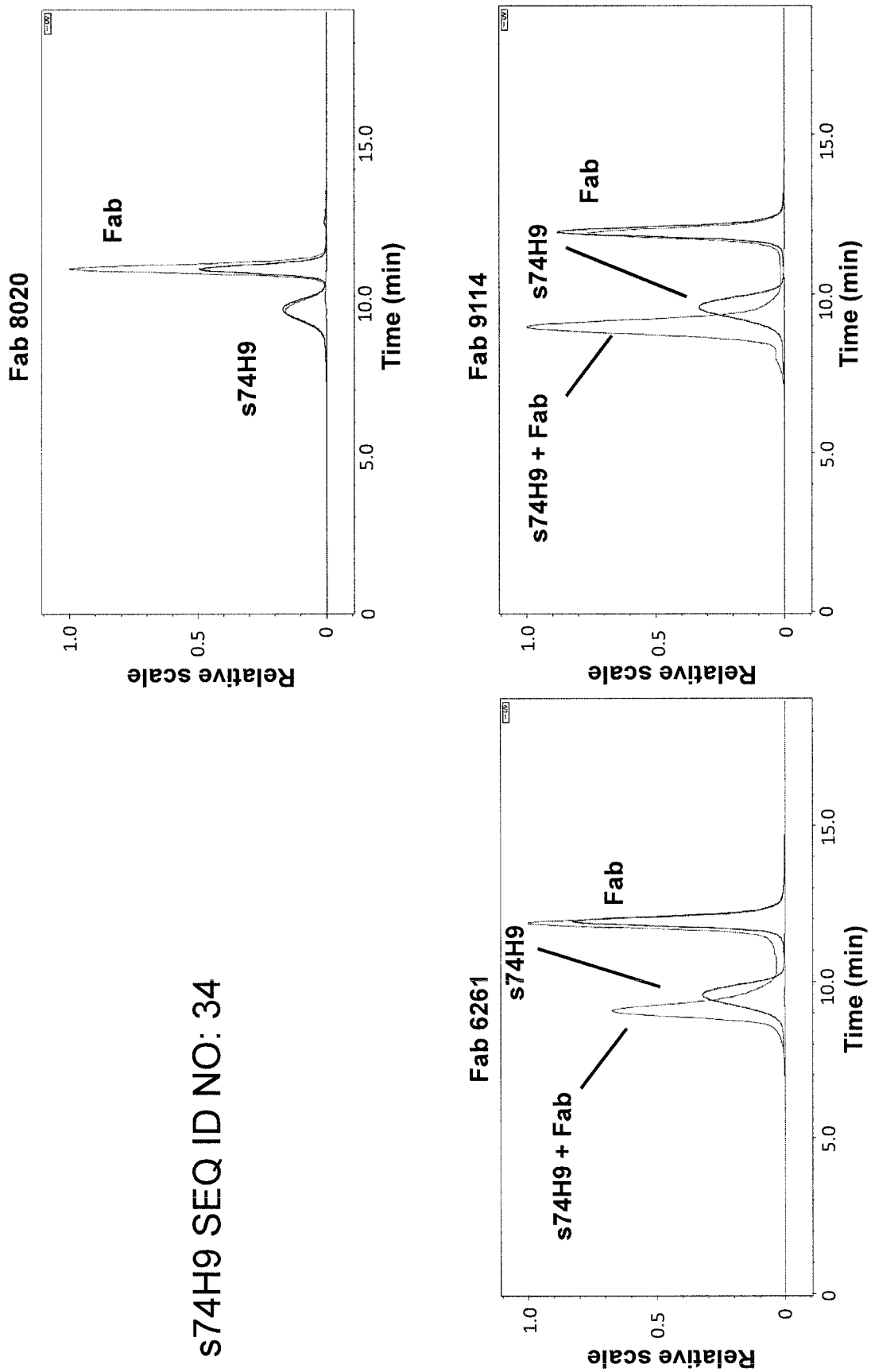
Figure 3D:
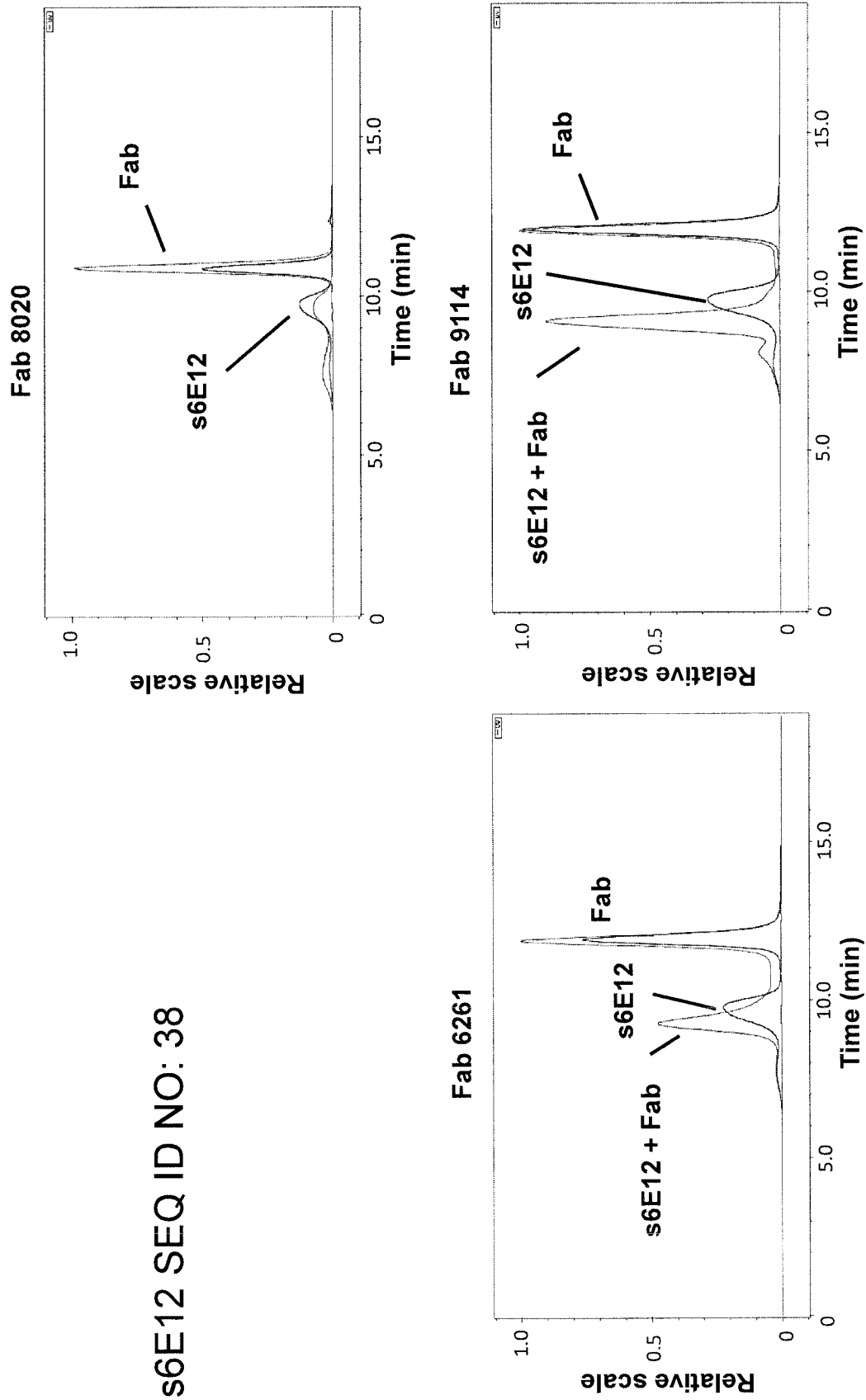
Figure 3E:
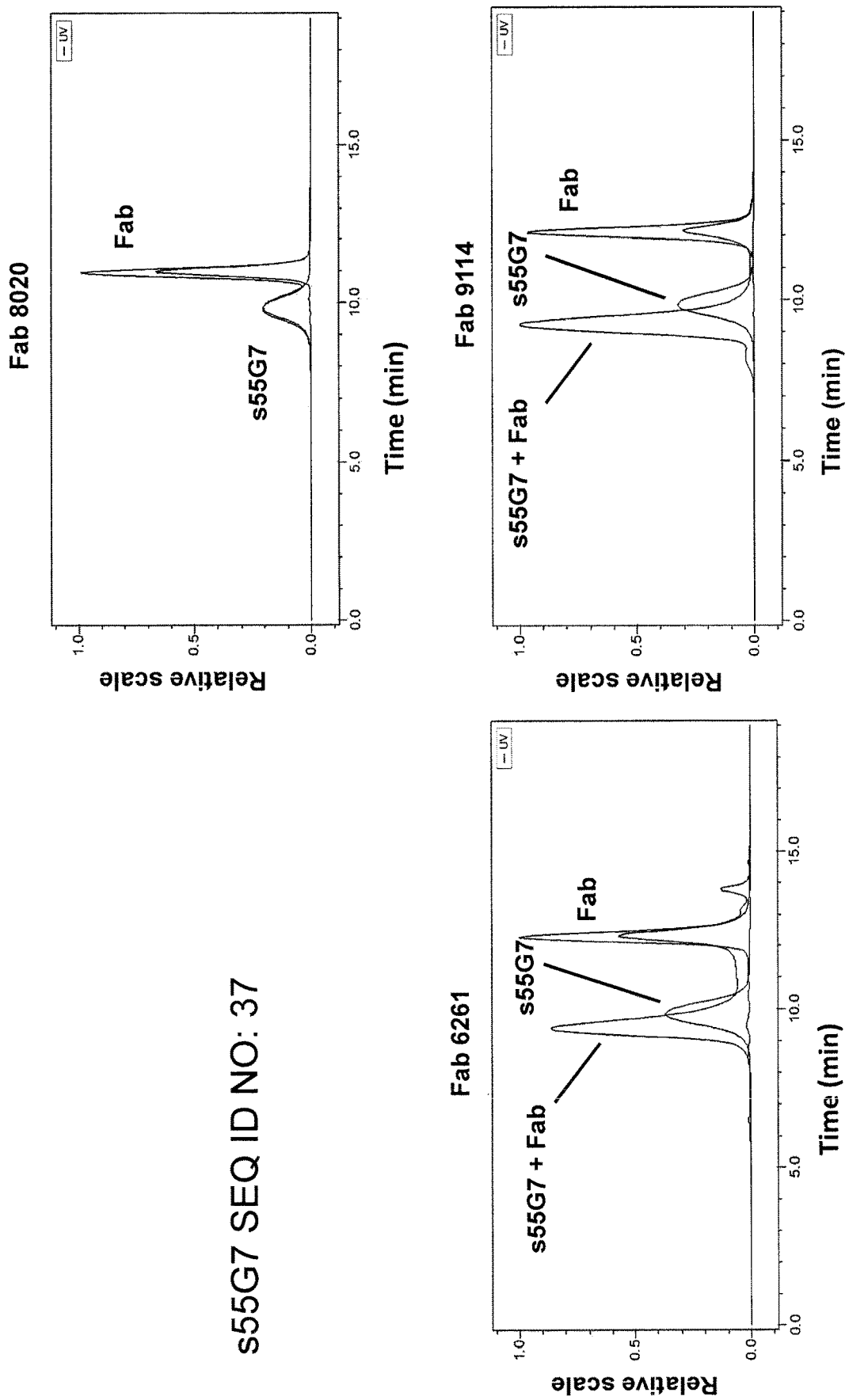

Definitions of terms as used in this disclosure are given below.

An "amino acid" as described herein can be any of the twenty naturally occurring (or "standard" amino acids) or variants thereof, such as, e.g., D-proline (the D-enantiomer of proline), or any variants that are not naturally found in proteins, such as, e.g., norleucine. The standard amino acids can be divided into several groups based on their properties. Important factors are charge, hydrophilicity or hydrophobicity, size and functional groups. These properties are important for protein structure and protein—protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 2 shows the abbreviations and properties of the standard amino acids.

The term "amino acid sequence identity" refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, are determined using sequence alignment techniques well-known in the art, such as by visual inspection and mathematical calculation, or, more preferably, the comparison is done by comparing sequence information using a computer program. An exemplary, preferred computer program is the Genetics Computer Group (GCG; Madison, Wis.) Wisconsin package version 10.0 program, "GAP" (Devereux et al. (1984)).

"Conservative substitution" refers to replacement of an amino acid of one class with another amino acid of the same class. In particular embodiments, a conservative substitution does not alter the structure or function, or both, of a polypeptide. Classes of amino acids, for the purposes of conservative substitution, include hydrophobic (e.g., Met, Ala, Val, Leu), neutral hydrophilic (e.g., Cys, Ser, Thr), acidic (e.g., Asp, Glu), basic (e.g., Asn, Gln, His, Lys, Arg), conformation disrupters (e.g., Gly, Pro) and aromatic (e.g., Trp, Tyr, Phe).

As used herein, the terms "disease" and "disorder" are used interchangeably to refer to a condition in a subject. In some embodiments, the condition is a viral infection, in particular, an influenza virus infection. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As used herein, the term "effective amount" in the context of administering a therapy to a subject refers to the amount of a therapy that has a prophylactic and/or therapeutic effect(s). In certain embodiments, an "effective amount" in the context of administration of a therapy to a subject refers to the amount of a therapy that is sufficient to achieve a reduction or amelioration of the severity of an influenza virus infection, disease or symptom associated therewith, such as, but not limited to, a reduction in the duration of an influenza virus infection, disease or symptom associated therewith, the prevention of the progression of an influenza virus infection, disease or symptom associated therewith, the prevention of the development or onset or recurrence of an influenza virus infection, disease or symptom associated therewith, the prevention or reduction of the spread of an influenza virus from one subject to another subject, the reduction of hospitalization of a subject and/or hospitalization length, an increase of the survival of a subject with an influenza virus infection or disease associated therewith, elimination of an influenza virus infection or disease associated therewith, inhibition or reduction of influenza virus replication, reduction of influenza virus titer; and/or enhancement and/or improvement of the prophylactic or therapeutic effect(s) of another therapy. In certain embodiments, the effective amount does not result in complete protection from an influenza virus disease, but results in a lower titer or reduced number of influenza viruses compared to an untreated subject. Benefits of a reduction in the titer, number or total burden of influenza virus include, but are not limited to, less severe symptoms of the infection, fewer symptoms of the infection and a reduction in the length of the disease associated with the infection.

The term "host," as used herein, is intended to refer to an organism or a cell into which a vector, such as a cloning vector or an expression vector, has been introduced. The organism or cell can be prokaryotic or eukaryotic. Preferably, the host comprises isolated host cells, e.g., host cells in culture. The term "host cells" merely signifies that the cells are modified for the (over)-expression of the polypeptides of the disclosure. It should be understood that the term "host" is intended to refer not only to the particular subject organism or cell but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

The term "included" or "including" as used herein is deemed to be followed by the words "without limitation."

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

Influenza viruses are classified into influenza virus types: genus A, B and C. The term "influenza virus subtype" as used herein refers to influenza A virus variants that are characterized by combinations of the hemagglutinin (H) and neuramidase (N) viral surface proteins. According to this disclosure, influenza virus subtypes may be referred to by their H number, such as, for example, "influenza virus comprising HA of the H3 subtype," "influenza virus of the H3 subtype" or "H3 influenza," or by a combination of an H number and an N number, such as, for example, "influenza virus subtype H3N2" or "H3N2." The term "subtype" specifically includes all individual "strains" within each subtype, which usually result from mutations and show different pathogenic profiles, including natural isolates as well as man-made mutants or reassortants and the like. Such strains may also be referred to as various "isolates" of a viral subtype. Accordingly, as used herein, the terms "strains" and "isolates" may be used interchangeably. The current nomenclature for human influenza virus strains or isolates includes the type (genus) of virus, i.e., A, B or C, the geographical location of the first isolation, strain number and year of isolation, usually with the antigenic description of HA and NA given in brackets, e.g., A/Moscow/10/00 (H3N2). Non-human strains also include the host of origin in the nomenclature. The influenza A virus subtypes can further be classified by reference to their phylogenetic group. Phylogenetic analysis has demonstrated a subdivision of hemagglutinins into two main groups: inter alia, the H1, H2, H5 and H9 subtypes in phylogenetic group 1 ("group 1" influenza viruses) and, inter alia, the H3, H4, H7 and H10 subtypes in phylogenetic group 2 ("group 2" influenza viruses).

As used herein, the term "influenza virus disease" refers to the pathological state resulting from the presence of an influenza virus, e.g., an influenza A or B virus in a cell or subject or the invasion of a cell or subject by an influenza virus. In specific embodiments, the term refers to a respiratory illness caused by an influenza virus.

As used herein, the term "nucleic acid" or "nucleic acid moledule" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acid molecules, etc.). A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

As used herein, in certain embodiments, the numbering of the amino acids in HA is based on the numbering of amino acids in HA0 of a wild-type influenza virus, e.g., the numbering of the amino acids of the H1N1 influenza strain A/Brisbane/59/2007 (SEQ ID NO:1). As used in this disclosure, the wording "the amino acid at position "x" in HA" thus means the amino acid corresponding to the amino acid at position x in HA0 of the particular wild-type influenza virus, e.g., A/Brisbane/59/2007 (SEQ ID NO:1; wherein the amino acids of the HA2 domain have been indicated in italics). Once being apprised hereof, it will be understood by the person of ordinary skill in the art that equivalent amino acids in other influenza virus strains and/or subtypes can be determined by multiple sequence alignment. Note that, in the numbering system used throughout this application, "1" refers to the N-terminal amino acid of an immature HA0 protein (SEQ ID NO:1). The mature sequence starts, e.g., on position 18 of SEQ ID NO:1. Once being apprised hereof, it will be understood by the person of ordinary skill in the art that the leader sequence (or signal sequence) that directs transport of a protein during production (e.g., corresponding to amino acids 1-17 of SEQ ID NO:1), generally is not present in the final polypeptide, that is, e.g., used in a vaccine. In certain embodiments, the polypeptides as described herein thus comprise an amino acid sequence without the leader sequence, i.e., the amino acid sequence is based on the amino acid sequence of HA0 without the signal sequence.

"Polypeptide" or "peptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example, by post-translational processing such as signal peptide cleavage, disulfide bond formation, glycosylation (e.g., N-linked and O-linked glycosylation), protease cleavage and lipid modification (e.g., S-palmitoylation).

"Stem domain polypeptide" refers to a polypeptide that comprises one or more polypeptide chains that make up a stem domain of a naturally occurring (or wild-type) hemagglutinin (HA). Typically, a stem domain polypeptide is a single polypeptide chain (i.e., corresponding to the stem domain of a hemagglutinin HA0 polypeptide) or two polypeptide chains (i.e., corresponding to the stem domain of a hemagglutinin HA1 polypeptide in association with a hemagglutinin HA2 polypeptide). As described herein, a stem domain polypeptide comprises one or more mutations as compared to the wild-type HA molecule, in particular, one or more amino acid residues of the wild-type HA may have been substituted by other amino acids, not naturally occurring on the corresponding position in a particular wild-type HA. Stem domain polypeptides hereof can, furthermore, comprise one or more linking sequences, as described below.

The term "vector" denotes a nucleic acid molecule into which a second nucleic acid molecule can be inserted for introduction into a host where it will be replicated and, in some cases, expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC), and yeast artificial chromosomes (YAC), and vectors derived from bacteriophages or plant or animal (including human) viruses. Vectors comprise an origin of replication recognized by the proposed host and, in the case of expression vectors, promoter and other regulatory regions recognized by the host. Certain vectors are capable of autonomous replication in a host into which they are introduced (e.g., vectors having a bacterial origin of replication can replicate in bacteria). Other vectors can be integrated into the genome of a host upon introduction into the host and, thereby, are replicated along with the host genome.

As used herein, the term "wild-type" in the context of a virus refers to influenza viruses that are prevalent, circulating naturally and producing typical outbreaks of disease.

Description

Influenza viruses have a significant impact on global public health, causing millions of cases of severe illness each year, thousands of deaths, and considerable economic losses. Current trivalent influenza vaccines elicit a potent neutralizing antibody response to the vaccine strains and closely related isolates, but rarely extend to more diverged strains within a subtype or to other subtypes. In addition, selection of the appropriate vaccine strains presents many challenges and frequently results in sub-optimal protection. Furthermore, predicting the subtype of the next pandemic virus, including when and where it will arise, is currently impossible.

Hemagglutinin (HA) is the major envelope glycoprotein from influenza A viruses, which is the major target of neutralizing antibodies. Hemagglutinin has two main functions during the entry process. First, hemagglutinin mediates attachment of the virus to the surface of target cells through interactions with sialic acid receptors. Second, after endocytosis of the virus, hemagglutinin subsequently triggers the fusion of the viral and endosomal membranes to release its genome into the cytoplasm of the target cell. HA comprises a large ectodomain of ~500 amino acids that is cleaved by host-derived enzymes to generate 2 polypeptides that remain linked by a disulfide bond. The majority of the N-terminal fragment (HA1, 320-330 amino acids) forms a membrane-distal globular domain that contains the receptor-binding site and most determinants recognized by virus-neutralizing antibodies. The smaller C-terminal portion (HA2, ~180 amino acids) forms a stem-like structure that anchors the globular domain to the cellular or viral membrane. The degree of sequence homology between subtypes is smaller in the HA1 polypeptides (34%-59% homology between subtypes) than in the HA2 polypeptide (51%-80% homology). The most conserved region is the sequence around the cleavage site, particularly the HA2 N-terminal 23 amino acids, which is conserved among all influenza A virus subtypes (Lorieau et al., 2010). Part of this region is exposed as a surface loop in the HA precursor molecule (HA0), but becomes inaccessible when HA0 is cleaved into HA1 and HA2.

Most neutralizing antibodies bind to the loops that surround the receptor binding site and interfere with receptor binding and attachment. Since these loops are highly variable, most antibodies targeting these regions are strain-specific, explaining why current vaccines elicit such limited, strain-specific immunity. Recently, however, fully human monoclonal antibodies against influenza virus hemagglutinin with broad cross-neutralizing potency were generated. Functional and structural analysis have revealed that these antibodies interfere with the membrane fusion process and are directed against highly conserved epitopes in the stem domain of the influenza HA protein (Throsby et al., 2008; Ekiert et al., 2009; WO 2008/028946, WO 2010/130636, WO 2013/007770).

Stem domain polypeptides stably presenting the epitopes of these antibodies are described in patent application PCT/EP2012/073706. At least some of the stem domain polypeptides described herein stably present the epitope of CR6261 and/or CR9114 and are immunogenic in mice. At least some of the stem domain polypeptides described herein stably present the epitope of CR8020 and are immunogenic in mice.

As described herein, new HA stem domain polypeptides have been designed presenting these epitopes. These polypeptides can be used to create a universal epitope-based vaccine inducing protection against a broad range of influenza strains. Like in the previously described stem domain polypeptides, the highly variable and immunodominant part, i.e., the head domain, is first removed from the full-length HA molecule to create a stem domain polypeptide, also called mini-HA, in order to redirect the immune response toward the stem domain where the epitopes for the broadly neutralizing antibodies are located. The broadly neutralizing antibodies mentioned above were used to probe the correct folding of the newly created molecules, and to confirm the presence of the neutralizing epitopes.

The new stem domain polypeptides of the disclosure show increased binding of the antibodies, in particular, CR6261 and/or CR9114, as compared to binding of those antibodies to the stem polypeptides described earlier (PCT/EP2012/073706).

The stem domain polypeptides of this disclosure are capable of presenting the conserved epitopes of the membrane proximal stem domain HA molecule to the immune system in the absence of dominant epitopes that are present in the membrane distal head domain. To this end, part of the primary sequence of the HA0 protein making up the head domain is removed and reconnected, either directly or, in some embodiments, by introducing a short flexible linking sequence ("linker") to restore the continuity of the polypeptide chain. The resulting polypeptide sequence is further modified by introducing specific mutations that stabilize the native three-dimensional structure of the remaining part of the HA0 molecule.

This disclosure thus provides polypeptides comprising (a) an influenza hemagglutinin HA1 domain that comprises an HA1 N-terminal stem segment, covalently linked by a linking sequence of 0-50 amino acid residues to an HA1 C-terminal stem segment, and (b) an influenza hemagglutinin HA2 domain, wherein the hemagglutinin stem domain polypeptide is resistant to protease cleavage at the junction between HA1 and HA, and wherein one or more amino acids in the HA1 and HA2 domains have been mutated. In the polypeptides of the disclosure, the HA1 and HA2 domains thus comprise one or more mutations as compared to the HA1 and HA2 domain of a wild-type influenza hemagglutinin on which the HA stem domain polypeptide is based.

As described herein, the stem domain polypeptides are based on HA of an influenza virus comprising HA of the H1 subtype.

In certain embodiments, the polypeptides comprise one or more mutations on position 337, 340, 352 or 353 of SEQ ID NO:1, or equivalent positions in other influenza viruses.

In certain embodiments, the polypeptides comprise at least one mutation on position 352 of SEQ ID NO:1, or on an equivalent position of other influenza viruses.

In certain embodiments, the polypeptides comprise at least one mutation on position 353 of SEQ ID NO:1, or on an equivalent position of other influenza viruses.

In certain embodiments, the polypeptides comprise at least one mutation on position 337 of SEQ ID NO:1, or on an equivalent position of other influenza viruses.

In certain embodiments, the polypeptides comprise at least one mutation on position 340 of SEQ ID NO:1, or on an equivalent position of other influenza viruses.

In certain embodiments, the polypeptides comprise one or more mutations in the HA2 amino acid sequence connecting the C-terminal residue of helix A to the N-terminal residue of helix CD, as indicated in FIG. 1.

In certain embodiments, one or more of the amino acids on positions 402, 406, 409, 413 and 416 (numbering refers to SEQ ID NO:1), or equivalent positions in other influenza viruses.

In certain embodiments, the polypeptides comprise at least one mutation on position 402 of SEQ ID NO:1, or on an equivalent position of other influenza viruses.

In certain embodiments, the polypeptides comprise at least one mutation on position 406 of SEQ ID NO:1, or on an equivalent position of other influenza viruses.

In certain embodiments, the polypeptides comprise at least one mutation on position 409 of SEQ ID NO:1, or on an equivalent position of other influenza viruses.

In certain embodiments, the polypeptides comprise at least one mutation on position 413 of SEQ ID NO:1, or on an equivalent position of other influenza viruses.

In certain embodiments, the polypeptides comprise at least one mutation on position 416 of SEQ ID NO:1, or on an equivalent position of other influenza viruses.

The polypeptides of the disclosure do not comprise the full-length HA1.

In certain embodiments, the immunogenic polypeptides are substantially smaller than HA0, preferably lacking all or substantially all of the globular head of HA. Preferably, the immunogenic polypeptides are no more than 360, preferably no more than 350, 340, 330, 320, 310, 305, 300, 295, 290, 285, 280, 275, or 270 amino acids in length. In certain embodiments, the immunogenic polypeptides are from about 250 to about 350, preferably from about 260 to about 340, preferably from about 270 to about 330, preferably from about 270 to about 330 amino acids in length.

In certain embodiments, the polypeptides further comprise one or more additional mutations in the HA1 and/or HA2 domains, as compared to the amino acid sequence of the HA of which the HA1 and HA2 domains are derived. Thus, the stability of the stem polypeptides is further increased. The "HA1 N-terminal segment" refers to a polypeptide segment that corresponds to the amino-terminal portion of the HA1 domain of an influenza hemagglutinin (HA) molecule. In certain embodiments, the HA1 N-terminal polypeptide segment comprises the amino acids from position 1 to position x of the HA1 domain, wherein amino acid on position x is an amino acid residue within HA1. The term "HA1 C-terminal segment" refers to a polypeptide segment that corresponds to the carboxy-terminal portion of an influenza hemagglutinin domain. In certain embodiments, the HA1 C-terminal polypeptide segment comprises the amino acids from position y to and including the C-terminal amino acid of the HA1 domain, wherein the amino acid on position y is an amino acid residue within HA1. As described herein, y is greater than x, thus, a segment of the HA1 domain between the HA1 N-terminal segment and the HA1 C-terminal segment, i.e., between the amino acid on position x and the amino acid on position y of HA1, has been deleted, and in some embodiments, replaced by a linking sequence.

In certain embodiments, the HA1 N-terminal stem segment comprises the amino acids 1-x of HA1, and the HA1 C-terminal stem segment comprises the amino acids y-end of HA1. Thus, in certain embodiments, the deletion in the HA1 segment comprises the amino acid sequence from the amino acid at position x+1 up to and including the amino acid at position y-1.

In certain embodiments, the polypeptides do not comprise the signal sequence. Thus, in certain embodiments, the HA1 N-terminal segment comprises the amino acid p-x of HA1, wherein p is the first amino acid of the mature HA molecule (e.g., p=18 in the case of SEQ ID NO:1). Once being apprised hereof, the person of ordinary skill in the art will be able to prepare the polypeptides described herein without the signal peptides (e.g., amino acids 1-17 of SEQ ID NO:1).

In certain embodiments, the polypeptides of the disclosure contain the intracellular sequences of HA and the transmembrane domain. In other embodiments, the polypeptides do not comprise the intracellular sequences of HA and the transmembrane domain. In certain embodiments, the intracellular and transmembrane sequences, e.g., the amino acid sequence from position (or the equivalent of) 519, 520, 521, 522, 523, 524, 525, 526, 527, 526, 528, 529, or 530 of the HA2 domain to the C-terminus of the HA2 domain, have been removed.

As described herein, the hemagglutinin stem domain polypeptides are resistant to protease cleavage at the junction between HA1 and HA2. It is known to those of skill in the art that the Arg (R)-Gly (G) sequence spanning HA1 and HA2 is a recognition site for trypsin and trypsin-like proteases and is typically cleaved for hemagglutinin activation. Since the HA stem domain polypeptides described herein should not be activated, the influenza hemagglutinin stem domain polypeptides are resistant to protease cleavage. As described herein, the protease cleavage site is, thus, removed or the protease site spanning HA1 and HA2 is mutated to a sequence that is resistant to protease cleavage.

In certain embodiments, the C-terminal amino acid residue of the HA1 C-terminal stem segment is any amino acid other than arginine (R) or lysine (K). In certain embodiments, the HA1 C-terminal amino acid is glutamine (Q), serine (S), threonine (T), asparagine (N), aspartic acid (D) or glutamic acid (E). In certain embodiments, the C-terminal amino acid residue of the HA1 C-terminal stem segment is glutamine (Q).

In certain embodiments, the polypeptides are glycosylated.

As described herein, the influenza hemagglutinin stem domain polypeptides are based on HA of influenza viruses of the H1 subtype. With "based on" it is meant that the N-terminal segments and/or C-terminal segments of the HA1 domain and/or the HA2 domains have at least 70%, 75%, 80%, 85%, 90%, 95%, 96%, 97%, 98%, or 99% amino acid sequence identity with the corresponding N-terminal and/or C-terminal segments of HA1 and/or the HA2 domains of any naturally occurring influenza hemagglutinin of a H1, H3 and/or H5 subtype known to those of skill in the art or later discovered. In certain embodiments, the influenza hemagglutinin stem domain polypeptides are based on an influenza hemagglutinin of a group 1 influenza A virus.

As described herein, the polypeptides are based on H1 HA, i.e., HA comprising an amino acid sequence from an influenza virus of the H1 subtype. In a particular embodiment, the polypeptides comprise hemagglutinin stem domains from or based on HA of an influenza A virus comprising HA of the H1 subtype, such as from the influenza virus A/Brisbane/59/2007 (H1N1) (SEQ ID NO:1), as described below. Once being apprised hereof, it will be understood by the person of ordinary skill in the art that other influenza A viruses also comprising HA of the H1 subtype may be used as described herein. In certain embodiments, the polypeptides comprise hemagglutinin stem domains based on HA of an influenza A H1 virus selected from Table 3.

In certain embodiments, the polypeptides comprise an HA1 N-terminal polypeptide segment comprising the amino acids from position 1 to position x of the H1 HA1 domain, wherein x is any amino acid between the amino acid on position 46 and the amino acid on position 60, such as the amino acid on position 47, 48, 49, 50, 51, 52, 53, 54, 55, 56, 57, 58, or 59, preferably wherein x is 52. 53, 55 or 59. Preferably, the polypeptides comprise an HA1 N-terminal segment without the signal sequence, i.e., an HA1 N-terminal segment comprising the amino acids from position 18 (e.g., for H1 HA, such as SEQ ID NO:1), or an equivalent position in other H1 influenza virus strains (see, e.g., Table 3), to position x of the HA1 domain. In certain embodiments, the HA1 N-terminal segment thus comprises the amino acids from position p (wherein p=18 for H1 HA in SEQ ID NO:1 or an equivalent position on other H1 HAs), to position x of the HA1 domain.

In certain embodiments, the HA1 C-terminal polypeptide segment comprises the amino acids from position y to and including the C-terminal amino acid of the H1 HA1 domain, wherein y is any amino acid between the amino acid on positions 290 and the amino acid on position 325 of H1 HA1, preferably wherein y is 291, 303, 318, or 321.

In certain embodiments, x is 52 and y is 321.

As described herein, the stem polypeptides comprise one or more mutations, i.e., amino acid substitutions, in the HA1 domain and/or the HA2 domain, as compared to the amino acid sequence of corresponding wild-type influenza virus HA1 and/or HA2 domains, i.e., the influenza virus on which the stem polypeptides are based.

In certain embodiments, one or more amino acid residues close to the HA0 cleavage site (residue 343 in SEQ ID NO:1) have been mutated. In certain embodiments, one or more of the amino acid residues on position 337, 340, 352, or 353 of SEQ ID NO:1, or equivalent positions in other influenza viruses, have been mutated, i.e., are substituted by an amino acid that is not occurring at the corresponding position in the amino acid sequence of the HA of the wild-type influenza virus on which the stem polypeptide is based. Table 7 shows the the naturally occurring amino acid variation.

In certain embodiments, the polypeptides comprise at least one mutation on position 352 of SEQ ID NO:1, or on an equivalent position of other influenza viruses.

In certain embodiments, the polypeptides comprise at least one mutation on position 353 of SEQ ID NO:1, or on an equivalent position of other influenza viruses.

In certain embodiments, the polypeptides comprise at least one mutation on position 337 of SEQ ID NO:1, or on an equivalent position of other influenza viruses.

In certain embodiments, the polypeptides comprise at least one mutation on position 340 of SEQ ID NO:1, or on an equivalent position of other influenza viruses.

In certain embodiments, the polypeptides comprise one or more of the mutations as indicated in Table 1.

In certain embodiments, the mutated amino acid residue on position 337 (HA1 domain) is selected from the group consisting of I, E, K, V, A, and T.

In certain embodiments, the mutated amino acid residue on position 340 (HA1 domain) is selected from the group consisting of I, K, R, T, F, N, S and Y.

In certain embodiments, the mutated amino acid residue on position 352 (HA2 domain) is selected from the group consisting of D, V, Y, A, I, N, S, and T.

In certain embodiments, the mutated amino acid residue on position 353 (HA2 domain) is selected from the group consisting of K, R, T, E, G, and V.

In certain embodiments, the mutated amino acid introduces a consensus N-glycosylation, e.g., N-X-T/S (where X is any naturally occurring amino acid except P), in the sequence as is, for example, the case for I340N in SEQ ID NO:6.

In certain embodiments, the mutated amino acid is an amino acid that does not naturally occur in sequences of the same subtype.

It is again noted that the numbering of the amino acids is based on the numbering of amino acids in H1 HA0, in particular, the numbering of the amino acids of the H1N1 influenza strain A/Brisbane/59/2007 (SEQ ID NO:1). Once being apprised hereof, the person of ordinary skill in the art will be able to determine the equivalent amino acids in HA of other influenza viruses and, thus, will be able to determine equivalent mutations, see, e.g., Table 3 for the sequence alignment of different H1 influenza viruses.

In certain embodiments, the HA2 domain comprises one or more mutations in the HA2 amino acid sequence connecting the C-terminal residue of helix A to the N-terminal residue of helix CD (FIG. 1). The H1 HA2 amino acid sequence connecting the C-terminal residue of helix A and the N-terminal residue of helix CD comprises the amino acid sequence comprising residues 402-418 of influenza HA (numbering according to SEQ ID NO:1), comprising the amino acid sequence MNTQFTAVGKEFN(H/K)LE(K/R) (SEQ ID NO:8).

In certain embodiments, the amino acid sequence connecting the C-terminal residue of helix A to the N-terminal residue of helix CD, i.e., the region comprising the amino acid residues 402-418 of influenza HA of serotype H1 (numbering according to SEQ ID NO:1) comprises the amino acid sequence $X_1$NTQ$X_2$TA$X_3$GKE$X_4$N(H/K)$X_5$E (K/R) (SEQ ID NO:52).

In certain embodiments, the polypeptides comprise one or more of the mutations in the H1 HA2 domain as indicated in Table 1.

In certain embodiments, one or more of the amino acids on positions 402, 406, 409, 413 and 416 (numbering refers to SEQ ID NO:1), i.e., one or more of the amino acids $X_1$, $X_2$, $X_3$, $X_4$ and $X_5$ have been mutated, i.e., comprise an amino acid that is not occurring at those positions in a wild-type influenza virus on which the stem polypeptide is based.

In certain embodiments, the mutated amino acid on position 402, i.e., $X_1$ is an amino acid selected from the group consisting of M, E, K, V, R, and T.

In certain embodiments, the mutated amino acid on position 406, i.e., $X_2$ is an amino acid selected from the group consisting of F, I, N, T, H, L, and Y, preferably I, L, or Y.

In certain embodiments, the mutated amino acid on position 409, i.e., $X_3$, is an amino acid selected from the group consisting of V, A, G, I, R, F, and S, preferably A, I, or F.

In certain embodiments, the mutated amino acid on position 413, i.e., $X_4$, is an amino acid selected from the group consisting of F, I, N, S, T, Y, E, K, M, and V, preferably I, Y, M, or V.

In certain embodiments, the mutated amino acid on position 416, i.e., $X_5$, is an amino acid selected from the group consisting of L, H, I, N, R, preferably I.

Combinations of these mutations are also possible.

In certain embodiments, the HA1 N-terminal stem segment comprises the amino acid residues 1-52 of HA1 preferably the amino acid residues 18-52 of HA1, and the HA1 C-terminal stem segment comprises the amino acid residues 321-343 of $HA_1$, wherein the amino acid on position 343, i.e., R343, has been mutated and is an amino acid other than R, preferably glutamine (Q). In certain embodiments, the HA1 N-terminal stem segment consists of the amino acid residues 1-52 of HA1, preferably the amino acid residues 18-52 of HA1, and the HA1 C-terminal stem segment consists of the amino acid residues 321-343 of HA1.

In certain embodiments, the polypeptides selectively bind to the antibodies CR6261 and/or CR9114. In an embodiment, the polypeptide does not bind to the antibody CR8057. In an embodiment, CR6261 comprises a heavy chain variable region comprising the amino acid sequence of SEQ ID NO:9 and a light chain variable region comprising the amino acid sequence of SEQ ID NO:10; CR9114 comprises a heavy chain variable region comprising the amino acid sequence of SEQ ID NO:11 and a light chain variable region comprising the amino acid sequence of SEQ ID NO:12. In an embodiment, CR8057 comprises a heavy chain variable region comprising the amino acid sequence of SEQ ID NO:13 and a light chain variable region comprising the amino acid sequence of SEQ ID NO:14.

As described above, the polypeptides comprise an influenza hemagglutinin HA1 domain that comprises an HA1 N-terminal stem segment that is covalently linked by a linking sequence of 0 to 50 amino acid residues to the HA1 C-terminal stem segment. The linking sequence does not occur in naturally occurring, or wild-type, HA. In certain embodiments, the linker is a peptide that comprises one amino acid residue, two or less amino acid residues, three or less amino acid residues, four or less amino acid residues, five or less amino acid residues, ten or less amino acid residues, 15 or less amino acid residues, 20 or less amino acid residues, 30 or less amino acid residues, 40 or less amino acid residues, or 50 or less amino acid residues. In a specific embodiment, the linking sequence is a sequence selected from the group consisting of G, GS, GGG, GSG, GSA, GSGS (SEQ ID NO:79), GSAG (SEQ ID NO:80), GGGG (SEQ ID NO:77), GSAGS (SEQ ID NO:78), GSGSG (SEQ ID NO:81), GSAGSA (SEQ ID NO:16), GSAGSAG (SEQ ID NO:15), and GSGSGSG (SEQ ID NO:82).

In certain embodiments, the HA1 N-terminal segment is directly linked to the HA1 C-terminal segment, i.e., the polypeptides do not comprise a linking sequence.

As described herein, removal of the cleavage site between HA1 and HA2 can be achieved by mutation of R (in a small number of cases K) to Q at the P1 position (see, e.g., Sun et al., 2010, for an explanation of the nomenclature of the cleavage site (position 343 in SEQ ID NO:1). A mutation to Q is preferred but S, T, N, D, or E are alternatives.

As described herein, one or more disulfide bridges are introduced in the stem domain polypeptides, preferably between amino acids of (or the equivalent of) positions 324 and 436 in H1 A/Brisbane/59/2007 (SEQ ID NO:1). In certain embodiments, the polypeptides thus further comprise the mutation R324C in the HA1 domain and T436C in the HA2 domain. Equivalent positions can be easily determined by those skilled in the art by aligning the sequences using a suitable algorithm such as Clustal, Muscle, etc. Engineered disulfide bridges are created by mutating at least one residue (if the other is already a cysteine), but usually two residues, that are spatially close into cysteine, that will spontaneously or by active oxidation form a covalent bond between the sulfur atoms of these residues.

Influenza HA in its native form exists as a trimer on the cell or virus membrane. In certain embodiments, the intracellular and transmembrane sequence is removed so that a secreted (soluble) polypeptide is produced following expression in cells. Methods to express and purify secreted ectodomains of HA have been described (see, e.g., Dopheide et al., 2009; Ekiert et al., 2009, 2011; Stevens et al., 2004, 2006; Wilson et al., 1981). Once being apprised hereof, a person of ordinary skill in the art will understand that these methods can also be applied directly to stem domain polypeptides of the disclosure in order to achieve expression of secreted (soluble) polypeptide. Therefore, these polypeptides are also encompassed in the disclosure.

In certain embodiments, the polypeptides hereof contain the intracellular sequences of HA and the transmembrane domain. In other embodiments, the intracellular and transmembrane sequences, e.g., the amino acid sequence from position (or the equivalent of) 519, 520, 521, 522, 523, 524, 525, 526, 527, 526, 528, 529, or 530 of the HA2 domain to the C-terminus of the HA2 domain (numbering according to SEQ ID NO:1) have been removed to produce a soluble polypeptide following expression in cells.

In certain embodiments, a soluble polypeptide hereof can be created by deletion of the polypeptide sequence from residue (or the equivalent of) 514 to the C-terminus (numbering according to SEQ ID NO:1). Alternatively, additional residues can be included in the polypeptide of the disclosure, e.g., by deleting the sequence from residue 515, 516, 517, 518, 519, 520, 521, 522, or 523. Optionally, a his-tag sequence (HHHHHH (SEQ ID NO:20) or HHHHHHH (SEQ ID NO:21)) may be added, for purification purposes, optionally connected through a linker. Optionally, the linker may contain a proteolytic cleavage site to enzymatically remove the his-tag after purification.

In certain embodiments, a soluble polypeptide can be created by deletion of the polypeptide sequence from residue (the equivalent of) 524, 525, 526, 527, 528, 529, 530, 531 or 532 (numbering according to SEQ ID NO:1). Optionally, a his-tag sequence (HHHHHH (SEQ ID NO:20) or HHHH-HHH (SEQ ID NO:21)) may be added, for purification purposes, optionally connected through a linker. Optionally, the linker may contain a proteolytic cleavage site to remove the his-tag after purification.

The soluble polypeptides can be further stabilized by introducing a sequence known to form trimeric structures, such as the foldon sequence (e.g., as described herein). Polypeptides obtained as described above are also encompassed herein.

The native HA exists as a trimer on the cell surface. Most of the interactions between the individual monomers that keep the trimer together are located in the head domain, while in the stem domain, trimerization is mediated by the formation of a trimeric coiled coil motif. After removal of the head, the tertiary structure is destabilized and, therefore, modifications are needed in order to increase protein stability. By strengthening the helical propensity of the helix CD, a more stable protein can be created. In certain embodiments, the sequence MKQIEDKIEEIESKQ (SEQ ID NO:5), derived from GCN4 and also known to trimerize, is introduced at (the equivalent of) positions 419-433.

In certain embodiments, the polypeptides are further stabilized by introducing a sequence known to form trimeric structures, i.e., GYIPEAPRDGQAYVRKDGEWVLLSTFL (SEQ ID NO:3) at the C-terminus of HA2, optionally connected through a linker. The linker may optionally contain a cleavage site for processing afterward, according to protocols well known to those skilled in the art. To facilitate purification of the soluble form, a tag sequence may be added, e.g., a his tag (HHHHHH (SEQ ID NO:20) or HHHHHH (SEQ ID NO:21)) or FLAG tag (DYKDDDDK) (SEQ ID NO:22)), or a combination of these, optionally connected via short linkers. The linker may optionally contain (part of) a proteolytic cleavage site, e.g., RSLVPR (SEQ ID NO:23) (thrombin) or IEGR (SEQ ID NO:24) (Factor X) for processing afterward, according to protocols well known to those skilled in the art. The processed proteins are also encompassed in the disclosure.

In certain embodiments, the C-terminal part of the HA2 domain from positions 520-565 has been deleted (numbering according to SEQ ID NO:1) and replaced by SGRDYKDDDDKLVPRGSPGSGYIPEAPRDGQAY-VRKDGEWVLLSTFLGHHHHHH (SEQ ID NO:4).

Applicants have previously identified broadly neutralizing antibodies isolated from primary human B-cells from vaccinated individuals, some of which were specific for group 1 (e.g., CR6261, as described in WO 2008/028946) and some of which were specific for group 2 influenza viruses (e.g., CR8020 as described in WO 2010/130636). Detailed analysis of the epitopes of these monoclonal antibodies has revealed the reason for the lack of cross-reactivity of these specific antibodies. In both cases, the presence of glycans in group 1 or group 2 HA molecules on different positions at least partly explained the fact that the antibodies are group-specific. With the identification of CR9114-like antibodies that cross-react with many groups 1 and 2 HA molecules, as described below, it has become clear that it is possible for the human immune system to elicit very broad neutralizing antibodies against influenza viruses. However, given the need for a yearly vaccination scheme, these antibodies are apparently not, or only to a very low extent, elicited following infection or vaccination with (seasonal) influenza viruses of subtypes H1 and/or H3.

According to the present disclosure, polypeptides are provided that mimic the specific epitopes of CR6261 and/or CR9114, and that can be used as immunogenic polypeptides, e.g., to elicit cross-neutralizing antibodies when administered in vivo, either alone or in combination with other prophylactic and/or therapeutic treatments. With "cross-neutralizing antibodies," antibodies are meant that are capable of neutralizing at least two, preferably at least three, four, or five different subtypes of influenza A viruses of phylogenetic group 1, and/or at least two, preferably at least three, four, or five, different subtypes of influenza A viruses of phylogenetic group 2, and/or at least two different subtypes of influenza B viruses, in particular, at least all virus strains that are neutralized by CR6261 and CR9114.

The polypeptides hereof do not comprise the full-length HA1. In certain embodiments, the immunogenic polypeptides are substantially smaller than HA0, preferably lacking all or substantially all of the globular head of HA. Preferably, the immunogenic polypeptides are no more than 360, preferably no more than 350, 340, 330, 320, 310, 305, 300, 295, 290, 285, 280, 275, or 270 amino acids in length. In an embodiment, the immunogenic polypeptide is from about 250 to about 350, preferably from about 260 to about 340, preferably from about 270 to about 330, or preferably from about 270 to about 330 amino acids in length.

In certain embodiments, the polypeptides selectively bind to the antibodies CR6261 and/or CR9114. In certain embodiments, the polypeptide does not bind to the antibody CR8057. CR6261 comprises a heavy chain variable region comprising the amino acid sequence (peptide) of SEQ ID NO:9 and a light chain variable region comprising the amino acid sequence of SEQ ID NO:10; CR9114 comprises a heavy chain variable region comprising the amino acid sequence of SEQ ID NO:11 and a light chain variable region comprising the amino acid sequence of SEQ ID NO:12; CR8020 comprises a heavy chain variable region comprising the amino acid sequence of SEQ ID NO:17 and a light chain variable region comprising the amino acid sequence of SEQ ID NO:18. CR8057 comprises a heavy chain variable region comprising the amino acid sequence of SEQ ID NO:13 and a light chain variable region comprising the amino acid sequence of SEQ ID NO:14.

As described above, the polypeptides comprise an influenza hemagglutinin HA1 domain that comprises an HA1 N-terminal stem segment that is covalently linked by a linking sequence of 0 to 50 amino acid residues to the HA1 C-terminal stem segment. The linking sequence, if present, does not occur in naturally occurring, or wild-type, HA. In certain embodiments, the linker is a peptide that comprises one amino acid residue, two or less amino acid residues, three or less amino acid residues, four or less amino acid residues, five or less amino acid residues, ten or less amino acid residues, 15 or less amino acid residues, 20 or less amino acid residues, 30 or less amino acid residues, 40 or less amino acid residues, or 50 or less amino acid residues. In a specific embodiment, the linking sequence is a sequence selected from the group consisting of G, GS, GGG, GSG, GSA, GSGS (SEQ ID NO:79), GSAG (SEQ ID NO:80), GGGG (SEQ ID NO:77), GSAGS (SEQ ID NO:78), GSGSG (SEQ ID NO:81), GSAGSA (SEQ ID NO:16), GSAGSAG (SEQ ID NO:15), and GSGSGSG (SEQ ID NO:82).

In certain embodiments, the polypeptides comprise the amino acid sequence:

(SEQ ID NO: 53)

DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDGVSGR

DYKDDDDKLVPRGSPGSGYIPEAPRDGQAYVRKDGEWVLLSTFLGHHHHH

H, wherein $X_1$ is an amino acid selected from the group consisting of E, I, K, V, A, and T;

$X_2$ is an amino acid selected from the group consisting of I, K, R, T, F, N, S, and Y;

$X_3$ is an amino acid selected from the group consisting of D, F, V, Y, A, I, N, S, and T;

$X_4$ is an amino acid selected from the group consisting of I, K, R, T, E, G, and V;

$X_5$ is an amino acid selected from the group consisting of E, K, M, V, R, and T;

$X_6$ is an amino acid selected from the group consisting of F, I, N, S, T, Y, H, and L;

$X_7$ is an amino acid selected from the group consisting of A, G, I, R, T, V, F, and S;

$X_8$ is an amino acid selected from the group consisting of F, I, N, S, T, Y, G, E, K, M, and V; and $X_9$ is an amino acid selected from the group consisting of H, I, L, N, R, and S.

In certain embodiments, the polypeptides comprise the amino acid sequence:

(SEQ ID NO: 54)

DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

-continued

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDG, wherein $X_1$ is an amino acid selected from the group consisting of E, I, K, V, A, and T;

$X_2$ is an amino acid selected from the group consisting of I, K, R, T, F, N, S, and Y;

$X_3$ is an amino acid selected from the group consisting of D, F, V, Y, A, I, N, S, and T;

$X_4$ is an amino acid selected from the group consisting of I, K, R, T, E, G, and V;

$X_5$ is an amino acid selected from the group consisting of E, K, M, V, R, and T;

$X_6$ is an amino acid selected from the group consisting of F, I, N, S, T, Y, H, and L;

$X_7$ is an amino acid selected from the group consisting of A, G, I, R, T, V, F, and S;

$X_8$ is an amino acid selected from the group consisting of F, I, N, S, T, Y, G, E, K, M, and V; and $X_9$ is an amino acid selected from the group consisting of H, I, L, N, R, and S.

In certain embodiments, the polypeptides comprise the amino acid sequence:

(SEQ ID NO: 70)

DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDGVKLE

SMGVYQIEG, wherein $X_1$ is an amino acid selected from the group consisting of E, I, K, V, A, and T;

$X_2$ is an amino acid selected from the group consisting of I, K, R, T, F, N, S, and Y;

$X_3$ is an amino acid selected from the group consisting of D, F, V, Y, A, I, N, S, and T;

$X_4$ is an amino acid selected from the group consisting of I, K, R, T, E, G, and V;

$X_5$ is an amino acid selected from the group consisting of E, K, M, V, R, and T;

$X_6$ is an amino acid selected from the group consisting of F, I, N, S, T, Y, H, and L;

$X_7$ is an amino acid selected from the group consisting of A, G, I, R, T, V, F, and S;

$X_8$ is an amino acid selected from the group consisting of F, I, N, S, T, Y, G, E, K, M, and V; and $X_9$ is an amino acid selected from the group consisting of H, I, L, N, R, and S.

In certain embodiments, the polypeptides comprise the amino acid sequence:

(SEQ ID NO: 71)

DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

```
-continued
EDKIEEIESKQIWCYNAELLVLLENERTLDFHDSNVKNLYEKVKSQLKNN

AKEIGNGCSEFYHKCNDECNIESVKNGTYDYPKYSEESKLNREKIDGVKL

ESMGVYQILAIYSTVASSLVLLVSLGAISFWMCSNGSLQCRICI,
``` wherein $X_1$ is an amino acid selected from the group consisting of E, I, K, V, A, and T;

$X_2$ is an amino acid selected from the group consisting of I, K, R, T, F, N, S, and Y;

$X_3$ is an amino acid selected from the group consisting of D, F, V, Y, A, I, N, S, and T;

$X_4$ is an amino acid selected from the group consisting of I, K, R, T, E, G, and V;

$X_5$ is an amino acid selected from the group consisting of E, K, M, V, R, and T;

$X_6$ is an amino acid selected from the group consisting of F, I, N, S, T, Y, H, and L;

$X_7$ is an amino acid selected from the group consisting of A, G, I, R, T, V, F, and S;

$X_8$ is an amino acid selected from the group consisting of F, I, N, S, T, Y, G, E, K, M, and V; and $X_9$ is an amino acid selected from the group consisting of H, I, L, N, R, and S.

The influenza hemagglutinin stem domain polypeptides can be prepared according to any technique deemed suitable to one of skill, including techniques described below.

Thus, the immunogenic polypeptides of the disclosure may be synthesized as DNA sequences by standard methods known in the art and cloned and subsequently expressed, in vitro or in vivo, using suitable restriction enzymes and methods known in the art. This disclosure thus also relates to nucleic acid molecules encoding the above-described polypeptides. The disclosure further relates to vectors comprising the nucleic acid molecules encoding the polypeptides of the disclosure. In certain embodiments, a nucleic acid molecule as described herein is part of a vector, e.g., a plasmid. Such vectors can easily be manipulated by methods well known to the person of ordinary skill in the art and can, for instance, be designed for being capable of replication in prokaryotic and/or eukaryotic cells. In addition, many vectors can directly, or in the form of an isolated desired fragment therefrom, be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. When host cells are used, it is preferred that the vector is an integrating vector. Alternatively, the vector may be an episomally replicating vector.

Once being apprised hereof, the person of ordinary skill in the art is capable of choosing suitable expression vectors, and inserting the nucleic acid sequences of the disclosure in a functional manner. To obtain expression of nucleic acid sequences encoding polypeptides, it is well known to those skilled in the art that sequences capable of driving expression can be functionally linked to the nucleic acid sequences encoding the polypeptide, resulting in recombinant nucleic acid molecules encoding a protein or polypeptide in expressible format. In general, the promoter sequence is placed upstream of the sequences that should be expressed. Many expression vectors are available in the art, e.g., the pcDNA and pEF vector series of INVITROGE®, pMSCV and pTK-Hyg from BD Sciences, pCMV-Script from STRATAGENE™, etc., which can be used to obtain suitable promoters and/or transcription terminator sequences, polyA sequences, and the like. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like. and combinations thereof. These should be capable of functioning in the host cell, thereby driving expression of the nucleic acid sequences that are functionally linked to them. The person of ordinary skill in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acid molecules of interest may be from the natural promoter or derivative thereof or from an entirely heterologous promoter (Kaufman, 2000). Some well-known and much-used promoters for expression in eukaryotic cells comprise promoters derived from viruses, such as adenovirus, e.g., the E1A promoter, promoters derived from cytomegalovirus (CMV), such as the CMV immediate early (IE) promoter (referred to herein as the "CMV promoter") (obtainable, for instance, from pcDNA, Invitrogen), promoters derived from Simian Virus 40 (SV40) (Das et al., 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001), actin promoter, an immunoglobulin promoter, heat shock promoters, and the like. Testing for promoter function and strength of a promoter is a matter of routine for a person of ordinary skill in the art and, in general, may, for instance, encompass cloning a test gene such as lacZ, luciferase, GFP, etc., behind the promoter sequence, and test for expression of the test gene. Of course, promoters may be altered by deletion, addition, mutation of sequences therein, and tested for functionality, to find new, attenuated, or improved promoter sequences. According to this disclosure, strong promoters that give high transcription levels in the eukaryotic cells of choice are preferred.

The constructs may be transfected into eukaryotic cells (e.g., plant, fungal, yeast or animal cells) or suitable prokaryotic expression systems like *E. coli* using methods that are well known to a person of ordinary skill in the art. In some cases, a suitable "tag" sequence (such as, for example, but not limited to, a his-, myc-, strep-, or flag-tag) or complete protein (such as, for example, but not limited to, maltose binding protein or glutathione S transferase) may be added to the sequences of the disclosure to allow for purification and/or identification of the polypeptides from the cells or supernatant. Optionally, a sequence containing a specific proteolytic site can be included to afterward remove the tag by proteolytic digestion.

Purified polypeptides can be analyzed by spectroscopic methods known in the art (e.g., circular dichroism spectroscopy, Fourier Transform Infrared spectroscopy and NMR spectroscopy or X-ray crystallography) to investigate the presence of desired structures like helices and beta sheets. ELISA, OCTET® and FACS® and the like can be used to investigate binding of the polypeptides of the disclosure to the broadly neutralizing antibodies described before (CR6261, CR9114, CR8057). Thus, polypeptides as described herein having the correct conformation can be selected.

The disclosure further relates to immunogenic compositions comprising a therapeutically effective amount of at least one of the polypeptides and/or nucleic acid molecules of the disclosure. In certain embodiments, the compositions comprise polypeptides comprising hemagglutinin stem domains from (or based on) HA of one influenza subtype, e.g., based on HA of an influenza virus comprising HA of, e.g., an H1 or H3 subtype. In certain embodiments, the compositions comprise polypeptides comprising hemagglutinin stem domains based on HA of two or more different influenza subtypes, e.g., compositions comprising both polypeptides comprising hemagglutinin stem domains based on HA of the H1 subtype and polypeptides comprising hemagglutinin stem domains based on HA of the H3 subtype.

The immunogenic compositions preferably further comprise a pharmaceutically acceptable carrier. In the present context, the term "pharmaceutically acceptable" means that the carrier, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The term "carrier" refers to a diluent, adjuvant, excipient, or vehicle with which the composition is administered. Saline solutions and aqueous dextrose and glycerol solutions can, e.g., be employed as liquid carriers, particularly for injectable solutions. The exact formulation should suit the mode of administration. The polypeptides and/or nucleic acid molecules preferably are formulated and administered as a sterile solution. Sterile solutions are prepared by sterile filtration or by other methods known per se in the art. The solutions can then be lyophilized or filled into pharmaceutical dosage containers. The pH of the solution generally is in the range of pH 3.0 to 9.5, e.g., pH 5.0 to 7.5.

The disclosure also relates to influenza HA stem domain polypeptides, nucleic acid molecules and/or vectors as described above for use in inducing an immune response against influenza HA protein. The disclosure also relates to methods for inducing an immune response in a subject, the method comprising administering to a subject a polypeptide, nucleic acid molecule and/or immunogenic composition as described above. A subject as described herein preferably is a mammal that is capable of being infected with an infectious disease-causing agent, in particular, an influenza virus, or otherwise can benefit from the induction of an immune response, such subject, for instance, being a rodent, e.g., a mouse, a ferret, or a domestic or farm animal, or a non-human primate, or a human. Preferably, the subject is a human subject. The disclosure thus provides methods for inducing an immune response to an influenza virus hemagglutinin (HA), in particular, of a group 1 and/or group 2 influenza A virus, such as an influenza virus comprising HA of the H1, H2, H3, H4, H5, H7 and/or H10 subtype, and/or of an influenza B virus in a subject utilizing the polypeptides, nucleic acid molecules and/or immunogenic compositions described herein. In some embodiments, the immune response induced is effective to prevent and/or treat an influenza virus infection caused group 1 and/or group 2 influenza A virus subtypes and/or influenza B viruses. In some embodiments, the immune response induced by the polypeptides, nucleic acid molecules and/or immunogenic compositions described herein is effective to prevent and/or treat an influenza A and/or B virus infection caused by two, three, four, five or six subtypes of influenza A and/or B viruses.

Small proteins and/or nucleic acid molecules do not always efficiently induce a potent immune response, so it may be necessary to increase the immunogenicity of the polypeptides and/or nucleic acid molecules by adding an adjuvant. In certain embodiments, the immunogenic compositions described herein comprise, or are administered in combination with, an adjuvant. The adjuvant for administration in combination with a composition described herein may be administered before, concomitantly with, or after administration of the composition. Examples of suitable adjuvants include aluminium salts such as aluminium hydroxide and/or aluminium phosphate; oil-emulsion compositions (or oil-in-water compositions), including squalene-water emulsions, such as MF59 (see, e.g., WO 90/14837); saponin formulations, such as, for example, QS21 and Immunostimulating Complexes (ISCOMS) (see, e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif-containing oligonucleotides, ADP-ribosylating bacterial toxins or mutants thereof, such as E. coli, heat labile enterotoxin LT, cholera toxin CT, pertussis toxin PT, or tetanus toxoid TT, Matrix M (Isconova). In addition, known immunopotentiating technologies may be used, such as fusing the polypeptides of the disclosure to proteins known in the art to enhance immune response (e.g., tetanus toxoid, CRM197, rCTB, bacterial flagellins or others) or including the polypeptides in virosomes, or combinations thereof. Other non-limiting examples that can be used are, e.g., disclosed by Coffman et al. (2010).

In an embodiment, the influenza hemagglutinin stem domain polypeptides of the disclosure are incorporated into viral-like particle (VLP) vectors. VLPs generally comprise a viral polypeptide(s) typically derived from a structural protein(s) of a virus. Preferably, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art.

In a specific embodiment, the polypeptide is incorporated into a virosome. A virosome containing a polypeptide hereof may be produced using techniques known to those skilled in the art. For example, a virosome may be produced by disrupting a purified virus, extracting the genome, and reassembling particles with the viral proteins (e.g., an influenza hemagglutinin stem domain polypeptide) and lipids to form lipid particles containing viral proteins.

The disclosure also relates to the above-described polypeptides, nucleic acid molecules and/or immunogenic compositions for inducing an immune response in a subject against influenza HA, in particular, for use as a vaccine. The influenza hemagglutinin stem domain polypeptides, nucleic acid molecules encoding such polypeptides, or vectors comprising such nucleic acid molecules or polypeptides described herein thus may be used to elicit neutralizing antibodies against influenza viruses, for example, against the stem region of influenza virus hemagglutinin. The disclosure, in particular, relates to polypeptides, nucleic acid molecules, and/or imunogenic compositions as described above for use as a vaccine in the prevention and/or treatment of a disease or condition caused by an influenza A virus of phylogenetic group 1 and/or phylogenetic group 2 and/or an influenza B virus. In an embodiment, the vaccine may be used in the prevention and/or treatment of diseases caused by two, three, four, five, six or more different subtypes of phylogenetic group 1 and/or 2 and/or influenza B viruses. The polypeptides hereof may be used after synthesis in vitro or in a suitable cellular expression system, including bacterial and eukaryotic cells or, alternatively, may be expressed in vivo in a subject in need thereof, by expressing a nucleic acid coding for the immunogenic polypeptide. Such nucleic acid vaccines may take any form, including naked DNA, plasmids, or viral vectors including adenoviral vectors.

Administration of the polypeptides, nucleic acid molecules, and/or immunogenic compositions hereof can be performed using standard routes of administration. Non-limiting examples include parenteral administration, such as intravenous, intradermal, transdermal, intramuscular, subcutaneous, etc., or mucosal administration, e.g., intranasal, oral, and the like. Once being apprised hereof, the person of ordinary skill in the art will be capable to determine the various possibilities to administer the polypeptides, nucleic acid molecules, and/or immunogenic compositions as described herein, in order to induce an immune response. In certain embodiments, the polypeptide, nucleic acid molecule, and/or immunogenic composition (or vaccine) is administered more than one time, i.e., in a so-called homologous prime-boost regimen. In certain embodiments where the polypeptide, nucleic acid molecule, and/or immunogenic composition is administered more than once, the administration of the second dose can be performed after a time interval of, for example, one week or more after the administration of the first dose, two weeks or more after the administration of the first dose, three weeks or more after the administration of the first dose, one month or more after the administration of the first dose, six weeks or more after the administration of the first dose, two months or more after the administration of the first dose, three months or more after the administration of the first dose, four months or more after the administration of the first dose, etc., up to several years after the administration of the first dose of the polypeptide, nucleic acid molecule, and/or immunogenic composition. It is also possible to administer the vaccine more than twice, e.g., three times, four times, etc., so that the first priming administration is followed by more than one boosting administration. In other embodiments, the polypeptide, nucleic acid molecule, and/or immunogenic composition as described herein is administered only once.

The polypeptides, nucleic acid molecules, and/or immunogenic compositions may also be administered, either as prime, or as boost, in a heterologous prime-boost regimen.

Further described are methods for preventing and/or treating an influenza virus disease in a subject utilizing the polypeptides, nucleic acid molecules and/or compositions described herein. In a specific embodiment, a method for preventing and/or treating an influenza virus disease in a subject comprises administering to a subject in need thereof an effective amount of a polypeptide, nucleic acid and/or immunogenic composition, as described above. A therapeutically effective amount refers to an amount of the polypeptide, nucleic acid, and/or composition as defined herein, that is effective for preventing, ameliorating and/or treating a disease or condition resulting from infection by a group 1 or 2 influenza A virus, and/or an influenza B virus. Prevention encompasses inhibiting or reducing the spread of influenza virus or inhibiting or reducing the onset, development or progression of one or more of the symptoms associated with infection by an influenza virus. "Amelioration" as used herein may refer to the reduction of visible or perceptible disease symptoms, viremia, or any other measurable manifestation of influenza infection.

Those in need of treatment include those already inflicted with a condition resulting from infection with a group 1 or a group 2 influenza A virus, or an influenza B virus, as well as those in which infection with influenza virus is to be prevented. The polypeptides, nucleic acid molecules and/or compositions of the disclosure thus may be administered to a naive subject, i.e., a subject that does not have a disease caused by influenza virus infection or has not been and is not currently infected with an influenza virus infection, or to subjects that already are and/or have been infected with an influenza virus.

In an embodiment, prevention and/or treatment may be targeted at patient groups that are susceptible to influenza virus infection. Such patient groups include, but are not limited to, e.g., the elderly (e.g., ≥50 years old, ≥60 years old, and preferably ≥65 years old), the young (e.g., ≤5 years old, ≤1 year old), hospitalized patients and patients who have been treated with an antiviral compound but have shown an inadequate antiviral response.

In another embodiment, the polypeptides, nucleic acid molecules and/or immunogenic compositions may be administered to a subject in combination with one or more other active agents, such as existing or future influenza vaccines, monoclonal antibodies and/or antiviral agents, and/or antibacterial, and/or immunomodulatory agents. The one or more other active agents may be beneficial in the treatment and/or prevention of an influenza virus disease or may ameliorate a symptom or condition associated with an influenza virus disease. In some embodiments, the one or more other active agents are pain relievers, anti-fever medications, or therapies that alleviate or assist with breathing.

Dosage regimens of the polypeptides and/or nucleic acid molecules hereof can be adjusted to provide the optimum desired response (e.g., a therapeutic response). A suitable dosage range may, for instance, be 0.1-100 mg/kg body weight, preferably 1-50 mg/kg body weight, preferably 0.5-15 mg/kg body weight. The precise dosage of the polypeptides and/or nucleic acid molecules to be employed will, e.g., depend on the route of administration and the seriousness of the infection or disease caused by it, and should be decided according to the judgment of the practitioner and each subject's circumstances. For example, effective doses vary depending upon target site, physiological state of the patient (including age, body weight, health), and whether treatment is prophylactic or therapeutic. Usually, the patient is a human, but non-human mammals including transgenic mammals can also be treated. Treatment dosages are optimally titrated to optimize safety and efficacy.

The polypeptides hereof may also be used to verify binding of monoclonal antibodies identified as potential therapeutic candidates. In addition, the polypeptides may be used as diagnostic tools, for example, to test the immune status of an individual by establishing whether there are antibodies in the serum of such individual capable of binding to the polypeptide of the disclosure. Thus also described is an in vitro diagnostic method for detecting the presence of an influenza infection in a patient, the method comprising the steps of a) contacting a biological sample obtained from the patient with a polypeptide as described herein; and b) detecting the presence of antibody-antigen complexes.

The polypeptides may also be used to identify new binding molecules or improve existing binding molecules, such as monoclonal antibodies and antiviral agents.

The disclosure is further illustrated in the following Examples and figures. The Examples are not intended to limit the scope of the disclosure in any way.

EXAMPLES

Example 1

Preparation of Stem-based Polypeptides

PCT/EP2012/073706 discloses influenza hemagglutinin stem domain polypeptides, compositions and vaccines and methods of their use in the field of prevention and/or treatment of influenza. Here, additional sequences of stem domain polypeptides derived from the full-length HA of H1N1 A/Brisbane/59/2007 (SEQ ID NO:1) are described. The stem domain polypeptides are obtained by site-directed mutation of H1-mini2-cluster1+5+6-GCN4 (SEQ ID NO:2) and present the broad influenza-neutralizing epitope of CR6261 (Throsby et al., 2009; Ekiert et al., 2010) and/or CR9114.

H1-mini2-cluster1+5+6-GCN4 (SEQ ID NO:2) was derived from the full-length HA of H1N1 A/Brisbane/59/2007 (SEQ ID NO:1) by taking the following steps:

1. Removal of the cleavage site in HA0. Cleavage of wild-type HA at this site results in HA1 and HA2. The removal can be achieved by mutation of R to Q at the P1 position (see, e.g., Sun et al., 2010, for an explanation of the nomenclature of the cleavage site (position 343 in SEQ ID NO:1).
2. Removal of the head domain by deleting amino acids 53 to 320 from SEQ ID NO:1. The remaining N- and C-terminal parts of the sequence were joined by a four-residue flexible linker, GGGG (SEQ ID NO:77).
3. Increasing the solubility of the loop (between the A-helix and the CD helix) formed by (the equivalent of) residues 402 to 418 in H1 A/Brisbane/59/2007 (SEQ ID NO:1) in order to both increase the stability of the pre-fusion conformation and to destabilize the post-fusion conformation of the modified HA. In H1-mini2-cluster1+5+6-GCN4 (SEQ ID NO:2), mutations F406S, V409T, F413G and L416S (numbering refers to SEQ ID NO:1) were introduced.
4. Introducing a disulfide bridge between amino acids at positions 324 and 436 in H1 A/Brisbane/59/2007; this is achieved by introducing mutations R324C and Y436C (numbering refers to SEQ ID NO:1).
5. Introducing the GCN4-derived sequence MKQIED-KIEEIESKQ (SEQ ID NO:5) that is known to trimerize, at positions 419-433 (numbering refers to SEQ ID NO:1).

In certain embodiments, the polypeptides of the disclosure contain the intracellular sequences of HA and the transmembrane domain. In other embodiments, the sequence of the transmembrane and intracellular domain have been deleted from position (or the equivalent thereof, as determined from sequence alignment) 519, 520, 521, 522, 523, 524, 525, 526, 526, 527, 528, 529, or 530 of HA2 to the C-terminus of HA2 (numbering according to SEQ ID NO:1) so that a secreted (soluble) polypeptide is produced following expression in cells. The soluble polypeptide can be further stabilized by introducing a sequence known to form trimeric structures, i.e., the foldon sequence AYVRKDGEWVLL (SEQ ID NO:3), optionally connected through a short linker, as described above. The linker may optionally contain a cleavage site for processing afterward, according to protocols well known to those skilled in the art. To facilitate purification and detection of the soluble form, a tag sequence may be optionally added, e.g., a histidine tag (HHHHHHH (SEQ ID NO:20) or HHHHHH (SEQ ID NO:21)) or a FLAG tag (DYKDDDDK; SEQ ID NO:22), or combination of these, optionally connected via short linkers. The linker may optionally contain (part of) a proteolytic cleavage site, e.g., LVPRGS (SEQ ID NO:23) (thrombin) or IEGR (SEQ ID NO:24) (Factor X), for processing afterward, according to protocols well known to those skilled in the art. The processed proteins are also encompassed in the disclosure.

An example of such a C-teminal sequence combining FLAG-tag, thrombin cleavage site, foldon, and His sequences is SEQ ID NO:4 FLAG- thrombin-foldon-His. This sequence was combined with a soluble form of H1-mini2-cluster1+5+6-GCN4 (SEQ ID NO:2) sequence to create the parental sequence (SEQ ID NO:6) that was used to create novel polypeptides of the disclosure by mutagenesis. This sequence does not contain the leader sequence corresponding to amino acids 1-17 of SEQ ID NOS:1 and 2.

The stem domain polypeptides are created by deleting the part of the hemagglutinin sequence that encodes the head domain of the molecule and reconnecting the N- and C-terminal parts of the sequence on either side of the deletion through a linker as described in PCT/2012/073706 and above. The removal of the head domain leaves part of the molecule that was previously shielded from the aqueous solvent exposed, potentially destabilizing the structure of the polypeptides of the disclosure. For this reason, residues in the B-loop (in particular, amino acid residue 406 (F and S in SEQ ID NOS:1 and 2, respectively), 409 (V and T) 413 (F and G) and 416 (L and S) were mutated in various combinations using parental sequence, SEQ ID NO:6, as the starting point. SEQ ID NO:6 was created from H1-mini2-cluster1+5+6-GCN4 (SEQ ID NO:2) by removing the leader sequence, and replacing residues 520-565 with a Flag-thrombin-foldon—his sequence (SEQ ID NO:4).

Similarly, in the area around the fusion peptide, a number of hydrophobic residues are exposed to the solvent, caused by the fact that, unlike the native full-length HA, the polypeptides of the disclosure cannot be cleaved and undergo the associated conformational change that buries the hydrophobic fusion peptide in the interior of the protein. To address this issue, some or all of the residues I337, I340, F352 and I353 in SEQ ID NO:2 were also mutated.

The helix A of HA is an important part of the epitopes of broadly neutralizing epitopes of CR6261, CR9114 and FI6.v3. The amino acid residue M402 (numbering refers to SEQ ID NO:1) sits at the C-terminal end of this helix, and to further stabilize the helix structure, this residue was also targeted to create novel polypeptides of the disclosure. Two different sets of mutant polypeptides are disclosed in Table 1.

TABLE I

Mutations created in SEQ ID NO: 6. Corresponding amino acids in SEQ ID NO: 1 (full-length, wt HA) and SEQ ID NO: 6 are also indicated.

| | Set 1 | | |
|---|---|---|---|
| Posi- | residue | | amino acids |
| tion | SEQ ID NO: 1 | SEQ ID NO:6 | introduced |
| 337 | I | I | E, I, K, V |
| 340 | I | I | I, K, R, T |

TABLE I-continued

Mutations created in SEQ ID NO: 6. Corresponding amino acids in SEQ ID NO: 1 (full-length, wt HA) and SEQ ID NO: 6 are also indicated.

| 352 | F | F | D, F, V, Y |
| 353 | I | I | I, K, R, T |
| 402 | M | M | E, K, M, V |
| 406 | F | S | F, I, N, T, Y, S |
| 409 | V | T | A, G, I, R, T, V |
| 413 | F | G | F, I, N, S, T, Y, G |
| 416 | L | S | H, I, L, N, R, S |

Set 2

| Position | residue SEQ ID NO: 1 | SEQ ID NO: 6 | amino acids introduced |
|---|---|---|---|
| 337 | I | I | A, E, I, K, T, V |
| 340 | I | I | F, I, N, S, T, Y |
| 352 | F | F | A, D, F, I, N, S, T, V, Y |
| 353 | I | I | E, G, I, K, R, V |
| 402 | M | M | M, R, T |
| 406 | F | S | F, H, L, Y, |
| 409 | V | T | F, I, S, T |
| 413 | F | G | E, K, M, V |
| 416 | L | S | I, L, R, S |

Example 2

Detection of Polypeptide Expression and Binding to Broadly Neutralizing Antibodies DNA sequences encoding the polypeptides of the disclosure were transformed into *Pichia pastoris* or transfected into HEK293F cells using protocols well known to a person of ordinary skill in the art. Constructs used for expression in mammalian cells contained the HA leader sequence (residue 1-17 in SEQ ID NOS:1 and 2), whereas, in constructs used for expression in *P. pastoris*, the HA leader sequence was replaced with the yeast alpha factor leader sequence (SEQ ID NO:7). In this way, expressed protein is directed toward the cell culture medium, thus allowing binding and expression to be determined without further purification of the polypeptides as described herein. All sequences contained the FLAG-foldon-HIS C-terminal sequence (SEQ ID NO:4).

Monoclonal antibody binding (CR6261, CR9114, CR8020) to polypeptides as described herein was determined by ELISA. To this end, ELISA plates were treated overnight with a 2 µg/ml monoclonal antibody solution (20 µl/well) at 4° C. After removal of the antibody solution, the remaining surface was blocked with 4% solution of non-fat dry milk powder in PBS for a minimum of 1 hour at room temperature. After washing of the plates, 20 µl of cell culture medium (neat or diluted) was added to each well and incubated for at least 1 hour at room temperature. ELISA plates were then washed and 20 µl of anti-FLAG-HRP antibody solution (Sigma A8952, 2000 times diluted in 4% non-fat dry milk in PBS-TWEEN®) was added. After incubation (1 hour at room temperature), plates were washed once more, and 20 µl luminescent substrate (Thermoscientific C#34078) was added to develop the signal. Alternatively, a colorimetric detection method can be used to develop the signal.

Expression of polypeptides as described herein was determined from a homogeneous time-resolved fluorescence assay (for a general description, see, e.g., Degorce et al., *Curr. Chem. Genomics* 2009 3:22-32). To this end, a mixture of Terbium (Tb)-labeled anti-FLAG monoclonal antibody (donor) and ALEXA FLUOR®-488-labeled anti-His monoclonal antibody (acceptor) (HTRF solution) was prepared by adding 210.5 µl Anti-FLAG-TB (stock solution 26 µg/ml) and 1.68 ml of anti-HIS-488 (stock solution 50 µg/ml) to 80 ml of a 1-to-1 mixture of culture medium and 50 mM HEPES+0.1% BSA. 19 µl of HTRF solution was added to each well of an ELISA plate and 1 µl of culture medium was added. Upon excitation and after a delay to allow interfering, short-lived background signals arising from other compounds (proteins, media components, etc.) to decay the ratio of fluorescence emission at 520 and 665 nm was determined. This is a measure of total protein content in the sample and is used to normalize the mAb binding signals between different experiments.

The polypeptides listed in Tables 4 and 5 were expressed in *P. pastoris* following protocols well known to those of ordinary skill in the art. Culture medium was collected and binding to CR6261; binding and expression of the stem domain polypeptides were determined as described above. Since the response in the binding assay scales with the concentration of expresses protein. ELISA binding signal was normalized for protein expression by comparing the ratio of binding signal over the signal in the HTRF assay for each expressed sequence. All expressed proteins exhibit higher ratios of CR626 binding to HTRF signal compared to the parental sequence of SEQ ID NO:6.

The polypeptides listed in Table 6 were expressed in HEK293F cells following protocols well known to those skilled in the art. Culture medium was collected and binding to CR6261; binding and expression of the stem domain polypeptides were determined as described above. The ratio of CR6261 binding to HTRF signals was calculated and compared to the ratio calculated for the parental sequence, SEQ ID NO:6. The results are listed in Table 6; all expressed proteins exhibit higher ratios, indicating that the stem polypeptides show increased binding of CR6261.

Example 3

Purification and Characterization of Polypeptides of the Disclosure

To further characterize polypeptides, the immunogens 127H1 (SEQ ID NO:55), 86B4 (SEQ ID NO:56), 74H9 (SEQ ID NO:57), 6E12 (SEQ ID NO:58) and 55G7 (SEQ ID NO:59) were cultured and purified to homogeneity. In order to obtain a highly pure preparation of a polypeptide of the disclosure, HEK293F cells were transfected with expression vector pcDNA2004 containing the genes encoding soluble forms of 127H1 (SEQ ID NO:55), 86B4 (SEQ ID NO:56), 74H9 (SEQ ID NO:57), 6E12 (SEQ ID NO:58) and 55G7 (SEQ ID NO:59). Soluble forms were created in this case by replacement of residues 519-565 (numbering refers to SEQ ID NO:1) with sequence RSLVPRGSPGHHHHHH (SEQ ID NO:69). It will be understood by the person of ordinary skill in the art that the leader sequence (or signal sequence) that directs transport of a protein during production (corresponding to amino acids 1-17 of SEQ ID NO:1) will not be present in the secreted final polypeptide. The amino acid sequences of the soluble secreted proteins are given as SEQ ID NOS:65 to 69.

To produce the polypeptides, $1.0*10^6$ vc/mL were seeded by spinning down HEK293F cells (INVITROGEN®) at 300 g for 5 minutes and resuspending in 300 mL pre-warmed Freestyle™ medium per SF1000 flask. This culture was incubated for 1 hour at 37° C., 10% $CO_2$ at 110 rpm in a multitron incubator. After 1 hour, the plasmid DNA was pipetted in 9.9 mL Optimem medium to a concentration of 1.0 µg/mL in the 300 mL culture volume. In parallel, 440 µL 293fectin® was pipetted in 9.9 mL Optimem medium and incubated for 5 minutes at room temperature. After 5 minutes, the plasmid DNA/Optimem mix was added to the 293fectin®/Optimem mix and incubated at room temperature for 20 minutes. After the incubation, the plasmid DNA/293fectin® mix was added dropwise to the cell suspension. The transfected cultured was incubated at 37° C., 10% $CO_2$, and 110 rpm in a multitron incubator. At day 7, cells were separated from the culture medium by centrifugation (30 minutes at 3000 g), while the supernatant containing the soluble polypeptides of the disclosure was filtrated over a 0.2 µm bottle top filter for further processing.

For purification purposes, ca 1400 ml culture supernatant from cells transfected with genes encoding the soluble forms (as described above) of polypeptides of the disclosure 127H1 (SEQ ID NO:55), 86B4 (SEQ ID NO:56), 741-19 (SEQ ID NO:57), 6E12 (SEQ ID NO:58) or 55G7 (SEQ ID NO:59) was applied to a 24 ml Ni Sepharose HP column, pre-equilibrated in wash buffer (20 mM TRIS, 500 mM NaCl, pH 7.8). Following a washing step with 10 mM Imidaze in wash buffer, the bound polypeptides of the disclosure were eluted with a step-wise gradient of 300 mM imidazole in wash buffer. The elution peaks were collected, buffer exchanged, concentrated, and applied to a size exclusion column for further purification (SUPERDEX® 200). Fractions were collected during elution and analyzed for protein content by SDS-PAGE and Western Blot (using a monoclonal antibody specific for histidine-tags). Fractions containing the purified polypeptides of the disclosure were collected and used for further analysis. Purity was determined by size-exclusion chromatography and was above 90% in all cases. Characteristics of the purification procedures are listed in Table 8.

To analyze the binding reaction between polypeptides and to confirm the presence of the conformational epitopes of CR6261 and CR9114, the complexation of these antibodies with the purified protein was studied by biolayer interferometry (Octet Red[384], Forte Bio). To this end, biotinylated CR6261, CR9114 were immobilized on streptavidin-coated sensors, which were subsequently exposed first to a solution of the purified polypeptide of the disclosure to measure the rate of association and then to a wash solution to measure the rate of dissociation. The immobilized CR6261and CR9114 both recognize the polypeptides of the disclosure as evidenced by the clear responses after exposure to the soluble form of polypeptides of the disclosure. To estimate the dissociation constant for the binding interaction, a titration was performed using a- two-fold dilution series. Sensors containing immobilized CR6261 were exposed to solutions containing the soluble polypeptides of the disclosure at concentrations of 750, 375, 163, 81, 40, 20 and 10 nM, respectively, except in the case of the purified s55G7 (SEQ ID NO:68) where a concentration range of 2000, 1000, 500, 250, 125, 63 and 31 nM was used. Similarly, sensors containing immobilized CR9114 were exposed to solutions containing the soluble polypeptides of the disclosure at concentrations of 300, 150, 75, 38, 19, 9 and 5 nM, respectively. In all cases, the final response after 4000 seconds was recorded, plotted as a function of the polypeptide concentration, and a fit to a steady-state 1:1 binding model was performed to calculate an apparent dissociation constant $K_d$ (see FIGS. 2A to 2E). Values determined in this way are listed in Table 8.

The binding between polypeptides s127H1 (SEQ ID NO:66), s86B4 (SEQ ID NO:67), s74H9 (SEQ ID NO:65), s6E12 (SEQ ID NO:69) and s55G7 (SEQ ID NO:68) and Fab fragments of CR6261, CR9114 and, as control, CR8020, were studied by analytical size exclusion chromatography combined with multi-angle light scattering (SEC-MALS). This technology allows the simultaneous separation and estimation of the molecular size for different molecular species and/or complexes. The results are shown in FIGS. 3A to 3E, and summarized in Table 9. The data indicate that the polypeptides are monomeric and form a 1:1 complex with Fab fragments of CR6261 and CR9114, but not CR8020. This is in line with the specificity of the binding reactions of the Fab fragments, since CR6261 and CR91 14 bind to HAs derived from group 1, whereas CR8020 does not.

In conclusion, it has been shown that soluble forms of polypeptides 127H1 (SEQ ID NO:55), 86B4 (SEQ ID NO:56), 74H9 (SEQ ID NO:57), 6E12 (SEQ ID NO:58), and 55G7 (SEQ ID NO:59) can be produced and purified to homogeneity. The purified soluble polypeptides are capable of binding broadly neutralizing monoclonal antibodies CR6261 and CR9114 with high affinity, confirming the presence of the corresponding neutralizing epitopes in these stem domain polypeptides.

Example 4

Figure 4A:
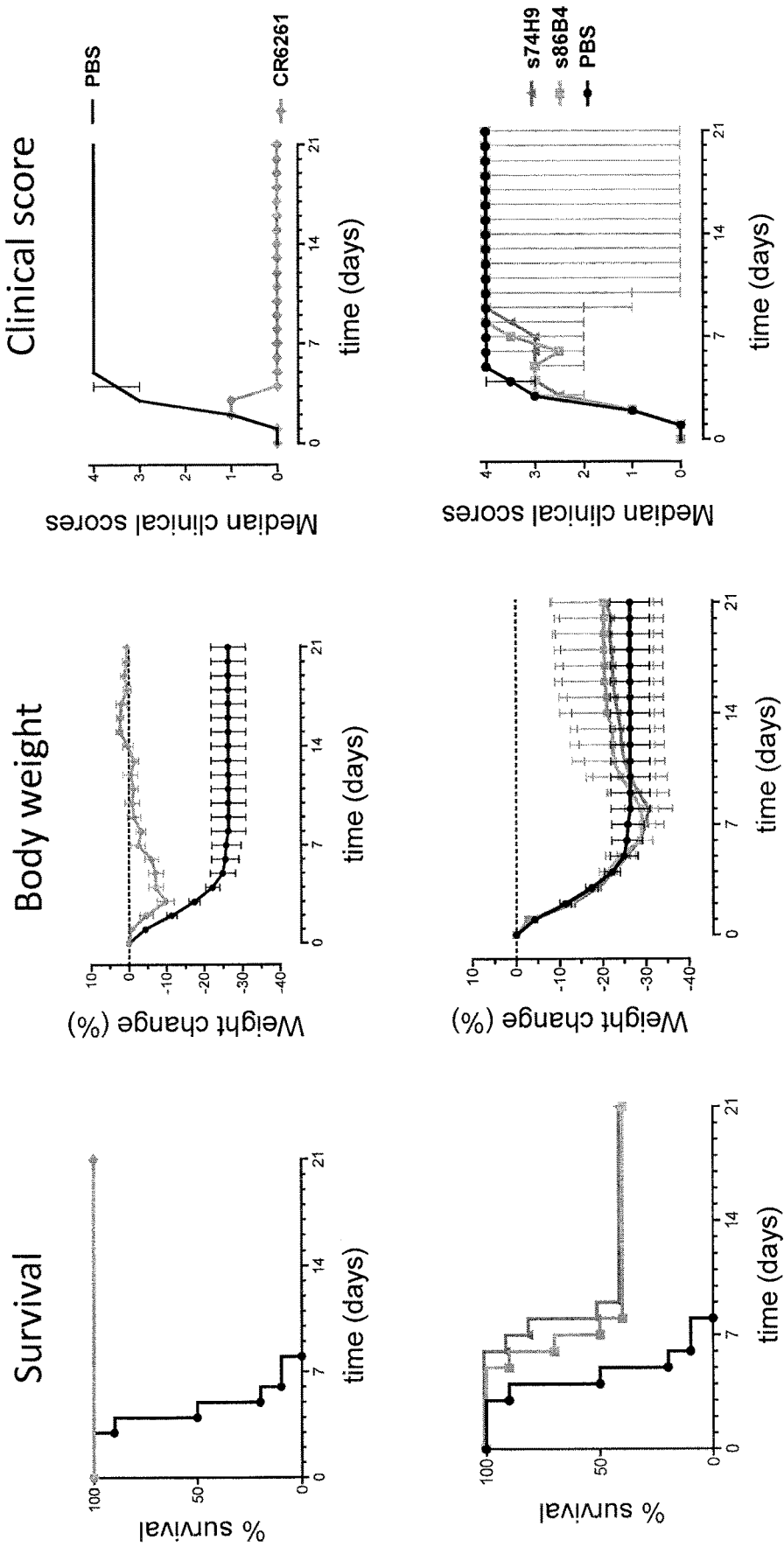
FIGS. 4A and 4B. Evaluation of protective efficacy of polypeptide of the disclosure s74H9 SEQ ID NO:65 and s86B4 SEQ ID NO:67 in a lethal influenza H1N1A/NL/602/09 challenge model.
Figure 4B:
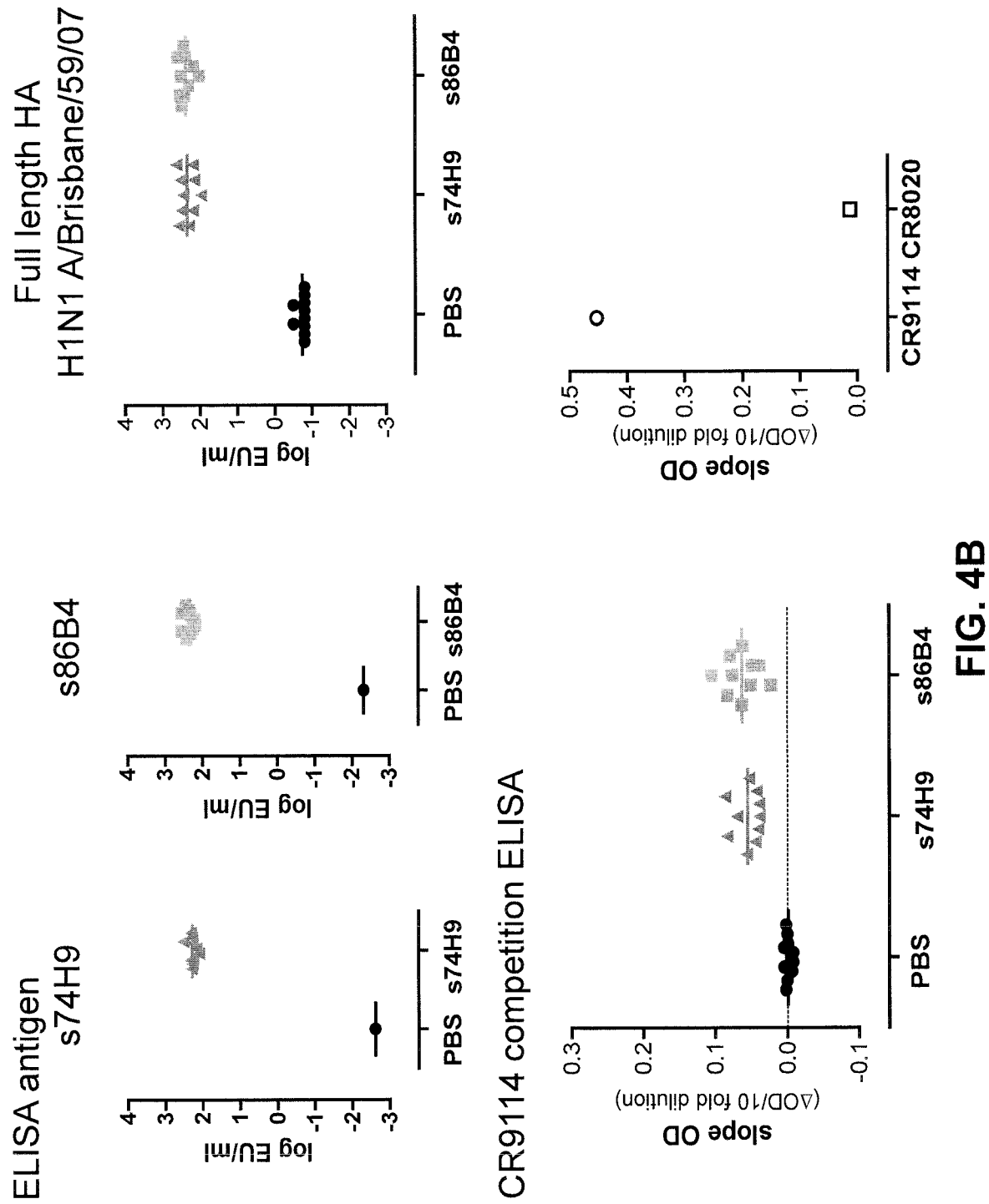
Figure 5A:
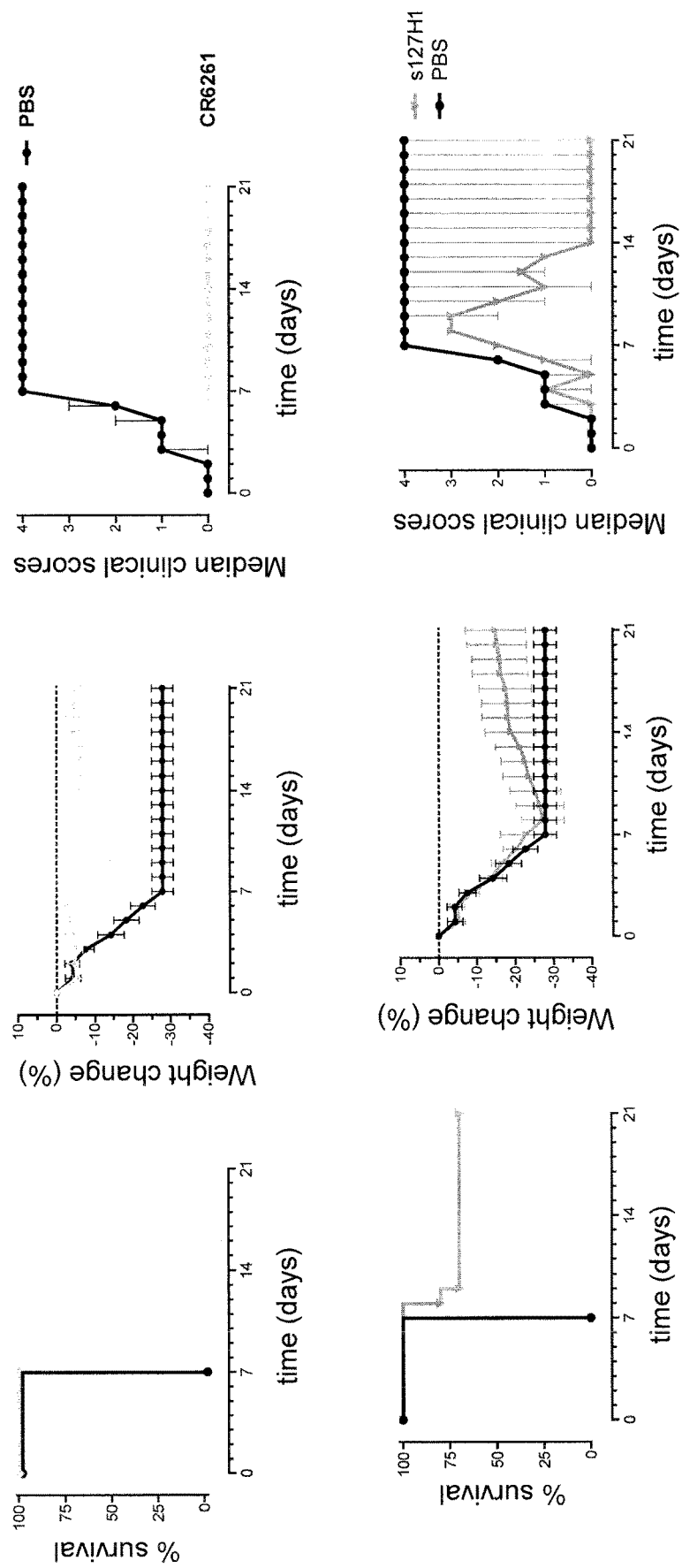
FIGS. 5A and 5B. Evaluation of protective efficacy of polypeptide of the disclosure s127H1 (SEQ ID NO:66) in a lethal influenza H1N1 A/Puerto Rico/8/1934 challenge model.
Figure 5B:
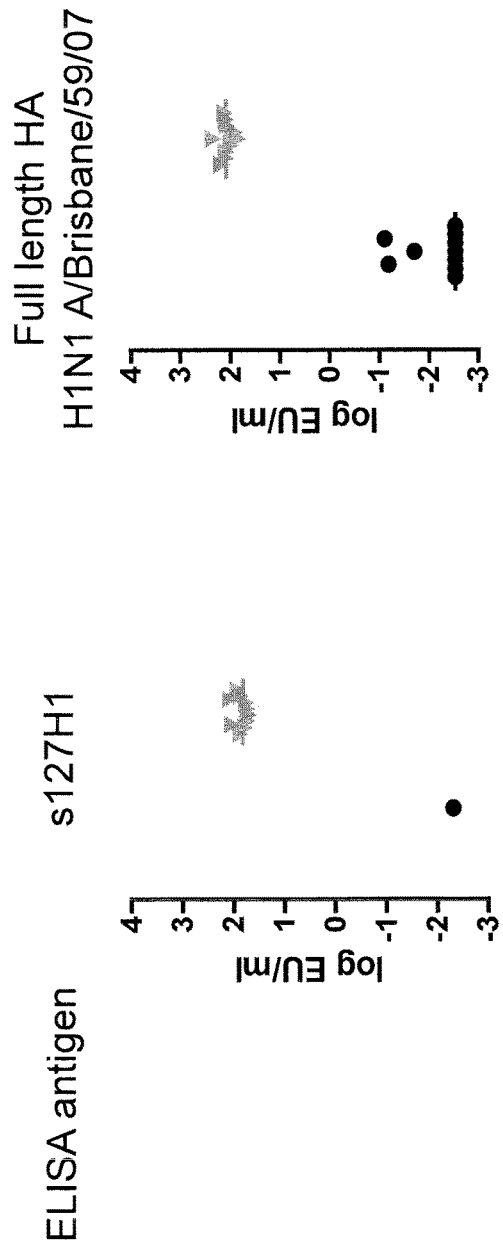
Figure 5B:
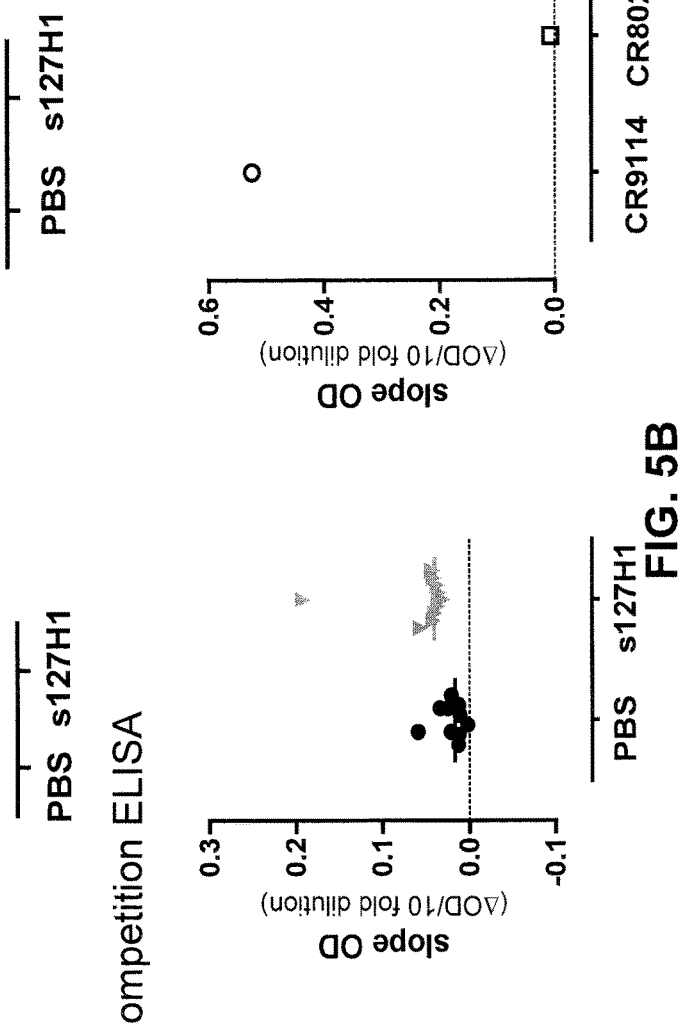
Figure 6:
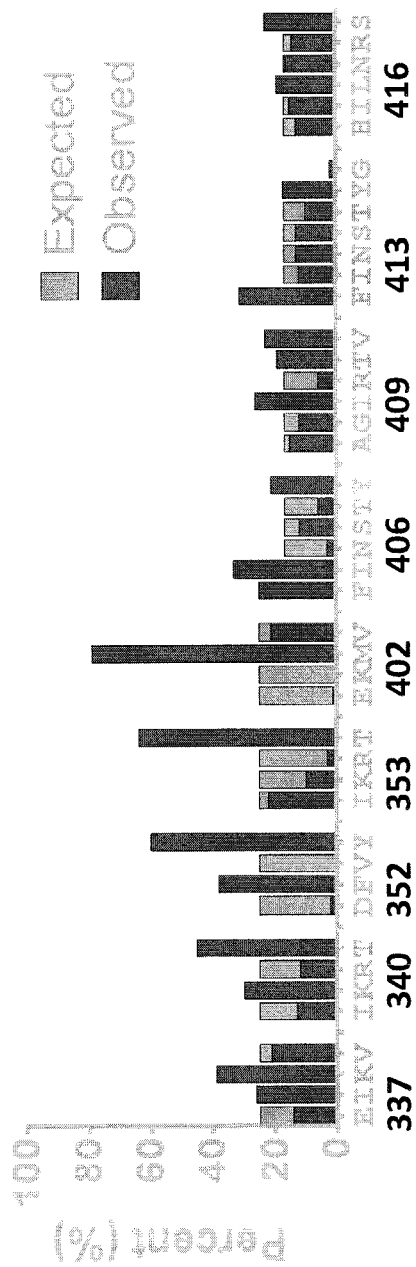
FIG. 6. Observed and expected frequency of occurrence of an amino acid at the indicated position in Set 1 sequences that show improved binding to CR6261. Values are expressed as percentage of the total number of Set 1 sequences that show improved CR6261 binding. Expected values are calculated as 100% divided by the number of variable amino acids at each position included in the set.

Evaluation of Protective Efficacy of Polypeptides of the Disclosure in a Lethal Influenza Challenge Model In order to evaluate the protective efficacy of polypeptides in a lethal influenza challenge model, groups of ten female BALB/c mice (ages 6 to 8 weeks) were immunized three times at three-week intervals with 30 µg of purified s86B4 (SEQ ID NO:67) and s74H9 (SEQ ID NO:65) adjuvated with 10 µg Matrix-M. As a positive control for the challenge model, CR6261 (15 mg/kg) was administered i.m. one day prior to challenge, while immunization with PBS served as a negative control. Four weeks after the last immunization, mice were challenged with 25xLD50 heterologous challenge virus (H1N1 A/NL/602/09) and monitored daily (survival, weight, and clinical scores) for three weeks. Pre-challenge serum is tested in ELISA assays for binding to the polypeptide of the disclosure used for immunization (to verify correct immunization), binding to soluble full-length HA form H1N1 A/Brisbane/59/07 and competition for binding to full-length HA with the broadly neutralizing antibody monoclonal antibody CR9114 (to determine whether induced antibodies bind at close proximity to the broadly neutralizing CR9114 epitope). The results are shown in FIGS. 4A and 4B.

The results show that the experiment is valid since all mice in the PBS control group succumb to infection at or before day 8 post challenge, whereas the positive control group (15 mg/kg CR6261, one day before challenge) is fully protected. In contrast to the PBS-treated mice, four out of ten mice immunized with polypeptide of the disclosure s86B4 (SEQ ID NO:67) or s74H9 (SEQ ID NO:65) survive the lethal challenge. This results in an increased survival time and reduced clinical score for groups immunized with polypeptide of the disclosure compared to the PBS control group.

The ELISA data (see FIG. 4B) using either the cognate antigen (i.e., either s86B4 or s74H9) or the full-length HA as the antigen indicate that both polypeptides, s74H9 and s86B4, are immunogenic and induce antibodies that are capable of recognizing full-length HA.

To further understand the immunological response to the immunization, a competition binding ELISA was performed. To this end, plate-bound full-length HA is incubated with serial-diluted serum samples, after which CR9114-biotin is added at a predetermined concentration. After further incubation, the amount of bound CR9114-biotin is quantified. Data are analyzed using linear regression of OD versus log dilution, expressed as "slope OD" (ΔOD/ten-fold dilution). The data show that the antibodies that are capable of competing for binding with the broadly neutralizing antibody CR9114 are induced by immunization with polypeptides. As a comparison, levels induced by unlabeled CR9114 (i.e., self-competition) and the non-binding monoclonal antibody CR8020, both serially diluted from 5 μg/ml starting concentration, are indicated in a separate graph.

In conclusion, these data show that immunization with polypeptides of the disclosure, such as s86B4 (SEQ ID NO:67) or s74H9 (SEQ ID NO:65), can protect mice against lethal infection with influenza. Both polypeptides are immunogenic, induce antibodies that can bind to full-length HA and at least part of these antibodies bind at, or close to, the epitope of the broadly neutralizing epitope of monoclonal antibody CR9114.

Example 5

Evaluation of Protective Efficacy of Another Polypeptide of the Disclosure in a Lethal Influenza Challenge Model In order to evaluate the protective efficacy of another polypeptide s127H1 (SEQ ID NO:66) in a lethal influenza challenge model, groups of ten female BALB/c mice (ages 6 to 8 weeks) were immunized three times at three-week intervals with 10 sg of purified s127H1 adjuvated with 10 μg Matrix-M. As a positive control for the challenge model, broadly neutralizing antibody monoclonal antibody CR6261 (15 mg/kg) was administered i.m. one day prior to challenge, while immunization with PBS served as a negative control. Four weeks after the last immunization, mice were challenged with 25xLD50 heterologous challenge virus (H1N1 A/Puerto Rico/8/34) and monitored daily (survival, weight, and clinical scores) for three weeks. Pre-challenge serum is tested in ELISA assays for binding to polypeptide of the disclosure s127H1 that was used for immunization (to verify correct immunization), binding to soluble H1N1 A/Brisbane/59/07 full-length HA and competition for binding to full-length HA with the broadly neutralizing antibody monoclonal antibody CR9114 (to determine whether induced antibodies bind at close proximity to the broadly neutralizing CR9114 epitope). The results are shown in FIGS. 5A and 5B.

The results show that the experiment is valid since all mice in the PBS control group succumb to infection at day 7 post challenge, whereas the positive control group (15 mg/kg CR6261, one day before challenge) is fully protected. In contrast to the PBS-treated mice, seven out of ten mice immunized with polypeptide, s127H1 (SEQ ID NO:66), survive the lethal challenge. This resulted in an increased survival proportion, increased survival time and reduced clinical score for groups immunized with polypeptide, s127H1, compared to the PBS control group.

The ELISA data using s127H1 or the soluble full-length HA as the antigen indicate that the polypeptide, s127H1, is immunogenic and induces antibodies that are capable of recognizing full-length HA (see FIG. 5B). To further understand the immunological response to the immunization, a competition binding ELISA was performed. To this end, plate-bound full-length HA is incubated with serial-diluted serum samples, after which CR9114-biotin is added at a predetermined titrated concentration. After further incubation, the amount of bound CR9114-biotin is quantified using streptavidin-conjugated horse radish peroxidase following protocols well known in the art. Data are analyzed using linear regression of OD versus log dilution, expressed as "slope OD" (ΔOD/ten-fold dilution). The data show that the antibodies that are capable of competing for binding with the broadly neutralizing antibody CR9114 are induced by immunization with polypeptides of the disclosure, as indicated by the elevated levels of competition observed in FIG. 5B. As a comparison, levels induced by unlabeled CR9114 (i.e., self-competition) and the non-binding monoclonal antibody CR8020, both serially diluted from 5 μg/ml starting concentration are indicated in a separate graph.

In conclusion, it is shown that immunization with polypeptides of the disclosure, such as s127H1 (SEQ ID NO:66), can protect mice against lethal infection with influenza. The polypeptide is immunogenic, induces antibodies that can bind to full-length HA and at least part of these antibodies bind at, or close to, the epitope of the broadly neutralizing epitope of monoclonal antibody CR9114.

Example 6

Analysis of Improved CR6261 Binders from Set 1 and set 2

To further understand which sequences can lead to increased binding of CR6261 compared to the parental sequence, SEQ ID NO:6, the sequences listed in Tables 4 and 5 were further analyzed. To this end, for each targeted position, the relative frequency of each of the variable amino acids present in the set of improved binders was calculated and compared to the expected frequency if there would be no preference for any of the variable amino acids (see FIGS. 6 and 8 for sequences of sets 1 and 2, respectively). The data show that some amino acids are more prevalent at certain positions in sequences that show improved CR6261 binding.

In both sets 1 and 2, high prevalence is observed for Met at position 402 (numbering refers to SEQ ID NO:1) in the sequences with improved binding, although in set 1, Val is also observed in some cases. Similarly, at position 352, high prevalence of the aromatic amino acids Phe and Tyr, at position 416, increased prevalence of Ser (although not very strong in set 1), and for position 337, increased prevalence of Lys is observed in both sets. It should be noted that Ser at position 416 introduces a putative N-glycosylation site at Asn414. Furthermore, at position 340, Asn is highly prevalent in improved CR6261 binders in set 2, whereas in set 1, Thr is more prevalent; both mutations introduce a putative glycosylation site at position 340: Asn leads to a putative N-glycosylation site, whereas Thr leads to a putative O-glycosylation site. At position 353, Thr is highly prevalent in improved binders from set 1, whereas in improved binders from set 2, Val is the most prevalent amino acid. At positions 406 and 409, the most prevalent amino acids in improved CR6261 binders are hydrophobic: at position 406, Ile and Phe (set 1) and Phe and Leu (set 2) are the most prevalent; at position 409, Ile and Val (set 1) and Phe and Ile (set 2) are the most prevalent. Finally, at position 413, Phe is the most prevalent amino acid among improved CR6261 binders from set 1, whereas Glu is the most prevalent among improved binders from set 2.

Figure 7A:
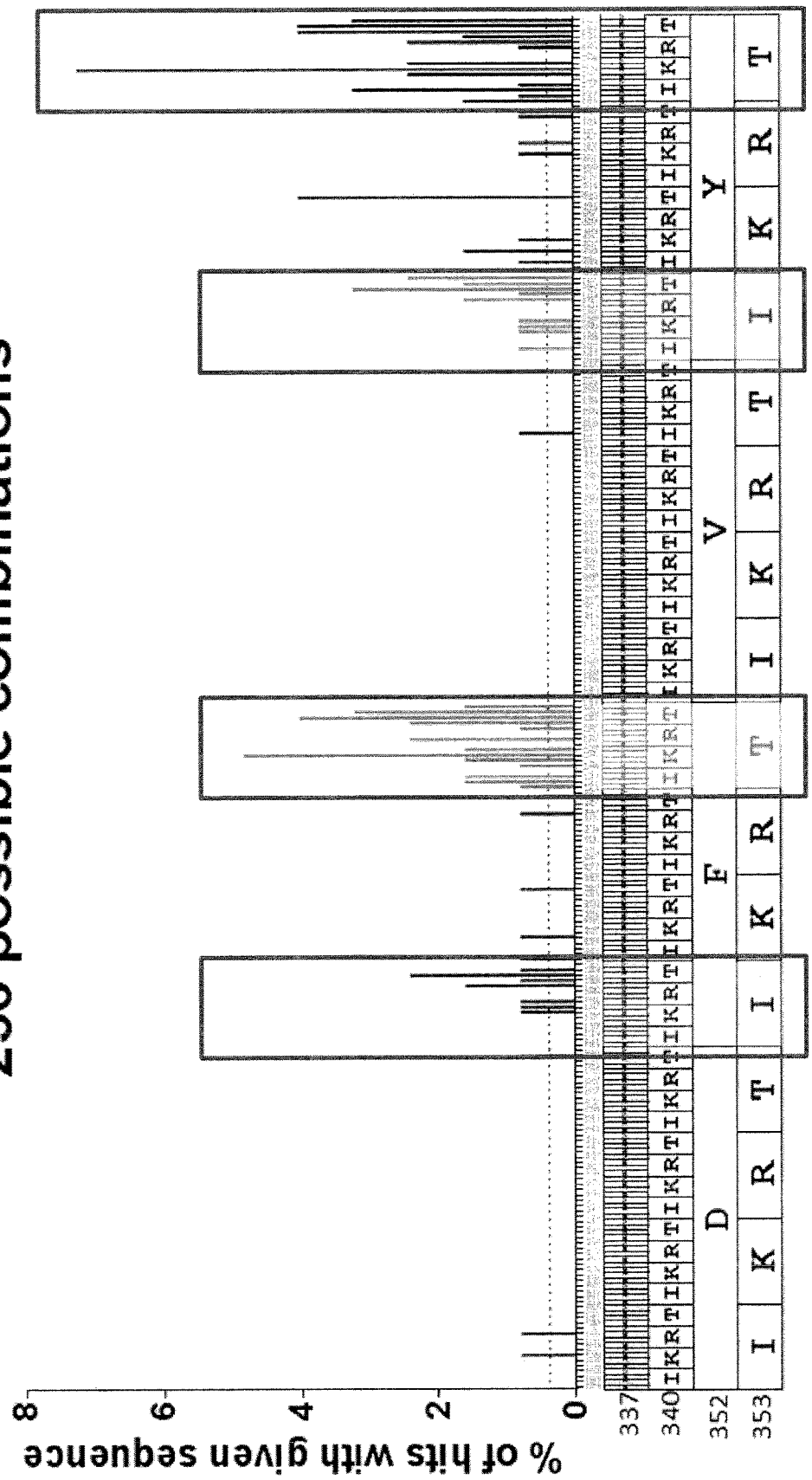
FIGS. 7A and 7B. Frequency of occurrence of combinations of amino acids in improved CR6261 binders from Set1. Sequences with improved binding to CR6261 were grouped according to the presence of amino acids at the positions indicated on the left, and the frequency of each combination was calculated as a percentage of the total number of Set 1 sequences that show improved CR6261 binding. Combinations that are more prevalent have been boxed.
Figure 7B:
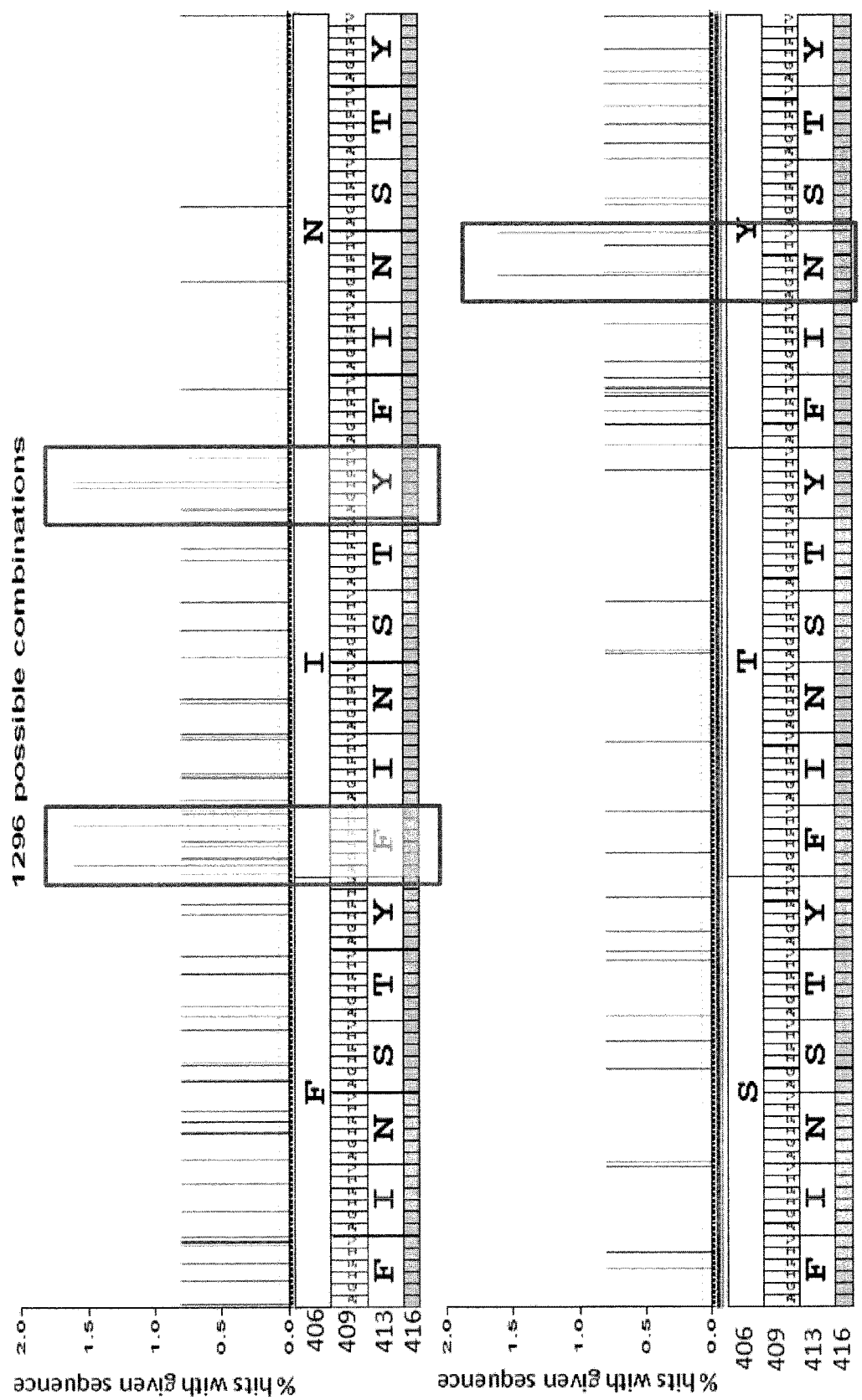
Figure 8:
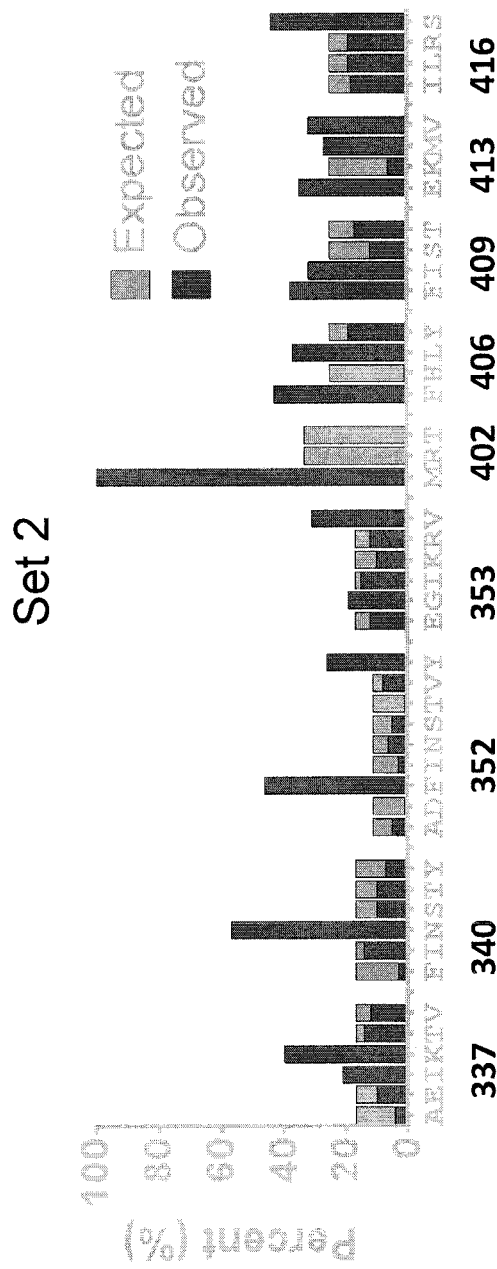
FIG. 8. Observed and expected frequency of occurrence of an amino acid at the indicated position in Set 2 sequences that show improved binding to CR6261 Values are expressed as percentage of the total number of Set 2 sequences that show improved CR6261 binding. Expected values are calculated as 100% divided by the number of variable amino acids at each position included in the set.
Figure 9A:
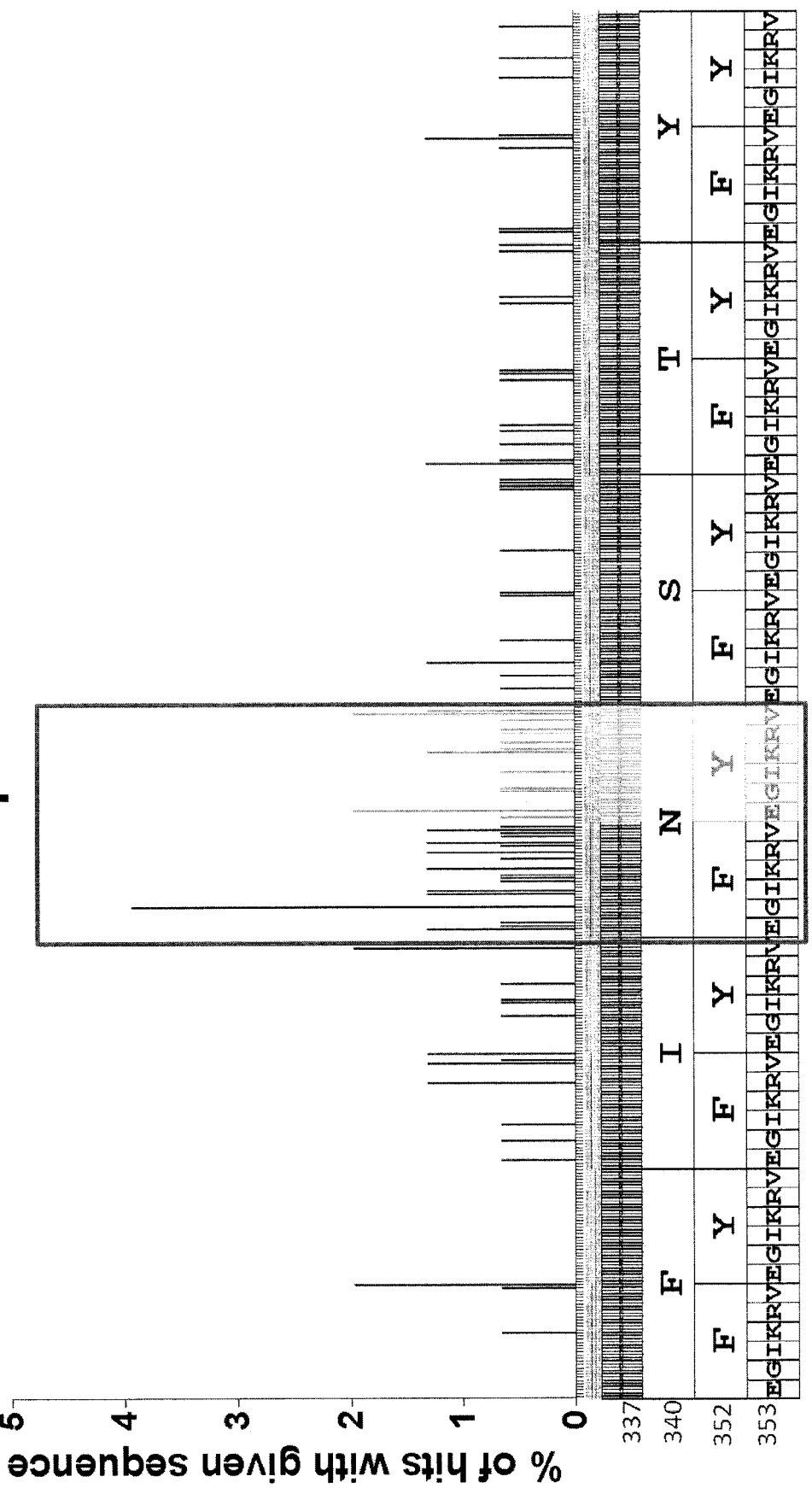
FIGS. 9A and 9B. Frequency of occurrence of combinations of amino acids in improved CR6261 binders from Set 2. Sequences with improved binding to CR6261 were grouped according to the presence of amino acids at the positions indicated on the left, and the frequency of each combination was calculated as a percentage of the total number of Set 2 sequences that show improved CR6261 binding. Combinations that are more prevalent have been boxed. Variation at position 402 was not included in the analysis as all improved binding sequences contain Met at this position, whereas, for position 352, only sequences containing either Phe or Tyr were taken into account.
Figure 9B:
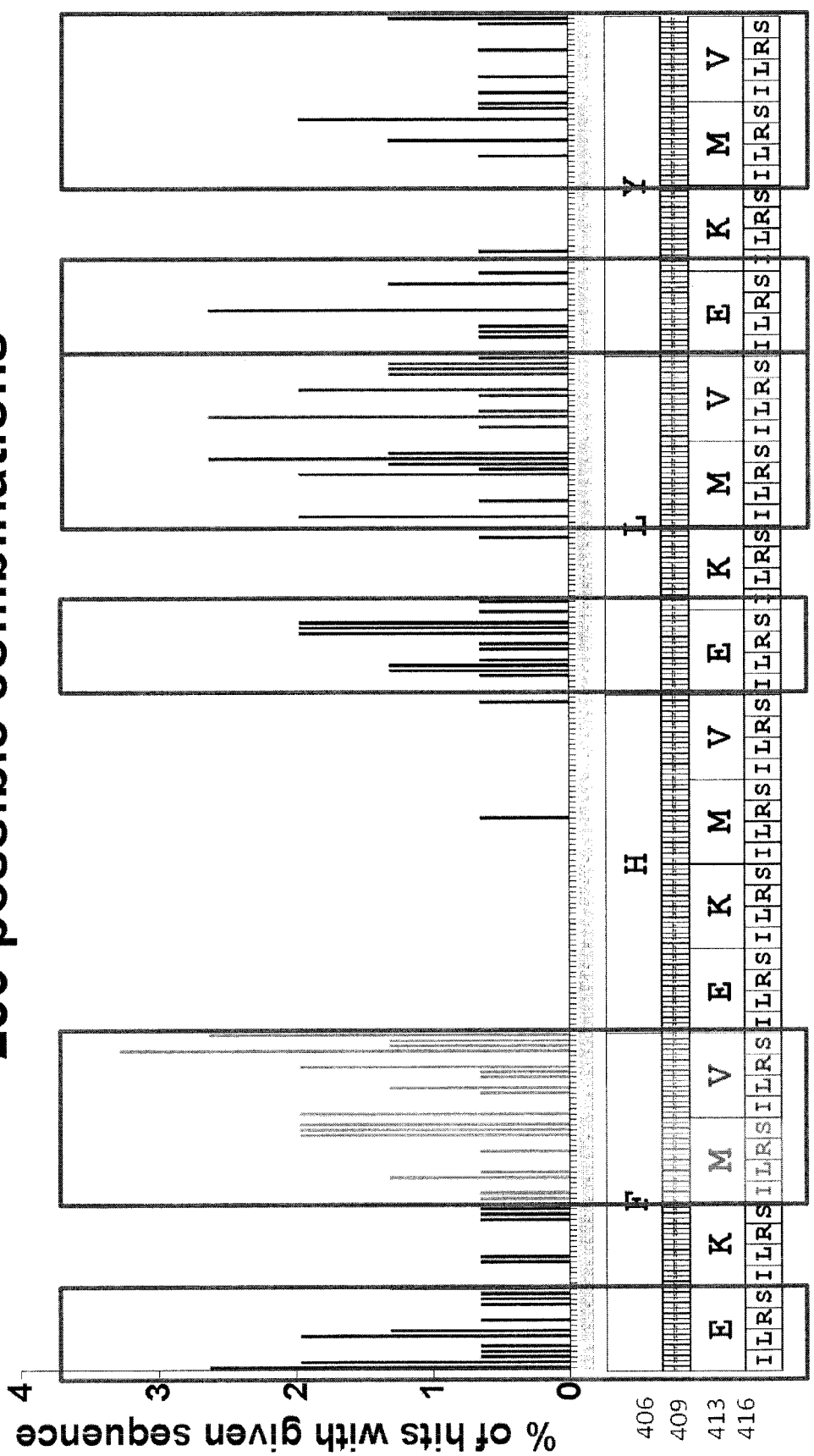

The sequences of the improved CR6261 binders were analyzed further to determine whether some combinations of amino acids were more prevalent among improved CR6261 binders than others. To this end, the number of improved binder sequences containing a particular combination of amino acids was counted and plotted as shown in FIGS. 7A, 7B (improved binders from set 1) and FIGS. 9A, 9B (set 2). The data were organized according to the different areas addressed in the mutant sets of polypeptides, i.e., the area of the fusion peptide (residue numbers 337, 340, 352 and 353; FIGS. 7A and 9A for improved binders from sets 1 and 2, respectively) and the B-loop (residue numbers 406, 409, 413 and 416; FIGS. 7B and 9B). In view of the very high prevalence of Met at position 402, this position was not included in the analysis to detect frequently occurring combinations as nearly all combinations of other positions with position 402 contain Met.

Among improved CR6261 binders from set 1, combinations of either Phe or Tyr at position 352 with either Ile or Thr at position 353 are most prevalent (boxed areas in FIG. 7A). With respect to combinations of amino acids in the B-loop area, Ile at position 406 combined with either Phe or Tyr (i.e., an aromatic amino acid) at position 413 and Tyr at position 406 combined with N at position 413, show increased prevalence among improved CR6261 binders (boxed areas in FIG. 7B).

For the analysis of sequences of improved CR6261 binders among the polypeptides from set 2 focusing on the fusion peptide area, only sequences containing either Phe or Tyr at position 352 were taken into account. Most prevalent among improved CR6261 binders with Phe or Tyr at position 352 are sequences with Asn at position 340 (see boxed area in FIG. 9A). The B-loop area sequences with either Phe, Leu or Tyr at position 406, in combination with either Glu, Met or Val at position 413 (boxed areas in FIG. 9B), are most prevalent among improved CR6261 binders.

In conclusion, the analysis shows that in the fusion peptide area, the introduction of Thr at position 353, in particular, in combination with an aromatic residue (Phe or Tyr) at position 352, can improve the binding of CR6261 to soluble polypeptides of the disclosure. Furthermore, Lys at position 337 or introduction of a putative N-glycosylation site by introducing Asn at position 340 can also contribute to improved binding of CR6261. In the B-loop area, a large hydrophobic residue (Phe, Tyr, Leu or Ile) can contribute to improved binding to CR6261. In particular, Phe, Leu, or Tyr at position 406 in combination with either Glu, Met, or Val at position 413 can improve binding of CR6261. Polypeptides of the disclosure comprising these residues at the described positions are preferred embodiments of the disclosure.

TABLE 2

Standard amino acids, abbreviations and properties.

| Amino Acid | 3-Letter | 1-Letter | Side chain polarity | Side chain charge (pH 7.4) |
|---|---|---|---|---|
| alanine | Ala | A | nonpolar | Neutral |
| arginine | Arg | R | polar | Positive |
| asparagine | Asn | N | polar | Neutral |
| aspartic acid | Asp | D | polar | Negative |
| cysteine | Cys | C | nonpolar | Neutral |
| glutamic acid | Glu | E | polar | Negative |
| glutamine | Gln | Q | polar | Neutral |
| glycine | Gly | G | nonpolar | Neutral |
| histidine | His | H | polar | positive (10%) neutral(90%) |
| isoleucine | Ile | I | nonpolar | Neutral |
| leucine | Leu | L | nonpolar | Neutral |
| lysine | Lys | K | polar | Positive |
| methionine | Met | M | nonpolar | Neutral |
| phenylalanine | Phe | F | nonpolar | Neutral |
| proline | Pro | P | nonpolar | Neutral |
| serine | Ser | S | polar | Neutral |
| threonine | Thr | T | polar | Neutral |
| tryptophan | Trp | W | nonpolar | Neutral |
| tyrosine | Tyr | Y | polar | Neutral |
| valine | Val | V | nonpolar | Neutral |

TABLE 3

Sequence alignment of H1 sequences according to particular embodiments of the disclosure.

```
 1. A/Solomon Islands/6/2003 (H1N1) (SEQ ID NO: 25)
 2. A/Brisbane/59/2007 (H1N1) (SEQ ID NO: 1)
 3. A/New Caledonia/20/1999(H1N1) (SEQ ID NO: 26)
 4. A/California/07/7009 (H1N1)(SEQ ID NO: 27)
 5. A/swine/Hubei/S1/2009(H1N1) (SEQ ID NO: 28)
 6. A/swine/Haseluenne/IDT2617/2003(H1N1) (SEQ ID NO: 29)
 7. A/NewYork/8/2006(H1N1) (SEQ ID NO: 30)
 8. A/SolomonIslands/3/2006(H1N1) (SEQ ID NO: 31)
 9. A/NewYork/146/2000(H1N1) (SEQ ID NO: 32)
10. A/NewYork/653/1996(H1N1) (SEQ ID NO: 33)
11. A/Beijing/262/1995(H1N1) (SEQ ID NO: 34)
12. A/Texas/36/1991(H1N1) (SEQ ID NO: 35)
13. A/Singapore/6/1986(H1N1) (SEQ ID NO: 36)
14. A/Chile/1/1983(H1N1) (SEQ ID NO: 37)
15. A/Baylor/11515/1982(H1N1) (SEQ ID NO: 38)
16. A/Brazil/11/1978(H1N1) (SEQ ID NO: 39)
17. A/USSR/90/1977(H1N1) (SEQ ID NO: 40)
18. A/NewJersey/8/1976(H1N1)(SEQ ID NO: 41)
19. A/Denver/1957(H1N1) (SEQ ID NO: 42)
20. A/Albany/4835/1948(H1N1) (SEQ ID NO: 43)
21. A/FortMonmouth/1/1947(H1N1) (SEQ ID NO: 44)
```

TABLE 3-continued

Sequence alignment of H1 sequences according to particular embodiments of the disclosure.

22. A/Cameron/1946(H1N1) (SEQ ID NO: 45)
23. A/Weiss/1943(H1N1) (SEQ ID NO: 46)
24. A/Iowa/1943(H1N1) (SEQ ID NO: 47)
25. A/Bellamy/1942(H1N1) (SEQ ID NO: 48)
26. A/PuertoRico/8/1934(H1N1) (SEQ ID NO: 49)
27. A/WSN/1933(H1N1) (SEQ ID NO: 50)
28. A/SouthCarolina/1/1918(H1N1) (SEQ ID NO: 51)

```
 1. MKVKLLVLLC TFTATYADTI CIGYHANNST DTVDTVLEKN VTVTHSVNLL EDSHNGKLCL  60
 2. MKVKLLVLLC TFTATYADTI CIGYHANNST DTVDTVLEKN VTVTHSVNLL ENSHNGKLCL  60
 3. MKAKLLVLLC TFTATYADTI CIGYHANNST DTVDTVLEKN VTVTHSVNLL EDSHNGKLCL  60
 4. MKAILVVLLY TFATANADTL CIGYHANNST DTVDTVLEKN VTVTHSVNLL EDKHNGKLCK  60
 5. MEAKLFVLFC AFTALKADTF CVGYHANYST HTVDTILEKN VTVTHSVNLL ENSHNGKLCS  60
 6. MEAKLFVLFC AFTALKADTI CVGYHANNST DTVDTILEKN VTVTHSINLL ENNHNGKLCS  60
 7. MKVKLLVLLC TFTATYADTI CIGYHANNST DTVDTVLEKN VTVTHSVNLL EDSHNGKLCL  60
 8. MKVKLLVLLC TFTATYADTI CIGYHANNST DTVDTVLEKN VTVTHSVNLL EDSHNGKLCL  60
 9. MKAKLLVLLC AFTATYADTI CIGYHANNST DTVDTVLEKN VTVTHSVNLL EDSHNGKLCR  60
10. MKAKLLVLLC AFTATYADTI CIGYHANNST DTVDTVLEKN VTVTHSVNLL EDSHNGKLCR  60
11. MKAKLLVLLC TFTATYADTI CIGYHANNST DTVDTVLEKN VTVTHSVNLL EDSHNGKLCL  60
12. MKAKLLVLLC AFTATYADTI CIGYHANNST DTVDTVLEKN VTVTHSVNLL EDSHNGKLCR  60
13. MKAKLLVLLC AFTATDADTI CIGYHANNST DTVDTVLEKN VTVTHSVNLL EDSHNGKLCR  60
14. MKAKLLVLLC ALSATDADTI CIGYHANNST DTVDTVLEKN VTVTHSVNLL EDNHNGKLCK  60
15. MKAKLLVLLC ALSATDADTI CIGYHANNST DTVDTVLEKN VTVTHSVNLL EDSHNGKLCR  60
16. MKAKLLVLLC ALSATDADTI CIGYHANNST DTVDTVLEKN VTVTHSVNLL EDSHNGKLCR  60
17. MKAKLLVLLC ALSATDADTI CIGYHANNST DTVDTVLEKN VTVTHSVNLL EDSHNGKLCR  60
18. MKAKLLVLLC AFTATDADTI CIGYHANNST DTVDTVLEKN VTVTHSVNLL EDSHNGKLCR  60
19. MKAKLLILLC ALSATDADTI CIGYHANNST DTVDTVLEKN VTVTHSVNLL EDSHNGKLCR  60
20. MKAKLLILLC ALSATDADTI CIGYHANNST DTVDTVLEKN VTVTHSVNLL EDSHNGKLCR  60
21. MKAKLLILLC ALTATDADTI CIGYHANNST DTVDTVLEKN VTVTHSVNLL EDSHNGKLCR  60
22. MKAKLLILLC ALSATDADTI CIGYHANNST DTVDTVLEKN VTVTHSVNLL EDSHNGKLCR  60
23. MKARLLVLLC ALAATDADTI CIGYHANNST DTVDTILEKN VTVTHSVNLL EDSHNGKLCR  60
24. MKARLLVLLC ALAATDADTI CIGYHANNST DTVDTVLEKN VTVTHSVNLL EDSHNGKLCR  60
25. MKARLLVLLC AIAATDADTI CIGYHANNST DTVDTILEKN VTVTHSVNLL EDSHNGKLCR  60
26. MKANLLVLLC ALAAADADTI CIGYHANNST DTVDTVLEKN VTVTHSVNLL EDSHNGKLCR  60
27. MKAKLLVLLY AFVATDADTI CIGYHANNST DTVDTIFEKN VAVTHSVNLL EDRHNGKLCK  60
28. MEARLLVLLC AFAATNADTI CIGYHANNST DTVDTVLEKN VTVTHSVNLL EDSHNGKLCK  60
     *:. *:.**   :: :: ***: ********** *****:.:*** *:.******** *: ******

1. LKGIAPLQLG NCSVAGWILG NPECELLISR ESWSYIVEKP NPENGTCYPG HFADYEELRE 120
 2. LKGIAPLQLG NCSVAGWILG NPECELLISK ESWSYIVEKP NPENGTCYPG HFADYEELRE 120
 3. LKGIAPLQLG NCSVAGWILG NPECELLISK ESWSYIVETP NPENGTCYPG YFADYEELRE 120
 4. LRGVAPLHLG KCNIAGWILG NPECESLSTA SSWSYIVETP SSDNGTCYPG DFIDYEELRE 120
 5. LNGKIPLQLG NCNVAGWILG NPKCDLLLTA NSSSYIIETS KSKNGACYPG EFADYEELKE 120
 6. LNGKAPLQLG NCNVAGWILG NPECDLLLTV DSWSYIIETS NSKNGACYPG EFADYEELRE 120
 7. LKGIAPLQLG NCSVAGWILG NPECELLISK ESWSYIVETP NPENGTCYPG YFADYEELRE 120
 8. LKGIAPLQLG NCSVAGWILG NPECELLISR ESWSYIVEKP NPENGTCYPG HFADYEELRE 120
 9. LKGTAPLQLG NCSIAGWILG NPECESLFSK ESWSYIAETP NPKNGTCYPG YFADYEELRE 120
10. LKGTAPLQLG NCSVAGWILG NPECESLFSK ESWSYIAETP NPENGTCYPG YFADYEELRE 120
11. LKGIAPLQLG NCSVAGWILG NPECESLISK ESWSYIVETP NPENGTCYPG YFADYEELRE 120
12. LKGIAPLQLG NCSVAGWILG NPKCESLFSK ESWSYIAETP NSENGTCYPG YFADYEELRE 120
13. LKGIAPLQLG NCSIAGWILG NPECESLFSK KSWSYIAETP NSENGTCYPG YFADYEELRE 120
14. LKGIAPLQLG KCSIAGWILG NPECESLFSK KSWSYIAETP NSENGTCYPG YFADYEELRE 120
15. LKGIAPLQLG KCSIAGWILG NPECESLFSK KSWSYIAETP NSENGTCYPG YFADYEELRE 120
16. LKGIAPLQLG KCSIAGWILG NPECESLFSK KSWSYIAETP NSENGTCYPG YFADYEELRE 120
17. LKGIAPLQLG KCNIAGWILG NPECESLFSK KSWSYIAETP NSENGTCYPG YFADYEELRE 120
18. LKGIAPLQLG NCSIAGWILG NPECESLFSK KSWSYIAETP NSENGTCYPG YFADYEELRE 120
19. LKGKAPLQLG NCNIAGWVLG NPECESLLSN RSWSYIAETP NSENGTCYPG DFADYEELRE 120
20. LKGIAPLQLG KCNIAGWILG NPECESLFSK KSWSYIAETP NSENGTCYPG YFADYEELRE 120
21. LKGIAPLQLG KCNIAGWILG NPECESLLSK RSWSYIAETP NSENGACYPG DFADYEELRE 120
22. LKGIAPLQLG KCNIAGWILG NPECESLLSK RSWSYIAETP NSENGACYPG DFADYEELRE 120
23. LKGIAPLQLG KCNIAGWILG NPECESLLSE RSWSYIVEIP NSENGTCYPG DFTDYEELRE 120
24. LKGIAPLQLG KCNIAGWILG NPECESLLSE RSWSYIVETP NSENGTCYPG DFIDYEELRE 120
25. LKGIAPLQLG KCNIAGWILG NPECESLLSE RSWSYIVETP NSENGTCYPG DFIDYEELRE 120
26. LKGIAPLQLG KCNIAGWLLG NPECDPLLPV RSWSYIVETP NSENGICYPG DFIDYEELRE 120
27. LKGIAPLQLG KCNITGWLLG NPECDSLLPA RSWSYIVETP NSENGACYPG DFIDYEELRE 120
28. LKGIAPLQLG KCNIAGWLLG NPECDLLLTA SSWSYIVETS NSENGTCYPG DFIDYEELRE 120
     *:* ***:**  :*:.::**:** **:*:  *  .     *****.* .   ...** ****   * *******

1. QLSSVSSFER FEIFPKESSW PNHTTT-GVS ASCSHNGESS FYKNLLWLTG KNGLYPNLSK 179
 2. QLSSVSSFER FEIFPKESSW PNHTVT-GVS ASCSHNGESS FYRNLLWLTG KNGLYPNLSK 179
 3. QLSSVSSFER FEIFPKESSW PNHTVT-GVS ASCSHNGKSS FYRNLLWLTG KNGLYPNLSK 179
 4. QLSSVSSFER FEIFPKTSSW PNHDSNKGVT AACPHAGAKS FYKNLIWLVK KGNSYPKLSK 180
 5. QLSTVSSFER FEIFPKAISW PDHDATRGTT VACSHSGVNS FYRNLLSTVK KGNSYPKLSK 180
 6. QLSTVSSFER FEIFPKATSW PNHDTTRGTT ISCSHSGANS FYRNLLWIVK KGNSYPKLSK 180
 7. QLSSVSSFER FEIFPKESSW PNHTVT-GVS ASCSHNGKSS FYRNLLWLTG KNGLYPNLSK 179
 8. QLSSVSSFER FEIFPKESSW PNHTTT-GVS ASCSHNGESS FYKNLLWLTG KNGLYPNLSK 179
```

TABLE 3-continued

Sequence alignment of H1 sequences according to particular embodiments of the disclosure.

```
 9. QLSSVSSFER FEIFPKDSSW PNHTVTKGVT ASCSHNGKSS FYKNLLWLTE KNGLYPNLSK  180
10. QLSSVSSFER FEIFPKESSW PNHTVTKGVT ASCSHNGKSS FYKNLLWLTE KNGLYPNLSK  180
11. QLSSVSSFER FEIFPKESSW PNHTVT-GVT ASCSHNGKSS FYRNLLWLTE KNGLYPNLSN  179
12. QLSSVSSFER FEIFPKESSW PNHTVTKGVT TSCSHNGKSS FYRNLLWLTE KNGLYPNVSK  180
13. QLSSVSSFER FEIFPKESSW PNHTVTKGVT ASCSHKGRSS FYRNLLWLTK KNGSYPNLSK  180
14. QLSSVSSFER FEIFPKESSW PKHNVTKGVT AACSHKGKSS FYRNLLWLTE KNGSYPNLSK  180
15. QLSSVSSFER FEIFPKESSW PKHSVTRGVT ASCSHKGKSS FYRNLLWLTE KNGSYPNLSK  180
16. QLSSVSSFER FEIFPKERSW PKHNITRGVT ASCSHKGKSS FYRNLLWLTE KNGSYPNLSK  180
17. QLSSVSSFER FEIFPKESSW PKHNVTRGVT ASCSHKGKSS FYRNLLWLTE KNGSYPNLSK  180
18. QLSSVSSFER FEIFPKESSW PNHTVTKGVT ASCSHKGRSS FYRNLLWLTK KNGSYPNLSK  180
19. QLSSVSSFER FEIFPKERSW PNHTTR-GVT AACPHARKSS FYKNLVWLTE ANGSYPNLSR  179
20. QLSSVSSFER FEIFPKERSW PKHNITRGVT AACSHKGKSS FYRNLLWLTE KNGSYPNLNK  180
21. QLSSVSSFER FEIFPKERSW PKHNITRGVT AACSHAGKSS FYKNLLWLTE TDGSYPKLSK  180
22. QLSSVSSFER FEIFPKERSW PEHNIDIGVT AACSHAGKSS FYRNLLWLTE KDGSYPNLNK  180
23. QLSSVSSFER FEIFPKESSW PKHNTARGVT AACSHAGKSS FYRNLLWLTE KDGSYPNLKN  180
24. QLSSVSSFER FEIFSKESSW PKHTTG-GVT AACSHAGKSS FYRNLLWLTE KDGSYPNLNN  179
25. QLSSVTSFER FEIFPKETSW PKHNTTKGVT AACSHAGKCS FYRNLLWLTE KDGSYPNLNN  180
26. QLSSVSSFER FEIFPKESSW PNHNTN-GVT AACSHEGKSS FYRNLLWLTE KEGSYPKLKN  179
27. QLSSVSSLER FEIFPKESSW PNHTFN-GVT VSCSHRGKSS FYRNLLWLTK KGDSYPKLTN  179
28. QLSSVSSFEK FEIFPKTSSW PNHETTKGVT AACSYAGASS FYRNLLWLTK KGSSYPKLSK  180
    *****:*:*: ****.*  ** *:*     **:  . :*.:    * **:**:**.  . **::..

1. SYANNKEKEV LVLWGVHHPP NIGDQRALYH KENAYVSVVS SHYSRKFTPE IAKRPKVRDQ  239
 2. SYANNKEKEV LVLWGVHHPP NIGNQKALYH TENAYVSVVS SHYSRKFTPE IAKRPKVRDQ  239
 3. SYVNNKEKEV LVLWGVHHPP NIGNQRALYH TENAYVSVVS SHYSRRFTPE IAKRPKVRDQ  239
 4. SYINDKGKEV LVLWGIHHPS TSADQQSLYQ NADAYVSVGS SRYSKKFKPE IAIRPKVRXX  240
 5. SYTNNKGKEV LVIWGVHHPP TDSVQQTLYQ NKHTYVSVGS SKYYKRFTPE IVARPKVRGQ  240
 6. SYTNNKGKEV LVIWGVHHPP TDSDQQTLYQ NNHTYVSVGS SKYYQRFTPE IVTRPKVRGQ  240
 7. SYANNKEKEV LVLWGVHHPP NIGDQRALYH TENAYVSVVS SHYSRRFTPE IAKRPKVRDQ  239
 8. SYANNKEKEV LVLWGVHHPP NIGDQRALYH KENAYVSVVS SHYSRKFTPE IAKRPKVRDQ  239
 9. SYVNKKGKEV LVLWGVHHPS NMGDQRAIYH KENAYVSVLS SHYSRRFTPE IAKRPKVRDQ  240
10. SYVNNKEKEV LVLWGVHHPS NIGDQRAIYH TENAYVSVVS SHYSRRFTPE ITKRPKVRDQ  240
11. SYVNNKEKEV LVLWGVHHPS NIRDQRAIYH TENAYVSVVS SHYSRRFTPE IAKRPKVRGQ  239
12. SYVNNKEKEV LVLWGVHHPS NIGDQRAIYH TENAYVSVVS SHYSRRFTPE IAKRPKVRDQ  240
13. SYVNNKEKEV LVLWGVHHPS NIGDQRAIYH TENAYVSVVS SHYNRRFTPE IAKRPKVRDQ  240
14. SYVNNKEKEV LVLWGVHHPS NIEDQKTIYR KENAYVSVVS SHYNRRFTPE IAKRPKVRNQ  240
15. SYVNDKEKEV LVLWGVHHPS NIEDQKTIYR KENAYVSVVS SHYNRRFTPE IAKRPKVRDQ  240
16. SYVNNKEKEV LVLWGVHHPS NIEDQKTIYR KENAYVSVVS SNYNRRFTPE IAKRPKVRGQ  240
17. SYVNNKEKEV LVLWGVHHPS NIEDQKTIYR KENAYVSVVS SNYNRRFTPE IAERPKVRGQ  240
18. SYVNNKEKEV LVLWGVHHPS NIGDQRAIYH TENAYVSVVS SHYNRRFTPE IAKRPKVRDQ  240
19. SYVNNQEKEV LVLWGVHHPS NIEEQRALYR KDNAYVSVVS SNYNRRFTPE IAKRPKVRDQ  239
20. SYVNNKEKEV LVLWGVHHPS NIEDQKTLYR KENAYVSVVS SNYNRRFTPE IAERPKVRGQ  240
21. SYVNNKEKEV LVLWGVHHPS NIEDQKTLYR KENAYVSVVS SNYNRRFTPE IAERPKVRGQ  240
22. SYVNKKEKEV LILWGVHHPP NIENQKTLYR KENAYVSVVS SNYNRRFTPE IAERPKVRGQ  240
23. SYVNKKGKEV LVLWGVHHPS SIKEQQTLYQ KENAYVSVVS SNYNRRFTPE IAERPKVRDQ  240
24. SYVNKKGKEV LVLWGVHHPS NIKDQQTLYQ KENAYVSVVS SNYNRRFTPE IAERPKVRGQ  239
25. SYVNKKGKEV LVLWGVHHPS NIKDQQTLYQ KENAYVSVVS SNYNRRFTPE IAERPKVRGQ  240
26. SYVNKKGKEV LVLWGIHHPP NSKEQQNLYQ NENAYVSVVT SNYNRRFTPE IAERPKVRDQ  239
27. SYVNNKGKEV LVLWGVHHPS SSDEQQSLYS NGNAYVSVAS SNYNRRFTPE IAARPKVKDQ  239
28. SYVNNKGKEV LVLWGVHHPP TGTDQQSLYQ NADAYVSVGS SKYNRRFTPE IAARPKVRDQ  240
    ** *.: *** *:***:***. .  :*: :*  . :*** * : *.*.::*.** *: ****:

1. EGRINYYWTL LEPGDTIIFE ANGNLIAPRY AFALSRGFGS GIINSNAPMD ECDAKCQTPQ  299
 2. EGRINYYWTL LEPGDTIIFE ANGNLIAPRY AFALSRGFGS GIINSNAPMD KCDAKCQTPQ  299
 3. EGRINYYWTL LEPGDTIIFE ANGNLIAPWY AFALSRGFGS GIITSNAPMD ECDAKCQTPQ  299
 4. EGRMNYYWTL VEPGDKITFE ATGNLVVPRY AFAMERNAGS GIIISDTPVH DCNTTCQTPK  300
 5. AGRMNYYWTL FDQGDTITFE ATGNLIAPWH AFALKGSSSS GIMLSDAQVH NCTTKCQTPH  300
 6. AGRMNYYWTL LDQGDTITFE ATGNLIAPWH AFALNKGFGS GIMISDAHVH NCTTKCQTPH  300
 7. EGRINYYWTL LEPGDTIIFE ANGNLIAPRF AFALSRGFGS GIITSNAPMD ECDAKCQTPQ  299
 8. EGRINYYWTL LEPGDTIIFE ANGNLIAPRY AFALSRGFGS GIINSNAPMD ECDAKCQTPQ  299
 9. EGRINYYWTL LEPGDTIIFE ANGNLIAPWY AFALSRGFGS GIIISNASMG ECDAKCQTPQ  300
10. EGRINYYWTL LEPGDTIIFE ANGNLIAPWY AFALSRGFGS GIIISNASMG ECDAKCQTPQ  300
11. EGRINYYWTL LEPGDTIIFE ANGNLIAPWY AFALSRGFGS GIITSNAPMN ECDAKCQTPQ  299
12. EGRINYYWTL LEPGDTIIFE ANGNLIAPWY AFALSRGFGS GIITSNASMD ECDAKCQTPQ  300
13. EGRINYYWTL LEPGDTIIFE ANGNLIAPWY AFALSRGFGS GIITSNASMD ECDAKCQTPQ  300
14. EGRINYYWTL LEPGDTIIFE ANGNLIAPWY AFALSRGFGS GIITSNASMD ECDAKCQTPQ  300
15. EGRINYYWTL LEPGDTIIFE ANGNLIAPWY AFALSRGFGS GIITSNVSMD ECDAKCQTPQ  300
16. EGRINYYWTL LEPGDTIIFE ANGNLIAPWY AFALSRGFGS GIITSNASMD ECDTKCQTPQ  300
17. AGRINYYWTL LEPGDTIIFE ANGNLIAPWH AFALNRGFGS GIITSNASMD ECDTKCQTPQ  300
18. EGRINYYWTL LEPGDTIIFE ANGNLIAPWY AFALSRGFGS GIITSNASMD ECDAKCQTPQ  300
19. SGRMNYYWTL LEPGDTIIFE ATGNLIAPWY AFALSRGPGS GIITSNAPLD ECDTKCQTPQ  299
20. AGRINYYWTL LEPGDTIIFE ANGNLIAPWH AFALSRGFGS GIITSNASMD ECDTKCQTPQ  300
21. AGRINYYWTL LEPGDTIIFE ANGNLIAPWY AFALSRDFGS GIITSNASMD ECDTKCQTPQ  300
22. AGRINYYWTL LEPGDTIIFE ANGNLIAPWY AFALNRGIGS GIITSNASMD ECDTKCQTPQ  300
23. AGRMNYYWTL LEPGDTIIFE ANGNLIAPWY AFALSRGFGS GIITSNASMH ECDTKCQTPQ  300
24. AGRINYYWTL LKPGDT1MFE ANGNLIAPWY AFALSRGFGS GIITSNASMH ECDTKCQTPQ  299
```

TABLE 3-continued

Sequence alignment of H1 sequences according to particular embodiments of the disclosure.

```
25.AGRMNYYWTL LEPGDTIIFE ANGNLIAPWY AFALSRGFGS GIITSNASMH ECNTKCQTPQ    300
26.AGRMNYYWTL LKPGDTIIFE ANGNLIAPMY AFALRRGFGS GIITSNASMH ECNTKCQTPL    299
27.HGRMNYYWTL LEPGDTIIFE ATGNLIAPWY AFALSRGFES GIITSNASMH ECNTKCQTPQ    299
28.AGRMNYYWTL LEPGDTITFE ATGNLIAPWY AFALNRGFGS GIITSDAPVH DCNTKCQTPH    300
    **:****** ::***.* ** *.***:.* . ***: *.  * *** *:..:  .*::.****

1.GAINSSLPFQ NVHPVTIGEC PKYVRSAKLR MVTGLRNIPS IQSRGLFGAI AGFIEGGWTG    359
 2.GAINSSLPFQ NVHPVTIGEC PKYVRSAKLR MVTGLRNIPS IQSRGLFGAI AGFIEGGWTG    359
 3.GAINSSLPFQ NVHPVTIGEC PKYVRSAKLR MVTGLRNIPS IQSRGLFGAI AGFIEGGWTG    359
 4.GAINTSLPFQ NIHPITIGKC PKYVKSTKLR LATGLRNIPS IQSRGLFGAI AGFIEGGWTG    360
 5.GALKNNLPLQ NVHPVTIGEC PKYVKSTQLR MATGLRNIPS IQSRGLFGAI AGFIEGGRTG    360
 6.GALKSNLPFQ NVHPSTIGEC PKYVKSTQLR MATGLRNIPS IQSRGLFGAI AGFIEGGWTG    360
 7.GAINSSLPFQ NVHPVTIGEC PKYVRSAKLR MVTGLRNIPS IQSRGLFGAI AGFIEGGWTG    359
 8.GAINSSLPFQ NVHPVTIGEC PKYVRSAKLR MVTGLRNIPS IQSRGLFGAI AGFIEGGWTG    359
 9.GAINSSLPFQ NVHPVTIGEC PKYVRSTKLR MVTGLRNVPS IQSRGLFGAI AGFIEGGWTG    360
10.GAINSSLPFQ NVHPVTIGEC PKYVRSTKLR MVTGLRNIPS IQSRGLFGAI AGFIEGGWTG    360
11.GAINSSLPFQ NVHPVTIGEC PKYVRSTKLR MVTGLRNIPS IQSRGLFGAI AGFIEGGWTG    359
12.GAINSSLPFQ NVHPVTIGEC PKYVRSTKLR MVTGLRNIPS IQSRGLFGAI AGFIEGGWTG    360
13.GAINSSLPFQ NVHPVTIGEC PKYVRSTKLR MVTGLRNIPS IQSRGLFGAI AGFIEGGWTG    360
14.GAINSSLPFQ NVHPVTIGEC PKYVRSTKLR MVTGLRNIPS IQSRGLFGAI AGFIEGGWTG    360
15.GAINSSLPFQ NVHPVTIGEC PKYVRSTKLR MVTGLRNIPS IQSRGLFGAI AGFIEGGWTG    360
16.GAINSSLPFQ NVHPVTIGEC PKYVRSTKLR MVTGLRNIPS IQSRGLFGAI AGFIEGGWTG    360
17.GAINSSLPFQ NIHPVTIGEC PKYVRSTKLR MVTGLRNIPS IQSRGLFGAI AGFIEGGWTG    360
18.GAINSSLPFQ NVHPVTIGEC PKYVRSTKLR MVTGLRNIPS IQSRGLFGAI AGFIEGGWTG    360
19.GAINSSLPFQ NIHPVTIGEC PKYVRSTKLR MVTGLRNIPS VQSRGLFGAI AGFIEGGWTG    359
20.GAINSSLPFQ NIHPVTIGEC PKYVRSTKLR MVTGLRNIPS IQSRGLFGAI AGFIEGGWTG    360
21.GAINSSLPFQ NIHPVTIGEC PKYVKSTKLR MVTGLRNIPS IQSRGLFGAI AGFIEGGWTG    360
22.GAINSSLPFQ NIHPFTIGEC PKYVRSTKLR MVTGLRNIPS IQSRGLFGAI AGFIEGGWDG    360
23.GAINSSLPFQ NIHPVTIGEC PKYVRSTKLR MVTGLRNIPS IQSRGLFGAI AGFIEGGWTG    360
24.GAINSSLPFQ NIHPVTIGEC PKYVRSTKLR MVTGLRNIPS IQSRGLFGAI AGFIEGGWTG    359
25.GAINSSLPFQ NIHPVTIGEC PKYVRSTKLR MVTGLRNIPS IQSRGLFGAI AGFIEGGWTG    360
26.GAINSSLPYQ NIHPVTIGEC PKYVRSAKLR MVTGLRNIPS IQSRGLFGAI AGFIEGGWTG    359
27.GSINSNLPFQ NIHPVTIGEC PKYVRSTKLR MVTGLRNIPS IQYRGLFGAI AGFIEGGWTG    359
28.GAINSSLPFQ NIHPVTIGEC PKYVRSTKLR MATGLRNIPS IQSRGLFGAI AGFIEGGWTG    360
   *:**:.**:* *:**.***:* ****:*:*** :.*****:** :* ******* ******** *

1.MVDGWYGYHH QNEQGSGYAA DQKSTQNAIN GITNKVNSVI EKMNTQFTAV GKEFNKLERR    419
 2.MVDGWYGYHH QNEQGSGYAA DQKSTQNAIN GITNKVNSVI EKMNTQFTAV GKEFNKLERR    419
 3.MVDGWYGYHH QNEQGSGYAA DQKSTQNAIN GITNKVNSVI EKMNTQFTAV GKEFNKLERR    419
 4.MVDGWYGYHH QNEQGSGYAA DLKSTQNAID EITNKVNSVI EKMNTQFTAV GKEFNHLEKR    420
 5.MIDGWYGYHH QNEQGSGYAA DQKSTQIAID GINNKANSVI GKMNIQLTSV GKEFNSLEKR    420
 6.MIDGWYGYHH QNEQGSGYAA DQKSTQIAID GINNKVNSII EKMNTQFTSV GKEFNDLEKR    420
 7.MVDGWYGYHH QNEQGSGYAA DQKSTQNAIN GITNKVNSVI EKMNTQFTAV GKEFNKLERR    419
 8.MVDGWYGYHH QNEQGSGYAA DQKSTQNAIN GITNKVNSVI EKMNTQFTAV GKEFNKLERR    419
 9.MIDGWYGYHH QNEQGSGYAA DQKSTQNAIN GITNKVNSII EKMNTQFTAV GKEFNKLEKR    420
10.MIDGWYGYHH QNEQGSGYAA DQKSTQNAID GITNKVNSVI EKMNTQFTAV GKEFNKLERR    420
11.MMDGWYGYHH QNEQGSGYAA DQKSTQNAIN GITNKVNSVI EKMNTQFTAV GKEFNKLERR    419
12.MIDGWYGYHH QNEQGSGYAA DQKSTQNAIN GITNKVNSVI EKMNTQFTAV GKEFNKLERR    420
13.MIDGWYGYHH QNEQGSGYAA DQKSTQNAIN GITNKVNSVI EKMNTQFTAV GKEFNKLERR    420
14.MIDGWYGYHH QNEQGSGYAA DQKSTQNAIN GITNKVNSII EKMNTQFTAV GKEFNKLEKR    420
15.MIDGWYGYHH QNEQGSGYAA DQKSTQNAIN GITNKVNSVI EKMNTQFTAV GKEFNKLEKR    420
16.MIDGWYGYHH QNEQGSGYAA DQKSTQNAIN GITNKVNSVI EKMNTQFTAV GKEFNKLEKR    420
17.MIDGWYGYHH QNEQGSGYAA DQKSTQNAIN GITNKVNSVI EKMNTQFTAV GKEFNKLEKR    420
18.MIDGWYGYHH QNEQGSGYAA DQKSTQNAIN GITNKVNSVI EKMNTQFTAV GKEFNKLERR    420
19.MMDGWYGYHH QNEQGSGYAA DQKSTQNAIN GITNKVNSVI EKMNTQFTAV GKEFNKLEKR    419
20.MIDGWYGYHH QNEQGSGYAA DQKSTQNAIN GITNKVNSVI EKMNTQFTAV GKEFNKLEKR    420
21.MIDGWYGYHH QNEQGSGYAA DQKSTQNAIN WITNKVNSVI EKMNTQFTAV GKEFNKLEKR    420
22.MIDGWYGYHH QNEQGSGYAA DQKSTQNAIN GITNKVNSVI EKMNTQFTAV GKEFNKLEKR    420
23.MIDGWYGYHH QNEQGSGYAA DQKSTQNAIN GITNKVNSVI EKMNTQFTAV GKEFNHLEKR    420
24.MIDGWYGYHH QNEQGSGYAA DQKSTQNAIN GITNKVNSVI EKMNTQFTAV GKEFNNLEKR    419
25.MIDGWYGYHH QNEQGSGYAA DQKSTQNAIN GITNKVNSVI EKMNTQFTAV GKEFNNLEKR    420
26.MIDGWYGYHH QNEQGSGYAA DQKSTQNAIN GITNKVNSVI EKMNIQFTAV GKEFNKLEKR    419
27.MIDGWYGYHH QNEQGSGYAA DQKSTQNAIN GITNKVNSVI EKMNTQFTAV GKEFNNLEKR    419
28.MIDGWYGYHH QNEQGSGYAA DQKSTQNAID GITNKVNSVI EKMNTQFTAV GKEFNNLERR    420
   *.******** ********** * *******:  *******:* **** ***** *****:**:*

1.MENLNKKVDD GFIDIWTYNA ELLVLLENER TLDFHDSNVK NLYEKVKSQL KNNAKEIGNG    479
 2.MENLNKKVDD GFIDIWTYNA ELLVLLENER TLDFHDSNVK NLYEKVKSQL KNNAKEIGNG    479
 3.MENLNKKVDD GFLDIWTYNA ELLVLLENER TLDFHDSNVK NLYEKVKSQL KNNAKEIGNG    479
 4.IENLNKKVDD GFLDIWTYNA ELLVLLENER TLDYHDSNVK NLYEKVRSQL KNNAKEIGNG    480
 5.KENLNKTVDD RFLDVWTFNA ELLVLLENQR TLEFHDLNIK SLYEKVKSHL RNNDKEIGNG    480
 6.IENLNKKVDD GFLDVWTYNA ELLILLENER TLDFHDFNVK NLYEKVKSQL RNNAKEIGNG    480
 7.MENLNKKVDD GFLDIWTYNA ELLVLLENER TLDFHDSNVK NLYEKVKSQL KNNAKEIGNG    479
 8.MENLNKKVDD GFIDIWTYNA ELLVLLENER TLDFHDSNVK NLYEKVKSQL KNNAKEIGNG    479
 9.MENLNKKVDD GFLDIWTYNA ELLVLLENER TLDFHDLNVK NLYEKVKNQL KNNAKEIGNG    480
10.MENLNKKVDD GFLDIWTYNA ELLVLLENER TLDFHDSNVK NLYEKVKTQL KNNAKEIGNG    480
```

TABLE 3-continued

Sequence alignment of H1 sequences according to particular embodiments of the disclosure.

```
11. MENLNKKVDD GFLDIWTYNA ELLVLLENER TLDFHDSNVK NLYEKVKSQL KNNAKEIGNG    479
12. MENLNKKVDD GFLDIWTYNA ELLVLLENGR TLDFHDSNVK NLYEKVKSQL KNNAKEIGNG    480
13. MENLNKKVDD GFLDIWTYNA ELLVLLENER TLDFHDSNVK NLYEKVKSQL KNNAKEIGNG    480
14. MENLNKKVDD GFLDIWTYNA ELLVLLENER TLDFHDSNVK NLYEKVKSQL KNNAKEIGNG    480
15. MENLNKKVDD GFLDIWTYNA ELLVLLENER TLDFHDSNVK NLYEKVKSQL KNNAKEIGNG    480
16. MENLNKKVDD GFLDIWTYNA ELLVLLENER TLDFHDSNVK NLYEKVKSQL KNNAKEIGNG    480
17. MENLNKKVDD GFLDIWTYNA ELLVLLENER TLDFHDSNVK NLYEKVKSQL KNNAKEIGNG    480
18. MENLNKKVDD GFLDIWTYNA ELLVLLENER TLDFHDSNVK NLYEKVKSQL KNNAKEIGNG    480
19. MENLNKKVDD GFMDIWTYNA ELLVLLENER TLDFHDSNVK NLYEKVKNQL RNNAKELGNG    479
20. MENLNKKVDD GFLDIWTYNA ELLVLLENER TLDFHDSNVK NLYEKVKSQL KNNAKEIGNG    480
21. MENLNKKVDD GFLDIWTYNA ELLVLLENER TLDFHDSNVK NLYEKVKNQL RNNAKEIGNG    480
22. MENLNKKVDD GFLDIWTYNA ELLVLLENER TLDFHDSNVK NLYEKVKNQL RNNAKEIGNG    480
23. MENLNKKVDD GFLDIWTYNA ELLILLENER TLDEHDSNVK NLYEKVKSQL RNNAKEIGNG    480
24. MENLNKKVDD GFLDIWTYNA ELLVLLENER TLDFHDSNVK NLYEKVKNQL RNNAKEIGNG    479
25. MENLNKKVDD GFLDIWTYNA ELLVLLENER TLDFHDSNVK NLYEKVKSQL RNNAKEIGNG    480
26. MENLNNKVDD GFLDIWTYNA ELLVLLENER TLDFHDSNVK NLYEKVKSQL KNNAKEIGNG    479
27. MENLNKKVDD GFLDIWTYNA ELLVLLENER TLDFHDLNVK NLYEKVKSQL KNNAKEIGNG    479
28. IENLNKKVDD GFLDIWTYNA ELLVLLENER TLDFHDSNVR NLYEKVKSQL KNNAKEIGNG    480
    :****:**** **:******* ***:**** * ***:** **: ******:.** :*****:***

1. CFEFYHKCND ECMESVKNGT YDYPKYSEES KLNREKIDGV KLESMGVYQI LAIYSTVASS    539
 2. CFEFYHKCND ECMESVKNGT YDYPKYSEES KLNREKIDGV KLESMGVYQI LAIYSTVASS    539
 3. CFEFYHKCNN ECMESVKNGT YDYPKYSEES KLNREKIDGV KLESMGVYQI LAIYSTVASS    539
 4. CFEFYHKCDN TCMESVKNGT YDYPKYSEEA KLNREEIDGV KLESTRIYQI LAIYSTVASS    540
 5. CFEFYHKRDN ECLECVKNGT YNYPKYSEES KFNREEIVGV KLESMGVHQI LAIYSTVASS    540
 6. CFEFYHKCDN ECMESVKNGT YNYPKYSEES KLNREKIDGV KLESMGVHQI LAIYSTVASS    540
 7. CFEFYHKCND ECMESVKNGT YDYPKYSEES KLNRERIDGV KLESMGVYQI LAIYSTVASS    539
 8. CFEFYHKCND ECMESVKNGT YDYPKYSEES KLNREKIDGV KLESMGVYQI LAIYSTVASS    539
 9. CFEFYHKCNN ECMESVKNGT YDYPKYSKES KLNREKIDGV KLESMGVYQI LAIYSTVASS    540
10. CFEFYHKCNN ECMESVKNGT YDYPKYSEES KLNREKIDGV KLESMGVYQI LAIYSTVASS    540
11. CFEFYHKCNN ECMESVKNGT YDYPKYSEES KLNREKIDGV KLESMGVYQI LAIYSTVASS    539
12. CFEFYHKCNN ECMESVKNGT YDYPKYSEES KLNRGKIDGV KLESMGVYQI LAIYSTVASS    540
13. CFEFYHKCNN ECMESVKNGT YDYPKYSEES KLNREKIDGV KLESMGVYQI LAIYSTVASS    540
14. CFEFYHKCNN ECMESVKNGT YDYPKYSEES KLNREKIDGV KLESMGVYQI LAIYSTVASS    540
15. CFEFYHKCNN ECMESVKNGT YDYPKYSEES KLNREKIDGV KLESMGVYQI LAIYSTVASS    540
16. CFEFYHKCNN ECMESVKNGT YDYPKYSEES KLNREKIDGV KLESMGVYQI LAIYSTVASS    540
17. CFEFYHKCNN ECMESVKNGT YDYPKYSEES KLNREKIDGV KLESMGVYQI LAIYSTVASS    540
18. CFEFYHKCNN ECMESVKNGT YDYPKYSEES KLNREKIDGV KLESMGVYQI LAIYSTVASS    540
19. CFEFYHKCDN ECMESVKNGT YDYPKYSEES KLNREKIDGV KLESMGVYRI LAIYSTVASS    539
20. CFEFYHKCNN ECMESVKNGT YDYPKYSEES KLNREKIDGV KLESMGVYQI LAIYSTVASS    540
21. CFEFYHKCNN ECMESVKNGT YDYPKYSEES KLNREKIDGV KLESMGVYQI LAIYSTVASS    540
22. CFEFYHKCNN ECMESVKNGT YDYPKFSEES KLNREKIDGV KLESMGVYQI LAIYSTVASS    540
23. CFEFYHKCNN ECMESVKNGT YDYPKYSEES KLNREKIDGV KLESMGVYQI LAIYSTVASS    540
24. CFEFYHKCNN ECMESVKNGT YDYPKYSEES KLNREKIDGV KLESMGVYQI LAIYSTAASS    539
25. CFEFYHKCNN ECMESVKNGT YDYPKYSEES KLNREKIDGV KLESMGVYQI LAIYSTVASS    540
26. CFEFYHKCDN ECMESVRNGT YDYPKYSEES KLNREKVDGV KLESMGIYQI LAIYSTVASS    539
27. CFEFYHKCDN ECMESVRNGT YDYPKYSEES KLNREKIDGV KLESMGVYQI LAIYSTVASS    539
28. CFEFYHKCDD ACMESVRNGT YDYPKYSEES KLNREEIDGV KLESMGVYQI LAIYSTVASS    540
    ********::  *****:*** *****:*:*: ****  .:*** ****   :*:* ******.***

1. LVLLVSLGAI SFWMCSNGSL QCRICI                                         565
 2. LVLLVSLGAI SFWMCSNGSL QCRICI                                         565
 3. LVLLVSLGAI SFWMCSNGSL QCRICI                                         565
 4. LVLVVSLGAI SFWMCSNGSL QCRICI                                         566
 5. LVLLVSLGAI SFWMCSNGSL QCRVCI                                         566
 6. LVLLVSLGAI SFWMCSNGSL QCRICI                                         566
 7. LVLLVSLGAI SFWMCSNGSL QCRICI                                         565
 8. LVLLVSLGAI SFWMCSNGSL QCRICI                                         565
 9. LVLLVSLGAI SFWMCSNGSL QCRICI                                         566
10. LVLLVSLGAI SFWMCSNGSL QCRICI                                         566
11. LVLLVSLGAI SFWMCSNGSL QCRICI                                         565
12. LVLLVSLGAI SFWMCSNGSL QCRICI                                         566
13. LVLLVSLGAI SFWMCSNGSL QCRICI                                         566
14. LVLLVSLGAI SFWMCSNGSL QCRICI                                         566
15. LVLLVSLGAI SFWMCSNGSL QCRICI                                         566
16. LVLLVSLGAI SFWMCSNGSL QCRICI                                         566
17. LVLLVSLGAI SFWMCSNGSL QCRICI                                         566
18. LVLLVSLGAI SFWMCSNGSL QCRICI                                         566
19. LVLLVSLGAI SFWMCSNGSL QCRICI                                         565
20. LVLLVSLGAI SFWMCSNGSL QCRICI                                         566
21. LVLLVSLGAI SFWMCSNGSL QCRICI                                         566
22. LVLLVSLGAI SFWMCSNGSL QCRICI                                         566
23. LVLLVSLGAI SFWMCSNGSL QCRICI                                         566
24. LVLLVSLGAI SFWMCSNGSL QCRICI                                         565
25. LVLLVSLGAI SFWMCSNGSL QCRICI                                         566
26. LVLLVSLGAI SFWMCSNGSL QCRICI                                         565
```

TABLE 3-continued

Sequence alignment of H1 sequences according to particular embodiments of the disclosure.

```
27. LVLLVSLGAI SFWMCSNGSL QCRICI                                        565
28. LVLLVSLGAI SFWMCSNGSL QCRICI                                        566
    ***.****** ********** ******
```

TABLE 4

Polypeptides expressed in *P. pastoris*. Expression and CR6261 binding were determined as described and the ratio of binding and expression signals calculated.

| SET1 clone | CR6261 binding signal | HTRF signal | ratio | fold increase of ratio over parental H1 mini-HA | Fusion peptide area 337 E, I, K, V | 340 I, K, R, T | 352 D, F, V, Y | 353 I, K, R, T | B-loop 402 E, K, M, V | 406 F, I, N, S, T, Y | 409 A, G, I, R, T, V | 413 F, I, N, S, T, Y | 416 H, I, L, N, R, S |
|---|---|---|---|---|---|---|---|---|---|---|---|---|---|
| 239E11 | 1076944 | 1492 | 721.81 | 121.52 | K | I | Y | T | M | F | I | N | R |
| 127H1 | 800024 | 6572 | 121.73 | 20.49 | K | K | F | T | M | Y | I | Y | S |
| 171E5 | 879704 | 11508 | 76.44 | 12.87 | K | T | F | T | M | I | A | F | S |
| 239D2 | 570424 | 9279 | 61.47 | 10.35 | K | K | F | T | M | I | V | F | N |
| 247B2 | 414984 | 7583 | 54.73 | 9.21 | K | I | Y | T | V | Y | I | F | S |
| 253D4 | 395824 | 7546 | 52.45 | 8.83 | K | T | F | T | M | Y | A | Y | H |
| 252F5 | 421824 | 8621 | 48.93 | 8.24 | V | K | Y | T | M | Y | V | Y | N |
| 220C9 | 1086064 | 22606 | 48.04 | 8.09 | K | T | F | T | M | F | T | Y | L |
| 125D3 | 139824 | 2937 | 47.61 | 8.02 | K | K | F | T | M | Y | G | T | H |
| 137C11 | 416504 | 9167 | 45.44 | 7.65 | V | K | F | T | M | Y | I | N | H |
| 131B5 | 844344 | 20419 | 41.35 | 6.96 | K | T | F | T | M | I | V | Y | H |
| 233F11 | 583024 | 14389 | 40.52 | 6.82 | K | K | Y | T | M | T | I | G | S |
| 234C5 | 377864 | 9465 | 39.92 | 6.72 | I | I | Y | T | M | F | T | N | L |
| 115A1 | 1176904 | 30389 | 38.73 | 6.52 | K | K | Y | T | M | I | V | Y | I |
| 185G7 | 505864 | 13560 | 37.31 | 6.28 | K | K | Y | T | M | I | V | I | S |
| 275D4 | 327344 | 9030 | 36.25 | 6.10 | K | K | Y | T | M | T | T | S | S |
| 244B8 | 273744 | 7757 | 35.29 | 5.94 | I | T | Y | T | M | Y | A | I | S |
| 252B8 | 284984 | 8252 | 34.54 | 5.81 | K | I | Y | T | M | S | I | N | L |
| 213C11 | 667024 | 20624 | 32.34 | 5.44 | V | K | Y | T | M | I | V | F | H |
| 174G3 | 491184 | 15320 | 32.06 | 5.40 | K | T | Y | K | V | S | G | Y | L |
| 125D10 | 133904 | 4241 | 31.57 | 5.31 | K | I | Y | T | M | Y | V | N | R |
| 127A7 | 233064 | 7498 | 31.08 | 5.23 | E | T | Y | T | M | I | I | I | L |
| 304G11 | 110504 | 3588 | 30.8 | 5.19 | K | K | Y | K | M | F | T | F | S |
| 162A11 | 364024 | 11939 | 30.49 | 5.13 | V | K | Y | T | M | F | A | F | I |
| 271F10 | 315304 | 10348 | 30.47 | 5.13 | I | K | Y | T | M | I | A | I | L |
| 218G11 | 958504 | 33710 | 28.43 | 4.79 | I | T | Y | I | M | I | I | I | N |
| 251C8 | 269544 | 9634 | 27.98 | 4.71 | K | K | Y | K | M | Y | I | N | L |
| 258A6 | 165624 | 6004 | 27.59 | 4.64 | I | K | Y | T | M | Y | T | F | H |
| 134A4 | 456304 | 17366 | 26.28 | 4.42 | K | I | Y | I | M | I | A | Y | N |
| 214C11 | 317904 | 12120 | 26.23 | 4.42 | E | I | Y | T | M | Y | V | S | S |
| 182G8 | 399864 | 15262 | 26.2 | 4.41 | K | K | Y | T | M | T | V | I | I |
| 113E7 | 966064 | 38018 | 25.41 | 4.28 | K | K | F | T | M | Y | T | I | H |
| 230G9 | 854584 | 34093 | 25.07 | 4.22 | K | K | Y | T | M | Y | T | F | R |
| 222G4 | 419064 | 16996 | 24.66 | 4.15 | K | T | F | I | V | I | I | Y | L |
| 182D7 | 418944 | 17096 | 24.51 | 4.13 | I | T | Y | T | M | I | I | F | N |
| 272H2 | 263264 | 10844 | 24.28 | 4.09 | K | T | Y | T | M | S | A | N | H |
| 191C8 | 309064 | 12753 | 24.23 | 4.08 | I | T | Y | T | V | I | A | F | I |
| 123C10 | 237824 | 9843 | 24.16 | 4.07 | K | I | Y | K | M | F | A | T | L |
| 284B9 | 1663504 | 70812 | 23.49 | 3.95 | K | T | Y | R | M | I | R | T | L |
| 134A3 | 531784 | 23414 | 22.71 | 3.82 | K | K | F | I | M | I | I | N | S |
| 188F4 | 287384 | 12888 | 22.3 | 3.75 | K | K | Y | T | M | S | V | T | H |
| 189B7 | 336344 | 15207 | 22.12 | 3.72 | E | T | F | T | M | Y | V | F | N |
| 148D5 | 329144 | 14994 | 21.95 | 3.70 | E | T | Y | I | M | F | G | S | H |
| 194C8 | 242304 | 11113 | 21.8 | 3.67 | I | T | F | T | M | F | V | F | I |
| 188A8 | 279144 | 13001 | 21.47 | 3.61 | K | T | Y | K | M | F | V | S | I |
| 162B3 | 279584 | 13159 | 21.25 | 3.58 | V | T | Y | T | M | Y | T | N | N |
| 204C5 | 832784 | 39330 | 21.17 | 3.56 | V | K | F | T | V | I | I | Y | L |
| 216E5 | 334904 | 15873 | 21.1 | 3.55 | V | T | F | T | M | F | R | Y | R |
| 129C2 | 199464 | 9486 | 21.03 | 3.54 | V | R | Y | I | M | I | I | Y | S |
| 286E8 | 158704 | 7662 | 20.71 | 3.49 | E | I | F | T | M | F | I | Y | S |
| 264G4 | 180504 | 8751 | 20.63 | 3.47 | K | R | Y | T | V | I | V | F | S |
| 214C4 | 302264 | 14709 | 20.55 | 3.46 | I | I | F | T | V | F | A | S | S |
| 125A8 | 212224 | 10327 | 20.55 | 3.46 | K | I | Y | T | V | I | V | Y | I |
| 123G2 | 498584 | 24442 | 20.4 | 3.43 | I | T | Y | I | M | Y | T | F | L |
| 187C6 | 345464 | 16932 | 20.4 | 3.43 | E | K | Y | K | M | F | I | I | H |
| 134H10 | 591704 | 29253 | 20.23 | 3.41 | K | T | Y | T | V | I | T | F | I |
| 187H10 | 299224 | 15289 | 19.57 | 3.29 | K | T | Y | I | M | I | G | F | L |
| 101D4 | 336584 | 17243 | 19.52 | 3.29 | I | K | Y | I | M | I | I | S | N |

TABLE 4-continued

Polypeptides expressed in *P. pastoris*. Expression and CR6261 binding were determined as described and the ratio of binding and expression signals calculated.

| SET1 clone | CR6261 binding signal | HTRF signal | ratio | fold increase of ratio over parental H1 mini-HA | Fusion peptide area | | | | B-loop | | | | |
|---|---|---|---|---|---|---|---|---|---|---|---|---|---|
| | | | | | 337 E, I, K, V | 340 I, K, R, T | 352 D, F, V, Y | 353 I, K, R, T | 402 E, K, M, V | 406 F, I, N, S, T, Y | 409 A, G, I, R, T, V | 413 F, I, N, S, T, Y | 416 H, I, L, N, R, S |
| 193B6 | 206904 | 10650 | 19.43 | 3.27 | K | K | Y | R | M | F | I | S | N |
| 137C5 | 295944 | 15406 | 19.21 | 3.23 | I | R | F | T | V | I | I | N | N |
| 112F3 | 449824 | 24169 | 18.61 | 3.13 | V | R | F | I | M | I | I | Y | S |
| 176A5 | 193104 | 10476 | 18.43 | 3.10 | I | T | F | T | V | F | I | F | I |
| 213B2 | 131704 | 7178 | 18.35 | 3.09 | K | K | Y | T | M | T | V | F | L |
| 307A10 | 114984 | 6348 | 18.11 | 3.05 | I | K | F | T | M | Y | G | Y | H |
| 126C3 | 219944 | 12413 | 17.72 | 2.98 | E | T | F | I | M | F | G | T | I |
| 263B6 | 151184 | 8800 | 17.18 | 2.89 | I | T | Y | I | M | S | T | Y | I |
| 138F11 | 147864 | 8788 | 16.83 | 2.83 | E | R | Y | R | M | F | V | F | L |
| 134D3 | 303504 | 18129 | 16.74 | 2.82 | E | R | F | I | M | Y | T | F | S |
| 131D5 | 344504 | 20857 | 16.52 | 2.78 | V | T | Y | I | V | I | A | F | S |
| 138F8 | 347704 | 21081 | 16.49 | 2.78 | K | T | Y | I | M | Y | A | F | H |
| 301F11 | 116904 | 7108 | 16.45 | 2.77 | V | T | F | T | V | Y | I | S | H |
| 112G6 | 543944 | 33149 | 16.41 | 2.76 | V | R | Y | I | M | F | I | S | I |
| 245C9 | 180024 | 10980 | 16.4 | 2.76 | V | R | F | T | M | F | V | T | L |
| 123E2 | 477064 | 29184 | 16.35 | 2.75 | V | T | Y | T | V | F | V | F | S |
| 266A11 | 90584 | 5696 | 15.9 | 2.68 | V | T | Y | T | M | Y | I | T | R |
| 104C4 | 521224 | 34458 | 15.13 | 2.55 | V | K | Y | I | M | F | G | F | N |
| 194E4 | 408584 | 27424 | 14.9 | 2.51 | E | K | F | T | M | I | T | F | I |
| 206B11 | 358744 | 24697 | 14.53 | 2.45 | V | R | Y | T | M | F | T | I | L |
| 192C4 | 343184 | 23932 | 14.34 | 2.41 | K | T | Y | K | M | I | V | T | N |
| 125H3 | 317384 | 22785 | 13.93 | 2.35 | I | T | F | T | M | I | A | Y | R |
| 145C9 | 182344 | 13108 | 13.91 | 2.34 | I | T | F | I | V | Y | I | S | N |
| 243D6 | 132144 | 9596 | 13.77 | 2.32 | I | R | F | T | M | N | V | Y | R |
| 182D3 | 142664 | 10487 | 13.6 | 2.29 | I | T | Y | R | M | F | A | G | S |
| 181H9 | 310504 | 23153 | 13.41 | 2.26 | V | K | F | I | M | F | V | F | N |
| 163E3 | 183544 | 14033 | 13.08 | 2.20 | E | K | Y | K | M | I | V | I | L |
| 145E7 | 132224 | 10312 | 12.82 | 2.16 | I | T | F | K | V | I | I | F | S |
| 275G3 | 115104 | 9180 | 12.54 | 2.11 | V | T | Y | I | M | T | A | S | S |
| 191D5 | 123824 | 10048 | 12.32 | 2.07 | I | R | F | T | M | T | G | F | S |
| 188G10 | 142504 | 11593 | 12.29 | 2.07 | V | T | Y | I | V | I | A | F | S |
| 171F6 | 140464 | 11555 | 12.16 | 2.05 | K | T | Y | T | M | S | T | Y | L |
| 125C2 | 83624 | 7009 | 11.93 | 2.01 | I | I | F | T | V | I | T | S | S |
| 206B8 | 285824 | 24166 | 11.83 | 1.99 | V | I | Y | T | M | I | T | F | H |
| 145F2 | 498504 | 42457 | 11.74 | 1.98 | I | K | F | T | M | F | R | F | S |
| 199F3 | 328504 | 29850 | 11.01 | 1.85 | K | T | Y | T | M | N | G | S | S |
| 181H11 | 186664 | 17205 | 10.85 | 1.83 | V | T | Y | T | M | I | I | N | R |
| 188C8 | 113344 | 10520 | 10.77 | 1.81 | I | K | Y | T | M | S | T | Y | L |
| 189E10 | 188864 | 18252 | 10.35 | 1.74 | K | T | Y | T | M | S | G | S | S |
| 146G7 | 533864 | 52422 | 10.18 | 1.71 | V | T | Y | I | M | Y | T | T | I |
| 182H2 | 109624 | 10976 | 9.99 | 1.68 | K | I | F | T | V | I | I | T | L |
| 262B9 | 94744 | 9584 | 9.89 | 1.66 | I | K | Y | T | M | F | R | F | R |
| 145E8 | 211504 | 21732 | 9.73 | 1.64 | E | K | F | K | V | I | V | F | I |
| 249B11 | 145184 | 14995 | 9.68 | 1.63 | K | K | F | T | M | S | T | G | H |
| 182C6 | 92944 | 9939 | 9.35 | 1.57 | K | R | D | I | M | F | I | N | N |
| SEQ ID NO: 6 AV + 2SD | | | 9.28 | 1.56 | | | | | | | | | |
| SEQ ID NO: 6 AV | 238077 | 40100 | 5.94 | 1.00 | | | | | | | | | |

TABLE 5

Polypeptides expressed in *P. pastoris*. Expression and CR6261 binding were determined as described and the ratio of binding and expression signals calculated.

| Set 2 clone | CR6261 binding signal | HTRF signal | ratio | fold increase of ratio over parental SEQ ID NO: 6 | Fusion peptide area | | | | B-loop | | | | |
|---|---|---|---|---|---|---|---|---|---|---|---|---|---|
| | | | | | 337 A, E, I, K, T, V | 340 F, I, N, S, T, Y | 352 A, D, F, I, N, S, T, V, Y | 353 E, G, I, K, R, V | 402 M, R, T | 406 F, H, L, Y | 409 F, I, S, T | 413 E, K, M, V | 416 I, L, R, S |
| 86B4 | 1077144 | 13862 | 77.7 | 13.08 | K | N | Y | K | M | F | I | M | I |
| 7A7 | 987824 | 13452 | 73.43 | 12.36 | T | N | Y | V | M | Y | F | E | R |
| 55G7 | 616184 | 8767 | 70.28 | 11.83 | K | N | Y | V | M | Y | I | M | L |
| 71H2 | 1109984 | 16750 | 66.27 | 11.16 | K | N | F | K | M | L | I | V | S |
| 86B3 | 900904 | 14448 | 62.35 | 10.50 | K | N | Y | K | M | L | I | V | R |
| 71A4 | 1064144 | 17597 | 60.47 | 10.18 | T | N | Y | V | M | Y | F | E | R |

TABLE 5-continued

Polypeptides expressed in *P. pastoris*. Expression and CR6261 binding were determined as described and the ratio of binding and expression signals calculated.

| | | | | fold increase of ratio over parental SEQ ID NO: 6 | Fusion peptide area | | | | B-loop | | | | |
|---|---|---|---|---|---|---|---|---|---|---|---|---|---|
| | | | | | | | 352 | | | | | | |
| Set 2 clone | CR6261 binding signal | HTRF signal | ratio | | 337 A, E, I, K, T, V | 340 F, I, N, S, T, Y | A, D, F, I, N, S, T, V, Y | 353 E, G, I, K, R, V | 402 M, R, T | 406 F, H, L, Y | 409 F, I, S, T | 413 E, K, M, V | 416 I. L. R. S |
| 51G3 | 460304 | 7773 | 59.22 | 9.97 | T | I | F | V | M | L | F | E | S |
| 84B8 | 582144 | 10091 | 57.69 | 9.71 | K | N | Y | I | M | F | F | M | S |
| 79C2 | 364184 | 7116 | 51.18 | 8.62 | T | N | Y | R | M | F | T | V | S |
| 69G8 | 481344 | 9479 | 50.78 | 8.55 | I | N | F | R | M | L | I | V | L |
| 79D5 | 702584 | 13981 | 50.25 | 8.46 | A | N | F | K | M | L | F | V | L |
| 54H4 | 291744 | 5857 | 49.81 | 8.39 | K | I | Y | K | M | L | I | E | L |
| 11H6 | 427384 | 9146 | 46.73 | 7.87 | K | N | Y | E | M | F | T | E | S |
| 90A9 | 413664 | 9025 | 45.84 | 7.72 | K | S | Y | V | M | Y | T | V | S |
| 75G5 | 1011384 | 26695 | 37.89 | 6.38 | E | S | Y | V | M | L | F | E | R |
| 8A10 | 360104 | 9630 | 37.39 | 6.29 | K | N | Y | V | M | L | I | V | R |
| 72D4 | 329944 | 8881 | 37.15 | 6.25 | V | N | F | R | M | F | S | M | S |
| 74H9 | 1283144 | 35494 | 36.15 | 6.09 | K | N | F | K | M | Y | F | M | S |
| 88C5 | 471424 | 13355 | 35.3 | 5.94 | K | N | Y | R | M | L | I | V | R |
| 61A9 | 383064 | 10864 | 35.26 | 5.94 | T | N | F | R | M | F | F | E | L |
| 86H9 | 457344 | 13340 | 34.28 | 5.77 | K | N | F | G | M | F | T | V | S |
| 71D3 | 1573024 | 46711 | 33.68 | 5.67 | I | S | Y | V | M | F | I | V | L |
| 9C6 | 270984 | 8235 | 32.91 | 5.54 | K | T | Y | V | M | Y | T | K | I |
| 81F11 | 317824 | 9964 | 31.9 | 5.37 | K | I | F | V | M | F | F | V | S |
| 84E10 | 255064 | 7996 | 31.9 | 5.37 | I | N | F | R | M | F | S | V | S |
| 71C4 | 1350144 | 44339 | 30.45 | 5.13 | K | N | F | G | M | F | I | V | S |
| 84D3 | 84424 | 2920 | 28.91 | 4.87 | E | N | F | K | M | L | I | E | S |
| 96H8 | 205904 | 7224 | 28.5 | 4.80 | K | Y | Y | K | M | F | I | M | S |
| 85A7 | 235704 | 8416 | 28.01 | 4.72 | K | N | Y | E | M | L | F | V | R |
| 50G10 | 264144 | 9470 | 27.89 | 4.70 | T | N | F | E | M | F | F | V | S |
| 6A1 | 299824 | 10912 | 27.48 | 4.63 | A | N | F | R | M | F | F | M | S |
| 91C4 | 1157424 | 44837 | 25.81 | 4.35 | K | N | F | G | M | L | I | M | R |
| 2C4 | 258264 | 10139 | 25.47 | 4.29 | I | N | F | V | M | F | I | V | L |
| 63C3 | 188184 | 7625 | 24.68 | 4.15 | E | T | Y | K | M | L | F | V | L |
| 850 | 196024 | 8115 | 24.16 | 4.07 | K | N | V | G | M | F | F | V | I |
| 67C10 | 306104 | 12907 | 23.72 | 3.99 | E | T | F | V | M | F | F | M | L |
| 10F9 | 165984 | 7113 | 23.34 | 3.93 | I | I | Y | V | M | Y | F | E | R |
| 4C1 | 385504 | 16548 | 23.3 | 3.92 | K | N | S | V | M | F | I | E | I |
| 86G3 | 183944 | 7995 | 23.01 | 3.87 | T | S | Y | V | M | F | T | V | L |
| 51G10 | 215264 | 9727 | 22.13 | 3.73 | A | N | Y | R | M | F | I | K | S |
| 58A5 | 90744 | 4142 | 21.91 | 3.69 | V | T | F | R | M | L | I | M | S |
| 56F8 | 235344 | 10823 | 21.74 | 3.66 | I | N | F | E | M | F | T | E | L |
| 67C11 | 209184 | 9856 | 21.22 | 3.57 | K | Y | Y | I | M | F | F | E | I |
| 91C8 | 333584 | 16012 | 20.83 | 3.51 | K | N | F | G | M | L | I | K | S |
| 48B11 | 302864 | 14946 | 20.26 | 3.41 | I | N | A | G | M | L | I | E | S |
| 78F11 | 84104 | 4155 | 20.24 | 3.41 | I | I | F | R | M | Y | F | E | I |
| 76A10 | 136984 | 6841 | 20.02 | 3.37 | I | Y | F | V | M | Y | F | E | I |
| 55H2 | 58104 | 2984 | 19.47 | 3.28 | I | I | Y | V | M | F | F | V | S |
| 74D7 | 358784 | 18453 | 19.44 | 3.27 | K | N | A | G | M | F | I | M | S |
| 11B4 | 166464 | 8679 | 19.18 | 3.23 | T | S | F | V | M | Y | T | V | S |
| 56F4 | 185984 | 9740 | 19.09 | 3.21 | T | T | F | E | M | F | S | M | S |
| 71E7 | 202704 | 10688 | 18.97 | 3.19 | K | N | S | R | M | Y | I | E | S |
| 48B10 | 102904 | 5480 | 18.78 | 3.16 | I | F | F | K | M | L | F | M | S |
| 48D11 | 120584 | 6807 | 17.71 | 2.98 | E | Y | Y | V | M | F | T | V | S |
| 35H3 | 106224 | 6092 | 17.44 | 2.94 | V | S | F | V | M | L | S | M | R |
| 53G10 | 107784 | 6188 | 17.42 | 2.93 | T | N | F | V | M | L | T | V | S |
| 86F1 | 158624 | 9145 | 17.35 | 2.92 | I | I | F | V | M | Y | I | V | I |
| 9C10 | 114144 | 6595 | 17.31 | 2.91 | I | I | Y | V | M | H | S | V | S |
| 6E12 | 372504 | 22044 | 16.9 | 2.85 | E | N | F | I | M | L | F | V | L |
| 2D9 | 316024 | 19245 | 16.42 | 2.76 | K | N | N | I | M | Y | F | E | L |
| 27B10 | 187344 | 11465 | 16.34 | 2.75 | K | N | N | V | M | L | F | E | S |
| 79F8 | 185264 | 11801 | 15.7 | 2.64 | I | N | V | I | M | F | T | E | S |
| 11F4 | 150824 | 9996 | 15.09 | 2.54 | I | Y | F | V | M | Y | F | V | L |
| 60A2 | 92664 | 6166 | 15.03 | 2.53 | E | N | Y | V | M | F | S | E | L |
| 58C8 | 277144 | 18603 | 14.9 | 2.51 | A | S | Y | I | M | L | S | E | L |
| 12C6 | 289184 | 20023 | 14.44 | 2.43 | I | N | S | V | M | L | I | E | L |
| 89F11 | 84824 | 5908 | 14.36 | 2.42 | T | I | Y | I | M | L | S | V | S |
| 96G5 | 108264 | 7589 | 14.27 | 2.40 | V | N | F | I | M | Y | F | M | S |
| 29C2 | 177904 | 12921 | 13.77 | 2.32 | K | N | F | G | M | Y | F | M | R |
| 56D2 | 145624 | 10658 | 13.66 | 2.30 | E | T | F | I | M | F | F | K | S |
| 66C8 | 184544 | 13591 | 13.58 | 2.29 | K | N | V | I | M | L | F | V | L |
| 69D2 | 445704 | 34266 | 13.01 | 2.19 | V | F | F | V | M | Y | T | E | S |
| 75E9 | 134504 | 10422 | 12.91 | 2.17 | I | I | F | G | M | F | S | E | I |
| 97G10 | 253104 | 20061 | 12.62 | 2.12 | E | S | F | I | M | F | F | E | I |
| 36E4 | 196104 | 15917 | 12.32 | 2.07 | I | N | N | K | M | F | F | V | L |

TABLE 5-continued

Polypeptides expressed in *P. pastoris*. Expression and CR6261 binding were determined as described and the ratio of binding and expression signals calculated.

| | | | | fold increase of ratio over parental SEQ ID NO: 6 | Fusion peptide area | | | | B-loop | | | | |
|---|---|---|---|---|---|---|---|---|---|---|---|---|---|
| | | | | | | | 352 | | | | | | |
| Set 2 clone | CR6261 binding signal | HTRF signal | ratio | | 337 A, E, I, K, T, V | 340 F, I, N, S, T, Y | A, D, F, I, N, S, T, V, Y | 353 E, G, I, K, R, V | 402 M, R, T | 406 F, H, L, Y | 409 F, I, S, T | 413 E, K, M, V | 416 I, L, R, S |
| 7D9 | 77824 | 6320 | 12.31 | 2.07 | K | N | F | V | M | F | F | M | L |
| 1F2 | 148544 | 12244 | 12.13 | 2.04 | K | N | Y | V | M | F | F | M | I |
| 76D10 | 113664 | 9729 | 11.68 | 1.97 | T | N | A | K | M | L | T | E | S |
| 36H2 | 171144 | 14761 | 11.59 | 1.95 | T | N | Y | K | M | H | F | M | R |
| 86G2 | 69704 | 6069 | 11.49 | 1.93 | E | N | F | V | M | L | I | E | R |
| 63D3 | 145784 | 13100 | 11.13 | 1.87 | K | N | I | G | M | F | T | E | L |
| 96A7 | 83304 | 7575 | 11 | 1.85 | V | I | F | V | M | F | S | V | S |
| 36D6 | 71304 | 6569 | 10.85 | 1.83 | I | N | A | G | M | F | T | E | I |
| 91F10 | 14784 | 1394 | 10.6 | 1.78 | T | N | Y | G | M | F | I | E | R |
| 80F10 | 90864 | 8609 | 10.55 | 1.78 | I | S | V | V | M | L | I | E | S |
| 75H8 | 103304 | 10074 | 10.25 | 1.73 | A | N | N | V | M | F | F | M | S |
| 57B8 | 58384 | 5800 | 10.07 | 1.70 | K | I | Y | I | M | F | F | V | I |
| 8D7 | 73424 | 7324 | 10.03 | 1.69 | K | N | F | V | M | L | F | E | L |
| 58A11 | 53264 | 5363 | 9.93 | 1.67 | V | T | Y | I | M | F | T | V | S |
| 7B6 | 60384 | 6137 | 9.84 | 1.66 | K | I | S | E | M | F | I | M | S |
| 87H5 | 78104 | 7994 | 9.77 | 1.64 | E | I | F | I | M | F | F | V | S |
| 70F6 | 418624 | 43334 | 9.66 | 1.63 | K | N | I | G | M | L | T | E | R |
| 26H1 | 79744 | 8268 | 9.64 | 1.62 | E | N | F | I | M | L | S | V | I |
| 78G2 | 56704 | 6055 | 9.36 | 1.58 | V | I | Y | G | M | L | F | E | S |
| SEQ ID NO: 6 AV + 2SD | | | 9.28 | 1.56 | | | | | | | | | |
| SEQ ID NO | 238077 | 40100 | 5.94 | 1.00 | | | | | | | | | |

TABLE 6

Polypeptides expressed in HEK293F. Expression and CR6261 binding were determined as described and the ratio of binding and expression signals calculated. The mutations included in each clone are indicated in Tables 4 and 5.

| Clone | CR6261 binding signal | HTRF signal | ratio | fold increase of ratio over parental SEQ ID NO: 6 |
|---|---|---|---|---|
| 127H1 | 24150000 | 327363 | 73.77 | 4.25 |
| 86B4 | 19970680 | 334887 | 59.63 | 3.44 |
| 171E5 | 6625080 | 235511 | 28.13 | 1.62 |
| 7A7 | 6191080 | 242461 | 25.53 | 1.47 |
| 71H2 | 21080360 | 336346 | 62.67 | 3.61 |
| 220C9 | 8493560 | 162872 | 52.15 | 3.00 |
| 131B5 | 5725640 | 139561 | 41.03 | 2.36 |
| 115A1 | 9557640 | 175377 | 54.50 | 3.14 |
| 74H9 | 26144240 | 344988 | 75.78 | 4.37 |
| 71C4 | 6413600 | 214495 | 29.90 | 1.72 |
| 91C4 | 8442400 | 245138 | 34.44 | 1.98 |
| 113E7 | 13005960 | 260748 | 49.88 | 2.87 |
| 6E12 | 15326000 | 309443 | 49.53 | 2.85 |
| 181H9 | 11892520 | 324690 | 36.63 | 2.11 |
| SEQ ID NO: 6 AV | 5661550 | 326077 | 17.36 | 1.00 |

TABLE 7

Naturally occuring sequence variation at the indicated positions in percentage of total number of sequences for each subtype.

| position | amino acid | H1 | H3 | H5 | H7 |
|---|---|---|---|---|---|
| 337 | V | 67 | 99 | 19 | 100 |
| | I | 32 | 1 | 2 | |
| | T | 0.8 | | 3 | |
| | S | | | 73 | |
| | Y | | | 0.1 | |
| | N | | | 0.5 | |
| | A | | | 2 | |

TABLE 7-continued

Naturally occuring sequence variation at the indicated positions in percentage of total number of sequences for each subtype.

| position | amino acid | H1 | H3 | H5 | H7 |
|---|---|---|---|---|---|
| 340 | G | | | 0.1 | |
| | I | 99 | | 21 | 98 |
| | V | 0.43 | | | |
| | T | 0.03 | | 0.5 | |
| | K | | 97 | | |
| | R | | 2 | 47 | |
| | G | | | 29 | |
| | E | | | 0.3 | |
| | S | | | | 2 |
| 352 | F | 100 | 100 | 100 | 100 |
| 353 | I | 99.9 | 100 | 100 | 100 |
| | L | 0.1 | | | |
| 402 | M | 100 | | 100 | |
| | T | | 99.8 | | 100 |
| | S | | 0.02 | | |

TABLE 8

Purification and strength of mAb binding of polypeptides of the disclosure.

| | SEQ ID NO: | Volume supernatant (ml) | Yield (mg/l of culture) | Purity from HP-SEC (%) | $K_d^{app}$ CR6261 (nM) | $K_d^{app}$ CR9114 (nM) |
|---|---|---|---|---|---|---|
| s127H1 | 35 | 1376 | 9.0 | 100.0 | 130 | 10 |
| s86B4 | 36 | 1380 | 9.0 | 96.0 | 150 | 13 |
| s55G7 | 37 | 1460 | 18.1 | 100.0 | 150 | 9 |
| s74H9 | 34 | 1335 | 11.3 | 99.7 | 130 | 10 |
| s6E12 | 38 | 1479 | 13.1 | 90.8 | 390 | 34 |

TABLE 9

Molecular weights as determined by SEC-MALS for polypeptides of the disclosure and their complexes with Fab fragments of CR6261 and CR9114. Theoretical (theor) values are estimated on the basis of the sequence of the polypeptide of the disclosure (assuming a monomer) and an additional contribution of approximately 10 kDa from attached glycans. The molecular weights of the Fab fragments of CR6261, CR9114 and CR8020 were also determined by SEC-MALS, and were 48, 49 and 47 kDa, respectively.

| | SEQ ID NO: | MW (kDa) Theor | MW (kDa) Observed | MW complex with CR6261 (kDa) Theor | MW complex with CR6261 (kDa) Observed | MW complex with CR9114 (kDa) Theor | MW complex with CR9114 (kDa) Observed |
|---|---|---|---|---|---|---|---|
| s127H1 | 35 | 40 | 39 | 87 | 74 | 86 | 83 |
| s86B4 | 36 | 40 | 40 | 88 | 75 | 87 | 83 |
| s55G7 | 37 | 40 | 40 | 90 | 66 | 87 | 80 |
| s74H9 | 34 | 40 | 41 | 89 | 72 | 88 | 83 |
| s6E12 | 38 | 40 | 40 | 88 | 67 | 87 | 80 |

REFERENCES

Bommakanti et al. (2010), *PNAS* 107(31):13701-13706.
Bommakanti et al. (2012), *J. Virol.* 86:13434.
Coffman et al. (2010), *Immunity* 33:492.
Devereux et al. (1984), *Nucl. Acids Res.* 12:387.
Dopheide T. A., and C. W. Ward (1981), *J. Gen. Virol.* 367-370.
Ekiert et al. (2009), *Science* 324:246.
Ekiert et al. (2011), *Science* 333:844.
Ferguson et al. (2003), *Nature* 422:428-443.
Lorieau et al. 2010, *Proc. Natl. Acad. Sci. U.S.A.* 107:11341.
Steel et al. (2010), *mBio.* 1(1):1-9.
Steven et al. (2004), *Science* 303:1866.
Steven et al. (2006), *Science* 312:404.
Throsby et al. (2008), *Plos One* 12(3):1-15.
Wilson et al. (1981), *Nature* 289:366.

SEQUENCES

```
SEQ ID NO: 1: H1 Full length (A/Brisbane/59/2007)
MKVKLLVLLC  TFTATYADTI  CIGYHANNST  DTVDTVLEKN  VTVTHSVNLL        50
ENSHNGKLCL  LKGIAPLQLG  NCSVAGWILG  NPECELLISK  ESWSYIVEKP       100
NPENGTCYPG  HFADYEELRE  QLSSVSSFER  FEIFPKESSW  PNHTVTGVSA       150
SCSHNGESSF  YRNLLWLTGK  NGLYPNLSKS  YANNKEKEVL  VLWGVHHPPN       200
IGDQKALYHT  ENAYVSVVSS  HYSRKFTPEI  AKRPKVRDQE  GRINYYWTLL       250
EPGDTIIFEA  NGNLIAPRYA  FALSRGFGSG  IINSNAPMDK  CDAKCQTPQG       300
AINSSLPFQN  VHPVTIGECP  KYVRSAKLRM  VTGLRNIPSI  QSRGLFGAIA       350
GFIEGGWTGM  VDGWYGYHHQ  NEQGSGYAAD  QKSTQNAING  ITNKVNSVIE       400
KMNTQFTAVG  KEFNKLERRM  ENLNKKVDDG  FIDIWTYNAE  LLVLLENERT       450
LDFHDSNVKN  LYEKVKSQLK  NNAKEIGNGC  FEFYHKCNDE  CMESVKNGTY       500
DYPKYSEESK  LNREKIDGVK  LESMGVYQIL  AIYSTVASSL  VLLVSLGAIS       550
FWMCSNGSLQ  CRICI                                                 565

SEQ ID NO: 2: H1-mini2-cluster1 + 5 + 6-GCN4
MKVKLLVLLC  TFTATYADTI  CIGYHANNST  DTVDTVLEKN  VTVTHSVNLL        50
ENGGGGKYVC  SAKLRMVTGL  RNIPSIQSQG  LFGAIAGFIE  GGWTGMVDGW       100
YGYHHQNEQG  SGYAADQKST  QNAINGITNK  VNSVIEKMNT  QSTATGKEGN       150
KSERMKQIED  KIEEIESKQI  WCYNAELLVL  LENERTLDFH  DSNVKNLYEK       200
VKSQLKNNAK  EIGNGCFEFY  HKCNDECMES  VKNGTYDYPK  YSEESKLNRE       250
KIDGVKLESM  GVYQILAIYS  TVASSLVLLV  SLGAISFWMC  SNGSLQCRIC       300
I                                                                  301

SEQ ID NO: 3: foldon
GYIPEAPRDGQAYVRKDGEWVLLSTFL

SEQ ID NO: 4: FLAG-thrombin-foldon-HIS
SGRDYKDDDDKLVPRGSPGSGYIPEAPRDGQAYVRKDGEWVLLSTFLGHHHHHH

SEQ ID NO: 5:
MKQIEDKIEEIESKQ

SEQ ID NO: 6: H1-mini2-cluster1 +30 5 +30 6-GCN4 without leader sequence and with
FLAG-thrombin-foldon-HIS
DTICIGYHANNSTDTVDTVLEKNVTVTHSVNLLENGGGGKYVCSAKLRMVTGLRNIPSIQSQGLFGAIAGFIEGGWT
GMVDGWYGYHHQNEQGSGYAADQKSTQNAINGITNKVNSVIEKMNTQSTATGKEGNKSERMKQIEDKIEEIESKQIW
CYNAELLVLLENERTLDFHDSNVKNLYEKVKSQLKNNAKEIGNGCFEFYHKCNDECMESVKNGTYDYPKYSEESKLN
REKIDGVSGRDYKDDDDKLVPRGSPGSGYIPEAPRDGQAYVRKDGEWVLLSTFLGHHHHHH SEQ ID NO: 7:
MREPSIFTAVLFAASSALAAPVNTTTEDETAQIPAEAVIGYSDLEGDFDVAVLPFSNSTNNGLLFINTTIASIAAKE
EGVSLEKREAEA SEQ ID NO: 8: H1 consensus sequence residue 402-418 (numbering according to
SEQ ID NO: 1)
402 MNTQFTAVG KEFN(H/K)LE(K/R) 418

>SC09-114 VH PROTEIN (SEQ ID NO: 11)
QVQLVQSGAEVKKPGSSVKVSCKSSGGTSNNYAISWVRQAPGQGLDWMGGISPIFGSTAYAQKFQGRVTISADIFSN
TAYMELNSLTSEDTAVYFCARHGNYYYSGMDVWGQGTTVTVSS
```

| SEQUENCES |
| --- |

>SC09-114 VL PROTEIN (SEQ ID NO: 12)
SYVLTQPPAVSGTPGQRVTISCSGSDSNIGRRSVNWYQQFPGTAPKLLIYSNDQRPSVVPDRFSGSKSGTSASLAIS
GLQSEDEAEYYCAAWDDSLKGAVFGGGTQLTVL

>CR6261 VH PROTEIN (SEQ ID NO: 9)
E V Q L V E S G A E V K K P G S S V K V S C K A S G G P F R S Y A I S W V R Q
A P G Q G P E W M G G I I P I F G T T K Y A P K F Q G R V T I T A D D F A G T
V Y M E L S S L R S E D T A M Y Y C A K H M G Y Q V R E T M D V W G K G T T V
T V S S

>CR6261 VL PROTEIN (SEQ ID NO: 10)
Q S V L T Q P P S V S A A P G Q K V T I S C S G S S S N I G N D Y V S W Y Q Q
L P G T A P K L L I Y D N N K R P S G I P D R F S G S K S G T S A T L G I T G
L Q T G D E A N Y Y C A T W D R R P T A Y V V F G G G T K L T V L G

>SC08-057 VH PROTEIN (SEQ ID NO: 13)
EVQLVESGGGLVQPGGSLRLSCAASGFTDSVIFMSWVRQAPGKGLECVSIIYIDDSTYYADSVKGRFTISRHNSMGT
VFLEMNSLRPDDTAVYYCATESGDFGDQTGPYHYYAMDV

>SC08-057 VL PROTEIN (SEQ ID NO: 14)
QSALTQPASVSGSPGQSITISCTGSSGDIGGYNAVSWYQHHPGKAPKLMIYEVTSRPSGVSDRFSASRSGDTASLTV
SGLQAEDEAHYYCCSFADSNILI

>SC08-020 VH PROTEIN (SEQ ID NO: 17)
QVQLQQSGAEVKTPGASVKVSCKASGYTFTRFGVSWIRQAPGQGLEWIGWISAYNGDTYYAQKFQARVTMTTDTSTT
TAYMEMRSLRSDDTAVYYCAREPPLFYSSWSLDN

>SC08-020 VL PROTEIN (SEQ ID NO: 18)
EIVXTQSPGTLSLSPGERATLSCRASQSVSMNYLAWFQQKPGQAPRLLIYGASRRATGIPDRISGSGSGTDFTLTIS
RLEPADFAVYYCQQYGTSPRT

SEQ ID NO: 55: 127H1
MKVKLLVLLCTFTATYADTICIGYHANNSTDTVDTVLEKNVTVTHSVNLLENGGGGKYVCSAKLRMVTGLRNKPSKQ
SQGLFGAIAGFTEGGWTGMVDGWYGYHHQNEQGSGYAADQKSTQNAINGITNKVNSVIEKMNTQYTAIGKEYNKSER
MKQIEDKIEEIESKQIWCYNAELLVLLENERTLDFHDSNVKNLYEKVKSQLKNNAKEIGNGCFEFYHKCNDECMESV
KNGTYDYPKYSEESKLNREKIDGVKLESMGVYQILAIYSTVASSLVLLVSLGAISFWMCSNGSLQCRICI

SEQ ID NO: 56: 86B4
MKVKLLVLLCTFTATYADTICIGYHANNSTDTVDTVLEKNVTVTHSVNLLENGGGGKYVCSAKLRMVTGLRNKPSNQ
SQGLFGAIAGYKEGGWTGMVDGWYGYHHQNEQGSGYAADQKSTQNAINGITNKVNSVIEKMNTQFTAIGKEMNKIER
MKQIEDKIEEIESKQIWCYNAELLVLLENERTLDFHDSNVKNLYEKVKSQLKNNAKEIGNGCFEFYHKCNDECMESV
KNGTYDYPKYSEESKLNREKIDGVKLESMGVYQILAIYSTVASSLVLLVSLGAISFWMCSNGSLQCRICI

SEQ ID NO: 59: 55G7
MKVKLLVLLCTFTATYADTICIGYHANNSTDTVDTVLEKNVTVTHSVNLLENGGGGKYVCSAKLRMVTGLRNKPSNQ
SQGLFGAIAGYVEGGWTGMVDGWYGYHHQNEQGSGYAADQKSTQNAINGITNKVNSVIEKMNTQYTAIGKEMNKLER
MKQIEDKIEEIESKQIWCYNAELLVLLENERTLDFHDSNVKNLYEKVKSQLKNNAKEIGNGCFEFYHKCNDECMESV
KNGTYDYPKYSEESKLNREKIDGVKLESMGVYQILAIYSTVASSLVLLVSLGAISFWMCSNGSLQCRICI

SEQ ID NO: 57: 74H9
MKVKLLVLLCTFTATYADTICIGYHANNSIDTVDTVLEKNVTVTHSVNLLENGGGGKYVCSAKLRMVTGLRNKPSNQ
SQGLFGAIAGEKEGGWTGMVDGWYGYHHQNEQGSGYAADQKSTQNAINGITNKVNSVIEKMNIQYTAFGKEMNKSER
MKQIEDKIEEIESKQIWCYNAELLVLLENERTLDFHDSNVKNLYEKVKSQLKNNAKEIGNGCFEFYHKCNDECMESV
KNGTYDYPKYSEESKLNREKIDGVKLESMGVYQILAIYSTVASSLVLLVSLGAISFWMCSNGSLQCRICI

SEQ ID NO: 60: 115A1
MKVKLLVLLCTFTATYADTICIGYHANNSTDTVDTVLEKNVTVTHSVNLLENGGGGKYVCSAKLRMVTGLRNKPSKQ
SQGLFGAIAGYTEGGWTGMVDGWYGYHHQNEQGSGYAADQKSTQNAINGITNKVNSVIEKMNTQITAVGKEYNKIER
MKQIEDKIEEIESKQIWCYNAELLVLLENERTLDFHDSNVKNLYEKVKSQLKNNAKEIGNGCFEFYHKCNDECMESV
KNGTYDYPKYSEESKLNREKIDG VKLESMGVYQILAIYSTVASSLVLLVSLGAISFWMCSNGSLQCRICI

SEQ ID NO: 61: 71H2
MKVKLLVLLCTFTATYADTICIGYHANNSTDTVDTVLEKNVTVTHSVNLLENGGGGKYVCSAKLRMVTGLRNKPSNQ
SQGLFGAIAGFKEGGWTGMVDGWYGYHHQNEQGSGYAADQKSTQNAINGITNKVNSVIEKMNTQLTAIGKEVNKSER
MKQIEDKIEEIESKQIWCYNAELLVLLENERILDFHDSNVKNLYEKVKSQLKNNAKEIGNGCFEFYHKCNDECMESV
KNGTYDYPKYSEESKLNREKIDGVKLESMGVYQILAIYSTVASSLVLLVSLGAISFWMCSNGSLQCRICI

SEQ ID NO: 62: 181H9
MKVKLLVLLCIFTATYADTICIGYHANNSTDTVDTVLEKNVTVTHSVNLLENGGGGKYVCSAKLRMVTGLRNVPSKQ
SQGLFGAIAGFIEGGWTGMVDGWYGYHHQNEQGSGYAADQKSTQNAINGITNKVNSVIEKMNTQFTAVGKEFNKNER
MKQIEDKIEEIESKQIWCYNAELLVLLENERILDFHDSNVKNLYEKVKSQLKNNAKEIGNGCFEFYHKCNDECMESV
KNGTYDYPKYSEESKLNREKIDGVKLESMGVYQILAIYSTVASSLVLLVSLGAISFWMCSNGSLQCRICI

SEQ ID NO: 58: 6E12
MKVKLLVLLQTFTATYADTICIGYHANNSTDTVDTVLEKNVIVTHSVNLLENGGGGKYVCSAKLRMVTGLRNEPSNQ
SQGLFGAIAGFIEGGWIGMVDGWYGYHHQNEQGSGYAADQKSTQNAINGITNKVNSVIEKMNTQLTAFGKEVNKLER

| SEQUENCES |
|---|
| MKQIEDKIEEIESKQIWCYNAELLVLLENERTLDFHDSNVKNLYEKVKSQLKNNAKEIGNGCFEFYHKCNDECMESV<br>KNGTYDYPKYSEESKLNREKIDGVKLESMGVYQILAIYSTVASSLVLLVSLGAISFWMCSNGSLQCRICI<br><br>SEQ ID NO: 63: 220C9<br>MKVKLLVLLCTFTATYADTICIGYHANNSTDTVDTVLEKNVTVTHSVNLLENGGGGKYVCSAKLRMVTGLRNKPSTQ<br>SQGLFGAIAGFTEGGWTGMVDGWYGYHHQNEQGSGYAADQKSTQNAINGITNKVNSVIEKMNTQFTATGKEYNKLER<br>MKQIEDKIEEIESKQIWCYNAELLVLLENERTLDFHDSNVKNLYEKVKSQLKNNAKEIGNGCFEFYHKCNDECMESV<br>KNGTYDYPKYSEESKLNREKIDGVKLESMGVYQILAIYSTVASSLVLLVSLGAISFWMCSNGSLQCRICI<br><br>SEQ ID NO: 64: 113E7<br>MKVKLLVLLCTFTATYADTICIGYHANNSTDTVDTVLEKNVTVIHSVNLLENGGGGKYVCSAKLRMVTGLRNKPSKQ<br>SQGLFGAIAGFTEGGWTGMVDGWYGYHHQNEQGSGYAADQKSTQNAINGITNKVNSVIEKMNTQYTATGKEINKHER<br>MKQIEDKIEEIESKQIWCYNAELLVLLENERTLDFHDSNVKNLYEKVKSQLKNNAKEIGNGCFEFYHKCNDECMESV<br>KNGTYDYPKYSEESKLNREKIDGVKLESMGVYQILAIYSTVASSLVLLVSLGAISFWMCSNGSLQCRICI<br><br>SEQ ID NO: 65: s74H9<br>DTICIGYHANNSTDTVDTVLEKNVTVTHSVNLLENGGGGKYVCSAKLRMVTGLRNKPSNQSQGLFGAIAGFKEGGWT<br>GMVDGWYGYHHQNEQGSGYAADQKSTQNAINGITNKVNSVIEKMNTQYTAFGKEMNKSERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGRSLVPRGSPGHHHHHH<br><br>SEQ ID NO: 66: s127H1<br>DTICIGYHANNSTDTVDTVLEKNVTVTHSVNLLENGGGGKYVCSAKLRMVTGLRNKPSKQSQGLFGAIAGFTEGGWT<br>GMVDGWYGYHHQNEQGSGYAADQKSTQNAINGITNKVNSVIEKMNTQYTAIGKEYNKSERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGRSLVPRGSPGHHHHHH<br><br>SEQ ID NO: 67: s86B4<br>DTICIGYHANNSTDTVDTVLEKNVTVTHSVNLLENGGGGKYVCSAKLRMVTGLRNKPSNQSQGLFGAIAGYKEGGWT<br>GMVDGWYGYHHQNEQGSGYAADQKSTQNAINGITNKVNSVIEKMNTQFTAIGKEMNKIERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGRSLVPRGSPGHHHHHH<br><br>SEQ ID NO: 68: s55G7<br>DTICIGYHANNSTDTVDTVLEKNVTVTHSVNLLENGGGGKYVCSAKLRMVTGLRNKPSNQSQGLFGAIAGYVEGGWT<br>GMVDGWYGYHHQNEQGSGYAADQKSTQNAINGITNKVNSVIEKMNTQYTAIGKEMNKLERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGRSLVPRGSPGHHHHHH<br><br>SEQ ID NO: 69: s6E12<br>DTICIGYHANNSTDTVDTVLEKNVTVTHSVNLLENGGGGKYVCSAKLRMVTGLRNEPSNQSQGLFGAIAGFIEGGWT<br>GMVDGWYGYHHQNEQGSGYAADQKSTQNAINGITNKVNSVIEKMNTQLTAFGKEVNKLERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGRSLVPRGSPGHHHHHH<br><br>SEQ ID NO: 72: s74H9-long<br>DTICIGYHANNSTDTVDTVLEKNVTVTHSVNLLENGGGGKYVCSAKLRMVTGLRNKPSNQSQGLFGAIAGEKEGGWT<br>GMVDGWYGYHHQNEQGSGYAADQKSTQNAINGITNKVNSVIEKMNTQYTAFGKEMNKSERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGVKLESMGVYQIEG<br><br>SEQ ID NO: 73: s127H1-long<br>DTICIGYHANNSTDTVDTVLEKNVTVTHSVNLLENGGGGKYVCSAKLRMVTGLRNKPSKQSQGLFGAIAGFTEGGWT<br>GMVDGWYGYHHQNEQGSGYAADQKSTQNAINGITNKVNSVIEKMNTQYTAIGKEYNKSERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGVKLESMGVYQIEG<br><br>SEQ ID NO: 74: s86B4-long<br>DTICIGYHANNSTDTVDTVLEKNVTVTHSVNLLENGGGGKYVCSAKLRMVTGLRNKPSNQSQGLFGAIAGYKEGGWT<br>GMVDGWYGYHHQNEQGSGYAADQKSTQNAINGITNKVNSVIEKMNTQFTAIGKEMNKIERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>RE KIDGVKLESMGVYQIEG<br><br>SEQ ID NO: 75: s55G7-long<br>DTICIGYHANNSTDTVDTVLEKNVTVTHSVNLLENGGGGKYVCSAKLRMVTGLRNKPSNQSQGLFGAIAGYVEGGWT<br>GMVDGWYGYHHQNEQGSGYAADQKSTQNAINGITNKVNSVIEKMNTQYTAIGKEMNKLERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGVKLESMGVYQIEG<br><br>SEQ ID NO: 76: s6E12-long<br>DTICIGYHANNSTDTVDTVLEKNVTVTHSVNLLENGGGGKYVCSAKLRMVTGLRNEPSNQSQGLFGAIAGFIEGGWT<br>GMVDGWYGYHHQNEQGSGYAADQKSTQNAINGITNKVNSVIEKMNTQLTAFGKEVNKLERMKQIEDKIEEIESKQIW<br>CYNAELLVLLENERTLDFHDSNVKNLYEKVKSQLKNNAKEIGNGCFEFYHKCNDECMESVKNGTYDYPKYSEESKLN<br>REKIDGVKLESMGVYQIEG |

What is claimed is:

1. An influenza hemagglutinin (HA) stem domain polypeptide comprising the amino acid sequence of SEQ ID NO: 53, 54, 70, or 71:

(SEQ ID NO: 53)
DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDGVSGR

DYKDDDDKLVPRGSPGSGYIPEAPRDGQAYVRKDGEWVLLSTFLGHHHHH

H, (SEQ ID NO: 54)
DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDG, (SEQ ID NO: 70)
DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDGVKLE

SMGVYQIEG, (SEQ ID NO: 71)
DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDGVKLE

SMGVYQILAIYSTVASSLVLLVSLGAISFWMCSNGSLQCRICI, wherein $X_1$ is an amino acid selected from the group consisting of E, I, K, V, A, and T;
$X_2$ is an amino acid selected from the group consisting of I, K, R, T, F, N, S and Y;
$X_3$ is an amino acid selected from the group consisting of D, F, V, Y, A, I, N, S, and T;
$X_4$ is an amino acid selected from the group consisting of I, K, R, T, E, G and V;
$X_5$ is an amino acid selected from the group consisting of E, K, M, V, R, and T;
$X_6$ is an amino acid selected from the group consisting of F, I, N, S, T, Y, H, and L;
$X_7$ is an amino acid selected from the group consisting of A, G, I, R, T, V, F, and S;
$X_8$ is an amino acid selected from the group consisting of F, I, N, S, T, Y, G, E, K, M, and V; and
$X_9$ is an amino acid selected from the group consisting of H, I, L, N, R, and S.

2. The influenza HA stem domain polypeptide of claim 1, wherein the polypeptide comprises the amino acid sequence of SEQ ID NO: 54:

(SEQ ID NO: 54)
DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDG.

3. The influenza HA stem domain polypeptide of claim 1, wherein the polypeptide comprises the amino acid sequence of SEQ ID NO: 70:

(SEQ ID NO: 70)
DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDGVKLE

SMGVYQIEG.

4. The influenza HA stem domain polypeptide of claim 1, wherein the polypeptide comprises the amino acid sequence of SEQ ID NO: 71:

(SEQ ID NO: 71)
DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDGVKLE

SMGVYQILAIYSTVASSLVLLVSLGAISFWMCSNGSLQCRICI.

5. An influenza hemagglutinin (HA) stem domain polypeptide, wherein the polypeptide comprises a peptide having the amino acid sequence selected from the group consisting of SEQ ID NO: 55 to SEQ ID NO:76.

6. An influenza hemagglutinin (HA) stem domain polypeptide, wherein the polypeptide comprises a peptide having the amino acid sequence selected from the group consisting of SEQ ID NO: 55, SEQ ID NO: 66 and SEQ ID NO: 73.

7. A nucleic acid molecule encoding the influenza HA stem domain polypeptide of claim 1.

8. A vector comprising the nucleic acid molecule of claim 7.

9. A composition comprising the influenza HA stem domain polypeptide of claim 1.

10. A vaccine comprising an effective amount of the influenza HA stem domain polypeptide of claim 1.

11. A method of inducing an immune response against influenza HA protein in a subject, the method comprising:

administering an effective amount of the influenza HA stem domain polypeptide of claim 1 to the subject to induce an immune response against influenza HA protein.

12. The influenza HA stem domain polypeptide of claim 6, wherein the polypeptide comprises SEQ ID NO: 55.

13. The influenza HA stem domain polypeptide of claim 6, wherein the polypeptide comprises SEQ ID NO: 66.

14. The influenza HA stem domain polypeptide of claim 6, wherein the polypeptide comprises SEQ ID NO: 73.

15. The influenza HA stem domain polypeptide of claim 1, wherein the polypeptide comprises the amino acid sequence of SEQ ID NO: 53:

(SEQ ID NO: 53)
DTICIGYHANNSTDTVDTVLEKNVTVTHSVNLLENGGGGKYVCSAKLRMV

TGLRNX$_1$PSX$_2$QSQGLFGAIAGX$_3$X$_4$EGGWTGMVDGWYGYHHQNEQGSGY

AADQKSTQNAINGITNKVNSVIEKX$_5$NTQX$_6$TAX$_7$GKEX$_8$NKX$_9$ERMKQI

EDKIEEIESKQIWCYNAELLVLLENERTLDFHDSNVKNLYEKVKSQLKNN

AKEIGNGCFEFYHKCNDECMESVKNGTYDYPKYSEESKLNREKIDGVSGR

DYKDDDDKLVPRGSPGSGYIPEAPRDGQAYVRKDGEWVLLSTFLGHHHHH

H.

16. A composition comprising the influenza HA stem domain polypeptide of claim 5.

17. A composition comprising the influenza HA stem domain polypeptide of claim 6.

18. A method of inducing an immune response against influenza HA protein in a subject, the method comprising:
administering an effective amount of the influenza HA stem domain polypeptide of claim 5 to the subject to induce an immune response against influenza HA protein.

19. A method of inducing an immune response against influenza HA protein in a subject, the method comprising:
administering an effective amount of the influenza HA stem domain polypeptide of claim 6 to the subject to induce an immune response against influenza HA protein.

20. The influenza HA stem domain polypeptide of claim 1, wherein the HA stem domain polypeptide comprises an influenza HA1 domain and an influenza HA2 domain, and the HA stem domain polypeptide is resistant to protease cleavage at the junction between the HA1 domain and the HA2 domain.

21. A nucleic acid molecule encoding the influenza HA stem domain polypeptide of claim 5.

22. A vector comprising the nucleic acid molecule of claim 21.

23. A nucleic acid molecule encoding the influenza HA stem domain polypeptide of claim 6.

24. A vector comprising the nucleic acid molecule of claim 23.

25. A vaccine comprising an effective amount of the influenza HA stem domain polypeptide of claim 5.

26. A vaccine comprising an effective amount of the influenza HA stem domain polypeptide of claim 6.

* * * * *

SEQUENCE LISTING

<160> NUMBER OF SEQ ID NOS: 82

<210> SEQ ID NO 1
<211> LENGTH: 565
<212> TYPE: PRT
<213> ORGANISM: Artificial Sequence
<220> FEATURE:
<223> OTHER INFORMATION: H1 Full length (A/Brisbane/59/2007)

<400> SEQUENCE: 1

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
```

```
                355                 360                 365
His Gln Asn Glu Gln Gly Ser Gly Tyr Ala Ala Asp Gln Lys Ser Thr
            370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Ile
            420                 425                 430
Asp Ile Trp Thr Tyr Asn Ala Glu Leu Leu Val Leu Leu Glu Asn Glu
                435                 440                 445
Arg Thr Leu Asp Phe His Asp Ser Asn Val Lys Asn Leu Tyr Glu Lys
            450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Lys Ile Asp Gly Val Lys Leu Glu Ser Met Gly Val Tyr Gln
            515                 520                 525
Ile Leu Ala Ile Tyr Ser Thr Val Ala Ser Ser Leu Val Leu Leu Val
            530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 2
<211> LENGTH: 301
<212> TYPE: PRT
<213> ORGANISM: Artificial Sequence
<220> FEATURE:
<223> OTHER INFORMATION: H1-mini2-cluster1+5+6-GCN4

<400> SEQUENCE: 2

Met Lys Val Lys Leu Leu Val Leu Leu Cys Thr Phe Thr Ala Thr Tyr
1               5                   10                  15
Ala Asp Thr Ile Cys Ile Gly Tyr His Ala Asn Asn Ser Thr Asp Thr
                20                  25                  30
Val Asp Thr Val Leu Glu Lys Asn Val Thr Val Thr His Ser Val Asn
            35                  40                  45
Leu Leu Glu Asn Gly Gly Gly Gly Lys Tyr Val Cys Ser Ala Lys Leu
50                  55                  60
Arg Met Val Thr Gly Leu Arg Asn Ile Pro Ser Ile Gln Ser Gln Gly
65                  70                  75                  80
Leu Phe Gly Ala Ile Ala Gly Phe Ile Glu Gly Gly Trp Thr Gly Met
                85                  90                  95
Val Asp Gly Trp Tyr Gly Tyr His His Gln Asn Glu Gln Gly Ser Gly
            100                 105                 110
Tyr Ala Ala Asp Gln Lys Ser Thr Gln Asn Ala Ile Asn Gly Ile Thr
            115                 120                 125
Asn Lys Val Asn Ser Val Ile Glu Lys Met Asn Thr Gln Ser Thr Ala
            130                 135                 140
Thr Gly Lys Glu Gly Asn Lys Ser Glu Arg Met Lys Gln Ile Glu Asp
```

```
            145                 150                 155                 160
Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 3
<211> LENGTH: 12
<212> TYPE: PRT
<213> ORGANISM: Artificial Sequence
<220> FEATURE:
<223> OTHER INFORMATION: foldon

<400> SEQUENCE: 3

Ala Tyr Val Arg Lys Asp Gly Glu Trp Val Leu Leu
1               5                   10

<210> SEQ ID NO 4
<211> LENGTH: 54
<212> TYPE: PRT
<213> ORGANISM: Artificial Sequence
<220> FEATURE:
<223> OTHER INFORMATION: FLAG-thrombin-foldon-HIS

<400> SEQUENCE: 4

Ser Gly Arg Asp Tyr Lys Asp Asp Asp Lys Leu Val Pro Arg Gly
1               5                   10                  15

Ser Pro Gly Ser Gly Tyr Ile Pro Glu Ala Pro Arg Asp Gly Gln Ala
            20                  25                  30

Tyr Val Arg Lys Asp Gly Glu Trp Val Leu Leu Ser Thr Phe Leu Gly
        35                  40                  45

His His His His His His
    50

<210> SEQ ID NO 5
<211> LENGTH: 15
<212> TYPE: PRT
<213> ORGANISM: Artificial Sequence
<220> FEATURE:
<223> OTHER INFORMATION: Trimerization domain

<400> SEQUENCE: 5

Met Lys Gln Ile Glu Asp Lys Ile Glu Glu Ile Glu Ser Lys Gln
1               5                   10                  15

<210> SEQ ID NO 6
```

```
<211> LENGTH: 292
<212> TYPE: PRT
<213> ORGANISM: Artificial Sequence
<220> FEATURE:
<223> OTHER INFORMATION: H1-mini2-cluster1+5+6-GCN4 without leader
      sequence and with FLAG-thrombin-foldon-HIS

<400> SEQUENCE: 6
```

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Ile Pro Ser Ile Gln Ser Gln Gly Leu
    50                  55                  60

Phe Gly Ala Ile Ala Gly Phe Ile Glu Gly Gly Trp Thr Gly Met Val
65              70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Ser Thr Ala Thr
        115                 120                 125

Gly Lys Glu Gly Asn Lys Ser Glu Arg Met Lys Gln Ile Glu Asp Lys
130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Ser Gly
225                 230                 235                 240

Arg Asp Tyr Lys Asp Asp Asp Lys Leu Val Pro Arg Gly Ser Pro
                245                 250                 255

Gly Ser Gly Tyr Ile Pro Glu Ala Pro Arg Asp Gly Gln Ala Tyr Val
            260                 265                 270

Arg Lys Asp Gly Glu Trp Val Leu Leu Ser Thr Phe Leu Gly His His
        275                 280                 285

His His His His
    290

```
<210> SEQ ID NO 7
<211> LENGTH: 89
<212> TYPE: PRT
<213> ORGANISM: Artificial Sequence
<220> FEATURE:
<223> OTHER INFORMATION: alpha factor leader sequence

<400> SEQUENCE: 7
```

Met Arg Phe Pro Ser Ile Phe Thr Ala Val Leu Phe Ala Ala Ser Ser
1               5                   10                  15

```
Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Lys Glu Glu Gly Val
65              70                  75                  80

Ser Leu Glu Lys Arg Glu Ala Glu Ala
                85

<210> SEQ ID NO 8
<211> LENGTH: 19
<212> TYPE: PRT
<213> ORGANISM: Artificial Sequence
<220> FEATURE:
<223> OTHER INFORMATION: H1 HA2 amino acid sequence connecting the
      C-terminal residue of helix A and the N-terminal residue of helix
      CD

<400> SEQUENCE: 8

Met Asn Thr Gln Phe Thr Ala Val Gly Lys Glu Phe Asn His Lys Leu
1               5                   10                  15

Glu Lys Arg

<210> SEQ ID NO 9
<211> LENGTH: 121
<212> TYPE: PRT
<213> ORGANISM: Artificial Sequence
<220> FEATURE:
<223> OTHER INFORMATION: CR6261 VH

<400> SEQUENCE: 9

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65              70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

<210> SEQ ID NO 10
<211> LENGTH: 112
<212> TYPE: PRT
<213> ORGANISM: Artificial Sequence
<220> FEATURE:
<223> OTHER INFORMATION: CR6261 VL PROTEIN

<400> SEQUENCE: 10

Gln Ser Val Leu Thr Gln Pro Pro Ser Val Ser Ala Ala Pro Gly Gln
1               5                   10                  15
```

Lys Val Thr Ile Ser Cys Ser Gly Ser Ser Asn Ile Gly Asn Asp
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
             85                  90                  95

Thr Ala Tyr Val Val Phe Gly Gly Gly Thr Lys Leu Thr Val Leu Gly
            100                 105                 110

<210> SEQ ID NO 11
<211> LENGTH: 121
<212> TYPE: PRT
<213> ORGANISM: Artificial Sequence
<220> FEATURE:
<223> OTHER INFORMATION: SC09-114 VH PROTEIN

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
             20                  25                  30

Ala Ile Ser Trp Val Arg Gln Ala Pro Gly Gln Gly Leu Asp Trp Met
         35                  40                  45

Gly Gly Ile Ser Pro Ile Phe Gly Ser Thr Ala Tyr Ala Gln Lys Phe
 50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
             85                  90                  95

Ala Arg His Gly Asn Tyr Tyr Tyr Ser Gly Met Asp Val Trp Gly
            100                 105                 110

Gln Gly Thr Thr Val Thr Val Ser Ser
        115                 120

<210> SEQ ID NO 12
<211> LENGTH: 110
<212> TYPE: PRT
<213> ORGANISM: Artificial Sequence
<220> FEATURE:
<223> OTHER INFORMATION: SC09-114 VL PROTEIN

<400> SEQUENCE: 12

Ser Tyr Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
             20                  25                  30

Ser Val Asn Trp Tyr Gln Gln Phe Pro Gly Thr Ala Pro Lys Leu Leu
         35                  40                  45

Ile Tyr Ser Asn Asp Gln Arg Pro Ser Val Val Pro Asp Arg Phe Ser
 50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Ser Ser Leu
             85                  90                  95

Lys Gly Ala Val Phe Gly Gly Gly Thr Gln Leu Thr Val Leu
            100                 105                 110

<210> SEQ ID NO 13
<211> LENGTH: 116
<212> TYPE: PRT
<213> ORGANISM: Artificial Sequence
<220> FEATURE:
<223> OTHER INFORMATION: SC08-057 VH PROTEIN

<400> SEQUENCE: 13

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Asp Ser Val Ile
            20                  25                  30

Phe Met Ser Trp Val Arg Gln Ala Pro Gly Lys Gly Leu Glu Cys Val
            35                  40                  45

Ser Ile Ile Tyr Ile Asp Asp Ser Thr Tyr Tyr Ala Asp Ser Val Lys
            50                  55                  60

Gly Arg Phe Thr Ile Ser Arg His Asn Ser Met Gly Thr Val Phe Leu
65                  70                  75                  80

Glu Met Asn Ser Leu Arg Pro Asp Asp Thr Ala Val Tyr Tyr Cys Ala
                85                  90                  95

Thr Glu Ser Gly Asp Phe Gly Asp Gln Thr Gly Pro Tyr His Tyr Tyr
            100                 105                 110

Ala Met Asp Val
        115

<210> SEQ ID NO 14
<211> LENGTH: 100
<212> TYPE: PRT
<213> ORGANISM: Artificial Sequence
<220> FEATURE:
<223> OTHER INFORMATION: SC08-057 VL PROTEIN

<400> SEQUENCE: 14

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Ile Gly Gly Tyr
            20                  25                  30

Asn Ala Val Ser Trp Tyr Gln His Pro Gly Lys Ala Pro Lys Leu
            35                  40                  45

Met Ile Tyr Glu Val Thr Ser Arg Pro Ser Gly Val Ser Asp Arg Phe
            50                  55                  60

Ser Ala Ser Arg Ser Gly Asp Thr Ala Ser Leu Thr Val Ser Gly Leu
65                  70                  75                  80

Gln Ala Glu Asp Glu Ala His Tyr Tyr Cys Cys Ser Phe Ala Asp Ser
                85                  90                  95

Asn Ile Leu Ile
        100

<210> SEQ ID NO 15
<211> LENGTH: 7
<212> TYPE: PRT
<213> ORGANISM: Artificial Sequence
<220> FEATURE:
<223> OTHER INFORMATION: Synthesized sequence

<400> SEQUENCE: 15

Gly Ser Ala Gly Ser Ala Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthesized sequence

<400> SEQUENCE: 16

Gly Ser Ala Gly Ser Ala
1               5

<210> SEQ ID NO 17
<211> LENGTH: 111
<212> TYPE: PRT
<213> ORGANISM: Artificial Sequence
<220> FEATURE:
<223> OTHER INFORMATION: SC08-020 VH

<400> SEQUENCE: 17

Gln Val Gln Leu Gln Gln Ser Gly Ala Glu Val Lys Thr Pro Gly Ala
1               5                   10                  15

Ser Val Lys Val Ser Cys Lys Ala Ser Gly Tyr Thr Phe Thr Arg Phe
                20                  25                  30

Gly Val Ser Trp Ile Arg Gln Ala Pro Gly Gln Gly Leu Glu Trp Ile
            35                  40                  45

Gly Trp Ile Ser Ala Tyr Asn Gly Asp Thr Tyr Tyr Ala Gln Lys Phe
    50                  55                  60

Gln Ala Arg Val Thr Met Thr Thr Asp Thr Ser Thr Thr Thr Ala Tyr
65                  70                  75                  80

Met Glu Met Arg Ser Leu Arg Ser Asp Asp Thr Ala Val Tyr Tyr Cys
                85                  90                  95

Ala Arg Glu Pro Pro Leu Phe Tyr Ser Ser Trp Ser Leu Asp Asn
            100                 105                 110

<210> SEQ ID NO 18
<211> LENGTH: 98
<212> TYPE: PRT
<213> ORGANISM: Artificial Sequence
<220> FEATURE:
<223> OTHER INFORMATION: SC08-020 VL
<220> FEATURE:
<221> NAME/KEY: misc_feature
<222> LOCATION: (4)..(4)
<223> OTHER INFORMATION: Xaa can be any naturally occurring amino acid

<400> SEQUENCE: 18

Glu Ile Val Xaa Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Asn
                20                  25                  30

Tyr Leu Ala Trp Phe Gln Gln Lys Pro Gly Gln Ala Pro Arg Leu Leu
            35                  40                  45

Ile Tyr Gly Ala Ser Arg Arg Ala Thr Gly Ile Pro Asp Arg Ile Ser
    50                  55                  60

Gly Ser Gly Ser Gly Thr Asp Phe Thr Leu Thr Ile Ser Arg Leu Glu
65                  70                  75                  80

Pro Ala Asp Phe Ala Val Tyr Tyr Cys Gln Gln Tyr Gly Thr Ser Pro
                85                  90                  95

Arg Thr

<210> SEQ ID NO 19

<400> SEQUENCE: 19

000

<210> SEQ ID NO 20
<211> LENGTH: 7
<212> TYPE: PRT
<213> ORGANISM: Artificial Sequence
<220> FEATURE:
<223> OTHER INFORMATION: His Tag

<400> SEQUENCE: 20

His His His His His His His
1               5

<210> SEQ ID NO 21
<211> LENGTH: 6
<212> TYPE: PRT
<213> ORGANISM: Artificial Sequence
<220> FEATURE:
<223> OTHER INFORMATION: His Tag

<400> SEQUENCE: 21

His His His His His His
1               5

<210> SEQ ID NO 22
<211> LENGTH: 8
<212> TYPE: PRT
<213> ORGANISM: Artificial Sequence
<220> FEATURE:
<223> OTHER INFORMATION: FLAG tag

<400> SEQUENCE: 22

Asp Tyr Lys Asp Asp Asp Asp Lys
1               5

<210> SEQ ID NO 23
<211> LENGTH: 6
<212> TYPE: PRT
<213> ORGANISM: Artificial Sequence
<220> FEATURE:
<223> OTHER INFORMATION: thrombin proteolytic site

<400> SEQUENCE: 23

Arg Ser Leu Val Pro Arg
1               5

<210> SEQ ID NO 24
<211> LENGTH: 4
<212> TYPE: PRT
<213> ORGANISM: Artificial Sequence
<220> FEATURE:
<223> OTHER INFORMATION: Factor X proteolytic site

<400> SEQUENCE: 24

Ile Glu Gly Arg
1

<210> SEQ ID NO 25
<211> LENGTH: 565
<212> TYPE: PRT
<213> ORGANISM: Artificial Sequence
<220> FEATURE:
<223> OTHER INFORMATION: A/Solomon ISlands/6/2003

<400> SEQUENCE: 25

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Lys Glu Asn Ala Tyr Val Ser Val Val Ser Ser His Tyr Ser Arg
210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
            275                 280                 285

Asp Glu Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
370                 375                 380

Gln Asn Ala Ile Asn Gly Ile Thr Asn Lys Val Asn Ser Val Ile Glu
385                 390                 395                 400
```

```
Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 26
<211> LENGTH: 564
<212> TYPE: PRT
<213> ORGANISM: Artificial Sequence
<220> FEATURE:
<223> OTHER INFORMATION: A/New Caledonia/20/1999

<400> SEQUENCE: 26

Lys Ala Lys Leu Leu Val Leu Leu Cys Thr Phe Thr Ala Thr Tyr Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Ser His Asn Gly Lys Leu Cys Leu Leu Lys Gly Ile Ala
    50                  55                  60

Pro Leu Gln Leu Gly Asn Cys Ser Val Ala Gly Trp Ile Leu Gly Asn
65                  70                  75                  80

Pro Glu Cys Glu Leu Leu Ile Ser Lys Glu Ser Trp Ser Tyr Ile Val
                85                  90                  95

Glu Thr Pro Asn Pro Glu Asn Gly Thr Cys Tyr Pro Gly Tyr Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Ser Ser Trp Pro Asn His Thr Val
    130                 135                 140

Thr Gly Val Ser Ala Ser Cys Ser His Asn Gly Lys Ser Ser Phe Tyr
145                 150                 155                 160

Arg Asn Leu Leu Trp Leu Thr Gly Lys Asn Gly Leu Tyr Pro Asn Leu
                165                 170                 175

Ser Lys Ser Tyr Val Asn Asn Lys Glu Lys Glu Val Leu Val Leu Trp
            180                 185                 190
```

```
Gly Val His His Pro Pro Asn Ile Gly Asn Gln Arg Ala Leu Tyr His
        195                 200                 205

Thr Glu Asn Ala Tyr Val Ser Val Val Ser Ser His Tyr Ser Arg Arg
    210                 215                 220

Phe Thr Pro Glu Ile Ala Lys Arg Pro Lys Val Arg Asp Gln Glu Gly
225                 230                 235                 240

Arg Ile Asn Tyr Tyr Trp Thr Leu Leu Glu Pro Gly Asp Thr Ile Ile
                245                 250                 255

Phe Glu Ala Asn Gly Asn Leu Ile Ala Pro Trp Tyr Ala Phe Ala Leu
                260                 265                 270

Ser Arg Gly Phe Gly Ser Gly Ile Ile Thr Ser Asn Ala Pro Met Asp
                275                 280                 285

Glu Cys Asp Ala Lys Cys Gln Thr Pro Gln Gly Ala Ile Asn Ser Ser
                290                 295                 300

Leu Pro Phe Gln Asn Val His Pro Val Thr Ile Gly Glu Cys Pro Lys
305                 310                 315                 320

Tyr Val Arg Ser Ala Lys Leu Arg Met Val Thr Gly Leu Arg Asn Ile
                325                 330                 335

Pro Ser Ile Gln Ser Arg Gly Leu Phe Gly Ala Ile Ala Gly Phe Ile
                340                 345                 350

Glu Gly Gly Trp Thr Gly Met Val Asp Gly Trp Tyr Gly Tyr His His
                355                 360                 365

Gln Asn Glu Gln Gly Ser Gly Tyr Ala Ala Asp Gln Lys Ser Thr Gln
                370                 375                 380

Asn Ala Ile Asn Gly Ile Thr Asn Lys Val Asn Ser Val Ile Glu Lys
385                 390                 395                 400

Met Asn Thr Gln Phe Thr Ala Val Gly Lys Glu Phe Asn Lys Leu Glu
                405                 410                 415

Arg Arg Met Glu Asn Leu Asn Lys Lys Val Asp Asp Gly Phe Leu Asp
                420                 425                 430

Ile Trp Thr Tyr Asn Ala Glu Leu Leu Val Leu Leu Glu Asn Glu Arg
                435                 440                 445

Thr Leu Asp Phe His Asp Ser Asn Val Lys Asn Leu Tyr Glu Lys Val
    450                 455                 460

Lys Ser Gln Leu Lys Asn Asn Ala Lys Glu Ile Gly Asn Gly Cys Phe
465                 470                 475                 480

Glu Phe Tyr His Lys Cys Asn Asn Glu Cys Met Glu Ser Val Lys Asn
                485                 490                 495

Gly Thr Tyr Asp Tyr Pro Lys Tyr Ser Glu Glu Ser Lys Leu Asn Arg
                500                 505                 510

Glu Lys Ile Asp Gly Val Lys Leu Glu Ser Met Gly Val Tyr Gln Ile
                515                 520                 525

Leu Ala Ile Tyr Ser Thr Val Ala Ser Ser Leu Val Leu Leu Val Ser
    530                 535                 540

Leu Gly Ala Ile Ser Phe Trp Met Cys Ser Asn Gly Ser Leu Gln Cys
545                 550                 555                 560

Arg Ile Cys Ile

<210> SEQ ID NO 27
<211> LENGTH: 566
<212> TYPE: PRT
<213> ORGANISM: Artificial Sequence
<220> FEATURE:
<223> OTHER INFORMATION: A/California/07/2009
```

<400> SEQUENCE: 27

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
```

```
                    405                 410                 415
Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
            530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

```
<210> SEQ ID NO 28
<211> LENGTH: 566
<212> TYPE: PRT
<213> ORGANISM: Artificial Sequence
<220> FEATURE:
<223> OTHER INFORMATION: A/swine/Hubei/S1/2009

<400> SEQUENCE: 28

Met Glu Ala Lys Leu Phe Val Leu Phe Cys Ala Phe Thr Ala Leu Lys
1               5                   10                  15

Ala Asp Thr Phe Cys Val Gly Tyr His Ala Asn Tyr Ser Thr His Thr
            20                  25                  30

Val Asp Thr Ile Leu Glu Lys Asn Val Thr Val Thr His Ser Val Asn
            35                  40                  45

Leu Leu Glu Asn Ser His Asn Gly Lys Leu Cys Ser Leu Asn Gly Lys
        50                  55                  60

Ile Pro Leu Gln Leu Gly Asn Cys Asn Val Ala Gly Trp Ile Leu Gly
65                  70                  75                  80

Asn Pro Lys Cys Asp Leu Leu Leu Thr Ala Asn Ser Ser Ser Tyr Ile
                85                  90                  95

Ile Glu Thr Ser Lys Ser Lys Asn Gly Ala Cys Tyr Pro Gly Glu Phe
            100                 105                 110

Ala Asp Tyr Glu Glu Leu Lys Glu Gln Leu Ser Thr Val Ser Ser Phe
            115                 120                 125

Glu Arg Phe Glu Ile Phe Pro Lys Ala Ile Ser Trp Pro Asp His Asp
        130                 135                 140

Ala Thr Arg Gly Thr Thr Val Ala Cys Ser His Ser Gly Val Asn Ser
145                 150                 155                 160

Phe Tyr Arg Asn Leu Leu Ser Thr Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asp Ser Val Gln Gln Thr Leu
```

```
            195                 200                 205
Tyr Gln Asn Lys His Thr Tyr Val Ser Val Gly Ser Ser Lys Tyr Tyr
210                 215                 220

Lys Arg Phe Thr Pro Glu Ile Val Ala Arg Pro Lys Val Arg Gly Gln
225                 230                 235                 240

Ala Gly Arg Met Asn Tyr Tyr Trp Thr Leu Phe Asp Gln Gly Asp Thr
                245                 250                 255

Ile Thr Phe Glu Ala Thr Gly Asn Leu Ile Ala Pro Trp His Ala Phe
                260                 265                 270

Ala Leu Lys Lys Gly Ser Ser Ser Gly Ile Met Leu Ser Asp Ala Gln
            275                 280                 285

Val His Asn Cys Thr Thr Lys Cys Gln Thr Pro His Gly Ala Leu Lys
        290                 295                 300

Asn Asn Leu Pro Leu Gln Asn Val His Leu Phe Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Arg Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Ile Ala Ile Asp Gly Ile Asn Asn Lys Ala Asn Ser Val Ile
385                 390                 395                 400

Gly Lys Met Asn Ile Gln Leu Thr Ser Val Gly Lys Glu Phe Asn Ser
                405                 410                 415

Leu Glu Lys Arg Lys Glu Asn Leu Asn Lys Thr Val Asp Asp Arg Phe
                420                 425                 430

Leu Asp Val Trp Thr Phe Asn Ala Glu Leu Leu Val Leu Leu Glu Asn
            435                 440                 445

Gln Arg Thr Leu Glu Phe His Asp Leu Asn Ile Lys Ser Leu Tyr Glu
        450                 455                 460

Lys Val Lys Ser His Leu Arg Asn Asn Asp Lys Glu Ile Gly Asn Gly
465                 470                 475                 480

Cys Phe Glu Phe Tyr His Lys Arg Asp Asn Glu Cys Leu Glu Cys Val
                485                 490                 495

Lys Asn Gly Thr Tyr Asn Tyr Pro Lys Tyr Ser Glu Glu Ser Lys Phe
                500                 505                 510

Asn Arg Glu Glu Ile Val Gly Val Lys Leu Glu Ser Met Gly Ile His
            515                 520                 525

Gln Ile Leu Ala Ile Tyr Ser Thr Val Ala Ser Ser Leu Val Leu Leu
        530                 535                 540

Val Ser Leu Gly Ala Ile Ser Phe Trp Met Cys Ser Asn Gly Ser Leu
545                 550                 555                 560

Gln Cys Arg Val Cys Ile
                565

<210> SEQ ID NO 29
<211> LENGTH: 566
<212> TYPE: PRT
<213> ORGANISM: Artificial Sequence
<220> FEATURE:
<223> OTHER INFORMATION: A/swine/Haseluenne/IDT2617/2003
```

<400> SEQUENCE: 29

```
Met Glu Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Ile Asn
        35                  40                  45

Leu Leu Glu Asn Asn His Asn Gly Lys Leu Cys Ser Leu Asn Gly Lys
    50                  55                  60

Ala Pro Leu Gln Leu Gly Asn Cys Asn Val Ala Gly Trp Ile Leu Gly
65              70                  75                  80

Asn Pro Glu Cys Asp Leu Leu Leu Thr Val Asp Ser Trp Ser Tyr Ile
                85                  90                  95

Ile Glu Thr Ser Asn Ser Lys Asn Gly Ala Cys Tyr Pro Gly Glu Phe
            100                 105                 110

Ala Asp Tyr Glu Glu Leu Arg Glu Gln Leu Ser Thr Val Ser Ser Phe
        115                 120                 125

Glu Arg Phe Glu Ile Phe Pro Lys Ala Thr Ser Trp Pro Asn His Asp
    130                 135                 140

Thr Thr Arg Gly Thr Thr Ile Ser Cys Ser His Ser Gly Ala Asn Ser
145                 150                 155                 160

Phe Tyr Arg Asn Leu Leu Trp Ile Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asp Ser Asp Gln Gln Thr Leu
        195                 200                 205

Tyr Gln Asn Asn His Thr Tyr Val Ser Val Gly Ser Ser Lys Tyr Tyr
    210                 215                 220

Gln Arg Phe Thr Pro Glu Ile Val Thr Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp His Ala Phe
            260                 265                 270

Ala Leu Asn Lys Gly Pro Ser Ser Gly Ile Met Ile Ser Asp Ala His
        275                 280                 285

Val His Asn Cys Thr Thr Lys Cys Gln Thr Pro His Gly Ala Leu Lys
    290                 295                 300

Ser Asn Leu Pro Phe Gln Asn Val His Pro Ser Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Ile Ala Ile Asp Gly Ile Asn Asn Lys Val Asn Ser Ile Ile
385                 390                 395                 400

Glu Lys Met Asn Thr Gln Phe Thr Ser Val Gly Lys Glu Phe Asn Asp
                405                 410                 415
```

```
Leu Glu Lys Arg Ile Glu Asn Leu Asn Lys Val Asp Asp Gly Phe
                420                 425                 430
Leu Asp Val Trp Thr Tyr Asn Ala Glu Leu Leu Ile Leu Leu Glu Asn
        435                 440                 445
Glu Arg Thr Leu Asp Phe His Asp Phe Asn Val Lys Asn Leu Tyr Glu
    450                 455                 460
Lys Val Lys Ser Gln Leu Arg Asn Asn Ala Lys Glu Ile Gly Asn Gly
465                 470                 475                 480
Cys Phe Glu Phe Tyr His Lys Cys Asp Asn Glu Cys Met Glu Ser Val
            485                 490                 495
Lys Asn Gly Thr Tyr Asn Tyr Pro Lys Tyr Ser Glu Glu Ser Lys Leu
            500                 505                 510
Asn Arg Glu Lys Ile Asp Gly Val Lys Leu Glu Ser Met Gly Val His
            515                 520                 525
Gln Ile Leu Ala Ile Tyr Ser Thr Val Ala Ser Ser Leu Val Leu Leu
        530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 30
<211> LENGTH: 565
<212> TYPE: PRT
<213> ORGANISM: Artificial Sequence
<220> FEATURE:
<223> OTHER INFORMATION: A/New York/8/2006

<400> SEQUENCE: 30

Met Lys Val Lys Leu Leu Val Leu Leu Cys Thr Phe Thr Ala Thr Tyr
1               5                   10                  15
Ala Asp Thr Ile Cys Ile Gly Tyr His Ala Asn Asn Ser Thr Asp Thr
            20                  25                  30
Val Asp Thr Val Leu Gl

His Thr Glu Asn Ala Tyr Val Ser Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Phe Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Arg Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 31
<211> LENGTH: 565
<212> TYPE: PRT
<213> ORGANISM: Artificial Sequence
<220> FEATURE:
<223> OTHER INFORMATION: A/Solomon Islands/3/2006

<400> SEQUENCE: 31

```
Met Lys Val Lys Leu Leu Val Leu Leu Cys Thr Phe Thr Ala Thr Tyr
1               5                   10                  15
Ala Asp Thr Ile Cys Ile Gly Tyr His Ala Asn Asn Ser Thr Asp Thr
                20                  25                  30
Val Asp Thr Val Leu Glu Lys Asn Val Thr Val Thr His Ser Val Asn
            35                  40                  45
Leu Leu Glu Asp Ser His Asn Gly Lys Leu Cys Leu Leu Lys Gly Ile
50                  55                  60
Ala Pro Leu Gln Leu Gly Asn Cys Ser Val Ala Gly Trp Ile Leu Gly
65                  70                  75                  80
Asn Pro Glu Cys Glu Leu Leu Ile Ser Arg Glu Ser Trp Ser Tyr Ile
                85                  90                  95
Val Glu Lys Pro Asn Pro Glu Asn Gly Thr Cys Tyr Pro Gly His Phe
                100                 105                 110
Ala Asp Tyr Glu Glu Leu Arg Glu Gln Leu Ser Ser Val Ser Ser Phe
            115                 120                 125
Glu Arg Phe Glu Ile Phe Pro Lys Glu Ser Ser Trp Pro Asn His Thr
        130                 135                 140
Thr Thr Gly Val Ser Ala Ser Cys Ser His Asn Gly Glu Ser Ser Phe
145                 150                 155                 160
Tyr Lys Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
            180                 185                 190
Trp Gly Val His His Pro Pro Asn Ile Gly Asp Gln Arg Ala Leu Tyr
        195                 200                 205
His Lys Glu Asn Ala Tyr Val Ser Val Val Ser Ser His Tyr Ser Arg
210                 215                 220
Lys Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
            260                 265                 270
Leu Ser Arg Gly Phe Gly Ser Gly Ile Ile Asn Ser Asn Ala Pro Met
        275                 280                 285
Asp Glu Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
    370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
```

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
    435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 32
<211> LENGTH: 566
<212> TYPE: PRT
<213> ORGANISM: Artificial Sequence
<220> FEATURE:
<223> OTHER INFORMATION: A/New York/146/2000

<400> SEQUENCE: 32

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Thr
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Ala Glu Thr Pro Asn Pro Lys Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Asp Ser Ser Trp Pro Asn His Thr
130                 135                 140

Val Thr Lys Gly Val Thr Ala Ser Cys Ser His Asn Gly Lys Ser Ser
145                 150                 155                 160

Phe Tyr Lys Asn Leu Leu Trp Leu Thr Glu Lys Asn Gly Leu Tyr Pro
                165                 170                 175

Asn Leu Ser Lys Ser Tyr Val Asn Lys Lys Gly Lys Glu Val Leu Val
            180                 185                 190

Leu Trp Gly Val His His Pro Ser Asn Met Gly Asp Gln Arg Ala Ile
        195                 200                 205

Tyr His Lys Glu Asn Ala Tyr Val Ser Val Leu Ser Ser His Tyr Ser
210                215                      220

Arg Arg Phe Thr Pro Glu Ile Ala Lys Arg Pro Lys Val Arg Asp Gln
225                230                  235                240

Glu Gly Arg Ile Asn Tyr Tyr Trp Thr Leu Leu Glu Pro Gly Asp Thr
                245                250                  255

Ile Ile Phe Glu Ala Asn Gly Asn Leu Ile Ala Pro Trp Tyr Ala Phe
                260              265                  270

Ala Leu Ser Arg Gly Phe Gly Ser Gly Ile Ile Ile Ser Asn Ala Ser
            275              280                  285

Met Gly Glu Cys Asp Ala Lys Cys Gln Thr Pro Gln Gly Ala Ile Asn
290                  295              300

Ser Ser Leu Pro Phe Gln Asn Val His Pro Val Thr Ile Gly Glu Cys
305              310                  315                  320

Pro Lys Tyr Val Arg Ser Thr Lys Leu Arg Met Val Thr Gly Leu Arg
                325              330                  335

Asn Val Pro Ser Ile Gln Ser Arg Gly Leu Phe Gly Ala Ile Ala Gly
            340                  345              350

Phe Ile Glu Gly Gly Trp Thr Gly Met Ile Asp Gly Trp Tyr Gly Tyr
            355                  360              365

His His Gln Asn Glu Gln Gly Ser Gly Tyr Ala Ala Asp Gln Lys Ser
    370                  375              380

Thr Gln Asn Ala Ile Asn Gly Ile Thr Asn Lys Val Asn Ser Ile Ile
385                  390              395                  400

Glu Lys Met Asn Thr Gln Phe Thr Ala Val Gly Lys Glu Phe Asn Lys
                405              410                  415

Leu Glu Lys Arg Met Glu Asn Leu Asn Lys Lys Val Asp Asp Gly Phe
            420              425              430

Leu Asp Ile Trp Thr Tyr Asn Ala Glu Leu Leu Val Leu Leu Glu Asn
        435              440              445

Glu Arg Thr Leu Asp Phe His Asp Leu Asn Val Lys Asn Leu Tyr Glu
    450                  455              460

Lys Val Lys Asn Gln Leu Lys Asn Asn Ala Lys Glu Ile Gly Asn Gly
465              470                  475              480

Cys Phe Glu Phe Tyr His Lys Cys Asn Asn Glu Cys Met Glu Ser Val
                485              490              495

Lys Asn Gly Thr Tyr Asp Tyr Pro Lys Tyr Ser Lys Glu Ser Lys Leu
            500              505              510

Asn Arg Glu Lys Ile Asp Gly Val Lys Leu Glu Ser Met Gly Val Tyr
            515              520              525

Gln Ile Leu Ala Ile Tyr Ser Thr Val Ala Ser Ser Leu Val Leu Leu
530              535              540

Val Ser Leu Gly Ala Ile Ser Phe Trp Met Cys Ser Asn Gly Ser Leu
545              550              555              560

Gln Cys Arg Ile Cys Ile
            565

<210> SEQ ID NO 33
<211> LENGTH: 566
<212> TYPE: PRT
<213> ORGANISM: Artificial Sequence
<220> FEATURE:
<223> OTHER INFORMATION: A/New York/653/1996

<400> SEQUENCE: 33

```
Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Thr
50                      55                  60

Ala Pro Leu Gln Leu Gly Asn Cys Ser Val Ala Gly Trp Ile Leu Gly
65                      70                  75                  80

Asn Pro Glu Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
            130                 135                 140

Val Thr Lys Gly Val Thr Ala Ser Cys Ser His Asn Gly Lys Ser Ser
145                 150                 155                 160

Phe Tyr Lys Asn Leu Leu Trp Leu Thr Glu Lys Asn Gly Leu Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
            195                 200                 205

Tyr His Thr Glu Asn Ala Tyr Val Ser Val Val Ser Ser His Tyr Ser
            210                 215                 220

Arg Arg Phe Thr Pro Glu Ile Thr Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ser
            275                 280                 285

Met Gly Glu Cys Asp Ala Lys Cys Gln Thr Pro Gln Gly Ala Ile Asn
            290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
```

```
                420             425             430
Leu Asp Ile Trp Thr Tyr Asn Ala Glu Leu Leu Val Leu Leu Glu Asn
            435             440             445

Glu Arg Thr Leu Asp Phe His Asp Ser Asn Val Lys Asn Leu Tyr Glu
        450             455             460

Lys Val Lys Thr Gln Leu Lys Asn Asn Ala Lys Glu Ile Gly Asn Gly
465             470             475             480

Cys Phe Glu Phe Tyr His Lys Cys Asn Asn Glu Cys Met Glu Ser Val
                485             490             495

Lys Asn Gly Thr Tyr Asp Tyr Pro Lys Tyr Ser Glu Glu Ser Lys Leu
            500             505             510

Asn Arg Glu Lys Ile Asp Gly Val Lys Leu Glu Ser Met Gly Val Tyr
        515             520             525

Gln Ile Leu Ala Ile Tyr Ser Thr Val Ala Ser Ser Leu Val Leu Leu
    530             535             540

Val Ser Leu Gly Ala Ile Ser Phe Trp Met Cys Ser Asn Gly Ser Leu
545             550             555             560

Gln Cys Arg Ile Cys Ile
            565

<210> SEQ ID NO 34
<211> LENGTH: 565
<212> TYPE: PRT
<213> ORGANISM: Artificial Sequence
<220> FEATURE:
<223> OTHER INFORMATION: A/Beijing/262/1995

<400> SEQUENCE: 34

Met Lys Ala Lys Leu Leu Val Leu Leu Cys Thr Phe Thr Ala Thr Tyr
1               5               10              15

Ala Asp Thr Ile Cys Ile Gly Tyr His Ala Asn Asn Ser Thr Asp Thr
            20              25              30

Val Asp Thr Val Leu Glu Lys Asn Val Thr Val Thr His Ser Val Asn
        35              40              45

Leu Leu Glu Asp Ser His Asn Gly Lys Leu Cys Leu Leu Lys Gly Ile
    50              55              60

Ala Pro Leu Gln Leu Gly Asn Cys Ser Val Ala Gly Trp Ile Leu Gly
65              70              75              80

Asn Pro Glu Cys Glu Ser Leu Ile Ser Lys Glu Ser Trp Ser Tyr Ile
                85              90              95

Val Glu Thr Pro Asn Pro Glu Asn Gly Thr Cys Tyr Pro Gly Tyr Phe
            100             105             110

Ala Asp Tyr Glu Glu Leu Arg Glu Gln Leu Ser Ser Val Ser Ser Phe
        115             120             125

Glu Arg Phe Glu Ile Phe Pro Lys Glu Ser Ser Trp Pro Asn His Thr
    130             135             140

Val Thr Gly Val Thr Ala Ser Cys Ser His Asn Gly Lys Ser Ser Phe
145             150             155             160

Tyr Arg Asn Leu Leu Trp Leu Thr Glu Lys Asn Gly Leu Tyr Pro Asn
                165             170             175

Leu Ser Asn Ser Tyr Val Asn Asn Lys Glu Lys Glu Val Leu Val Leu
            180             185             190

Trp Gly Val His His Pro Ser Asn Ile Arg Asp Gln Arg Ala Ile Tyr
        195             200             205

His Thr Glu Asn Ala Tyr Val Ser Val Val Ser Ser His Tyr Ser Arg
```

```
                    210                 215                 220
Arg Phe Thr Pro Glu Ile Ala Lys Arg Pro Lys Val Arg Gly Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
                260                 265                 270

Leu Ser Arg Gly Phe Gly Ser Gly Ile Ile Thr Ser Asn Ala Pro Met
            275                 280                 285

Asn Glu Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Met Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 35
<211> LENGTH: 600
<212> TYPE: PRT
<213> ORGANISM: Artificial Sequence
<220> FEATURE:
<223> OTHER INFORMATION: A/Texas/36/1991

<400> SEQUENCE: 35

Met Lys Ala Lys Leu Leu Val Leu Leu Cys Ala Phe Thr Ala Thr Tyr
```

```
1               5                   10                  15
Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Val Ala Gly Trp Ile Leu Gly
65                  70                  75                  80

Asn Pro Lys Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
                130                 135                 140

Val Thr Lys Gly Val Thr Thr Ser Cys Ser His Asn Gly Lys Ser Ser
145                 150                 155                 160

Phe Tyr Arg Asn Leu Leu Trp Leu Thr Lys Lys Asn Gly Leu Tyr Pro
                165                 170                 175

Asn Val Ser Lys Ser Tyr Val Asn Asn Lys Glu Lys Glu Val Leu Val
                180                 185                 190

Leu Trp Gly Val His His Pro Ser Asn Ile Gly Asp Gln Arg Ala Ile
                195                 200                 205

Tyr His Thr Glu Asn Ala Tyr Val Ser Val Val Ser Ser His Tyr Ser
                210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ser
                275                 280                 285

Met Asp Glu Cys Asp Ala Lys Cys Gln Thr Pro Gln Gly Ala Ile Asn
                290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
                355                 360                 365

His His Gln Asn Glu Gln Gly Ser Gly Tyr Ala Ala Asp Gln Lys Ser
                370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
                420                 425                 430
```

```
Leu Asp Ile Trp Thr Tyr Asn Ala Glu Leu Leu Val Leu Leu Glu Asn
        435                 440                 445

Gly Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Met Glu Asn Leu Asn Lys Lys Val Asp Gly Phe Leu Asp Ile Trp
            485                 490                 495

Thr Tyr Asn Ala Glu Leu Leu Val Leu Leu Glu Asn Glu Arg Thr Leu
                500                 505                 510

Asp Phe His Asp Ser Asn Val Lys Asn Leu Tyr Glu Lys Val Lys Ser
        515                 520                 525

Gln Leu Lys Asn Asn Ala Lys Glu Ile Gly Asn Gly Cys Phe Glu Phe
    530                 535                 540

Tyr His Lys Cys Asn Asn Glu Cys Met Glu Ser Val Lys Asn Gly Thr
545                 550                 555                 560

Tyr Asp Tyr Pro Lys Tyr Ser Glu Glu Ser Lys Leu Asn Arg Gly Lys
                565                 570                 575

Ile Asp Gly Val Lys Leu Glu Ser Met Gly Val Tyr Gln Ile Leu Ala
            580                 585                 590

Ile Tyr Ser Thr Val Ala Ser Ser
        595                 600

<210> SEQ ID NO 36
<211> LENGTH: 566
<212> TYPE: PRT
<213> ORGANISM: Artificial Sequence
<220> FEATURE:
<223> OTHER INFORMATION: A/Singapore/6/1986

<400> SEQUENCE: 36

Met Lys Ala Lys Leu Leu Val Leu Leu Cys Ala Phe Thr Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Lys Gly Arg Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
            180                 185                 190
```

```
Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Asn
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
                260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
                500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 37
<211> LENGTH: 506
<212> TYPE: PRT
<213> ORGANISM: Artificial Sequence
<220> FEATURE:
```

-continued

<223> OTHER INFORMATION: A/Chile/1/1983

<400> SEQUENCE: 37

```
Met Lys Ala Lys Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Ser Tyr Val Asn Asn Lys Glu Lys
        115                 120                 125

Glu Val Leu Val Leu Trp Gly Val His His Pro Ser Asn Ile Glu Asp
    130                 135                 140

Gln Lys Thr Ile Tyr Arg Lys Glu Asn Ala Tyr Val Ser Val Val Ser
145                 150                 155                 160

Ser His Tyr Asn Arg Arg Phe Thr Pro Glu Ile Ala Lys Arg Pro Lys
                165                 170                 175

Val Arg Asn Gln Glu Gly Arg Ile Asn Tyr Tyr Trp Thr Leu Leu Glu
            180                 185                 190

Pro Gly Asp Thr Ile Ile Phe Glu Ala Asn Gly Asn Leu Ile Ala Pro
        195                 200                 205

Trp Tyr Ala Phe Ala Leu Ser Arg Gly Phe Gly Ser Gly Ile Ile Thr
    210                 215                 220

Ser Asn Ala Ser Met Asp Glu Cys Asp Ala Lys Cys Gln Thr Pro Gln
225                 230                 235                 240

Gly Ala Ile Asn Ser Ser Leu Pro Phe Gln Asn Val His Pro Val Thr
                245                 250                 255

Ile Gly Glu Cys Pro Lys Tyr Val Arg Ser Thr Lys Leu Arg Met Val
            260                 265                 270

Thr Gly Leu Arg Asn Ile Pro Ser Ile Gln Ser Arg Gly Leu Phe Gly
        275                 280                 285

Ala Ile Ala Gly Phe Ile Glu Gly Gly Trp Thr Gly Met Ile Asp Gly
    290                 295                 300

Trp Tyr Gly Tyr His His Gln Asn Glu Gln Gly Ser Gly Tyr Ala Ala
305                 310                 315                 320

Asp Gln Lys Ser Thr Gln Asn Ala Ile Asn Gly Ile Thr Asn Lys Val
                325                 330                 335

Asn Ser Ile Ile Glu Lys Met Asn Thr Gln Phe Thr Ala Val Gly Lys
            340                 345                 350

Glu Phe Asn Lys Leu Glu Lys Arg Met Glu Asn Leu Asn Lys Lys Val
        355                 360                 365

Asp Asp Gly Phe Leu Asp Ile Trp Thr Tyr Asn Ala Glu Leu Leu Val
    370                 375                 380

Leu Leu Glu Asn Glu Arg Thr Leu Asp Phe His Asp Ser Asn Val Lys
385                 390                 395                 400
```

```
Asn Leu Tyr Glu Lys Val Lys Ser Gln Leu Lys Asn Asn Ala Lys Glu
                405             410             415

Ile Gly Asn Gly Cys Phe Glu Phe Tyr His Lys Cys Asn Asn Glu Cys
            420             425             430

Met Glu Ser Val Lys Asn Gly Thr Tyr Asp Tyr Pro Lys Tyr Ser Glu
            435             440             445

Glu Ser Lys Leu Asn Arg Glu Lys Ile Asp Gly Val Lys Leu Glu Ser
        450             455             460

Met Gly Val Tyr Gln Ile Leu Ala Ile Tyr Ser Thr Val Ala Ser Ser
465             470             475             480

Leu Val Leu Leu Val Ser Leu Gly Ala Ile Ser Phe Trp Met Cys Ser
                485             490             495

Asn Gly Ser Leu Gln Cys Arg Ile Cys Ile
                500             505

<210> SEQ ID NO 38
<211> LENGTH: 566
<212> TYPE: PRT
<213> ORGANISM: Artificial Sequence
<220> FEATURE:
<223> OTHER INFORMATION: A/Baylor/11515/1982

<400> SEQUENCE: 38

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Ser Ile Ala Gly Trp Ile Leu Gly
65              70                  75                  80

Asn Pro Glu Cys Glu Ser Leu Phe Ser Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Ser
130                 135                 140

Val Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asp Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser His Tyr Asn
210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255
```

```
Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Val Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 39
<211> LENGTH: 505
<212> TYPE: PRT
<213> ORGANISM: Artificial Sequence
<220> FEATURE:
<223> OTHER INFORMATION: A/Brazil/11/1978

<400> SEQUENCE: 39

```
Lys Ala Lys Leu Leu Val Leu Leu Cys Ala Leu Ser Ala Thr Asp Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45
```

```
Leu Glu Asp Ser His Asn Gly Lys Leu Cys Arg Leu Lys Gly Ile Ala
 50                  55                  60

Pro Leu Gln Leu Gly Lys Cys Ser Ile Ala Gly Trp Ile Leu Gly Asn
 65                  70                  75                  80

Pro Glu Cys Glu Ser Leu Phe Ser Lys Ser Trp Ser Tyr Ile Ala
                 85                  90                  95

Glu Thr Pro Asn Ser Glu Asn Gly Thr Cys Tyr Pro Gly Tyr Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Arg Ser Trp Pro Lys His Asn Ile
    130                 135                 140

Thr Arg Gly Val Thr Ala Ser Cys Ser His Lys Gly Lys Ser Ser Phe
145                 150                 155                 160

Tyr Arg Asn Leu Leu Trp Leu Thr Glu Lys Asn Gly Ser Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Ser Asn Ile Glu Asp Gln Lys Thr Ile Tyr
        195                 200                 205

Arg Lys Glu Asn Ala Tyr Val Ser Val Val Ser Ser Asn Tyr Asn Arg
    210                 215                 220

Arg Phe Thr Pro Glu Ile Ala Lys Arg Pro Lys Val Arg Gly Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Ser Met
        275                 280                 285

Asp Glu Cys Asp Thr Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Leu
```

```
                    465                 470                 475                 480

Val Leu Leu Val Ser Leu Gly Ala Ile Ser Phe Trp Met Cys Ser Asn
                        485                 490                 495

Gly Ser Leu Gln Cys Arg Ile Cys Ile
                500                 505

<210> SEQ ID NO 40
<211> LENGTH: 566
<212> TYPE: PRT
<213> ORGANISM: Artificial Sequence
<220> FEATURE:
<223> OTHER INFORMATION: A/USSR/90/1977

<400> SEQUENCE: 40

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn

```
                    325                 330                 335
Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
                355                 360                 365

His His Gln Asn Glu Gln Gly Ser Gly Tyr Ala Ala Asp Gln Lys Ser
                370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Phe His Asp Ser Asn Val Lys Asn Leu Tyr Glu
                450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
                500                 505                 510

Asn Arg Glu Lys Ile Asp Gly Val Lys Leu Glu Ser Met Gly Val Tyr
                515                 520                 525

Gln Ile Leu Ala Ile Tyr Ser Thr Val Ala Ser Ser Leu Val Leu Leu
                530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 41
<211> LENGTH: 566
<212> TYPE: PRT
<213> ORGANISM: Artificial Sequence
<220> FEATURE:
<223> OTHER INFORMATION: A/New Jersey/8/1976

<400> SEQUENCE: 41

Met Lys Ala Lys Leu Leu Val Leu Leu Cys Ala Phe Thr Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His

-continued

```
            115                 120                 125
Glu Arg Phe Glu Ile Phe Pro Lys Glu Ser Ser Trp Pro Asn His Thr
130                 135                 140
Val Thr Lys Gly Val Thr Ala Ser Cys Ser His Lys Gly Arg Ser Ser
145                 150                 155                 160
Phe Tyr Arg Asn Leu Leu Trp Leu Thr Lys Asn Gly Ser Tyr Pro
            165                 170                 175
Asn Leu Ser Lys Ser Tyr Val Asn Asn Lys Glu Lys Glu Val Leu Val
                180                 185                 190
Leu Trp Gly Val His His Pro Ser Asn Ile Gly Asp Gln Arg Ala Ile
            195                 200                 205
Tyr His Thr Glu Asn Ala Tyr Val Ser Val Val Ser Ser His Tyr Asn
    210                 215                 220
Arg Arg Phe Thr Pro Glu Ile Ala Lys Arg Pro Lys Val Arg Asp Gln
225                 230                 235                 240
Glu Gly Arg Ile Asn Tyr Tyr Trp Thr Leu Leu Glu Pro Gly Asp Thr
            245                 250                 255
Ile Ile Phe Glu Ala Asn Gly Asn Leu Ile Ala Pro Trp Tyr Ala Phe
            260                 265                 270
Ala Leu Ser Arg Gly Phe Gly Ser Gly Ile Ile Thr Ser Asn Ala Ser
            275                 280                 285
Met Asp Glu Cys Asp Ala Lys Cys Gln Thr Pro Gln Gly Ala Ile Asn
    290                 295                 300
Ser Ser Leu Pro Phe Gln Asn Val His Pro Val Thr Ile Gly Glu Cys
305                 310                 315                 320
Pro Lys Tyr Val Arg Ser Thr Lys Leu Arg Met Val Thr Gly Leu Arg
            325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Ile Asp Gly Trp Tyr Gly Tyr
            355                 360                 365
His His Gln Asn Glu Gln Gly Ser Gly Tyr Ala Ala Asp Gln Lys Ser
    370                 375                 380
Thr Gln Asn Ala Ile Asn Gly Ile Thr Asn Lys Val Asn Ser Val Ile
385                 390                 395                 400
Glu Lys Met Asn Thr Gln Phe Thr Ala Val Gly Lys Glu Phe Asn Lys
            405                 410                 415
Leu Glu Arg Arg Met Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
            435                 440                 445
Glu Arg Thr Leu Asp Phe His Asp Ser Asn Val Lys Asn Leu Tyr Glu
    450                 455                 460
Lys Val Lys Ser Gln Leu Lys Asn Asn Ala Lys Glu Ile Gly Asn Gly
465                 470                 475                 480
Cys Phe Glu Phe Tyr His Lys Cys Asn Asn Glu Cys Met Glu Ser Val
            485                 490                 495
Lys Asn Gly Thr Tyr Asp Tyr Pro Lys Tyr Ser Glu Glu Ser Lys Leu
            500                 505                 510
Asn Arg Glu Lys Ile Asp Gly Val Lys Leu Glu Ser Met Gly Val Tyr
            515                 520                 525
Gln Ile Leu Ala Ile Tyr Ser Thr Val Ala Ser Ser Leu Val Leu Leu
            530                 535                 540
```

```
Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 42
<211> LENGTH: 565
<212> TYPE: PRT
<213> ORGANISM: Artificial Sequence
<220> FEATURE:
<223> OTHER INFORMATION: A/Denver/1957

<400> SEQUENCE: 42

```
Met Lys Ala Lys Leu Leu Ile Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Lys
50                  55                  60

Ala Pro Leu Gln Leu Gly Asn Cys Asn Ile Ala Gly Trp Val Leu Gly
65                  70                  75                  80

Asn Pro Glu Cys Glu Ser Leu Leu Ser Asn Arg Ser Trp Ser Tyr Ile
                85                  90                  95

Ala Glu Thr Pro Asn Ser Glu Asn Gly Thr Cys Tyr Pro Gly Asp Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Asn His Thr
130                 135                 140

Thr Arg Gly Val Thr Ala Ala Cys Pro His Ala Arg Lys Ser Ser Phe
145                 150                 155                 160

Tyr Lys Asn Leu Val Trp Leu Thr Glu Ala Asn Gly Ser Tyr Pro Asn
                165                 170                 175

Leu Ser Arg Ser Tyr Val Asn Asn Gln Glu Lys Glu Val Leu Val Leu
            180                 185                 190

Trp Gly Val His His Pro Ser Asn Ile Glu Glu Gln Arg Ala Leu Tyr
        195                 200                 205

Arg Lys Asp Asn Ala Tyr Val Ser Val Ser Ser Asn Tyr Asn Arg
210                 215                 220

Arg Phe Thr Pro Glu Ile Ala Lys Arg Pro Lys Val Arg Asp Gln Ser
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Pro Gly Ser Gly Ile Ile Thr Ser Asn Ala Pro Leu
        275                 280                 285

Asp Glu Cys Asp Thr Lys Cys Gln Thr Pro Gln Gly Ala Ile Asn Ser
290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335
```

-continued

```
Ile Pro Ser Val Gln Ser Arg Gly Leu Phe Gly Ala Ile Ala Gly Phe
                340                 345                 350

Ile Glu Gly Gly Trp Thr Gly Met Met Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Lys Arg Met Glu Asn Leu Asn Lys Lys Val Asp Asp Gly Phe Met
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Asn Gln Leu Arg Asn Asn Ala Lys Glu Leu Gly Asn Gly Cys
465                 470                 475                 480

Phe Glu Phe Tyr His Lys Cys Asp Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Arg
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 43
<211> LENGTH: 566
<212> TYPE: PRT
<213> ORGANISM: Artificial Sequence
<220> FEATURE:
<223> OTHER INFORMATION: A/Albany/4835/1948

<400> SEQUENCE: 43

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125
```

Glu Arg Phe Glu Ile Phe Pro Lys Glu Arg Ser Trp Pro Lys His Asn
    130                 135                 140
Ile Thr Arg Gly Val Thr Ala Ala Cys Ser His Lys Gly Lys Ser Ser
145                 150                 155                 160
Phe Tyr Arg Asn Leu Leu Trp Leu Thr Glu Lys Asn Gly Ser Tyr Pro
                165                 170                 175
Asn Leu Asn Lys Ser Tyr Val Asn Asn Lys Glu Lys Glu Val Leu Val
            180                 185                 190
Leu Trp Gly Val His His Pro Ser Asn Ile Glu Asp Gln Lys Thr Leu
        195                 200                 205
Tyr Arg Lys Glu Asn Ala Tyr Val Ser Val Val Ser Ser Asn Tyr Asn
    210                 215                 220
Arg Arg Phe Thr Pro Glu Ile Ala Glu Arg Pro Lys Val Arg Gly Gln
225                 230                 235                 240
Ala Gly Arg Ile Asn Tyr Tyr Trp Thr Leu Leu Glu Pro Gly Asp Thr
                245                 250                 255
Ile Ile Phe Glu Ala Asn Gly Asn Leu Ile Ala Pro Trp His Ala Phe
            260                 265                 270
Ala Leu Ser Arg Gly Phe Gly Ser Gly Ile Ile Thr Ser Asn Ala Ser
        275                 280                 285
Met Asp Glu Cys Asp Thr Lys Cys Gln Thr Pro Gln Gly Ala Ile Asn
    290                 295                 300
Ser Ser Leu Pro Phe Gln Asn Ile His Pro Val Thr Ile Gly Glu Cys
305                 310                 315                 320
Pro Lys Tyr Val Arg Ser Thr Lys Leu Arg Met Val Thr Gly Leu Arg
                325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Ile Asp Gly Trp Tyr Gly Tyr
        355                 360                 365
His His Gln Asn Glu Gln Gly Ser Gly Tyr Ala Ala Asp Gln Lys Ser
    370                 375                 380
Thr Gln Asn Ala Ile Asn Gly Ile Thr Asn Lys Val Asn Ser Val Ile
385                 390                 395                 400
Glu Lys Met Asn Thr Gln Phe Thr Ala Val Gly Lys Glu Phe Asn Lys
                405                 410                 415
Leu Glu Lys Arg Met Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
        435                 440                 445
Glu Arg Thr Leu Asp Phe His Asp Ser Asn Val Lys Asn Leu Tyr Glu
    450                 455                 460
Lys Val Lys Ser Gln Leu Lys Asn Asn Ala Lys Glu Ile Gly Asn Gly
465                 470                 475                 480
Cys Phe Glu Phe Tyr His Lys Cys Asn Asn Glu Cys Met Glu Ser Val
                485                 490                 495
Lys Asn Gly Thr Tyr Asp Tyr Pro Lys Tyr Ser Glu Glu Ser Lys Leu
            500                 505                 510
Asn Arg Glu Lys Ile Asp Gly Val Lys Leu Glu Ser Met Gly Val Tyr
        515                 520                 525
Gln Ile Leu Ala Ile Tyr Ser Thr Val Ala Ser Ser Leu Val Leu Leu
    530                 535                 540

```
Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 44
<211> LENGTH: 566
<212> TYPE: PRT
<213> ORGANISM: Artificial Sequence
<220> FEATURE:
<223> OTHER INFORMATION: A/FortMonmouth/1/1947

<400> SEQUENCE: 44

```
Met L

```
Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Asn Ala Ile Asn Trp Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Asn Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 45
<211> LENGTH: 566
<212> TYPE: PRT
<213> ORGANISM: Artificial Sequence
<220> FEATURE:
<223> OTHER INFORMATION: A/Cameron/1946

<400> SEQUENCE: 45

Met Lys Ala Lys Leu Leu Ile Leu Leu Cys Ala Leu Ser Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Lys Arg Ser Trp Ser Tyr Ile
                85                  90                  95

Ala Glu Thr Pro Asn Ser Glu Asn Gly Ala Cys Tyr Pro Gly Asp Phe
            100                 105                 110

Ala Asp Tyr Glu Glu Leu Arg Glu Gln Leu Ser Ser Val Ser Ser Phe
        115                 120                 125
```

```
Glu Arg Phe Glu Ile Phe Pro Lys Gly Arg Ser Trp Pro Glu His Asn
130                 135                 140

Ile Asp Ile Gly Val Thr Ala Ala Cys Ser His Ala Gly Lys Ser Ser
145                 150                 155                 160

Phe Tyr Lys Asn Leu Leu Trp Leu Thr Glu Lys Asp Gly Ser Tyr Pro
                165                 170                 175

Asn Leu Asn Lys Ser Tyr Val Asn Lys Lys Glu Lys Glu Val Leu Ile
            180                 185                 190

Leu Trp Gly Val His His Pro Pro Asn Ile Glu Asn Gln Lys Thr Leu
        195                 200                 205

Tyr Arg Lys Glu Asn Ala Tyr Val Ser Val Val Ser Ser Asn Tyr Asn
210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Asn Arg Gly Ile Gly Ser Gly Ile Ile Thr Ser Asn Ala Ser
        275                 280                 285

Met Asp Glu Cys Asp Thr Lys Cys Gln Thr Pro Gln Gly Ala Ile Asn
290                 295                 300

Ser Ser Leu Pro Phe Gln Asn Ile His Pro Phe Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Asp Gly Met Ile Asp Gly Trp Tyr Gly Tyr
        355                 360                 365

His His Gln Asn Glu Gln Gly Ser Gly Tyr Ala Ala Asp Gln Lys Ser
370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
450                 455                 460

Lys Val Lys Asn Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Phe Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
```

```
                545                 550                 555                 560

Gln Cys Arg Ile Cys Ile
                565

<210> SEQ ID NO 46
<211> LENGTH: 566
<212> TYPE: PRT
<213> ORGANISM: Artificial Sequence
<220> FEATURE:
<223> OTHER INFORMATION: A/Weiss/1943

<400> SEQUENCE: 46

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Ile Pro Asn Ser Glu Asn Gly Thr Cys Tyr Pro Gly Asp Phe
            100                 105                 110

Thr Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Thr Ala Arg Gly Val Thr Ala Ala Cys Ser His Ala Gly Lys Ser Ser
145                 150                 155                 160

Phe Tyr Arg Asn Leu Leu Trp Leu Thr Glu Lys Asp Gly Ser Tyr Pro
                165                 170                 175

Asn Leu Lys Asn Ser Tyr Val Asn Lys Lys Gly Lys Glu Val Leu Val
            180                 185                 190

Leu Trp Gly Val His His Pro Ser Ile Lys Glu Gln Gln Thr Leu
        195                 200                 205

Tyr Gln Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
```

```
                340                 345                 350
Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Ile Leu Leu Glu Asn
        435                 440                 445

Glu Arg Thr Leu Asp Phe His Asp Ser Asn Val Lys Asn Leu Tyr Glu
450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 47
<211> LENGTH: 565
<212> TYPE: PRT
<213> ORGANISM: Artificial Sequence
<220> FEATURE:
<223> OTHER INFORMATION: A/Iowa/1943

<400> SEQUENCE: 47

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Ser Lys Glu Ser Ser Trp Pro Lys His Thr
```

```
              130                 135                 140
Thr Gly Val Thr Ala Ala Cys Ser His Ala Gly Lys Ser Ser Phe
145                 150                 155                 160

Tyr Arg Asn Leu Leu Trp Leu Thr Glu Lys Asp Gly Ser Tyr Pro Asn
                165                 170                 175

Leu Asn Asn Ser Tyr Val Asn Lys Lys Gly Lys Glu Val Leu Val Leu
                180                 185                 190

Trp Gly Val His His Pro Ser Asn Ile Lys Asp Gln Gln Thr Leu Tyr
                195                 200                 205

Gln Lys Glu Asn Ala Tyr Val Ser Val Val Ser Ser Asn Tyr Asn Arg
            210                 215                 220

Arg Phe Thr Pro Glu Ile Ala Glu Arg Pro Lys Val Arg Gly Gln Ala
225                 230                 235                 240

Gly Arg Ile Asn Tyr Tyr Trp Thr Leu Leu Lys Pro Gly Asp Thr Ile
                245                 250                 255

Met Phe Glu Ala Asn Gly Asn Leu Ile Ala Pro Trp Tyr Ala Phe Ala
                260                 265                 270

Leu Ser Arg Gly Phe Gly Ser Gly Ile Ile Thr Ser Asn Ala Ser Met
            275                 280                 285

His Glu Cys Asp Thr Lys Cys Gln Thr Pro Gln Gly Ala Ile Asn Ser
    290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
    450                 455                 460

Val Lys Asn Gln Leu Arg Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
    515                 520                 525

Ile Leu Ala Ile Tyr Ser Thr Ala Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560
```

```
Cys Arg Ile Cys Ile
            565

<210> SEQ ID NO 48
<211> LENGTH: 446
<212> TYPE: PRT
<213> ORGANISM: Artificial Sequence
<220> FEATURE:
<223> OTHER INFORMATION: A/Bellamy/1942

<400> SEQUENCE: 48

Met Lys Ala Arg Leu Leu Val Leu Leu Cys Ala Ile Ala Ala Thr Asp
1               5                   10                  15

Ala Asp Thr Ile Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Thr Ser Phe
        115                 120                 125

Glu Arg Phe Glu Ile Phe Pro Lys Glu Thr Ser Trp Pro Lys His Asn
    130                 135                 140

Thr Thr Lys Gly Val Thr Ala Ala Cys Ser His Ala Gly Lys Cys Ser
145                 150                 155                 160

Phe Tyr Arg Asn Leu Leu Trp Leu Thr Glu Lys Asp Gly Ser Tyr Pro
                165                 170                 175

Asn Leu Asn Asn Ser Tyr Val Asn Lys Lys Gly Lys Glu Val Leu Val
            180                 185                 190

Leu Trp Gly Val His His Pro Ser Asn Ile Lys Asp Gln Gln Thr Leu
        195                 200                 205

Tyr Gln Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asn Thr Lys Cys Gln Thr Pro Gln Met Ile Asp Gly
    290                 295                 300

Trp Tyr Gly Tyr His His Gln Asn Glu Gln Gly Ser Gly Tyr Ala Ala
305                 310                 315                 320

Asp Gln Lys Ser Thr Gln Asn Ala Ile Asn Gly Ile Thr Asn Lys Val
                325                 330                 335

Asn Ser Val Ile Glu Lys Met Asn Thr Gln Phe Thr Ala Val Gly Lys
            340                 345                 350
```

```
Glu Phe Asn Asn Leu Glu Lys Arg Met Glu Asn Leu Asn Lys Lys Val
            355                 360                 365

Asp Asp Gly Phe Leu Asp Ile Trp Thr Tyr Asn Ala Glu Leu Leu Val
            370                 375                 380

Leu Leu Glu Asn Glu Arg Thr Leu Asp Phe His Asp Ser Asn Val Lys
385                 390                 395                 400

Asn Leu Tyr Glu Lys Val Lys Ser Gln Leu Arg Asn Asn Ala Lys Glu
                405                 410                 415

Ile Gly Asn Gly Leu Val Leu Val Ser Leu Gly Ala Ile Ser Phe
            420                 425                 430

Trp Met Cys Ser Asn Gly Ser Leu Gln Cys Arg Ile Cys Ile
            435                 440                 445

<210> SEQ ID NO 49
<211> LENGTH: 565
<212> TYPE: PRT
<213> ORGANISM: Artificial Sequence
<220> FEATURE:
<223> OTHER INFORMATION: A/Puerto Rico/8/1934

<400> SEQUENCE: 49

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
            130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
            195                 200                 205

Gln Asn Glu Asn Ala Tyr Val Ser Val Val Thr Ser Asn Tyr Asn Arg
        210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270
```

Leu Arg Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
        290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 50
<211> LENGTH: 565
<212> TYPE: PRT
<213> ORGANISM: Artificial Sequence
<220> FEATURE:
<223> OTHER INFORMATION: A/WSN/1933

<400> SEQUENCE: 50

Met Lys Ala Lys Leu Leu Val Leu Leu Tyr Ala Phe Val Ala Thr Asp
1               5                   10                  15

Ala Asp Thr Ile Cys Ile Gly Tyr His Ala Asn Asn Ser Thr Asp Thr
            20                  25                  30

Val Asp Thr Ile Phe Glu Lys Asn Val Ala Val Thr His Ser Val Asn
        35                  40                  45

Leu Leu Glu Asp Arg His Asn Gly Lys Leu Cys Lys Leu Lys Gly Ile
    50                  55                  60

```
Ala Pro Leu Gln Leu Gly Lys Cys Asn Ile Thr Gly Trp Leu Leu Gly
 65                  70                  75                  80

Asn Pro Glu Cys Asp Ser Leu Leu Pro Ala Arg Ser Trp Ser Tyr Ile
                 85                  90                  95

Val Glu Thr Pro Asn Ser Glu Asn Gly Ala Cys Tyr Pro Gly Asp Phe
            100                 105                 110

Ile Asp Tyr Glu Glu Leu Arg Glu Gln Leu Ser Ser Val Ser Ser Leu
        115                 120                 125

Glu Arg Phe Glu Ile Phe Pro Lys Glu Ser Ser Trp Pro Asn His Thr
    130                 135                 140

Phe Asn Gly Val Thr Val Ser Cys Ser His Arg Gly Lys Ser Ser Phe
145                 150                 155                 160

Tyr Arg Asn Leu Leu Trp Leu Thr Lys Lys Gly Asp Ser Tyr Pro Lys
                165                 170                 175

Leu Thr Asn Ser Tyr Val Asn Asn Lys Gly Lys Glu Val Leu Val Leu
            180                 185                 190

Trp Gly Val His His Pro Ser Ser Ser Asp Glu Gln Gln Ser Leu Tyr
        195                 200                 205

Ser Asn Gly Asn Ala Tyr Val Ser Val Ala Ser Ser Asn Tyr Asn Arg
210                 215                 220

Arg Phe Thr Pro Glu Ile Ala Ala Arg Pro Lys Val Lys Asp Gln His
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Phe Glu Ser Gly Ile Ile Thr Ser Asn Ala Ser Met
        275                 280                 285

His Glu Cys Asn Thr Lys Cys Gln Thr Pro Gln Gly Ser Ile Asn Ser
    290                 295                 300

Asn Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Tyr Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Leu Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480
```

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 51
<211> LENGTH: 566
<212> TYPE: PRT
<213> ORGANISM: Artificial Sequence
<220> FEATURE:
<223> OTHER INFORMATION: A/South Carolina/1/1918

<400> SEQUENCE: 51

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

```
Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 52
<211> LENGTH: 17
<212> TYPE: PRT
<213> ORGANISM: Artificial Sequence
<220> FEATURE:
<223> OTHER INFORMATION: amino acid residues 402-418 of influenza HA of serotype H1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature

```
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 52

Xaa Asn Thr Gln Xaa Thr Ala Xaa Gly Lys Glu Xaa Asn Xaa Xaa Glu
1               5                   10                  15

Xaa

<210> SEQ ID NO 53
<211> LENGTH: 292
<212> TYPE: PRT
<213> ORGANISM: Artificial Sequence
<220> FEATURE:
<223> OTHER INFORMATION: mini HA
<220> FEATURE:
<221> NAME/KEY: MISC_FEATURE
<222> LOCATION: (56)..(56)
<223> OTHER INFORMATION: x= E, I, K, V, A, T
<220> FEATURE:
<221> NAME/KEY: MISC_FEATURE
<222> LOCATION: (59)..(59)
<223> OTHER INFORMATION: I, K, R, T, F, N, S, Y
<220> FEATURE:
<221> NAME/KEY: MISC_FEATURE
<222> LOCATION: (71)..(71)
<223> OTHER INFORMATION: x= D, F, V, Y, A, I, N, S, T
<220> FEATURE:
<221> NAME/KEY: MISC_FEATURE
<222> LOCATION: (72)..(72)
<223> OTHER INFORMATION: x= I, K, R, T, E, G, V
<220> FEATURE:
<221> NAME/KEY: MISC_FEATURE
<222> LOCATION: (121)..(121)
<223> OTHER INFORMATION: x= E, K, M, V, R, T
<220> FEATURE:
<221> NAME/KEY: MISC_FEATURE
<222> LOCATION: (125)..(125)
<223> OTHER INFORMATION: x= F, I, N, S, T, Y, H, L
<220> FEATURE:
<221> NAME/KEY: MISC_FEATURE
<222> LOCATION: (128)..(128)
<223> OTHER INFORMATION: x= A, G, I, R, T, V, F, S
<220> FEATURE:
<221> NAME/KEY: MISC_FEATURE
<222> LOCATION: (131)..(131)
<223> OTHER INFORMATION: x= F, I, N, S, T, Y, G, E, K, V
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: MISC_FEATURE
<222> LOCATION: (134)..(134)
<223> OTHER INFORMATION: x= H, I, L, N, R, S
<220> FEATURE:
<221> NAME/KEY: misc_feature
<222> LOCATION: (135)..(135)
<223> OTHER INFORMATION: Xaa can be any naturally occurring amino acid

<400> SEQUENCE: 53

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asn Gly Gly Gly Gly Lys Tyr Val Cys Ser Ala Lys Leu Arg
```

```
                35                  40                  45
Met Val Thr Gly Leu Arg Asn Xaa Pro Ser Xaa Gln Ser Gln Gly Leu
 50                  55                  60

Phe Gly Ala Ile Ala Gly Xaa Xaa Glu Gly Gly Trp Thr Gly Met Val
 65                  70                  75                  80

Asp Gly Trp Tyr Gly Tyr His His Gln Asn Glu Gln Gly Ser Gly Tyr
                 85                  90                  95

Ala Ala Asp Gln Lys Ser Thr Gln Asn Ala Ile Asn Gly Ile Thr Asn
                100                 105                 110

Lys Val Asn Ser Val Ile Glu Lys Xaa Asn Thr Gln Xaa Thr Ala Xaa
                115                 120                 125

Gly Lys Glu Xaa Asn Lys Xaa Glu Arg Met Lys Gln Ile Glu Asp Lys
                130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
                180                 185                 190

Lys Glu Ile Gly Asn Gly Cys Phe Glu Phe Tyr His Lys Cys Asn Asp
                195                 200                 205

Glu Cys Met Glu Ser Val Lys Asn Gly Thr Tyr Asp Tyr Pro Lys Tyr
210                 215                 220

Ser Glu Glu Ser Lys Leu Asn Arg Glu Lys Ile Asp Gly Val Ser Gly
225                 230                 235                 240

Arg Asp Tyr Lys Asp Asp Asp Lys Leu Val Pro Arg Gly Ser Pro
                245                 250                 255

Gly Ser Gly Tyr Ile Pro Glu Ala Pro Arg Asp Gly Gln Ala Tyr Val
                260                 265                 270

Arg Lys Asp Gly Glu Trp Val Leu Leu Ser Thr Phe Leu Gly His His
                275                 280                 285

His His His His
        290

<210> SEQ ID NO 54
<211> LENGTH: 237
<212> TYPE: PRT
<213> ORGANISM: Artificial Sequence
<220> FEATURE:
<223> OTHER INFORMATION: mini HA
<220> FEATURE:
<221> NAME/KEY: MISC_FEATURE
<222> LOCATION: (56)..(56)
<223> OTHER INFORMATION: x= E, I, K, V, A, T
<220> FEATURE:
<221> NAME/KEY: MISC_FEATURE
<222> LOCATION: (59)..(59)
<223> OTHER INFORMATION: x= I, K, R, T, F, N, S, Y
<220> FEATURE:
<221> NAME/KEY: MISC_FEATURE
<222> LOCATION: (71)..(71)
<223> OTHER INFORMATION: x= D, F, V, Y, A, I, N, S, T
<220> FEATURE:
<221> NAME/KEY: MISC_FEATURE
<222> LOCATION: (72)..(72)
<223> OTHER INFORMATION: x= I, K, R, T, E, G, V
<220> FEATURE:
<221> NAME/KEY: MISC_FEATURE
<222> LOCATION: (121)..(121)
<223> OTHER INFORMATION: x= E, K, M, V, R, T
<220> FEATURE:
<221> NAME/KEY: MISC_FEATURE
```

```
<222> LOCATION: (125)..(125)
<223> OTHER INFORMATION: x= F, I, N, S, T, Y, H, L
<220> FEATURE:
<221> NAME/KEY: MISC_FEATURE
<222> LOCATION: (128)..(128)
<223> OTHER INFORMATION: x= A, G, I, R, T, V, F, S
<220> FEATURE:
<221> NAME/KEY: MISC_FEATURE
<222> LOCATION: (132)..(132)
<223> OTHER INFORMATION: x= F, I, N, S, T, Y, G, E, K, V
<220> FEATURE:
<221> NAME/KEY: MISC_FEATURE
<222> LOCATION: (135)..(135)
<223> OTHER INFORMATION: x= H, I, L, N, R, S

<400> SEQUENCE: 54

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Xaa Pro Ser Xaa Gln Ser Gln Gly Leu
    50                  55                  60

Phe Gly Ala Ile Ala Gly Xaa Xaa Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Xaa Asn Thr Gln Xaa Thr Ala Xaa
        115                 120                 125

Gly Lys Glu Xaa Asn Lys Xaa Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly
225                 230                 235

<210> SEQ ID NO 55
<211> LENGTH: 301
<212> TYPE: PRT
<213> ORGANISM: Artificial Sequence
<220> FEATURE:
<223> OTHER INFORMATION: 127H1

<400> SEQUENCE: 55

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
              35                  40                  45

Leu Leu Glu Asn Gly Gly Gly Lys Tyr Val Cys Ser Ala Lys Leu
         50                  55                  60

Arg Met Val Thr Gly Leu Arg Asn Lys Pro Ser Lys Gln Ser Gln Gly
 65                  70                  75                  80

Leu Phe Gly Ala Ile Ala Gly Phe Thr Glu Gly Gly Trp Thr Gly Met
                 85                  90                  95

Val Asp Gly Trp Tyr Gly Tyr His His Gln Asn Glu Gln Gly Ser Gly
                100                 105                 110

Tyr Ala Ala Asp Gln Lys Ser Thr Gln Asn Ala Ile Asn Gly Ile Thr
            115                 120                 125

Asn Lys Val Asn Ser Val Ile Glu Lys Met Asn Thr Gln Tyr Thr Ala
130                 135                 140

Ile Gly Lys Glu Tyr Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 56
<211> LENGTH: 301
<212> TYPE: PRT
<213> ORGANISM: Artificial Sequence
<220> FEATURE:
<223> OTHER INFORMATION: 86B4

<400> SEQUENCE: 56

Met Lys Val Lys Leu Leu Val Leu Leu Cys Thr Phe Thr Ala Thr Tyr
 1               5                  10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asn Gly Gly Gly Lys Tyr Val Cys Ser Ala Lys Leu
         50                  55                  60

Arg Met Val Thr Gly Leu Arg Asn Lys Pro Ser Asn Gln Ser Gln Gly
 65                  70                  75                  80

Leu Phe Gly Ala Ile Ala Gly Tyr Lys Glu Gly Gly Trp Thr Gly Met
                 85                  90                  95

Val Asp Gly Trp Tyr Gly Tyr His His Gln Asn Glu Gln Gly Ser Gly
```

```
            100                 105                 110
Tyr Ala Ala Asp Gln Lys Ser Thr Gln Asn Ala Ile Asn Gly Ile Thr
            115                 120                 125

Asn Lys Val Asn Ser Val Ile Glu Lys Met Asn Thr Gln Phe Thr Ala
        130                 135                 140

Ile Gly Lys Glu Met Asn Lys Ile Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 57
<211> LENGTH: 301
<212> TYPE: PRT
<213> ORGANISM: Artificial Sequence
<220> FEATURE:
<223> OTHER INFORMATION: 74H9

<400> SEQUENCE: 57

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Phe Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
            115                 120                 125

Asn Lys Val Asn Ser Val Ile Glu Lys Met Asn Thr Gln Tyr Thr Ala
        130                 135                 140

Phe Gly Lys Glu Met Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
```

```
                    165                 170                 175
Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
            195                 200                 205

Ala Lys Glu Ile Gly Asn Gly Cys Phe Glu Phe Tyr His Lys Cys Asn
            210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
            275                 280                 285

Met Cys Ser Asn Gly Ser Leu Gln Cys Arg Ile Cys Ile
            290                 295                 300

<210> SEQ ID NO 58
<211> LENGTH: 301
<212> TYPE: PRT
<213> ORGANISM: Artificial Sequence
<220> FEATURE:
<223> OTHER INFORMATION: 6E12

<400> SEQUENCE: 58

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asn Gly Gly Gly Gly Lys Tyr Val Cys Ser Ala Lys Leu
        50                  55                  60

Arg Met Val Thr Gly Leu Arg Asn Glu Pro Ser Asn Gln Ser Gln Gly
65                  70                  75                  80

Leu Phe Gly Ala Ile Ala Gly Phe Ile Glu Gly Gly Trp Thr Gly Met
            85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
            115                 120                 125

Asn Lys Val Asn Ser Val Ile Glu Lys Met Asn Thr Gln Leu Thr Ala
        130                 135                 140

Phe Gly Lys Glu Val Asn Lys Leu Glu Arg Met Lys Gln Ile Glu Asp
145                 150                 155                 160

Lys Ile Glu Glu Ile Glu Ser Lys Gln Ile Trp Cys Tyr Asn Ala Glu
            165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
            195                 200                 205

Ala Lys Glu Ile Gly Asn Gly Cys Phe Glu Phe Tyr His Lys Cys Asn
            210                 215                 220

Asp Glu Cys Met Glu Ser Val Lys Asn Gly Thr Tyr Asp Tyr Pro Lys
```

```
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
                260                 265                 270

Ala Ser Ser Leu Val Leu Leu Val Ser Leu Gly Ala Ile Ser Phe Trp
                275                 280                 285

Met Cys Ser Asn Gly Ser Leu Gln Cys Arg Ile Cys Ile
                290                 295                 300

<210> SEQ ID NO 59
<211> LENGTH: 301
<212> TYPE: PRT
<213> ORGANISM: Artificial Sequence
<220> FEATURE:
<223> OTHER INFORMATION: 55G7

<400> SEQUENCE: 59

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Leu Leu Glu Asn Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Tyr Val Glu Gly Gly Trp Thr Gly Met
                85                  90                  95

Val Asp Gly Trp Tyr Gly Tyr His His Gln Asn Glu Gln Gly Ser Gly
                100                 105                 110

Tyr Ala Ala Asp Gln Lys Ser Thr Gln Asn Ala Ile Asn Gly Ile Thr
                115                 120                 125

Asn Lys Val Asn Ser Val Ile Glu Lys Met Asn Thr Gln Tyr Thr Ala
                130                 135                 140

Ile Gly Lys Glu Met Asn Lys Leu Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
                180                 185                 190

Asn Val Lys Asn Leu Tyr Glu Lys Val Lys Ser Gln Leu Lys Asn Asn
                195                 200                 205

Ala Lys Glu Ile Gly Asn Gly Cys Phe Glu Phe Tyr His Lys Cys Asn
                210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
                260                 265                 270

Ala Ser Ser Leu Val Leu Leu Val Ser Leu Gly Ala Ile Ser Phe Trp
                275                 280                 285

Met Cys Ser Asn Gly Ser Leu Gln Cys Arg Ile Cys Ile
                290                 295                 300
```

<210> SEQ ID NO 60
<211> LENGTH: 301
<212> TYPE: PRT
<213> ORGANISM: Artificial Sequence
<220> FEATURE:
<223> OTHER INFORMATION: 115A1

<400> SEQUENCE: 60

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Tyr Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ile Thr Ala
    130                 135                 140

Val Gly Lys Glu Tyr Asn Lys Ile Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 61
<211> LENGTH: 301
<212> TYPE: PRT
<213> ORGANISM: Artificial Sequence
<220> FEATURE:
<223> OTHER INFORMATION: 71H2

<400> SEQUENCE: 61

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asn Gly Gly Gly Lys Tyr Val Cys Ser Ala Lys Leu
50                  55                  60

Arg Met Val Thr Gly Leu Arg Asn Lys Pro Ser Asn Gln Ser Gln Gly
65                  70                  75                  80

Leu Phe Gly Ala Ile Ala Gly Phe Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
            115                 120                 125

Asn Lys Val Asn Ser Val Ile Glu Lys Met Asn Thr Gln Leu Thr Ala
    130                 135                 140

Ile Gly Lys Glu Val Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
                180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
    275                 280                 285

Met Cys Ser Asn Gly Ser Leu Gln Cys Arg Ile Cys Ile
    290                 295                 300

<210> SEQ ID NO 62
<211> LENGTH: 301
<212> TYPE: PRT
<213> ORGANISM: Artificial Sequence
<220> FEATURE:
<223> OTHER INFORMATION: 181H9

<400> SEQUENCE: 62

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asn Gly Gly Gly Lys Tyr Val Cys Ser Ala Lys Leu
50                  55                  60
```

Arg Met Val Thr Gly Leu Arg Asn Val Pro Ser Lys Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Val Gly Lys Glu Phe Asn Lys Asn Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 63
<211> LENGTH: 301
<212> TYPE: PRT
<213> ORGANISM: Artificial Sequence
<220> FEATURE:
<223> OTHER INFORMATION: 220C9

<400> SEQUENCE: 63

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Lys Tyr Val Cys Ser Ala Lys Leu
    50                  55                  60

Arg Met Val Thr Gly Leu Arg Asn Lys Pro Ser Thr Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

```
Asn Lys Val Asn Ser Val Ile Glu Lys Met Asn Thr Gln Phe Thr Ala
            130                 135                 140

Thr Gly Lys Glu Tyr Asn Lys Leu Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 64
<211> LENGTH: 301
<212> TYPE: PRT
<213> ORGANISM: Artificial Sequence
<220> FEATURE:
<223> OTHER INFORMATION: 113E7

<400> SEQUENCE: 64

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Thr Gly Lys Glu Ile Asn Lys His Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190
```

```
Asn Val Lys Asn Leu Tyr Glu Lys Val Lys Ser Gln Leu Lys Asn Asn
            195                 200                 205

Ala Lys Glu Ile Gly Asn Gly Cys Phe Glu Phe Tyr His Lys Cys Asn
210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 65
<211> LENGTH: 253
<212> TYPE: PRT
<213> ORGANISM: Artificial Sequence
<220> FEATURE:
<223> OTHER INFORMATION: s74H9

<400> SEQUENCE: 65

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Phe
        115                 120                 125

Gly Lys Glu Met Asn Lys Ser Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250
```

```
<210> SEQ ID NO 66
<211> LENGTH: 253
<212> TYPE: PRT
<213> ORGANISM: Artificial Sequence
<220> FEATURE:
<223> OTHER INFORMATION: s127H1

<400> SEQUENCE: 66

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Tyr Asn Lys Ser Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His
                245                 250

<210> SEQ ID NO 67
<211> LENGTH: 253
<212> TYPE: PRT
<213> ORGANISM: Artificial Sequence
<220> FEATURE:
<223> OTHER INFORMATION: s86B4

<400> SEQUENCE: 67

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60
```

```
Phe Gly Ala Ile Ala Gly Tyr Lys Glu Gly Gly Trp Thr Gly Met Val
 65                  70                  75                  80

Asp Gly Trp Tyr Gly Tyr His His Gln Asn Glu Gln Gly Ser Gly Tyr
                 85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Ile
        115                 120                 125

Gly Lys Glu Met Asn Lys Ile Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250

<210> SEQ ID NO 68
<211> LENGTH: 253
<212> TYPE: PRT
<213> ORGANISM: Artificial Sequence
<220> FEATURE:
<223> OTHER INFORMATION: s55G7

<400> SEQUENCE: 68

Asp Thr Ile Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
             20                  25                  30

Leu Glu Asn Gly Gly Gly Gly Lys Tyr Val Cys Ser Ala Lys Leu Arg
         35                  40                  45

Met Val Thr Gly Leu Arg Asn Lys Pro Ser Asn Gln Ser Gln Gly Leu
     50                  55                  60

Phe Gly Ala Ile Ala Gly Tyr Val Glu Gly Gly Trp Thr Gly Met Val
 65                  70                  75                  80

Asp Gly Trp Tyr Gly Tyr His His Gln Asn Glu Gln Gly Ser Gly Tyr
                 85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Met Asn Lys Leu Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175
```

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His
                245                 250

<210> SEQ ID NO 69
<211> LENGTH: 253
<212> TYPE: PRT
<213> ORGANISM: Artificial Sequence
<220> FEATURE:
<223> OTHER INFORMATION: s6E12

<400> SEQUENCE: 69

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Glu Pro Ser Asn Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Phe
        115                 120                 125

Gly Lys Glu Val Asn Lys Leu Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His
                245                 250

<210> SEQ ID NO 70
<211> LENGTH: 250
<212> TYPE: PRT
<213> ORGANISM: Artificial Sequence

```
<220> FEATURE:
<223> OTHER INFORMATION: SEQ 70
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid

<400> SEQUENCE: 70

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Xaa Pro Ser Xaa Gln Ser Gln Gly Leu
    50                  55                  60

Phe Gly Ala Ile Ala Gly Xaa Xaa Glu Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Xaa Asn Thr Gln Xaa Thr Ala Xaa
        115                 120                 125

Gly Lys Glu Xaa Asn Lys Xaa Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220
```

-continued

```
Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250

<210> SEQ ID NO 71
<211> LENGTH: 284
<212> TYPE: PRT
<213> ORGANISM: Artificial Sequence
<220> FEATURE:
<223> OTHER INFORMATION: SEQ 71
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid

<400> SEQUENCE: 71

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asn Gly Gly Gly Lys Tyr Val Cys Ser Ala Lys Leu Arg
            35                  40                  45

Met Val Thr Gly Leu Arg Asn Xaa Pro Ser Xaa Gln Ser Gln Gly Leu
50                  55                  60

Phe Gly Ala Ile Ala Gly Xaa Xaa Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Xaa Asn Thr Gln Xaa Thr Ala Xaa
        115                 120                 125

Gly Lys Glu Xaa Asn Lys Xaa Glu Arg Met Lys Gln Ile Glu Asp Lys
        130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
```

```
                165                 170                 175
Val Lys Asn Leu Tyr Glu Lys Val Lys Ser Gln Leu Lys Asn Asn Ala
                180                 185                 190

Lys Glu Ile Gly Asn Gly Cys Phe Glu Phe Tyr His Lys Cys Asn Asp
            195                 200                 205

Glu Cys Met Glu Ser Val Lys Asn Gly Thr Tyr Asp Tyr Pro Lys Tyr
        210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Leu Ala Ile Tyr Ser Thr Val Ala
                245                 250                 255

Ser Ser Leu Val Leu Val Ser Leu Gly Ala Ile Ser Phe Trp Met
                260                 265                 270

Cys Ser Asn Gly Ser Leu Gln Cys Arg Ile Cys Ile
        275                 280

<210> SEQ ID NO 72
<211> LENGTH: 250
<212> TYPE: PRT
<213> ORGANISM: Artificial Sequence
<220> FEATURE:
<223> OTHER INFORMATION: s74H9-long

<400> SEQUENCE: 72

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asn Gly Gly Gly Gly Lys Tyr Val Cys Ser Ala Lys Leu Arg
            35                  40                  45

Met Val Thr Gly Leu Arg Asn Lys Pro Ser Asn Gln Ser Gln Gly Leu
        50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Phe
        115                 120                 125

Gly Lys Glu Met Asn Lys Ser Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
                180                 185                 190

Lys Glu Ile Gly Asn Gly Cys Phe Glu Phe Tyr His Lys Cys Asn Asp
            195                 200                 205

Glu Cys Met Glu Ser Val Lys Asn Gly Thr Tyr Asp Tyr Pro Lys Tyr
        210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
```

-continued

```
                245                 250

<210> SEQ ID NO 73
<211> LENGTH: 250
<212> TYPE: PRT
<213> ORGANISM: Artificial Sequence
<220> FEATURE:
<223> OTHER INFORMATION: s127H1-long

<400> SEQUENCE: 73

Asp Thr Ile Cys Ile Gly Tyr His Ala Asn Asn Ser Thr Asp Thr Val
1               5                  10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Tyr Asn Lys Ser Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250

<210> SEQ ID NO 74
<211> LENGTH: 250
<212> TYPE: PRT
<213> ORGANISM: Artificial Sequence
<220> FEATURE:
<223> OTHER INFORMATION: s86B4-long

<400> SEQUENCE: 74

Asp Thr Ile Cys Ile Gly Tyr His Ala Asn Asn Ser Thr Asp Thr Val
1               5                  10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45
```

```
Met Val Thr Gly Leu Arg Asn Lys Pro Ser Asn Gln Ser Gln Gly Leu
 50                  55                  60

Phe Gly Ala Ile Ala Gly Tyr Lys Glu Gly Trp Thr Gly Met Val
 65                  70                  75                  80

Asp Gly Trp Tyr Gly Tyr His His Gln Asn Glu Gln Gly Ser Gly Tyr
                 85                  90                  95

Ala Ala Asp Gln Lys Ser Thr Gln Asn Ala Ile Asn Gly Ile Thr Asn
                100                 105                 110

Lys Val Asn Ser Val Ile Glu Lys Met Asn Thr Gln Phe Thr Ala Ile
                115                 120                 125

Gly Lys Glu Met Asn Lys Ile Glu Arg Met Lys Gln Ile Glu Asp Lys
130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
                180                 185                 190

Lys Glu Ile Gly Asn Gly Cys Phe Glu Phe Tyr His Lys Cys Asn Asp
                195                 200                 205

Glu Cys Met Glu Ser Val Lys Asn Gly Thr Tyr Asp Tyr Pro Lys Tyr
210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250
```

<210> SEQ ID NO 75
<211> LENGTH: 250
<212> TYPE: PRT
<213> ORGANISM: Artificial Sequence
<220> FEATURE:
<223> OTHER INFORMATION: s55G7-long

<400> SEQUENCE: 75

```
Asp Thr Ile Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
                 20                  25                  30

Leu Glu Asn Gly Gly Gly Gly Lys Tyr Val Cys Ser Ala Lys Leu Arg
             35                  40                  45

Met Val Thr Gly Leu Arg Asn Lys Pro Ser Asn Gln Ser Gln Gly Leu
 50                  55                  60

Phe Gly Ala Ile Ala Gly Tyr Val Glu Gly Trp Thr Gly Met Val
 65                  70                  75                  80

Asp Gly Trp Tyr Gly Tyr His His Gln Asn Glu Gln Gly Ser Gly Tyr
                 85                  90                  95

Ala Ala Asp Gln Lys Ser Thr Gln Asn Ala Ile Asn Gly Ile Thr Asn
                100                 105                 110

Lys Val Asn Ser Val Ile Glu Lys Met Asn Thr Gln Tyr Thr Ala Ile
                115                 120                 125

Gly Lys Glu Met Asn Lys Leu Glu Arg Met Lys Gln Ile Glu Asp Lys
                130                 135                 140

Ile Glu Glu Ile Glu Ser Lys Gln Ile Trp Cys Tyr Asn Ala Glu Leu
145                 150                 155                 160
```

```
Leu Val Leu Leu Glu Asn Glu Arg Thr Leu Asp Phe His Asp Ser Asn
                165                 170                 175
Val Lys Asn Leu Tyr Glu Lys Val Lys Ser Gln Leu Lys Asn Asn Ala
            180                 185                 190
Lys Glu Ile Gly Asn Gly Cys Phe Glu Phe Tyr His Lys Cys Asn Asp
            195                 200                 205
Glu Cys Met Glu Ser Val Lys Asn Gly Thr Tyr Asp Tyr Pro Lys Tyr
            210                 215                 220
Ser Glu Glu Ser Lys Leu Asn Arg Glu Lys Ile Asp Gly Val Lys Leu
225                 230                 235                 240
Glu Ser Met Gly Val Tyr Gln Ile Glu Gly
                245                 250
```

<210> SEQ ID NO 76
<211> LENGTH: 250
<212> TYPE: PRT
<213> ORGANISM: Artificial Sequence
<220> FEATURE:
<223> OTHER INFORMATION: s6E12-long

<400> SEQUENCE: 76

```
Asp Thr Ile Cys Ile Gly Tyr His Ala Asn Asn Ser Thr Asp Thr Val
1               5                   10                  15
Asp Thr Val Leu Glu Lys Asn Val Thr Val Thr His Ser Val Asn Leu
            20                  25                  30
Leu Glu Asn Gly Gly Gly Gly Lys Tyr Val Cys Ser Ala Lys Leu Arg
            35                  40                  45
Met Val Thr Gly Leu Arg Asn Glu Pro Ser Asn Gln Ser Gln Gly Leu
50                  55                  60
Phe Gly Ala Ile Ala Gly Phe Ile Glu Gly Gly Trp Thr Gly Met Val
65                  70                  75                  80
Asp Gly Trp Tyr Gly Tyr His His Gln Asn Glu Gln Gly Ser Gly Tyr
                85                  90                  95
Ala Ala Asp Gln Lys Ser Thr Gln Asn Ala Ile Asn Gly Ile Thr Asn
                100                 105                 110
Lys Val Asn Ser Val Ile Glu Lys Met Asn Thr Gln Leu Thr Ala Phe
            115                 120                 125
Gly Lys Glu Val Asn Lys Leu Glu Arg Met Lys Gln Ile Glu Asp Lys
130                 135                 140
Ile Glu Glu Ile Glu Ser Lys Gln Ile Trp Cys Tyr Asn Ala Glu Leu
145                 150                 155                 160
Leu Val Leu Leu Glu Asn Glu Arg Thr Leu Asp Phe His Asp Ser Asn
                165                 170                 175
Val Lys Asn Leu Tyr Glu Lys Val Lys Ser Gln Leu Lys Asn Asn Ala
            180                 185                 190
Lys Glu Ile Gly Asn Gly Cys Phe Glu Phe Tyr His Lys Cys Asn Asp
            195                 200                 205
Glu Cys Met Glu Ser Val Lys Asn Gly Thr Tyr Asp Tyr Pro Lys Tyr
            210                 215                 220
Ser Glu Glu Ser Lys Leu Asn Arg Glu Lys Ile Asp Gly Val Lys Leu
225                 230                 235                 240
Glu Ser Met Gly Val Tyr Gln Ile Glu Gly
                245                 250
```

<210> SEQ ID NO 77
<211> LENGTH: 4

```
<212> TYPE: PRT
<213> ORGANISM: Artificial Sequence
<220> FEATURE:
<223> OTHER INFORMATION: Synthesized sequence

<400> SEQUENCE: 77

Gly Gly Gly Gly
1

<210> SEQ ID NO 78
<211> LENGTH: 5
<212> TYPE: PRT
<213> ORGANISM: Artificial Sequence
<220> FEATURE:
<223> OTHER INFORMATION: Synthesized sequence

<400> SEQUENCE: 78

Gly Ser Ala Gly Ser
1               5

<210> SEQ ID NO 79
<211> LENGTH: 4
<212> TYPE: PRT
<213> ORGANISM: Artificial Sequence
<220> FEATURE:
<223> OTHER INFORMATION: Synthesized sequence

<400> SEQUENCE: 79

Gly Ser Gly Ser
1

<210> SEQ ID NO 80
<211> LENGTH: 4
<212> TYPE: PRT
<213> ORGANISM: Artificial Sequence
<220> FEATURE:
<223> OTHER INFORMATION: Synthesized sequence

<400> SEQUENCE: 80

Gly Ser Ala Gly
1

<210> SEQ ID NO 81
<211> LENGTH: 5
<212> TYPE: PRT
<213> ORGANISM: Artificial Sequence
<220> FEATURE:
<223> OTHER INFORMATION: Synthesized sequence

<400> SEQUENCE: 81

Gly Ser Gly Ser Gly
1               5

<210> SEQ ID NO 82
<211> LENGTH: 7
<212> TYPE: PRT
<213> ORGANISM: Artificial Sequence
<220> FEATURE:
<223> OTHER INFORMATION: Synthesized sequence

<400> SEQUENCE: 82

Gly Ser Gly Ser Gly Ser Gly
1               5
```